US012806286B2

(12) United States Patent
Corey et al.

(10) Patent No.: US 12,806,286 B2
(45) Date of Patent: Nov. 24, 2026

(54) DUAL-AAV VECTOR DELIVERY OF PCDH15 AND USES THEREOF

(71) Applicant: President and Fellows of Harvard College, Cambridge, MA (US)

(72) Inventors: David P. Corey, Cambridge, MA (US); Eric M. Mulhall, Cambridge, MA (US); Maryna V. Ivanchenko, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 761 days.

(21) Appl. No.: 18/025,719

(22) PCT Filed: Sep. 14, 2021

(86) PCT No.: PCT/US2021/050188

§ 371 (c)(1),
(2) Date: Mar. 10, 2023

(87) PCT Pub. No.: WO2022/056440

PCT Pub. Date: Mar. 17, 2022

(65) Prior Publication Data

US 2024/0016955 A1 Jan. 18, 2024

Related U.S. Application Data

(60) Provisional application No. 63/077,911, filed on Sep. 14, 2020.

(51) Int. Cl.

| | |
|---|---|
| ***A61K 48/00*** | (2006.01) |
| ***A61K 38/00*** | (2006.01) |
| ***A61P 27/02*** | (2006.01) |
| ***A61P 27/16*** | (2006.01) |
| ***C07K 14/47*** | (2006.01) |
| ***C12N 15/86*** | (2006.01) |

(52) U.S. Cl.

CPC .......... *A61K 48/0041* (2013.01); *A61P 27/02* (2018.01); *A61P 27/16* (2018.01); *C07K 14/47* (2013.01); *C12N 15/86* (2013.01); *A61K 38/00* (2013.01); *C12N 2750/14143* (2013.01); *C12N 2750/14171* (2013.01); *C12N 2800/40* (2013.01)

(58) Field of Classification Search

CPC ..... C12N 15/85; C12N 15/86; C12N 15/8645
See application file for complete search history.

(56) References Cited

U.S. PATENT DOCUMENTS

| | | | |
|---|---|---|---|
| 5,399,363 | A | 3/1995 | Liversidge et al. |
| 5,478,745 | A | 12/1995 | Samulski et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,641,515 | A | 6/1997 | Ramtoola |
| 5,738,868 | A | 4/1998 | Shinkarenko |
| 5,741,516 | A | 4/1998 | Webb et al. |
| 5,795,587 | A | 8/1998 | Gao et al. |
| 6,001,650 | A | 12/1999 | Colosi |
| 6,156,303 | A | 12/2000 | Russell et al. |
| 10,167,457 | B2 | 1/2019 | Liu et al. |
| 11,167,042 | B2 | 11/2021 | Stankovic et al. |
| 11,730,827 | B2 | 8/2023 | Holt et al. |
| 2003/0138772 | A1 | 7/2003 | Gao et al. |
| 2013/0095071 | A1 | 4/2013 | Bance et al. |
| 2017/0037479 | A1 | 2/2017 | Kuznetsov et al. |
| 2018/0327779 | A1 | 11/2018 | Colella et al. |
| 2018/0369414 | A1 | 12/2018 | Stankovic et al. |
| 2019/0153050 | A1 | 5/2019 | Boye et al. |
| 2022/0315948 | A1 | 10/2022 | Corey et al. |

FOREIGN PATENT DOCUMENTS

| | | | |
|---|---|---|---|
| WO | WO 98/010088 | A1 | 3/1998 |
| WO | WO 2016/139321 | A1 | 9/2016 |
| WO | WO 2017/193059 | A1 | 11/2017 |
| WO | WO 2018/031683 | A1 | 2/2018 |
| WO | WO 2018/145111 | A1 | 8/2018 |
| WO | WO 2019/199689 | A1 | 10/2019 |
| WO | WO 2020/079034 | A2 | 4/2020 |
| WO | WO 2020/097372 | A1 | 5/2020 |
| WO | WO 2020/198737 | A1 | 10/2020 |

OTHER PUBLICATIONS

UniProt webpage capture for PCDH15 (Q96QU1). https://www.uniprot.org/uniprotkb/Q96QU1/entry. Captured Jun. 27, 2025. (Year: 2025).*
NCBI webpage capture for PCDH15 (NM_033056.3). https://www.ncbi.nlm.nih.gov/nuccore/NM_033056.3. Captured Apr. 16, 2025. (Year: 2025).*
Invitation to Pay Additional Fees for Application No. PCT/US2020/029968, mailed Aug. 3, 2020.
International Search Report and Written Opinion for Application No. PCT/US2020/029968, mailed Oct. 5, 2020.
International Preliminary Report on Patentability for Application No. PCT/US2020/029968, mailed Nov. 4, 2021.
International Search Report and Written Opinion for Application No. PCT/US2021/050188, mailed Dec. 20, 2021.
International Preliminary Report on Patentability for Application No. PCT/US2021/050188, mailed Mar. 23, 2023.
Ahmad et al., Restoration of connexin26 protein level in the cochlea completely rescues hearing in a mouse model of human connexin30-linked deafness. Proc Natl Acad Sci U S A. Jan. 23, 2007;104(4):1337-41. doi: 10.1073/pnas.0606855104. Epub Jan. 16, 2007.

(Continued)

*Primary Examiner* — Christopher M Babic
*Assistant Examiner* — Jennifer S Spence
(74) *Attorney, Agent, or Firm* — Wolf, Greenfield & Sacks, P.C.

(57) ABSTRACT

The present disclosure, at least in part, provides a dual-AAV vector system and compositions thereof for expression full-length PCDH15 in target cells. The present disclosure also provides the method of using the dual rAAV system for delivering full-length PCDH15 to a target cell (e.g., inner cells or cells in the eye) for treating deafness and/or blindness (e.g., Usher syndrome 1F).

4 Claims, 22 Drawing Sheets

Specification includes a Sequence Listing.

(56) References Cited

OTHER PUBLICATIONS

Ahmed et al., Mutations of the protocadherin gene PCDH15 cause Usher syndrome type 1F. Am J Hum Genet. Jul. 2001;69(1):25-34. doi: 10.1086/321277. Epub Jun. 7, 2001.
Ahmed et al., PCDH15 is expressed in the neurosensory epithelium of the eye and ear and mutant alleles are responsible for both USH1F and DFNB23. Hum Mol Genet. Dec. 15, 2003;12(24):3215-23. doi: 10.1093/hmg/ddg358. Epub Oct. 21, 2003.
Akil et al., Restoration of hearing in the VGLUT3 knockout mouse using virally mediated gene therapy. Neuron. Jul. 26, 2012;75(2):283-93. doi: 10.1016/j.neuron.2012.05.019.
Alagramam et al., Mutations in protocadherin 15 and cadherin 23 affect tip links and mechanotransduction in mammalian sensory hair cells. PLoS One. Apr. 21, 2011;6(4):e19183. doi: 10.1371/journal.pone.0019183.
Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.
Angueyra et al., Leveraging Zebrafish to Study Retinal Degeneration. Front Cell Dev Biol. Sep. 19, 2018;6:110. doi: 10.3389/fcell.2018.00110. eCollection 2018.
Araya-Secchi et al., An elastic element in the protocadherin-15 tip link of the inner ear. Nat Commun. Nov. 18, 2016;7:13458. doi: 10.1038/ncomms13458.
Assad et al., An active motor model for adaptation by vertebrate hair cells. J Neurosci. Sep. 1992;12(9):3291-309. doi: 10.1523/JNEUROSCI.12-09-03291.1992.
Assad et al., Tip-link integrity and mechanical transduction in vertebrate hair cells. Neuron. Dec. 1991;7(6):985-94. doi: 10.1016/0896-6273(91)90343-x.
Azaiez et al., Genomic Landscape and Mutational Signatures of Deafness-Associated Genes. Am J Hum Genet. Oct. 4, 2018;103(4):484-497. doi: 10.1016/j.ajhg.2018.08.006. Epub Sep. 20, 2018.
Ben-Yosef et al., A mutation of PCDH15 among Ashkenazi Jews with the type 1 Usher syndrome. N Engl J Med. Apr. 24, 2003;348(17):1664-70. doi: 10.1056/NEJMoa021502.
Bird et al., Harnessing molecular motors for nanoscale pulldown in live cells. Mol Biol Cell. Feb. 1, 2017;28(3):463-475. doi: 10.1091/mbc.E16-08-0583. Epub Dec. 8, 2016.
Boulay et al., Hearing is normal without connexin30. J Neurosci. Jan. 9, 2013;33(2):430-4. doi: 10.1523/JNEUROSCI.4240-12.2013.
Brownstein et al., The R245X mutation of PCDH15 in Ashkenazi Jewish children diagnosed with nonsyndromic hearing loss foreshadows retinitis pigmentosa. Pediatr Res. Jun. 2004;55(6):995-1000. doi: 10.1203/01.PDR.0000125258.58267.56. Epub Mar. 17, 2004.
Buenrostro et al., Transposition of native chromatin for fast and sensitive epigenomic profiling of open chromatin, DNA-binding proteins and nucleosome position. Nature Methods. Dec. 2013;10(12):1213-8. doi: 10.1038/nmeth.2688. Epub Oct. 6, 2013.
Burset et al., SpliceDB: database of canonical and noncanonical mammalian splice sites, Nucleic Acids Res. Jan. 1, 2001;29(1):255-9. doi: 10.1093/nar/29.1.255.
Chamberlain et al., Progress toward Gene Therapy for Duchenne Muscular Dystrophy. Mol Ther. May 3, 2017;25(5):1125-1131. doi: 10.1016/j.ymthe.2017.02.019. Epub Apr. 15, 2017.
Chang et al., Functional studies reveal new mechanisms for deafness caused by connexin mutations. Otol Neurotol. Feb. 2009;30(2):237-40. doi: 10.1097/MAO.0b013e318194f774.
Chang et al., Gap junction mediated intercellular metabolite transfer in the cochlea is compromised in connexin30 null mice. PloS One. 2008;3(12):e4088. doi: 10.1371/journal.pone.0004088. Epub Dec. 31, 2008.
Chang et al., Timed conditional null of connexin26 in mice reveals temporary requirements of connexin26 in key cochlear developmental events before the onset of hearing. Neurobiol Dis. Jan. 2015;73:418-27. doi: 10.1016/j.nbd.2014.09.005. Epub Sep. 22, 2014.
Chen et al., Characterization of a knock-in mouse model of the homozygous p. V37I variant in Gjb2. Sci Rep. Sep. 13, 2016;6:33279. doi: 10.1038/srep33279.
Chen et al., Developmental abnormalities in supporting cell phalangeal processes and cytoskeleton in the Gjb2 knockdown mouse model. Dis Model Mech. Feb. 26, 2018;11(2):dmm033019. doi: 10.1242/dmm.033019.
Chen et al., Down regulated connexin26 at different postnatal stage displayed different types of cellular degeneration and formation of organ of Corti. Biochem Biophys Res Commun. Feb. 28, 2014;445(1):71-7. doi: 10.1016/j.bbrc.2014.01.154. Epub Jan. 31, 2014.
Cheung et al., Ca2+ changes the force sensitivity of the hair-cell transduction channel. Biophys J. Jan. 1, 2006;90(1):124-39. doi: 10.1529/biophysj.105.061226. Epub Oct. 7, 2005.
Christensen et al., TRP channels in mechanosensation : Direct or indirect activation? Nat Rev Neurosci. Jul. 2007;8(7):510-21. doi: 10.1038/nrn2149.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cohen-Salmon et al., Targeted ablation of connexin26 in the inner ear epithelial gap junction network causes hearing impairment and cell death. Curr Biol. Jul. 9, 2002;12(13):1106-11. doi: 10.1016/s0960-9822(02)00904-1.
Corey et al., Kinetics of the receptor current in bullfrog saccular hair cells. J Neurosci. May 1983;3(5):962-76. doi: 10.1523/JNEUROSCI.03-05-00962.1983.
Corey et al., TRPA1 is a candidate for the mechanosensitive transduction channel of vertebrate hair cells. Nature. Dec. 9, 2004;432(7018):723-30. doi: 10.1038/nature03066. Epub Oct. 13, 2004.
Creyghton et al., Histone H3K27ac separates active from poised enhancers and predicts developmental state. Proc Natl Acad Sci U S A. Dec. 14, 2010;107(50):21931-6. doi: 10.1073/pnas.1016071107. Epub Nov. 24, 2010.
Crispino et al., BAAV mediated GJB2 gene transfer restores gap junction coupling in cochlear organotypic cultures from deaf Cx26Sox10Cre mice. PloS One. 2011;6(8):e23279. doi: 10.1371/journal.pone.0023279. Epub Aug. 18, 2011.
Crispino et al., In vivo genetic manipulation of inner ear connexin expression by bovine adeno-associated viral vectors. Sci Rep. Aug. 4, 2017;7(1):6567. doi: 10.1038/s41598-017-06759-y.
Darcy et al. Dual adeno-associated viral Anc80 vector efficiently transduces inner ear cells in non-human primates. ARO Abstract 691. 2020; 43: 447-448.
Degen et al., Connexin32 can restore hearing in connexin26 deficient mice. Eur J Cell Biol. Oct. 2011;90(10):817-24. doi: 10.1016/j.ejcb.2011.05.001. Epub Aug. 2, 2011.
Del Castillo et al., A novel deletion involving the connexin-30 gene, del(GJB6-d13s1854), found in trans with mutations in the GJB2 gene (connexin-26) in subjects with DFNB1 non-syndromic hearing impairment. J Med Genet. Jul. 2005;42(7):588-94. doi: 10.1136/jmg.2004.028324.
Del Castillo et al., DFNB1 Non-syndromic Hearing Impairment: Diversity of Mutations and Associated Phenotypes. Front Mol Neurosci. Dec. 22, 2017;10:428. doi: 10.3389/fnmol.2017.00428. eCollection 2017.
De-La-Torre et al., A Mechanically Weak Extracellular Membrane-Adjacent Domain Induces Dimerization of Protocadherin-15. Biophys J. Dec. 18, 2018;115(12):2368-2385. doi: 10.1016/j.bpj.2018.11.010. Epub Nov. 16, 2018.
Deltcheva et al., CRISPR RNA maturation by trans-encoded small RNA and host factor 10 RNase III. Nature. Mar. 31, 2011;471(7340):602-7. doi: 10.1038/nature09886.
Derby et al., Gene transfer into the mammalian inner ear using HSV-1 and vaccinia virus vectors. Hear Res. Aug. 1999;134(1-2):1-8. doi: 10.1016/s0378-5955(99)00045-3.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.

(56) References Cited

OTHER PUBLICATIONS

Dinh et al., Diverse deafness mechanisms of connexin mutations revealed by studies using in vitro approaches and mouse models. Brain Res. Jun. 24, 2009;1277:52-69. doi: 10.1016/j.brainres.2009.02.008. Epub Feb. 20, 2009.
Doucette et al., Profound, prelingual nonsyndromic deafness maps to chromosome 10q21 and is caused by a novel missense mutation in the Usher syndrome type IF gene PCDH15. Eur J Hum Genet. May 2009;17(5):554-64. doi: 10.1038/ejhg.2008.231. Epub Dec. 24, 2008.
Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.
Ellis et al., A survey of ex vivo/in vitro transduction efficiency of mammalian primary cells and cell lines with Nine natural adeno-associated virus (AAV1-9) and one engineered adeno-associated virus serotype. Virol J. Mar. 6, 2013;10:74. doi: 10.1186/1743-422X-10-74.
Feigenspan et al., Expression of connexin36 in cone pedicles and OFF-cone bipolar cells of the mouse retina. J Neurosci. Mar. 31, 2004;24(13):3325-34. doi: 10.1523/JNEUROSCI.5598-03.2004.
Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.
Fetoni et al., Cx26 partial loss causes accelerated presbycusis by redox imbalance and dysregulation of Nfr2 pathway. Redox Biol. Oct. 2018;19:301-317. doi: 10.1016/j.redox.2018.08.002. Epub Aug. 7, 2018.
Forge et al., Gap junctions and connexin expression in the inner ear. Novartis Found Symp. 1999;219:134-50; discussion 151-6. doi: 10.1002/9780470515587.ch9.
Forge et al., Gap junctions in the inner ear: comparison of distribution patterns in different vertebrates and assessement of connexin composition in mammals. J Comp Neurol. Dec. 8, 2003;467(2):207-31. doi: 10.1002/cne.10916.
Garcia et al., Localization of myosin-Iβ near both ends of tip links in frog saccular hair cells. J Neurosci. Nov. 1, 1998;18(21):8637-47. doi: 10.1523/JNEUROSCI.18-21-08637.1998.
Gaudelli et al., Programmable base editing of A*T to G*C in genomic DNA without DNA cleavage. Nature. Nov. 23, 2017;551(7681):464-471. doi: 10.1038/nature24644. Epub Oct. 25, 2017.
Ge et al., Structure of mouse protocadherin 15 of the stereocilia tip link in complex with LHFPL5. Elife. Aug. 2, 2018;7:e38770. doi: 10.7554/eLife.38770.
Genbank Submission. NCBI; Accession No. NC_000010, version NC_000010.10. *Homo sapiens* chromosome 10, GRCh37.p13 Primary Assembly. Aug. 13, 2013. No Author Listed. 3 pages.
Genbank Submission. NCBI; Accession No. NM_001142763, version NM_001142763.2. *Homo sapiens* protocadherin related 15 (PCDH15), transcript variant A, mRNA. Jun. 29, 2021. Choudhary et al. 9 pages.
Genbank Submission. NCBI; Accession No. NM_001142763, version NM_001142763.1. *Homo sapiens* protocadherin related 15 (PCDH15), transcript variant A, mRNA. Apr. 23, 2019. Schrauwen et al. 9 pages.
Genbank Submission. NCBI; Accession No. NM_001142769, version NM_001142769.2. *Homo sapiens* protocadherin related 15 (PCDH15), transcript variant I, mRNA. May 4, 2019. Schrauwen et al. 9 pages.
Genbank Submission. NCBI; Accession No. NM_001142769, version NM_001142769.3. *Homo sapiens* protocadherin related 15 (PCDH15), transcript variant I, mRNA. Jun. 29, 2021. Choudhary et al. 9 pages.
Genbank Submission. NCBI; Accession No. NM_001142771, version NM_001142771.1. *Homo sapiens* protocadherin related 15 (PCDH15), transcript variant K, mRNA. Apr. 23, 2019. Schrauwen et al. 10 pages.
Genbank Submission. NCBI; Accession No. NM_001142771, version NM_001142771.2. *Homo sapiens* protocadherin related 15 (PCDH15), transcript variant K, mRNA. Jun. 29, 2021. Choudhary et al. 9 pages.
Genbank Submission. NCBI; Accession No. NM_001142772, version NM_001142772.1. *Homo sapiens* protocadherin related 15 (PCDH15), transcript variant L, mRNA. Apr. 23, 2019. Schrauwen et al. 10 pages.
Genbank Submission. NCBI; Accession No. NM_033056, version NM_033056.3. *Homo sapiens* protocadherin related 15 (PCDH15), transcript variant C, mRNA. Apr. 23, 2019. Schrauwen et al. 9 pages.
Genbank Submission. NCBI; Accession No. NP_001136235, version NP_001136235.1. protocadherin-15 isoform CD1-1 precursor [*Homo sapiens* ]. Jun. 29, 2021. Choudhary et al. 5 pages.
Genbank Submission. NCBI; Accession No. NP_001136241, version NP_001136241.1. protocadherin-15 isoform CD2-1 precursor [*Homo sapiens* ]. Jun. 29, 2021. Choudhary et al. 5 pages.
Genbank Submission. NCBI; Accession No. NP_001341349, version NP_001341349.1. protocadherin-15 isoform CD3-a precursor [*Homo sapiens* ]. Jun. 29, 2021. Choudhary et al. 5 pages.
Gregorevic et al., rAAV6-microdystrophin preserves muscle function and extends lifespan in severely dystrophic mice. Nat Med. Jul. 2006;12(7):787-9. doi: 10.1038/nm1439. Epub Jul. 2, 2006.
Grimm et al., In vitro and in vivo gene therapy vector evolution via multispecies interbreeding and retargeting of adeno-associated viruses. J Virol. Jun. 2008;82(12):5887-911. doi: 10.1128/JVI.00254-08. Epub Apr. 9, 2008.
György et al., Allele-specific gene editing prevents deafness in a model of dominant progressive hearing loss. Nat Med. Jul. 2019;25(7):1123-1130. doi: 10.1038/s41591-019-0500-9. Epub Jul. 3, 2019.
György et al., Gene transfer with AAV9-PHP.B rescues hearing in a mouse model of usher syndrome 3A and transduces hair cells in a non-human primate. Mol Ther Methods Clin Dev. Nov. 20, 2018;13:1-13. doi: 10.1016/j.omtm.2018.11.003. eCollection Jun. 14, 2019.
György et al., Rescue of hearing by gene delivery to inner-ear hair cells using exosome-associated AAV. Mol Ther. Feb. 1, 2017;25(2):379-391. doi: 10.1016/j.ymthe.2016.12.010. Epub Jan. 9, 2017.
Hanlon et al., AAV-S: A novel AAV vector selected in brain transduces the inner ear with high efficiency. Mol Ther. Apr. 28, 2020; 18 (4S1): Abstract 151.
Hanlon et al., Selection of an Efficient AAV Vector for Robust CNS Transgene Expression. Mol Ther Methods Clin Dev. Oct. 23, 2019;15:320-332. doi: 10.1016/j.omtm.2019.10.007. eCollection Dec. 13, 2019.
Hasson et al., Unconventional myosins in inner-ear sensory epithelia J Cell Biol. Jun. 16, 1997;137(6):1287-307. doi: 10.1083/jcb.137.6.1287.
Haywood-Watson et al., Ames Waltzer deaf mice have reduced electroretinogram amplitudes and complex alternative splicing of Pcdh15 transcripts. Invest Ophthalmol Vis Sci. Jul. 2006;47(7):3074-84. doi: 10.1167/iovs.06-0108.
Hirsch et al., Delivering Transgenic DNA Exceeding the Carrying Capacity of AAV Vectors. Methods Mol Biol. 2016;1382:21-39. doi: 10.1007/978-1-4939-3271-9_2.
Holt et al., A chemical-genetic strategy demonstrates myosin 1c mediates sensory adaptation in hair cells. Cell. Feb. 8, 2002;108(3):371-81. doi: 10.1016/s0092-8674(02)00629-3.
Holt et al., Functional expression of exogenous proteins in mammalian sensory hair cells infected with adenoviral vectors. J Neurophysiol. Apr. 1999;81(4):1881-8. doi: 10.1152/jn.1999.81.4.1881.
Hrvatin et al., Single-cell analysis of experience-dependent transcriptomic states in the mouse visual cortex. Nat Neurosci. Jan. 2018;21(1):120-129. doi: 10.1038/s41593-017-0029-5. Epub Dec. 11, 2017.
Iizuka et al., Perinatal Gjb2 gene transfer rescues hearing in a mouse model of hereditary deafness. Hum Mol Genet. Jul. 1, 2015;24(13):3651-61. doi: 10.1093/hmg/ddv109. Epub Mar. 23, 2015.

(56) References Cited

OTHER PUBLICATIONS

Indzhykulian et al., Molecular remodeling of tip links underlies mechanosensory regeneration in auditory hair cells. PLoS Biol. 2013;11(6):e1001583. doi: 10.1371/journal.pbio. 1001583. Epub Jun. 11, 2013.
Isgrig et al., AAV2.7m8 is a powerful viral vector for inner ear gene therapy. Nat Commun. Jan. 25, 2019;10(1):427. doi: 10.1038/s41467-018-08243-1.
Ivanchenko, Preclinical testing of AAV9-PHP.B for transgene expression in the non-human primate cochlea. Hear Res. Sep. 1, 2020;394:107930. doi: 10.1016/j.heares.2020.107930. Epub Feb. 26, 2020.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Johnson et al., Connexin-Mediated Signaling in Nonsensory Cells Is Crucial for the Development of Sensory Inner Hair Cells in the Mouse Cochlea. J Neurosci. Jan. 11, 2017;37(2):258-268. doi: 10.1523/JNEUROSCI.2251-16.2016.
Kamiya et al., Assembly of the cochlear gap junction macromolecular complex requires connexin 26. J Clin Invest. Apr. 2014;124(4):1598-607. doi: 10.1172/JCI67621. Epub Mar. 3, 2014.
Karpati et al., The principles of gene therapy in Duchenne muscular dystrophy. Clin Invest Med. Oct. 1994;17(5):499-509.
Kazmierczak et al., Cadherin 23 and protocadherin 15 interact to form tip-link filaments in sensory hair cells. Nature. Sep. 6, 2007;449(7158):87-91. doi: 10.1038/nature06091.
Kelsell et al., Connexin 26 mutations in hereditary non-syndromic sensorineural deafness. Nature. May 1, 1997;387(6628):80-3. doi: 10.1038/387080a0.
Kenna et al., Audiologic phenotype and progression in GJB2 (Connexin 26) hearing loss. Arch Otolaryngol Head Neck Surg. Jan. 2010;136(1):81-7. doi: 10.1001/archoto.2009.202.
Kikuchi et al., Gap junctions in the rat cochlea: immunohistochemical and ultrastructural analysis. Anat Embryol (Berl) Feb. 1995;191(2):101-18. doi: 10.1007/BF00186783.
Kleinstiver et al., Broadening the targeting range of Staphylococcus aureus CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kodippili et al., Dual AAV Gene Therapy for Duchenne Muscular Dystrophy with a 7-kb Mini-Dystrophin Gene in the Canine Model. Hum Gene Ther. Mar. 2018;29(3):299-311. doi: 10.1089/hum.2017.095. Epub Aug. 4, 2017.
Koehler et al., Generation of inner ear organoids containing functional hair cells from human pluripotent stem cells. Nat Biotechnol. Jun. 2017;35(6):583-589. doi: 10.1038/nbt.3840. Epub May 1, 2017.
Kohrman et al., Gene therapy for deafness. Gene Ther. Dec. 2013;20(12):1119-23. doi: 10.1038/gt.2013.39. Epub Jul. 18, 2013.
Komor et al., Programmable editing of a target base in genomic DNA without double-stranded DNA cleavage. Nature. May 19, 2016;533(7603):420-4. doi: 10.1038/nature17946. Epub Apr. 20, 2016.
Kwan et al., TRPA1 contributes to cold, mechanical, and chemical nociception but is not essential for hair-cell transduction. Neuron. Apr. 20, 2006;50(2):277-89. doi: 10.1016/j.neuron.2006.03.042.
Lang et al., Effects of chronic furosemide treatment and age on cell division in the adult gerbil inner ear. J Assoc Res Otolaryngol. Jun. 2003;4(2):164-75. doi: 10.1007/s10162-002-2056-4.
Lee et al., Mice with conditional deletion of Cx26 exhibit no vestibular phenotype despite secondary loss of Cx30 in the vestibular end organs. Hear Res. Oct. 2015;328:102-12. doi: 10.1016/j.heares.2015.07.018. Epub Jul. 29, 2015.
Levy et al., Cytosine and adenine base editing of the brain, liver, retina, heart and skeletal muscle of mice via adeno-associated viruses. Nat Biomed Eng. Jan. 2020;4(1):97-110. doi: 10.1038/s41551-019-0501-5. Epub Jan. 14, 2020.
Li et al., Characterization of slow-cycling cells in the mouse cochlear lateral wall. PLoS One. Jun. 20, 2017;12(6):e0179293. doi: 10.1371/journal.pone.0179293. eCollection 2017.
Li et al., Notch inhibition induces mitotically generated hair cells in mammalian cochleae via activating the Wnt pathway. Proc Natl Acad Sci U S A. Jan. 6, 2015;112(1):166-71. doi: 10.1073/pnas.1415901112. Epub Dec. 22, 2014.
Lin et al., Hearing loss and incident dementia. Arch Neurol. Feb. 2011;68(2):214-20. doi: 10.1001/archneurol.2010.362.
Lin et al., Hearing loss prevalence in the United States. Arch Intern Med. Nov. 14, 2011;171(20):1851-2. doi: 10.1001/archinternmed.2011.506.
Lukashkina et al., Amplification mode differs along the length of the mouse cochlea as revealed by connexin 26 deletion from specific gap junctions. Sci Rep. Jul. 12, 2017;7(1):5185. doi: 10.1038/s41598-017-04279-3.
Lustig et al., Cochlear Gene Therapy. Cold Spring Harb Perspect Med. Sep. 3, 2019;9(9):a033191. doi: 10.1101/cshperspect.a033191.
Ma et al., Connexin 26 in mature ears influences survival of hair cells and neurons. ARO Abstract 404. 2020; 43:258-9.
Maguire et al., Efficacy, Safety, and Durability of Voretigene Neparvovec-rzyl in RPE65 Mutation-Associated Inherited Retinal Dystrophy: Results of Phase 1 and 3 Trials. Ophthalmology. Sep. 2019;126(9):1273-1285. doi: 10.1016/j.ophtha.2019.06.017. Epub Jun. 22, 2019.
Mahendrasingam et al., Subcellular distribution and relative expression of fibrocyte markers in the CD/1 mouse cochlea assessed by semiquantitative immunogold electron microscopy. J Histochem Cytochem. Nov. 2011;59(11):984-1000. doi: 10.1369/0022155411421801.
Mason et al., Universal infant hearing screening by automated auditory brainstem response measurement. Pediatrics. Feb. 1998;101(2):221-8. doi: 10.1542/peds.101.2.221.
McLean et al., GREAT improves functional interpretation of cis-regulatory regions. Nat Biotechnol. May 2010;28(5):495-501. doi: 10.1038/nbt.1630. Epub May 2, 2010.
Mei et al., A deafness mechanism of digenic Cx26 (GJB2) and Cx30 (GJB6) mutations: Reduction of endocochlear potential by impairment of heterogeneous gap junctional function in the cochlear lateral wall. Neurobiol Dis. Dec. 2017;108:195-203. doi: 10.1016/j.nbd.2017.08.002. Epub Aug. 17, 2017.
Mutai et al., Mitotic activity and specification of fibrocyte subtypes in the developing rat cochlear lateral wall. Neuroscience. Nov. 10, 2009;163(4):1255-63. doi: 10.1016/j.neuroscience.2009.07.059. Epub Aug. 4, 2009.
Narui et al., Tuning Inner-Ear Tip-Link Affinity Through Alternatively Spliced Variants of Protocadherin-15. Biochemistry. Mar. 20, 2018;57(11):1702-1710. doi: 10.1021/acs.biochem.7b01075. Epub Mar. 6, 2018.
Nickel et al., Gap junctions and connexins in the inner ear: their roles in homeostasis and deafness. Curr Opin Otolaryngol Head Neck Surg. Oct. 2008;16(5):452-7. doi: 10.1097/MOO.0b013e32830e20b0.
Olson et al., Post-translational tools expand the scope of synthetic biology. Curr Opin Chem Biol. Aug. 2012;16(3-4):300-6. doi: 10.1016/j.cbpa.2012.06.003. Epub Jul. 4, 2012.
Paige et al., RNA mimics of green fluorescent protein. Science. Jul. 29, 2011;333(6042):642-6. doi: 10.1126/science.1207339.
Pan et al., Gene therapy restores auditory and vestibular function in a mouse model of Usher syndrome type 1c. Nat Biotechnol. Mar. 2017;35(3):264-272. doi: 10.1038/nbt.3801. Epub Feb. 6, 2017.
Pepermans et al., The CD2 isoform of protocadherin-15 is an essential component of the tip-link complex in mature auditory hair cells. EMBO Mol Med. Jul. 2014;6(7):984-92. doi: 10.15252/emmm.201403976.
Plantier et al., A factor VIII minigene comprising the truncated intron I of factor IX highly improves the in vitro production of factor VIII. Thromb Haemost. Aug. 2001;86(2):596-603.

(56) References Cited

OTHER PUBLICATIONS

Powers et al., A Partial Calcium-Free Linker Confers Flexibility to Inner-Ear Protocadherin-15. Structure. Mar. 7, 2017;25(3):482-495. doi: 10.1016/j.str.2017.01.014. Epub Feb. 23, 2017.
Qi et al., Repurposing CRISPR as an RNA-Guided Platform for Sequence-Specific Control of Gene Expression. Cell. Feb. 28, 2013;152(5):1173-83. doi: 10.1016/j.cell.2013.02.022.
Rada-Iglesias et al., A unique chromatin signature uncovers early developmental enhancers in humans. Nature. Feb. 10, 2011;470(7333):279-83. doi: 10.1038/nature09692. Epub Dec. 15, 2010.
Rees et al., Base editing: precision chemistry on the genome and transcriptome of living cells. Nat Rev Genet. Dec. 2018;19(12):770-788. doi: 10.1038/s41576-018-0059-1.
Rodriguez-Paris et al., Comparative functional characterization of novel non-syndromic GJB2 gene variant p.Gly45Arg and lethal syndromic variant p.Gly45Glu. PeerJ. Oct. 11, 2016;4:e2494. doi: 10.7717/peerj.2494. eCollection 2016.
Sacheli et al., Gene transfer in inner ear cells: a challenging race. Gene Ther. Mar. 2013;20(3):237-47. doi: 10.1038/gt.2012.51. Epub Jun. 28, 2012.
Scheffer et al., Gene expression profiling identifies Hes6 as a transcriptional target of ATOH1 in cochlear hair cells. FEBS Lett. Oct. 2, 2007;581(24):4651-6. doi: 10.1016/j.febslet.2007.08.059. Epub Sep. 4, 2007.
Scheffer et al., The alphal subunit of nicotinic acetylcholine receptors in the inner ear: transcriptional regulation by ATOH1 and co-expression with the gamma subunit in hair cells. J Neurochem. Dec. 2007;103(6):2651-64. doi: 10.1111/j.1471-4159.2007.04980.x.
Scheffer et al., XIRP2, an actin-binding protein essential for inner ear hair-cell stereocilia. Cell Rep. Mar. 24, 2015;10(11):1811-8. doi: 10.1016/j.celrep.2015.02.042. Epub Mar. 12, 2015.
Senis et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014.
Shepherd et al., The extent of adaptation in bullfrog saccular hair cells. J Neurosci. Oct. 1994;14(10):6217-29. doi: 10.1523/JNEUROSCI.14-10-06217.1994.
Shu et al., Identification of Adeno-Associated Viral Vectors That Target Neonatal and Adult Mammalian Inner Ear Cell Subtypes. Hum Gene Ther. Sep. 2016;27(9):687-99. doi: 10.1089/hum.2016.053. Epub Jun. 24, 2016.
Solc et al., Molecular cloning of myosins from the bullfrog saccular macula: A candidate for the adaptation motor. Auditory Neurosci. 1994; 1:63-75.
Sotomayor et al., A Partial Calcium-Free Linker Confers Flexibility to Inner-Ear Protocadherin-15. Structure. Mar. 7, 2017;25(3):482-495. doi: 10.1016/j.str.2017.01.014. Epub Feb. 23, 2017.
Sotomayor et al., In search of the hair-cell gating spring: Elastic properties of ankyrin and cadherin repeats. Structure. Apr. 2005;13(4):669-82. doi: 10.1016/j.str.2005.03.001.
Sotomayor et al., Structural determinants of cadherin-23 function in hearing and deafness. Neuron. Apr. 15, 2010;66(1):85-100. doi: 10.1016/j.neuron.2010.03.028.
Sotomayor et al., Structure of a force-conveying cadherin bond essential for inner-ear mechanotransduction. Nature. Dec. 6, 2012;492(7427):128-32. doi: 10.1038/nature11590. Epub Nov. 7, 2012.
Sun et al., Connexin30 null and conditional connexin26 null mice display distinct pattern and time course of cellular degeneration in the cochlea. J Comp Neurol. Oct. 20, 2009;516(6):569-79. doi: 10.1002/cne.22117.
Takada et al., Connexin 26 null mice exhibit spiral ganglion degeneration that can be blocked by BDNF gene therapy. Hearing Res. Mar. 2014;309:124-35. doi: 10.1016/j.heares.2013.11.009. Epub Dec. 12, 2013.
Trapani et al., Effective delivery of large genes to the retina by dual AAV vectors. EMBO Mol Med. Feb. 2014;6(2):194-211. doi: 10.1002/emmm.201302948. Epub Dec. 15, 2013.
Trapani et al., Seeing the Light after 25 Years of Retinal Gene Therapy. Trends Mol Med. Aug. 2018;24(8):669-681. doi: 10.1016/j.molmed.2018.06.006. Epub Jul. 5, 2018.
Trapani, Dual AAV Vectors for Stargardt Disease. Methods Mol Biol. 2018;1715:153-175. doi: 10.1007/978-1-4939-7522-8_11.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Vogl, Tryptophan-rich basic protein (WRB) mediates insertion of the tail-anchored protein otoferlin and is required for hair cell exocytosis and hearing. EMBO J. Dec. 1, 2016;35(23):2536-2552. doi: 10.15252/embj.201593565. Epub Jul. 25, 2016.
Wang et al., Targeted connexin26 ablation arrests postnatal development of the organ of Corti. Biochem Biophys Res Commun. Jul. 17, 2009;385(1):33-7. doi: 10.1016/j.bbrc.2009.05.023. Epub May 9, 2009.
Wassmer et al., Exosome-associated AAV2 vector mediates robust gene delivery into the murine retina upon intravitreal injection. Sci Rep. Mar. 31, 2017;7:45329. doi: 10.1038/srep45329.
Watanabe et al., Expression of the Sox10 gene during mouse inner ear development. Brain Res Mol Brain Res. Dec. 8, 2000;84(1-2):141-5. doi: 10.1016/s0169-328x(00)00236-9.
Wilch et al., A novel DFNB1 deletion allele supports the existence of a distant cis-regulatory region that controls GJB2 and GJB6 expression. Clin Genet. Sep. 2010;78(3):267-74. doi: 10.1111/j.1399-0004.2010.01387.x. Epub Mar. 1, 2010.
Wingard et al., Cellular and Deafness Mechanisms Underlying Connexin Mutation-Induced Hearing Loss—A Common Hereditary Deafness. Front Cell Neurosci. May 29, 2015;9:202. doi: 10.3389/fncel.2015.00202. eCollection 2015.
Wise et al., The effect of deafness duration on neurotrophin gene therapy for spiral ganglion neuron protection. Hearing Res. Aug. 2011;278(1-2):69-76. doi: 10.1016/j.heares.2011.04.010. Epub May 1, 2011.
Wu et al., Hair-cell mechanotransduction persists in TRP channel knockout mice. PloS One. May 19, 2016;11(5):e0155577. doi: 10.1371/journal.pone.0155577. eCollection 2016.
Xia et al., Expression of connexin 26 and Na,K-ATPase in the developing mouse cochlear lateral wall: functional implications. Brain Res. Oct. 30, 1999;846(1):106-11. doi: 10.1016/s0006-8993(99)01996-4.
Xiao et al., Rescue of the albino phenotype by introducing a functional tyrosinase minigene into Kunming albino mice. World J Gastroenterol. Jan. 14, 2007;13(2):244-9. doi: 10.3748/wjg.v13.i2.244.
Yang et al., Gfil-Cre knock-in mouse line: A tool for inner ear hair cell-specific gene deletion. Genesis. Jun. 2010;48(6):400-6. doi: 10.1002/dvg.20632.
Yeh et al., In vivo base editing of post-mitotic sensory cells. Nature Commun. Jun. 5, 2018;9(1):2184. doi: 10.1038/s41467-018-04580-3.
Yeh et al., In vivo base editing rescues hearing in a mouse model of recessive deafness. ARO Abstract 172. 2020; 43:96-97.
Yu et al., Virally expressed connexin26 restores gap junction function in the cochlea of conditional Gjb2 knockout mice. Gene Ther. Jan. 2014;21(1):71-80. doi: 10.1038/gt.2013.59. Epub Nov. 14, 2013.
Zelante et al., Connexin26 mutations associated with the most common form of non-syndromic neurosensory autosomal recessive deafness (DFNB1) in Mediterraneans. Hum Mol Genet. Sep. 1997;6(9):1605-9. doi: 10.1093/hmg/6.9.1605.
Zhu et al., Active cochlear amplification is dependent on supporting cell gap junctions. Nature Commun. 2013;4:1786. doi: 10.1038/ncomms2806.
Extended European Search Report for Application No. 20794633.6, mailed Sep. 27, 2023.
Ahmed et al., Gene structure and mutant alleles of PCDH15: nonsyndromic deafness DFNB23 and type 1 Usher syndrome. Hum Genet. Oct. 2008;124(3):215-23. doi: 10.1007/s00439-008-0543-3. Epub Aug. 22, 2008.

(56) References Cited

OTHER PUBLICATIONS

Genbank Submission. NCBI; Accession No. NG_009115, version NG_009115.1. *Homo sapiens* rhodopsin (RHO), RefSeqGene on chromosome 3. Jan. 18, 2018. 7 pages.
Ivanchenko et al., Mini-PCDH15 gene therapy rescues hearing in a mouse model of Usher syndrome type 1F. Nat Commun. Apr. 26, 2023;14(1):2400. doi: 10.1038/s41467-023-38038-y.
Ostedgaard et al., A shortened adeno-associated virus expression cassette for CFTR gene transfer to cystic fibrosis airway epithelia. Proc Natl Acad Sci U S A. Feb. 22, 2005;102(8):2952-7. doi: 10.1073/pnas.0409845102. Epub Feb. 9, 2005.
Pepermans et al., The tip-link molecular complex of the auditory mechano-electrical transduction machinery. Hear Res. Dec. 2015;330(Pt A):10-7. doi: 10.1016/j.heares.2015.05.005. Epub Jun. 3, 2015.
Perreault-Micale et al., Truncating variants in the majority of the cytoplasmic domain of PCDH15 are unlikely to cause Usher syndrome 1F. J Mol Diagn. Nov. 2014;16(6):673-8. doi: 10.1016/j.jmoldx.2014.07.001.
Zhang et al., Cochlear Gene Therapy for Sensorineural Hearing Loss: Current Status and Major Remaining Hurdles for Translational Success. Front Mol Neurosci. Jun. 26, 2018:11:221. doi: 10.3389/fnmol.2018.00221. eCollection 2018.

* cited by examiner

SEQUENCE LISTING

```
<160> NUMBER OF SEQ ID NOS: 56

<210> SEQ ID NO 1
<211> LENGTH: 1962
<212> TYPE: PRT
<213> ORGANISM: Homo sapiens

<400> SEQUENCE: 1

Met Phe Arg Gln Phe Tyr Leu Trp Thr Cys Leu Ala Ser Gly Ile Ile
1               5                   10                  15

Leu Gly Ser Leu Phe Glu Ile Cys Leu Gly Gln Tyr Asp Asp Asp Trp
            20                  25                  30

Gln Tyr Glu Asp Cys Lys Leu Ala Arg Gly Gly Pro Pro Ala Thr Ile
        35                  40                  45

Val Ala Ile Asp Glu Glu Ser Arg Asn Gly Thr Ile Leu Val Asp Asn
    50                  55                  60

Met Leu Ile Lys Gly Thr Ala Gly Gly Pro Asp Pro Thr Ile Glu Leu
65                  70                  75                  80

Ser Leu Lys Asp Asn Val Asp Tyr Trp Val Leu Met Asp Pro Val Lys
                85                  90                  95

Gln Met Leu Phe Leu Asn Ser Thr Gly Arg Val Leu Asp Arg Asp Pro
            100                 105                 110

Pro Met Asn Ile His Ser Ile Val Val Gln Val Gln Cys Ile Asn Lys
        115                 120                 125

Lys Val Gly Thr Ile Ile Tyr His Glu Val Arg Ile Val Val Arg Asp
    130                 135                 140

Arg Asn Asp Asn Ser Pro Thr Phe Lys His Glu Ser Tyr Tyr Ala Thr
145                 150                 155                 160

Val Asn Glu Leu Thr Pro Val Gly Thr Thr Ile Phe Thr Gly Phe Ser
                165                 170                 175

Gly Asp Asn Gly Ala Thr Asp Ile Asp Asp Gly Pro Asn Gly Gln Ile
            180                 185                 190

Glu Tyr Val Ile Gln Tyr Asn Pro Asp Asp Pro Thr Ser Asn Asp Thr
        195                 200                 205

Phe Glu Ile Pro Leu Met Leu Thr Gly Asn Ile Val Leu Arg Lys Arg
    210                 215                 220

Leu Asn Tyr Glu Asp Lys Thr Arg Tyr Phe Val Ile Ile Gln Ala Asn
225                 230                 235                 240

Asp Arg Ala Gln Asn Leu Asn Glu Arg Arg Thr Thr Thr Thr Thr Leu
                245                 250                 255
```

```
Thr Val Asp Val Leu Asp Gly Asp Asp Leu Gly Pro Met Phe Leu Pro
            260                 265                 270

Cys Val Leu Val Pro Asn Thr Arg Asp Cys Arg Pro Leu Thr Tyr Gln
        275                 280                 285

Ala Ala Ile Pro Glu Leu Arg Thr Pro Glu Glu Leu Asn Pro Ile Ile
    290                 295                 300

Val Thr Pro Pro Ile Gln Ala Ile Asp Gln Asp Arg Asn Ile Gln Pro
305                 310                 315                 320

Pro Ser Asp Arg Pro Gly Ile Leu Tyr Ser Ile Leu Val Gly Thr Pro
                325                 330                 335

Glu Asp Tyr Pro Arg Phe Phe His Met His Pro Arg Thr Ala Glu Leu
            340                 345                 350

Ser Leu Leu Glu Pro Val Asn Arg Asp Phe His Gln Lys Phe Asp Leu
        355                 360                 365

Val Ile Lys Ala Glu Gln Asp Asn Gly His Pro Leu Pro Ala Phe Ala
    370                 375                 380

Gly Leu His Ile Glu Ile Leu Asp Glu Asn Asn Gln Ser Pro Tyr Phe
385                 390                 395                 400

Thr Met Pro Ser Tyr Gln Gly Tyr Ile Leu Glu Ser Ala Pro Val Gly
                405                 410                 415

Ala Thr Ile Ser Asp Ser Leu Asn Leu Thr Ser Pro Leu Arg Ile Val
            420                 425                 430

Ala Leu Asp Lys Asp Ile Glu Asp Thr Lys Asp Pro Glu Leu His Leu
        435                 440                 445

Phe Leu Asn Asp Tyr Thr Ser Val Phe Thr Val Thr Gln Thr Gly Ile
    450                 455                 460

Thr Arg Tyr Leu Thr Leu Leu Gln Pro Val Asp Arg Glu Glu Gln Gln
465                 470                 475                 480

Thr Tyr Thr Phe Ser Ile Thr Ala Phe Asp Gly Val Gln Glu Ser Glu
                485                 490                 495

Pro Val Ile Val Asn Ile Gln Val Met Asp Ala Asn Asp Asn Thr Pro
            500                 505                 510

Thr Phe Pro Glu Ile Ser Tyr Asp Val Tyr Val Tyr Thr Asp Met Arg
        515                 520                 525

Pro Gly Asp Ser Val Ile Gln Leu Thr Ala Val Asp Ala Asp Glu Gly
    530                 535                 540

Ser Asn Gly Glu Ile Thr Tyr Glu Ile Leu Val Gly Ala Gln Gly Asp
545                 550                 555                 560

Phe Ile Ile Asn Lys Thr Thr Gly Leu Ile Thr Ile Ala Pro Gly Val
                565                 570                 575

Glu Met Ile Val Gly Arg Thr Tyr Ala Leu Thr Val Gln Ala Ala Asp
            580                 585                 590

Asn Ala Pro Pro Ala Glu Arg Arg Asn Ser Ile Cys Thr Val Tyr Ile
        595                 600                 605

Glu Val Leu Pro Pro Asn Asn Gln Ser Pro Pro Arg Phe Pro Gln Leu
    610                 615                 620

Met Tyr Ser Leu Glu Ile Ser Glu Ala Met Arg Val Gly Ala Val Leu
625                 630                 635                 640

Leu Asn Leu Gln Ala Thr Asp Arg Glu Gly Asp Ser Ile Thr Tyr Ala
                645                 650                 655

Ile Glu Asn Gly Asp Pro Gln Arg Val Phe Asn Leu Ser Glu Thr Thr
            660                 665                 670
```

```
Gly Ile Leu Thr Leu Gly Lys Ala Leu Asp Arg Glu Ser Thr Asp Arg
        675                 680                 685

Tyr Ile Leu Ile Ile Thr Ala Ser Asp Gly Arg Pro Asp Gly Thr Ser
    690                 695                 700

Thr Ala Thr Val Asn Ile Val Val Thr Asp Val Asn Asp Asn Ala Pro
705                 710                 715                 720

Val Phe Asp Pro Tyr Leu Pro Arg Asn Leu Ser Val Val Glu Glu Glu
                725                 730                 735

Ala Asn Ala Phe Val Gly Gln Val Lys Ala Thr Asp Pro Asp Ala Gly
            740                 745                 750

Ile Asn Gly Gln Val His Tyr Ser Leu Gly Asn Phe Asn Asn Leu Phe
        755                 760                 765

Arg Ile Thr Ser Asn Gly Ser Ile Tyr Thr Ala Val Lys Leu Asn Arg
    770                 775                 780

Glu Val Arg Asp Tyr Tyr Glu Leu Val Val Val Ala Thr Asp Gly Ala
785                 790                 795                 800

Val His Pro Arg His Ser Thr Leu Thr Leu Ala Ile Lys Val Leu Asp
                805                 810                 815

Ile Asp Asp Asn Ser Pro Val Phe Thr Asn Ser Thr Tyr Thr Val Leu
            820                 825                 830

Val Glu Glu Asn Leu Pro Ala Gly Thr Thr Ile Leu Gln Ile Glu Ala
        835                 840                 845

Lys Asp Val Asp Leu Gly Ala Asn Val Ser Tyr Arg Ile Arg Ser Pro
    850                 855                 860

Glu Val Lys His Phe Phe Ala Leu His Pro Phe Thr Gly Glu Leu Ser
865                 870                 875                 880

Leu Leu Arg Ser Leu Asp Tyr Glu Ala Phe Pro Asp Gln Glu Ala Ser
                885                 890                 895

Ile Thr Phe Leu Val Glu Ala Phe Asp Ile Tyr Gly Thr Met Pro Pro
            900                 905                 910

Gly Ile Ala Thr Val Thr Val Ile Val Lys Asp Met Asn Asp Tyr Pro
        915                 920                 925

Pro Val Phe Ser Lys Arg Ile Tyr Lys Gly Met Val Ala Pro Asp Ala
    930                 935                 940

Val Lys Gly Thr Pro Ile Thr Thr Val Tyr Ala Glu Asp Ala Asp Pro
945                 950                 955                 960

Pro Gly Leu Pro Ala Ser Arg Val Arg Tyr Arg Val Asp Asp Val Gln
                965                 970                 975

Phe Pro Tyr Pro Ala Ser Ile Phe Glu Val Glu Glu Asp Ser Gly Arg
            980                 985                 990

Val Ile Thr Arg Val Asn Leu Asn  Glu Glu Pro Thr Thr  Ile Phe Lys
        995                 1000                1005

Leu Val  Val Val Ala Phe Asp  Asp Gly Glu Pro Val  Met Ser Ser
    1010                1015                1020

Ser Ala  Thr Val Lys Ile Leu  Val Leu His Pro Gly  Glu Ile Pro
    1025                1030                1035

Arg Phe  Thr Gln Glu Glu Tyr  Arg Pro Pro Pro Val  Ser Glu Leu
    1040                1045                1050

Ala Thr  Lys Gly Thr Met Val  Gly Val Ile Ser Ala  Ala Ala Ile
    1055                1060                1065

Asn Gln  Ser Ile Val Tyr Ser  Ile Val Ser Gly Asn  Glu Glu Asp
    1070                1075                1080
```

```
Thr Phe  Gly Ile Asn Asn Ile  Thr Gly Val Ile Tyr  Val Asn Gly
    1085                 1090                 1095

Pro Leu  Asp Tyr Glu Thr Arg  Thr Ser Tyr Val Leu  Arg Val Gln
    1100                 1105                 1110

Ala Asp  Ser Leu Glu Val Val  Leu Ala Asn Leu Arg  Val Pro Ser
    1115                 1120                 1125

Lys Ser  Asn Thr Ala Lys Val  Tyr Ile Glu Ile Gln  Asp Glu Asn
    1130                 1135                 1140

Asn His  Pro Pro Val Phe Gln  Lys Lys Phe Tyr Ile  Gly Gly Val
    1145                 1150                 1155

Ser Glu  Asp Ala Arg Met Phe  Thr Ser Val Leu Arg  Val Lys Ala
    1160                 1165                 1170

Thr Asp  Lys Asp Thr Gly Asn  Tyr Ser Val Met Ala  Tyr Arg Leu
    1175                 1180                 1185

Ile Ile  Pro Pro Ile Lys Glu  Gly Lys Glu Gly Phe  Val Val Glu
    1190                 1195                 1200

Thr Tyr  Thr Gly Leu Ile Lys  Thr Ala Met Leu Phe  His Asn Met
    1205                 1210                 1215

Arg Arg  Ser Tyr Phe Lys Phe  Gln Val Ile Ala Thr  Asp Asp Tyr
    1220                 1225                 1230

Gly Lys  Gly Leu Ser Gly Lys  Ala Asp Val Leu Val  Ser Val Val
    1235                 1240                 1245

Asn Gln  Leu Asp Met Gln Val  Ile Val Ser Asn Val  Pro Pro Thr
    1250                 1255                 1260

Leu Val  Glu Lys Lys Ile Glu  Asp Leu Thr Glu Ile  Leu Asp Arg
    1265                 1270                 1275

Tyr Val  Gln Glu Gln Ile Pro  Gly Ala Lys Val Val  Val Glu Ser
    1280                 1285                 1290

Ile Gly  Ala Arg Arg His Gly  Asp Ala Phe Ser Leu  Glu Asp Tyr
    1295                 1300                 1305

Thr Lys  Cys Asp Leu Thr Val  Tyr Ala Ile Asp Pro  Gln Thr Asn
    1310                 1315                 1320

Arg Ala  Ile Asp Arg Asn Glu  Leu Phe Lys Phe Leu  Asp Gly Lys
    1325                 1330                 1335

Leu Leu  Asp Ile Asn Lys Asp  Phe Gln Pro Tyr Tyr  Gly Glu Gly
    1340                 1345                 1350

Gly Arg  Ile Leu Glu Ile Arg  Thr Pro Glu Ala Val  Thr Ser Ile
    1355                 1360                 1365

Lys Lys  Arg Gly Glu Ser Leu  Gly Tyr Thr Glu Gly  Ala Leu Leu
    1370                 1375                 1380

Ala Leu  Ala Phe Ile Ile Ile  Leu Cys Cys Ile Pro  Ala Ile Leu
    1385                 1390                 1395

Val Val  Leu Val Ser Tyr Arg  Gln Phe Lys Val Arg  Gln Ala Glu
    1400                 1405                 1410

Cys Thr  Lys Thr Ala Arg Ile  Gln Ala Ala Leu Pro  Ala Ala Lys
    1415                 1420                 1425

Pro Ala  Val Pro Ala Pro Ala  Pro Val Ala Ala Pro  Pro Pro Pro
    1430                 1435                 1440

Pro Pro  Pro Pro Pro Gly Ala  His Leu Tyr Glu Glu  Leu Gly Asp
    1445                 1450                 1455

Ser Ser  Met His Asn Leu Phe  Leu Leu Tyr His Phe  Gln Gln Ser
    1460                 1465                 1470
```

```
Arg Gly  Asn Asn Ser Val Ser  Glu Asp Arg Lys His  Gln Gln Val
    1475                 1480                 1485

Val Met  Pro Phe Ser Ser Asn  Thr Ile Glu Ala His  Lys Ser Ala
    1490                 1495                 1500

His Val  Asp Gly Ser Leu Lys  Ser Asn Lys Leu Lys  Ser Ala Arg
    1505                 1510                 1515

Lys Phe  Thr Phe Leu Ser Asp  Glu Asp Asp Leu Ser  Ala His Asn
    1520                 1525                 1530

Pro Leu  Tyr Lys Glu Asn Ile  Ser Gln Val Ser Thr  Asn Ser Asp
    1535                 1540                 1545

Ile Ser  Gln Arg Thr Asp Phe  Val Asp Pro Phe Ser  Pro Lys Ile
    1550                 1555                 1560

Gln Ala  Lys Ser Lys Ser Leu  Arg Gly Pro Arg Glu  Lys Ile Gln
    1565                 1570                 1575

Arg Leu  Trp Ser Gln Ser Val  Ser Leu Pro Arg Arg  Leu Met Arg
    1580                 1585                 1590

Lys Val  Pro Asn Arg Pro Glu  Ile Ile Asp Leu Gln  Gln Trp Gln
    1595                 1600                 1605

Gly Thr  Arg Gln Lys Ala Glu  Asn Glu Asn Thr Gly  Ile Cys Thr
    1610                 1615                 1620

Asn Lys  Arg Gly Ser Ser Asn  Pro Leu Leu Thr Thr  Glu Glu Ala
    1625                 1630                 1635

Asn Leu  Thr Glu Lys Glu Glu  Ile Arg Gln Gly Glu  Thr Leu Met
    1640                 1645                 1650

Ile Glu  Gly Thr Glu Gln Leu  Lys Ser Leu Ser Ser  Asp Ser Ser
    1655                 1660                 1665

Phe Cys  Phe Pro Arg Pro His  Phe Ser Phe Ser Thr  Leu Pro Thr
    1670                 1675                 1680

Val Ser  Arg Thr Val Glu Leu  Lys Ser Glu Pro Asn  Val Ile Ser
    1685                 1690                 1695

Ser Pro  Ala Glu Cys Ser Leu  Glu Leu Ser Pro Ser  Arg Pro Cys
    1700                 1705                 1710

Val Leu  His Ser Ser Leu Ser  Arg Arg Glu Thr Pro  Ile Cys Met
    1715                 1720                 1725

Leu Pro  Ile Glu Thr Glu Arg  Asn Ile Phe Glu Asn  Phe Ala His
    1730                 1735                 1740

Pro Pro  Asn Ile Ser Pro Ser  Ala Cys Pro Leu Pro  Pro Pro Pro
    1745                 1750                 1755

Pro Ile  Ser Pro Pro Ser Pro  Pro Pro Ala Pro Ala  Pro Leu Ala
    1760                 1765                 1770

Pro Pro  Pro Asp Ile Ser Pro  Phe Ser Leu Phe Cys  Pro Pro Pro
    1775                 1780                 1785

Ser Pro  Pro Ser Ile Pro Leu  Pro Leu Pro Pro Pro  Thr Phe Phe
    1790                 1795                 1800

Pro Leu  Ser Val Ser Thr Ser  Gly Pro Pro Thr Pro  Pro Leu Leu
    1805                 1810                 1815

Pro Pro  Phe Pro Thr Pro Leu  Pro Pro Pro Pro Pro  Ser Ile Pro
    1820                 1825                 1830

Cys Pro  Pro Pro Pro Ser Ala  Ser Phe Leu Ser Thr  Glu Cys Val
    1835                 1840                 1845

Cys Ile  Thr Gly Val Lys Cys  Thr Thr Asn Leu Met  Pro Ala Glu
    1850                 1855                 1860
```

```
Lys Ile  Lys Ser Ser Met Thr  Gln Leu Ser Thr Thr  Thr Val Cys
    1865                1870                1875

Lys Thr  Asp Pro Gln Arg Glu  Pro Lys Gly Ile Leu  Arg His Val
    1880                1885                1890

Lys Asn  Leu Ala Glu Leu Glu  Lys Ser Val Ala Asn  Met Tyr Ser
    1895                1900                1905

Gln Ile  Glu Lys Asn Tyr Leu  Arg Thr Asn Val Ser  Glu Leu Gln
    1910                1915                1920

Thr Met  Cys Pro Ser Glu Val  Thr Asn Met Glu Ile  Thr Ser Glu
    1925                1930                1935

Gln Asn  Lys Gly Ser Leu Asn  Asn Ile Val Glu Gly  Thr Glu Lys
    1940                1945                1950

Gln Ser  His Ser Gln Ser Thr  Ser Leu
    1955                1960


<210> SEQ ID NO 2
<211> LENGTH: 1790
<212> TYPE: PRT
<213> ORGANISM: Homo sapiens

<400> SEQUENCE: 2

Met Phe Arg Gln Phe Tyr Leu Trp Thr Cys Leu Ala Ser Gly Ile Ile
1               5                   10                  15

Leu Gly Ser Leu Phe Glu Ile Cys Leu Gly Gln Tyr Asp Asp Asp Trp
            20                  25                  30

Gln Tyr Glu Asp Cys Lys Leu Ala Arg Gly Gly Pro Pro Ala Thr Ile
        35                  40                  45

Val Ala Ile Asp Glu Glu Ser Arg Asn Gly Thr Ile Leu Val Asp Asn
    50                  55                  60

Met Leu Ile Lys Gly Thr Ala Gly Gly Pro Asp Pro Thr Ile Glu Leu
65                  70                  75                  80

Ser Leu Lys Asp Asn Val Asp Tyr Trp Val Leu Met Asp Pro Val Lys
                85                  90                  95

Gln Met Leu Phe Leu Asn Ser Thr Gly Arg Val Leu Asp Arg Asp Pro
            100                 105                 110

Pro Met Asn Ile His Ser Ile Val Val Gln Val Gln Cys Ile Asn Lys
        115                 120                 125

Lys Val Gly Thr Ile Ile Tyr His Glu Val Arg Ile Val Val Arg Asp
    130                 135                 140

Arg Asn Asp Asn Ser Pro Thr Phe Lys His Glu Ser Tyr Tyr Ala Thr
145                 150                 155                 160

Val Asn Glu Leu Thr Pro Val Gly Thr Thr Ile Phe Thr Gly Phe Ser
                165                 170                 175

Gly Asp Asn Gly Ala Thr Asp Ile Asp Asp Gly Pro Asn Gly Gln Ile
            180                 185                 190

Glu Tyr Val Ile Gln Tyr Asn Pro Asp Asp Pro Thr Ser Asn Asp Thr
        195                 200                 205

Phe Glu Ile Pro Leu Met Leu Thr Gly Asn Ile Val Leu Arg Lys Arg
    210                 215                 220

Leu Asn Tyr Glu Asp Lys Thr Arg Tyr Phe Val Ile Ile Gln Ala Asn
225                 230                 235                 240

Asp Arg Ala Gln Asn Leu Asn Glu Arg Arg Thr Thr Thr Thr Thr Leu
                245                 250                 255
```

```
Thr Val Asp Val Leu Asp Gly Asp Asp Leu Gly Pro Met Phe Leu Pro
            260                 265                 270

Cys Val Leu Val Pro Asn Thr Arg Asp Cys Arg Pro Leu Thr Tyr Gln
        275                 280                 285

Ala Ala Ile Pro Glu Leu Arg Thr Pro Glu Glu Leu Asn Pro Ile Ile
    290                 295                 300

Val Thr Pro Pro Ile Gln Ala Ile Asp Gln Asp Arg Asn Ile Gln Pro
305                 310                 315                 320

Pro Ser Asp Arg Pro Gly Ile Leu Tyr Ser Ile Leu Val Gly Thr Pro
                325                 330                 335

Glu Asp Tyr Pro Arg Phe Phe His Met His Pro Arg Thr Ala Glu Leu
            340                 345                 350

Ser Leu Leu Glu Pro Val Asn Arg Asp Phe His Gln Lys Phe Asp Leu
        355                 360                 365

Val Ile Lys Ala Glu Gln Asp Asn Gly His Pro Leu Pro Ala Phe Ala
    370                 375                 380

Gly Leu His Ile Glu Ile Leu Asp Glu Asn Asn Gln Ser Pro Tyr Phe
385                 390                 395                 400

Thr Met Pro Ser Tyr Gln Gly Tyr Ile Leu Glu Ser Ala Pro Val Gly
                405                 410                 415

Ala Thr Ile Ser Asp Ser Leu Asn Leu Thr Ser Pro Leu Arg Ile Val
            420                 425                 430

Ala Leu Asp Lys Asp Ile Glu Asp Val Pro Pro Ser Gly Val Pro Thr
        435                 440                 445

Lys Asp Pro Glu Leu His Leu Phe Leu Asn Asp Tyr Thr Ser Val Phe
    450                 455                 460

Thr Val Thr Gln Thr Gly Ile Thr Arg Tyr Leu Thr Leu Leu Gln Pro
465                 470                 475                 480

Val Asp Arg Glu Glu Gln Gln Thr Tyr Thr Phe Ser Ile Thr Ala Phe
                485                 490                 495

Asp Gly Val Gln Glu Ser Glu Pro Val Ile Val Asn Ile Gln Val Met
            500                 505                 510

Asp Ala Asn Asp Asn Thr Pro Thr Phe Pro Glu Ile Ser Tyr Asp Val
        515                 520                 525

Tyr Val Tyr Thr Asp Met Arg Pro Gly Asp Ser Val Ile Gln Leu Thr
    530                 535                 540

Ala Val Asp Ala Asp Glu Gly Ser Asn Gly Glu Ile Thr Tyr Glu Ile
545                 550                 555                 560

Leu Val Gly Ala Gln Gly Asp Phe Ile Ile Asn Lys Thr Thr Gly Leu
                565                 570                 575

Ile Thr Ile Ala Pro Gly Val Glu Met Ile Val Gly Arg Thr Tyr Ala
            580                 585                 590

Leu Thr Val Gln Ala Ala Asp Asn Ala Pro Pro Ala Glu Arg Arg Asn
        595                 600                 605

Ser Ile Cys Thr Val Tyr Ile Glu Val Leu Pro Pro Asn Asn Gln Ser
    610                 615                 620

Pro Pro Arg Phe Pro Gln Leu Met Tyr Ser Leu Glu Ile Ser Glu Ala
625                 630                 635                 640

Met Arg Val Gly Ala Val Leu Leu Asn Leu Gln Ala Thr Asp Arg Glu
                645                 650                 655

Gly Asp Ser Ile Thr Tyr Ala Ile Glu Asn Gly Asp Pro Gln Arg Val
            660                 665                 670
```

-continued

```
Phe Asn Leu Ser Glu Thr Thr Gly Ile Leu Thr Leu Gly Lys Ala Leu
        675                 680                 685

Asp Arg Glu Ser Thr Asp Arg Tyr Ile Leu Ile Ile Thr Ala Ser Asp
    690                 695                 700

Gly Arg Pro Asp Gly Thr Ser Thr Ala Thr Val Asn Ile Val Val Thr
705                 710                 715                 720

Asp Val Asn Asp Asn Ala Pro Val Phe Asp Pro Tyr Leu Pro Arg Asn
                725                 730                 735

Leu Ser Val Val Glu Glu Glu Ala Asn Ala Phe Val Gly Gln Val Lys
            740                 745                 750

Ala Thr Asp Pro Asp Ala Gly Ile Asn Gly Gln Val His Tyr Ser Leu
        755                 760                 765

Gly Asn Phe Asn Asn Leu Phe Arg Ile Thr Ser Asn Gly Ser Ile Tyr
    770                 775                 780

Thr Ala Val Lys Leu Asn Arg Glu Val Arg Asp Tyr Tyr Glu Leu Val
785                 790                 795                 800

Val Val Ala Thr Asp Gly Ala Val His Pro Arg His Ser Thr Leu Thr
                805                 810                 815

Leu Ala Ile Lys Val Leu Asp Ile Asp Asp Asn Ser Pro Val Phe Thr
            820                 825                 830

Asn Ser Thr Tyr Thr Val Leu Val Glu Glu Asn Leu Pro Ala Gly Thr
        835                 840                 845

Thr Ile Leu Gln Ile Glu Ala Lys Asp Val Asp Leu Gly Ala Asn Val
    850                 855                 860

Ser Tyr Arg Ile Arg Ser Pro Glu Val Lys His Phe Phe Ala Leu His
865                 870                 875                 880

Pro Phe Thr Gly Glu Leu Ser Leu Leu Arg Ser Leu Asp Tyr Glu Ala
                885                 890                 895

Phe Pro Asp Gln Glu Ala Ser Ile Thr Phe Leu Val Glu Ala Phe Asp
            900                 905                 910

Ile Tyr Gly Thr Met Pro Pro Gly Ile Ala Thr Val Thr Val Ile Val
        915                 920                 925

Lys Asp Met Asn Asp Tyr Pro Pro Val Phe Ser Lys Arg Ile Tyr Lys
    930                 935                 940

Gly Met Val Ala Pro Asp Ala Val Lys Gly Thr Pro Ile Thr Thr Val
945                 950                 955                 960

Tyr Ala Glu Asp Ala Asp Pro Pro Gly Leu Pro Ala Ser Arg Val Arg
                965                 970                 975

Tyr Arg Val Asp Asp Val Gln Phe Pro Tyr Pro Ala Ser Ile Phe Glu
            980                 985                 990

Val Glu Glu Asp Ser Gly Arg Val  Ile Thr Arg Val Asn  Leu Asn Glu
        995                 1000                1005

Glu Pro  Thr Thr Ile Phe Lys  Leu Val Val Val Ala  Phe Asp Asp
    1010                1015                1020

Gly Glu  Pro Val Met Ser Ser  Ser Ala Thr Val Lys  Ile Leu Val
    1025                1030                1035

Leu His  Pro Gly Glu Ile Pro  Arg Phe Thr Gln Glu  Glu Tyr Arg
    1040                1045                1050

Pro Pro  Pro Val Ser Glu Leu  Ala Thr Lys Gly Thr  Met Val Gly
    1055                1060                1065

Val Ile  Ser Ala Ala Ala Ile  Asn Gln Ser Ile Val  Tyr Ser Ile
    1070                1075                1080
```

```
Val Ser  Gly Asn Glu Glu Asp  Thr Phe Gly Ile Asn  Asn Ile Thr
    1085                 1090                 1095

Gly Val  Ile Tyr Val Asn Gly  Pro Leu Asp Tyr Glu  Thr Arg Thr
    1100                 1105                 1110

Ser Tyr  Val Leu Arg Val Gln  Ala Asp Ser Leu Glu  Val Val Leu
    1115                 1120                 1125

Ala Asn  Leu Arg Val Pro Ser  Lys Ser Asn Thr Ala  Lys Val Tyr
    1130                 1135                 1140

Ile Glu  Ile Gln Asp Glu Asn  Asn His Pro Pro Val  Phe Gln Lys
    1145                 1150                 1155

Lys Phe  Tyr Ile Gly Gly Val  Ser Glu Asp Ala Arg  Met Phe Thr
    1160                 1165                 1170

Ser Val  Leu Arg Val Lys Ala  Thr Asp Lys Asp Thr  Gly Asn Tyr
    1175                 1180                 1185

Ser Val  Met Ala Tyr Arg Leu  Ile Ile Pro Pro Ile  Lys Glu Gly
    1190                 1195                 1200

Lys Glu  Gly Phe Val Val Glu  Thr Tyr Thr Gly Leu  Ile Lys Thr
    1205                 1210                 1215

Ala Met  Leu Phe His Asn Met  Arg Arg Ser Tyr Phe  Lys Phe Gln
    1220                 1225                 1230

Val Ile  Ala Thr Asp Asp Tyr  Gly Lys Gly Leu Ser  Gly Lys Ala
    1235                 1240                 1245

Asp Val  Leu Val Ser Val Val  Asn Gln Leu Asp Met  Gln Val Ile
    1250                 1255                 1260

Val Ser  Asn Val Pro Pro Thr  Leu Val Glu Lys Lys  Ile Glu Asp
    1265                 1270                 1275

Leu Thr  Glu Ile Leu Asp Arg  Tyr Val Gln Glu Gln  Ile Pro Gly
    1280                 1285                 1290

Ala Lys  Val Val Val Glu Ser  Ile Gly Ala Arg Arg  His Gly Asp
    1295                 1300                 1305

Ala Phe  Ser Leu Glu Asp Tyr  Thr Lys Cys Asp Leu  Thr Val Tyr
    1310                 1315                 1320

Ala Ile  Asp Pro Gln Thr Asn  Arg Ala Ile Asp Arg  Asn Glu Leu
    1325                 1330                 1335

Phe Lys  Phe Leu Asp Gly Lys  Leu Leu Asp Ile Asn  Lys Asp Phe
    1340                 1345                 1350

Gln Pro  Tyr Tyr Gly Glu Gly  Gly Arg Ile Leu Glu  Ile Arg Thr
    1355                 1360                 1365

Pro Glu  Ala Val Thr Ser Ile  Lys Lys Arg Gly Glu  Ser Leu Gly
    1370                 1375                 1380

Tyr Thr  Glu Gly Ala Leu Leu  Ala Leu Ala Phe Ile  Ile Ile Leu
    1385                 1390                 1395

Cys Cys  Ile Pro Ala Ile Leu  Val Val Leu Val Ser  Tyr Arg Gln
    1400                 1405                 1410

Phe Lys  Val Arg Gln Ala Glu  Cys Thr Lys Thr Ala  Arg Ile Gln
    1415                 1420                 1425

Ala Ala  Leu Pro Ala Ala Lys  Pro Ala Val Pro Ala  Pro Ala Pro
    1430                 1435                 1440

Val Ala  Ala Pro Pro Pro Pro  Pro Pro Pro Pro Pro  Gly Ala His
    1445                 1450                 1455

Leu Tyr  Glu Glu Leu Gly Asp  Ser Ser Met His Lys  Tyr Glu Met
    1460                 1465                 1470
```

Pro Gln Tyr Gly Ser Arg Arg Arg Leu Leu Pro Pro Ala Gly Gln
1475 1480 1485

Glu Glu Tyr Gly Glu Val Val Gly Glu Ala Glu Glu Glu Tyr Glu
1490 1495 1500

Glu Glu Glu Glu Glu Pro Lys Lys Ile Lys Lys Pro Lys Val Glu
1505 1510 1515

Ile Arg Glu Pro Ser Glu Glu Glu Glu Val Val Val Thr Ile Glu
1520 1525 1530

Lys Pro Pro Ala Ala Glu Pro Thr Tyr Thr Thr Trp Lys Arg Ala
1535 1540 1545

Arg Ile Phe Pro Met Ile Phe Lys Lys Val Arg Gly Leu Ala Asp
1550 1555 1560

Lys Arg Gly Ile Val Asp Leu Glu Gly Glu Glu Trp Gln Arg Arg
1565 1570 1575

Leu Glu Glu Glu Asp Lys Asp Tyr Leu Lys Leu Thr Leu Asp Gln
1580 1585 1590

Glu Glu Ala Thr Glu Ser Thr Val Glu Ser Glu Glu Glu Ser Ser
1595 1600 1605

Ser Asp Tyr Thr Glu Tyr Ser Glu Glu Glu Ser Glu Phe Ser Glu
1610 1615 1620

Ser Glu Thr Thr Glu Glu Glu Ser Glu Ser Glu Thr Pro Ser Glu
1625 1630 1635

Glu Glu Glu Ser Ser Thr Pro Glu Ser Glu Glu Ser Glu Ser Thr
1640 1645 1650

Glu Ser Glu Gly Glu Lys Ala Arg Lys Asn Ile Val Leu Ala Arg
1655 1660 1665

Arg Arg Pro Met Val Glu Glu Val Lys Glu Val Lys Gly Arg Lys
1670 1675 1680

Glu Glu Pro Gln Glu Glu Gln Lys Glu Pro Lys Met Glu Glu Glu
1685 1690 1695

Glu His Ser Glu Glu Glu Glu Ser Gly Pro Ala Pro Val Glu Glu
1700 1705 1710

Ser Thr Asp Pro Glu Ala Gln Asp Ile Pro Glu Glu Gly Ser Ala
1715 1720 1725

Glu Ser Ala Ser Val Glu Gly Gly Val Glu Ser Glu Glu Glu Ser
1730 1735 1740

Glu Ser Gly Ser Ser Ser Ser Ser Ser Glu Ser Gln Ser Gly Gly
1745 1750 1755

Pro Trp Gly Tyr Gln Val Pro Ala Tyr Asp Arg Ser Lys Asn Ala
1760 1765 1770

Asn Gln Lys Lys Ser Pro Gly Ala Asn Ser Glu Gly Tyr Asn Thr
1775 1780 1785

Ala Leu
1790

<210> SEQ ID NO 3
<211> LENGTH: 1675
<212> TYPE: PRT
<213> ORGANISM: Homo sapiens

<400> SEQUENCE: 3

Met Phe Arg Gln Phe Tyr Leu Trp Thr Cys Leu Ala Ser Gly Ile Ile
1 5 10 15

Leu Gly Ser Leu Phe Glu Ile Cys Leu Gly Gln Tyr Asp Asp Asp Cys
20 25 30

```
Lys Leu Ala Arg Gly Gly Pro Pro Ala Thr Ile Val Ala Ile Asp Glu
        35                  40                  45

Glu Ser Arg Asn Gly Thr Ile Leu Val Asp Asn Met Leu Ile Lys Gly
    50                  55                  60

Thr Ala Gly Gly Pro Asp Pro Thr Ile Glu Leu Ser Leu Lys Asp Asn
65                  70                  75                  80

Val Asp Tyr Trp Val Leu Met Asp Pro Val Lys Gln Met Leu Phe Leu
                85                  90                  95

Asn Ser Thr Gly Arg Val Leu Asp Arg Asp Pro Pro Met Asn Ile His
            100                 105                 110

Ser Ile Val Val Gln Val Gln Cys Ile Asn Lys Lys Val Gly Thr Ile
        115                 120                 125

Ile Tyr His Glu Val Arg Ile Val Val Arg Asp Arg Asn Asp Asn Ser
    130                 135                 140

Pro Thr Phe Lys His Glu Ser Tyr Tyr Ala Thr Val Asn Glu Leu Thr
145                 150                 155                 160

Pro Val Gly Thr Thr Ile Phe Thr Gly Phe Ser Gly Asp Asn Gly Ala
                165                 170                 175

Thr Asp Ile Asp Asp Gly Pro Asn Gly Gln Ile Glu Tyr Val Ile Gln
            180                 185                 190

Tyr Asn Pro Asp Asp Pro Thr Ser Asn Asp Thr Phe Glu Ile Pro Leu
        195                 200                 205

Met Leu Thr Gly Asn Ile Val Leu Arg Lys Arg Leu Asn Tyr Glu Asp
    210                 215                 220

Lys Thr Arg Tyr Phe Val Ile Ile Gln Ala Asn Asp Arg Ala Gln Asn
225                 230                 235                 240

Leu Asn Glu Arg Arg Thr Thr Thr Thr Thr Leu Thr Val Asp Val Leu
                245                 250                 255

Asp Gly Asp Asp Leu Gly Pro Met Phe Leu Pro Cys Val Leu Val Pro
            260                 265                 270

Asn Thr Arg Asp Cys Arg Pro Leu Thr Tyr Gln Ala Ala Ile Pro Glu
        275                 280                 285

Leu Arg Thr Pro Glu Glu Leu Asn Pro Ile Ile Val Thr Pro Pro Ile
    290                 295                 300

Gln Ala Ile Asp Gln Asp Arg Asn Ile Gln Pro Pro Ser Asp Arg Pro
305                 310                 315                 320

Gly Ile Leu Tyr Ser Ile Leu Val Gly Thr Pro Glu Asp Tyr Pro Arg
                325                 330                 335

Phe Phe His Met His Pro Arg Thr Ala Glu Leu Ser Leu Leu Glu Pro
            340                 345                 350

Val Asn Arg Asp Phe His Gln Lys Phe Asp Leu Val Ile Lys Ala Glu
        355                 360                 365

Gln Asp Asn Gly His Pro Leu Pro Ala Phe Ala Gly Leu His Ile Glu
    370                 375                 380

Ile Leu Asp Glu Asn Asn Gln Ser Pro Tyr Phe Thr Met Pro Ser Tyr
385                 390                 395                 400

Gln Gly Tyr Ile Leu Glu Ser Ala Pro Val Gly Ala Thr Ile Ser Asp
                405                 410                 415

Ser Leu Asn Leu Thr Ser Pro Leu Arg Ile Val Ala Leu Asp Lys Asp
            420                 425                 430

Ile Glu Asp Thr Lys Asp Pro Glu Leu His Leu Phe Leu Asn Asp Tyr
        435                 440                 445
```

-continued

```
Thr Ser Val Phe Thr Val Thr Gln Thr Gly Ile Thr Arg Tyr Leu Thr
    450                 455                 460

Leu Leu Gln Pro Val Asp Arg Glu Glu Gln Gln Thr Tyr Thr Phe Ser
465                 470                 475                 480

Ile Thr Ala Phe Asp Gly Val Gln Glu Ser Glu Pro Val Ile Val Asn
                485                 490                 495

Ile Gln Val Met Asp Ala Asn Asp Asn Thr Pro Thr Phe Pro Glu Ile
            500                 505                 510

Ser Tyr Asp Val Tyr Val Tyr Thr Asp Met Arg Pro Gly Asp Ser Val
        515                 520                 525

Ile Gln Leu Thr Ala Val Asp Ala Asp Glu Gly Ser Asn Gly Glu Ile
    530                 535                 540

Thr Tyr Glu Ile Leu Val Gly Ala Gln Gly Asp Phe Ile Ile Asn Lys
545                 550                 555                 560

Thr Thr Gly Leu Ile Thr Ile Ala Pro Gly Val Glu Met Ile Val Gly
                565                 570                 575

Arg Thr Tyr Ala Leu Thr Val Gln Ala Ala Asp Asn Ala Pro Pro Ala
            580                 585                 590

Glu Arg Arg Asn Ser Ile Cys Thr Val Tyr Ile Glu Val Leu Pro Pro
        595                 600                 605

Asn Asn Gln Ser Pro Pro Arg Phe Pro Gln Leu Met Tyr Ser Leu Glu
    610                 615                 620

Ile Ser Glu Ala Met Arg Val Gly Ala Val Leu Leu Asn Leu Gln Ala
625                 630                 635                 640

Thr Asp Arg Glu Gly Asp Ser Ile Thr Tyr Ala Ile Glu Asn Gly Asp
                645                 650                 655

Pro Gln Arg Val Phe Asn Leu Ser Glu Thr Thr Gly Ile Leu Thr Leu
            660                 665                 670

Gly Lys Ala Leu Asp Arg Glu Ser Thr Asp Arg Tyr Ile Leu Ile Ile
        675                 680                 685

Thr Ala Ser Asp Gly Arg Pro Asp Gly Thr Ser Thr Ala Thr Val Asn
    690                 695                 700

Ile Val Val Thr Asp Val Asn Asp Asn Ala Pro Val Phe Asp Pro Tyr
705                 710                 715                 720

Leu Pro Arg Asn Leu Ser Val Val Glu Glu Glu Ala Asn Ala Phe Val
                725                 730                 735

Gly Gln Val Lys Ala Thr Asp Pro Asp Ala Gly Ile Asn Gly Gln Val
            740                 745                 750

His Tyr Ser Leu Gly Asn Phe Asn Asn Leu Phe Arg Ile Thr Ser Asn
        755                 760                 765

Gly Ser Ile Tyr Thr Ala Val Lys Leu Asn Arg Glu Val Arg Asp Tyr
    770                 775                 780

Tyr Glu Leu Val Val Val Ala Thr Asp Gly Ala Val His Pro Arg His
785                 790                 795                 800

Ser Thr Leu Thr Leu Ala Ile Lys Val Leu Asp Ile Asp Asp Asn Ser
                805                 810                 815

Pro Val Phe Thr Asn Ser Thr Tyr Thr Val Leu Val Glu Glu Asn Leu
            820                 825                 830

Pro Ala Gly Thr Thr Ile Leu Gln Ile Glu Ala Lys Asp Val Asp Leu
        835                 840                 845

Gly Ala Asn Val Ser Tyr Arg Ile Arg Ser Pro Glu Val Lys His Phe
    850                 855                 860
```

```
Phe Ala Leu His Pro Phe Thr Gly Glu Leu Ser Leu Leu Arg Ser Leu
865                 870                 875                 880

Asp Tyr Glu Ala Phe Pro Asp Gln Glu Ala Ser Ile Thr Phe Leu Val
                885                 890                 895

Glu Ala Phe Asp Ile Tyr Gly Thr Met Pro Pro Gly Ile Ala Thr Val
            900                 905                 910

Thr Val Ile Val Lys Asp Met Asn Asp Tyr Pro Pro Val Phe Ser Lys
        915                 920                 925

Arg Ile Tyr Lys Gly Met Val Ala Pro Asp Ala Val Lys Gly Thr Pro
    930                 935                 940

Ile Thr Thr Val Tyr Ala Glu Asp Ala Asp Pro Pro Gly Leu Pro Ala
945                 950                 955                 960

Ser Arg Val Arg Tyr Arg Val Asp Asp Val Gln Phe Pro Tyr Pro Ala
                965                 970                 975

Ser Ile Phe Glu Val Glu Glu Asp Ser Gly Arg Val Ile Thr Arg Val
            980                 985                 990

Asn Leu Asn Glu Glu Pro Thr Thr  Ile Phe Lys Leu Val  Val Val Ala
        995                 1000                1005

Phe Asp  Asp Gly Glu Pro Val  Met Ser Ser Ser Ala  Thr Val Lys
    1010                 1015                 1020

Ile Leu  Val Leu His Pro Gly  Glu Ile Pro Arg Phe  Thr Gln Glu
    1025                 1030                 1035

Glu Tyr  Arg Pro Pro Pro Val  Ser Glu Leu Ala Thr  Lys Gly Thr
    1040                 1045                 1050

Met Val  Gly Val Ile Ser Ala  Ala Ala Ile Asn Gln  Ser Ile Val
    1055                 1060                 1065

Tyr Ser  Ile Val Ser Gly Asn  Glu Glu Asp Thr Phe  Gly Ile Asn
    1070                 1075                 1080

Asn Ile  Thr Gly Val Ile Tyr  Val Asn Gly Pro Leu  Asp Tyr Glu
    1085                 1090                 1095

Thr Arg  Thr Ser Tyr Val Leu  Arg Val Gln Ala Asp  Ser Leu Glu
    1100                 1105                 1110

Val Val  Leu Ala Asn Leu Arg  Val Pro Ser Lys Ser  Asn Thr Ala
    1115                 1120                 1125

Lys Val  Tyr Ile Glu Ile Gln  Asp Glu Asn Asn His  Pro Pro Val
    1130                 1135                 1140

Phe Gln  Lys Lys Phe Tyr Ile  Gly Gly Val Ser Glu  Asp Ala Arg
    1145                 1150                 1155

Met Phe  Thr Ser Val Leu Arg  Val Lys Ala Thr Asp  Lys Asp Thr
    1160                 1165                 1170

Gly Asn  Tyr Ser Val Met Ala  Tyr Arg Leu Ile Ile  Pro Pro Ile
    1175                 1180                 1185

Lys Glu  Gly Lys Glu Gly Phe  Val Val Glu Thr Tyr  Thr Gly Leu
    1190                 1195                 1200

Ile Lys  Thr Ala Met Leu Phe  His Asn Met Arg Arg  Ser Tyr Phe
    1205                 1210                 1215

Lys Phe  Gln Val Ile Ala Thr  Asp Asp Tyr Gly Lys  Gly Leu Ser
    1220                 1225                 1230

Gly Lys  Ala Asp Val Leu Val  Ser Val Val Asn Gln  Leu Asp Met
    1235                 1240                 1245

Gln Val  Ile Val Ser Asn Val  Pro Pro Thr Leu Val  Glu Lys Lys
    1250                 1255                 1260
```

-continued

```
Ile Glu  Asp Leu Thr Glu Ile  Leu Asp Arg Tyr Val  Gln Glu Gln
    1265                 1270                 1275

Ile Pro  Gly Ala Lys Val Val  Val Glu Ser Ile Gly  Ala Arg Arg
    1280                 1285                 1290

His Gly  Asp Ala Phe Ser Leu  Glu Asp Tyr Thr Lys  Cys Asp Leu
    1295                 1300                 1305

Thr Val  Tyr Ala Ile Asp Pro  Gln Thr Asn Arg Ala  Ile Asp Arg
    1310                 1315                 1320

Asn Glu  Leu Phe Lys Phe Leu  Asp Gly Lys Leu Leu  Asp Ile Asn
    1325                 1330                 1335

Lys Asp  Phe Gln Pro Tyr Tyr  Gly Glu Gly Gly Arg  Ile Leu Glu
    1340                 1345                 1350

Ile Arg  Thr Pro Glu Ala Val  Thr Ser Ile Lys Lys  Arg Gly Glu
    1355                 1360                 1365

Ser Leu  Gly Tyr Thr Glu Gly  Ala Leu Leu Ala Leu  Ala Phe Ile
    1370                 1375                 1380

Ile Ile  Leu Cys Cys Ile Pro  Ala Ile Leu Val Val  Leu Val Ser
    1385                 1390                 1395

Tyr Arg  Gln Phe Lys Val Arg  Gln Ala Glu Cys Thr  Lys Thr Ala
    1400                 1405                 1410

Arg Ile  Gln Ala Ala Leu Pro  Ala Ala Lys Pro Ala  Val Pro Ala
    1415                 1420                 1425

Pro Ala  Pro Val Ala Ala Pro  Pro Pro Pro Pro Pro  Pro Pro Pro
    1430                 1435                 1440

Gly Ala  His Leu Tyr Glu Glu  Leu Gly Asp Ser Ser  Met Tyr Glu
    1445                 1450                 1455

Met Pro  Gln Tyr Gly Ser Arg  Arg Arg Leu Leu Pro  Pro Ala Gly
    1460                 1465                 1470

Gln Glu  Glu Tyr Gly Glu Val  Val Gly Glu Ala Glu  Glu Glu Tyr
    1475                 1480                 1485

Glu Glu  Glu Glu Trp Ala Arg  Lys Arg Met Ile Lys  Leu Val Val
    1490                 1495                 1500

Asp Arg  Glu Tyr Glu Thr Ser  Ser Thr Gly Glu Asp  Ser Ala Pro
    1505                 1510                 1515

Glu Cys  Gln Arg Asn Arg Leu  His His Pro Ser Ile  His Ser Asn
    1520                 1525                 1530

Ile Asn  Gly Asn Ile Tyr Ile  Ala Gln Asn Gly Ser  Val Val Arg
    1535                 1540                 1545

Thr Arg  Arg Ala Cys Leu Thr  Asp Asn Leu Lys Val  Ala Ser Pro
    1550                 1555                 1560

Val Arg  Leu Gly Gly Pro Phe  Lys Lys Leu Asp Lys  Leu Ala Val
    1565                 1570                 1575

Thr His  Glu Glu Asn Val Pro  Leu Asn Thr Leu Ser  Lys Gly Pro
    1580                 1585                 1590

Phe Ser  Thr Glu Lys Met Asn  Ala Arg Pro Thr Leu  Val Thr Phe
    1595                 1600                 1605

Ala Pro  Cys Pro Val Gly Thr  Asp Asn Thr Ala Val  Lys Pro Leu
    1610                 1615                 1620

Arg Asn  Arg Leu Lys Ser Thr  Val Glu Gln Glu Ser  Met Ile Asp
    1625                 1630                 1635

Ser Lys  Asn Ile Lys Glu Ala  Leu Glu Phe His Ser  Asp His Thr
    1640                 1645                 1650
```

```
Gln Ser  Asp Asp Glu Glu Leu  Trp Met Gly Pro Trp  Asn Asn Leu
    1655                 1660                 1665

His Ile  Pro Met Thr Lys Leu
    1670                 1675
```

<210> SEQ ID NO 4
<211> LENGTH: 3504
<212> TYPE: DNA
<213> ORGANISM: Artificial Sequence
<220> FEATURE:
<223> OTHER INFORMATION: Synthetic

<400> SEQUENCE: 4

```
atgtttcgac agttttatct ctggacatgt ttagcttcag ggatcatcct gggctctctc     60

tttgaaatct gcttgggcca gtatgatgat gactggcaat atgaggattg caaactagct    120

aggggaggac caccagctac catagttgct attgatgaag aaagtcggaa tggtacaatt    180

ctggtggaca acatgctgat caaagggact gctggaggac cagaccccac catagaactt    240

tctttaaagg ataatgtgga ttactgggtg ttgatggatc ctgttaagca aatgcttttc    300

ctgaacagca ccggaagagt tctggataga gatccaccga tgaacataca ctccattgtg    360

gtgcaggtcc agtgcatcaa caaaaaagtg ggcactatta tctaccatga agtgcgaata    420

gtggtgagag acaggaatga caactcaccc actttcaagc atgaaagcta ctatgccaca    480

gtgaatgagc tcactccagt tggtaccaca atattcacag gattttcagg agacaatgga    540

gctacagata tagatgatgg accaaatgga cagatagagt atgttattca gtataatcca    600

gatgatccga catccaatga cacctttgaa attcccctaa tgttgactgg aaatatagtg    660

ttaaggaaga ggctcaacta tgaagataag actcgctact ttgtcataat ccaagctaat    720

gaccgtgccc aaaatctgaa tgagaggcga accaccacca ccactctcac agtggatgtt    780

ctggatggag atgacttggg tccaatgttt cttccttgtg tccttgtgcc aaacactcgt    840

gattgccgtc cactcactta tcaagctgcc atacctgagt tgagaactcc ggaagaactg    900

aaccccatta ttgttacgcc accaatccaa gccattgatc aggaccggaa tattcaaccg    960

ccatcagata ggccaggaat cctctattcc atccttgttg ggactcctga ggattaccca   1020

cgatttttcc atatgcatcc taggacagca gaacttagtc tcctggagcc agtaaacaga   1080

gactttcacc agaaatttga tttggttatt aaggctgaac aagacaatgg tcatcctctt   1140

cctgcctttg ccggtctaca cattgaaata ctggatgaaa acaatcaaag tccatatttt   1200

acaatgccca gttatcaagg ctatatcctg gaatctgccc cagtgggagc aaccatttcg   1260

gacagtctca atttgacttc acctttaaga atagtagctc tggacaagga catagaagat   1320

gttccaccca gtggagttcc tacaaaagac ccagagcttc acctttttct gaatgactac   1380

acctcagtct tcaccgtcac acagactggt attactcgct acctcacctt acttcaacca   1440

gtggacaggg aagaacagca aacttacacc ttttcgataa cagcatttga tggtgtacaa   1500

gaaagtgagc cagtcatcgt caatattcaa gtgatggatg caaatgataa cacgccaacc   1560

ttccctgaaa tatcctatga tgtgtatgtt tatacagaca tgagacctgg ggacagtgtc   1620

atacagctca ctgcagtcga cgcagacgaa gggtcaaatg gggagatcac atatgaaatc   1680

cttgttgggg ctcagggaga cttcatcatc aataaaacaa cagggcttat caccatcgct   1740

ccaggggtgg aaatgatagt cgggcggact tacgcactca cggtccaagc agcggataat   1800

gctcctcctg cagagcgaag gaactccatc tgcactgtgt atattgaagt gcttccacca   1860
```

```
aataatcaaa gccctcctcg cttcccacag ctgatgtata gccttgaaat tagtgaagcc   1920
atgagggttg gtgctgtttt attaaatcta caggcaactg atcgagaggg agactcaata   1980
acatatgcca ttgagaatgg agatcctcag agagttttta atctttcaga aaccacgggg   2040
attctaacct tagggaaagc actggacagg gaaagcactg atcgctacat tctgatcatc   2100
acagcttcag atggcaggcc agatgggacc tcaactgcca cagtaaacat agtggtgaca   2160
gatgtcaatg acaatgctcc agtgtttgat ccttatctgc caagaaattt atctgtggtg   2220
gaagaagaag ccaatgcctt tgtgggtcaa gtaaaagcaa cagaccctga tgctggaata   2280
aatggtcaag tgcactacag tttgggtaac tttaataatc tttttcgtat cacatccaat   2340
gggagcattt acacagcagt gaagcttaac agagaagtca gggactacta tgaacttgtt   2400
gttgtggcaa cagatggagc agtacaccct cgtcattcaa ctctaacctt ggccatcaag   2460
gttttggaca ttgatgataa cagtcctgtg ttcaccaatt caacatacac tgtccttgtt   2520
gaagagaatt tgccagctgg gactaccatc cttcaaatag aggccaaaga tgtcgacctt   2580
ggagcaaatg tgtcttaccg gataagaagc ccagaagtga agcacttttt tgcactacat   2640
ccatttacag gagaactatc gcttttaagg agtttagatt atgaggcatt tccagaccaa   2700
gaagcaagta tcacttttct ggtagaggcc tttgatattt atggaacaat gccacctggt   2760
attgctactg tcacagtgat tgtaaaggat atgaatgatt atcctcctgt ctttagtaaa   2820
cgaatataca aagggatggt ggctccggat gcagtcaagg gtacacctat cacaacagtt   2880
tatgctgaag atgcagaccc tcctggatta cctgcaagtc gtgtgaggta tagagtagat   2940
gatgtacagt ttccttaccc tgccagtatt tttgaagtgg aagaagattc tggaagagta   3000
ataacacgag tcaatcttaa tgaagaacct acaacaattt ttaagttggt ggtggttgct   3060
tttgatgatg gggagcctgt gatgtccagc agtgccacag tgaagattct tgtcttacat   3120
cctggtgaga tcccacgctt cacacaggag gaatatagac ctcctccagt aagtgaactt   3180
gccaccaaag ggaccatggt tggtgtaatt tctgctgctg ccattaatca aagtattgtg   3240
tactccattg tttcaggaaa tgaagaagat acatttggaa ttaataacat cacaggtgtt   3300
atctatgtga atggacctct ggattatgag accaggacaa gctatgtact tcgagtccaa   3360
gctgattccc tggaagtggt ccttgccaat ctccgagttc cttcaaaaag caatacagct   3420
aaagtataca ttgagattca ggatgaaaat aatcatcccc cagtgtttca gaaaaaattc   3480
tacatcggag gtgtatctga agat                                          3504
```

<210> SEQ ID NO 5
<211> LENGTH: 2406
<212> TYPE: DNA
<213> ORGANISM: Artificial Sequence
<220> FEATURE:
<223> OTHER INFORMATION: Synthetic

<400> SEQUENCE: 5

```
gcaagaatgt ttacttctgt actcagagtg aaggctactg ataaagatac tggcaattat     60
agtgtcatgg cctacagact cataatacca ccaattaaag agggaaaaga aggatttgta    120
gtggaaacat atacagggct tatcaaaact gctatgctct tccataatat gaggagatcc    180
tacttcaagt ttcaagttat tgcaactgac gactatggga agggactgag cggcaaagcc    240
gatgtactcg tctccgtggt caatcagctg gatatgcaag tcattgtttc caatgtgcct    300
cctactctag tggaaaaaaa gatagaagat cttacagaga tcttggatcg ctatgttcag    360
gaacaaattc ctggtgccaa ggtcgtagtg gagtccattg gagctcgccg gcatggagat    420
```

gccttttccc tagaagatta caccaaatgt gacttgactg tctatgcaat tgaccccccaa 480 accaacagag ccatcgatag aaatgagctt tttaaatttt tggatggcaa actacttgat 540
atcaataaag actttcagcc gtattatggg gaaggaggac gcattctgga gatccggact 600
ccagaggcag tgaccagcat taaaaagaga ggagaaagtc taggatacac agaaggggcc 660
ttgttggctc tggccttcat catcatcctc tgctgcattc ctgccatctt ggtggttttg 720
gtcagctaca gacagtttaa agtacgtcaa gctgagtgta caaagactgc acgaattcag 780
gccgcattac ccgcggctaa accagcagtg ccggctcctg caccagtggc agcgcccccg 840
ccgccgccgc cgcctccgcc aggtgcgcat ctctatgaag aacttggaga cagctcaatg 900
cataatcttt tccttctcta ccattttcaa caaagcaggg gaaataactc agtctcagaa 960
gacaggaaac atcaacaagt tgtgatgccc ttttcttcca atactattga ggctcacaag 1020
tcagctcatg tagacggatc acttaagagc aacaaactga agtctgcaag aaaattcaca 1080
tttctatctg atgaggatga cttaagtgcc cataatcccc tttataagga aaacataagt 1140
caagtatcaa caaattcaga catttcacag agaacagatt ttgtagaccc attttcaccc 1200
aaaatacaag ccaagagtaa gtctctgagg ggcccaagag aaaagattca gaggctgtgg 1260
agtcagtcag tcagcttacc caggaggctg atgaggaaag ttccaaatag accagagatc 1320
atagatctgc agcagtggca aggcaccagg cagaaagctg aaaatgaaaa cactggaatc 1380
tgtacaaaca aaagaggtag cagcaatcca ttgcttacaa ctgaagaggc aaatttgaca 1440
gagaaagagg aaataaggca aggtgaaaca ctgatgatag aaggaacaga acagttgaaa 1500
tctctctctt cagactcttc attttgcttt cccaggcctc acttctcatt ctccactttg 1560
ccaactgttt caagaactgt ggaactcaaa tcagaaccta atgtcatcag ttctcctgct 1620
gagtgttcct tggaactttc tccttcaagg ccttgtgttt tacattcttc actctctagg 1680
agagagacac ctatttgtat gttacctatt gaaaccgaaa gaaatatttt tgaaaatttt 1740
gcccatccac caaacatctc tccttctgcc tgtccccttc cccctcctcc tcctatttct 1800
cctccttctc ctcctcctgc tcctgctcct cttgctcctc ctcctgacat ttctcctttt 1860
tctctttttt gtcctcctcc ctctcctcct tctatccctc ttcctcttcc tcctcctaca 1920
ttttttccac tttccgtttc aacgtctggt cccccaacac cacctcttct acctccattt 1980
ccaactcctc ttcctccacc acctccttct attccttgcc ctccacctcc ttcagcttca 2040
tttctgtcca cagagtgtgt ctgtataaca ggtgttaaat gcacgaccaa cttgatgcct 2100
gccgagaaaa ttaagtcctc tatgacacag ctatcaacaa cgacagtgtg taaaacagac 2160
cctcagagag aaccaaaagg catcctcaga cacgttaaaa acttagcaga acttgaaaaa 2220
tcagtagcta acatgtacag tcaaatagaa aaaaactatc tacgcacaaa tgtttcagaa 2280
cttcaaacta tgtgcccttc agaagtaaca aatatggaaa tcacatctga acaaaacaag 2340
gggagtttga acaatattgt cgagggaact gaaaaacaat ctcacagtca atctacttca 2400
ctgtaa 2406

<210> SEQ ID NO 6
<211> LENGTH: 1869
<212> TYPE: DNA
<213> ORGANISM: Artificial Sequence
<220> FEATURE:
<223> OTHER INFORMATION: Synthetic

<400> SEQUENCE: 6
gcaagaatgt ttacttctgt actcagagtg aaggctactg ataaagatac tggcaattat 60
agtgtcatgg cctacagact cataatacca ccaattaaag agggaaaaga aggatttgta 120
gtggaaacat atacagggct tatcaaaact gctatgctct tccataatat gaggagatcc 180
tacttcaagt ttcaagttat tgcaactgac gactatggga agggactgag cggcaaagcc 240
gatgtactcg tctccgtggt caatcagctg gatatgcaag tcattgtttc caatgtgcct 300
cctactctag tggaaaaaaa gatagaagat cttacagaga tcttggatcg ctatgttcag 360
gaacaaattc ctggtgccaa ggtcgtagtg gagtccattg gagctcgccg gcatggagat 420
gccttttccc tagaagatta caccaaatgt gacttgactg tctatgcaat tgacccccaa 480
accaacagag ccatcgatag aaatgagctt tttaaatttt tggatggcaa actacttgat 540
atcaataaag actttcagcc gtattatggg gaaggaggac gcattctgga gatccggact 600
ccagaggcag tgaccagcat taaaaagaga ggagaaagtc taggatacac agaaggggcc 660
ttgttggctc tggccttcat catcatcctc tgctgcattc ctgccatctt ggtggttttg 720
gtcagctaca gacagtttaa agtacgtcaa gctgagtgta caaagactgc acgaattcag 780
gccgcattac ccgcggctaa accagcagtg ccggctcctg caccagtggc agcgcccccg 840
ccgccgccgc cgcctccgcc aggtgcgcat ctctatgaag aacttggaga cagctcaatg 900
cataagtatg aaatgcctca atatgggagt cgccgtcgat tgttaccacc agctggacag 960
gaggaatatg gtgaggtggt tggtgaagct gaggaagaat atgaggagga agaggaagag 1020
ccaaagaaaa ttaaaaaacc aaaggttgaa attagagagc ctagtgagga ggaagaagta 1080
gttgtaacta tcgaaaaacc accagcagct gagcctacat acacaacatg gaagagagcc 1140
agaatattcc ccatgatttt taagaaagtt agaggattag ctgataaaag aggaatcgtt 1200
gaccttgagg gtgaagagtg gcagagacgc cttgaggaag aagataaaga ttatttgaaa 1260
ctcactctgg accaagagga agcaacagaa agcactgtag aatcagagga ggaatcctcc 1320
agcgactata ctgaatacag tgaagaagag tctgagttca gtgagtctga gactacagaa 1380
gaggaatctg agtcagagac accctctgag gaggaggaga gttccacccc tgaatcagaa 1440
gaatcggaat ccacagagtc agaaggagaa aaagcaagga aaaacattgt gcttgcaaga 1500
agaaggccca tggttgagga ggtcaaggaa gtcaagggta ggaaagagga gccacaagaa 1560
gaacaaaaag aacctaagat ggaagaagaa gaacactcag aagaagaaga aagtggacca 1620
gcccctgtgg aagaaagtac agaccctgaa gctcaagata tccctgaaga gggcagtgca 1680
gaatcagctt cggtggaagg aggtgtggaa agtgaggagg aatcagaatc aggtagtagt 1740
agcagtagta gcgaaagtca gtctggaggt ccatggggct atcaggtacc agcgtatgac 1800
agaagcaaga atgcaaacca aaagaagtcg ccaggagcaa actctgaagg ttacaacaca 1860
gcactttga 1869

<210> SEQ ID NO 7
<211> LENGTH: 1560
<212> TYPE: DNA
<213> ORGANISM: Artificial Sequence
<220> FEATURE:
<223> OTHER INFORMATION: Synthetic

<400> SEQUENCE: 7
gcaagaatgt ttacttctgt actcagagtg aaggctactg ataaagatac tggcaattat 60
agtgtcatgg cctacagact cataatacca ccaattaaag agggaaaaga aggatttgta 120
gtggaaacat atacagggct tatcaaaact gctatgctct tccataatat gaggagatcc 180
tacttcaagt ttcaagttat tgcaactgac gactatggga agggactgag cggcaaagcc 240
gatgtactcg tctccgtggt caatcagctg gatatgcaag tcattgtttc caatgtgcct 300
cctactctag tggaaaaaaa gatagaagat cttacagaga tcttggatcg ctatgttcag 360
gaacaaattc ctggtgccaa ggtcgtagtg gagtccattg gagctcgccg gcatggagat 420
gccttttccc tagaagatta caccaaatgt gacttgactg tctatgcaat tgacccccaa 480
accaacagag ccatcgatag aaatgagctt tttaaatttt tggatggcaa actacttgat 540
atcaataaag actttcagcc gtattatggg gaaggaggac gcattctgga gatccggact 600
ccagaggcag tgaccagcat taaaaagaga ggagaaagtc taggatacac agaaggggcc 660
ttgttggctc tggccttcat catcatcctc tgctgcattc ctgccatctt ggtggttttg 720
gtcagctaca gacagtttaa agtacgtcaa gctgagtgta caaagactgc acgaattcag 780
gccgcattac ccgcggctaa accagcagtg ccggctcctg caccagtggc agcgcccccg 840
ccgccgccgc cgcctccgcc aggtgcgcat ctctatgaag aacttggaga cagctcaatg 900
tatgaaatgc ctcaatatgg gagtcgccgt cgattgttac caccagctgg acaggaggaa 960
tatggtgagg tggttggtga agctgaggaa gaatatgagg aggaagagtg ggcaagaaaa 1020
agaatgatca agttagttgt tgatcgagag tatgaaacca gctcaactgg agaagacagt 1080
gctcctgaat gtcagagaaa ccgtcttcac catcctagta tccacagtaa tatcaacggc 1140
aatatatata ttgcacagaa tggttctgtg gtgagaaccc gccgtgcctg cctcacggac 1200
aacttaaaag ttgcttcccc tgttcgactg ggagggccct ttaagaaact agacaagttg 1260
gcagtgacac atgaggagaa tgtacctctg aacacattat caaaggggcc attttctact 1320
gaaaaaatga atgcaagacc aactctggtt acatttgccc cttgccctgt ggggactgac 1380
aatacagcgg tgaagccact aaggaacagg ctgaaaagca cagttgaaca ggagtccatg 1440
attgacagta agaacatcaa ggaggctttg gaatttcata gtgaccacac acagtctgat 1500
gatgaagagc tttggatggg cccctggaac aacctccata taccaatgac aaaactgtga 1560

<210> SEQ ID NO 8
<211> LENGTH: 596
<212> TYPE: DNA
<213> ORGANISM: Artificial Sequence
<220> FEATURE:
<223> OTHER INFORMATION: Synthetic

<400> SEQUENCE: 8
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtgatgcggt tttggcagta catcaatggg cgtggatagc 420

```
ggtttgactc acggggattt ccaagtctcc accccattga cgtcaatggg agtttgtttt    480

ggcaccaaaa tcaacgggac tttccaaaat gtcgtaacaa ctccgcccca ttgacgcaaa    540

tgggcggtag gcgtgtacgg tgggaggtct atataagcag agctctctgg ctaact        596
```

<210> SEQ ID NO 9
<211> LENGTH: 242
<212> TYPE: DNA
<213> ORGANISM: Homo sapiens

<400> SEQUENCE: 9

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

ag                                                                   242
```

<210> SEQ ID NO 10
<211> LENGTH: 1226
<212> TYPE: DNA
<213> ORGANISM: Artificial Sequence
<220> FEATURE:
<223> OTHER INFORMATION: Synthetic

<400> SEQUENCE: 10

```
ctagcacagc actaggctaa agcgtactga gcccttgtct tccgtgggag ctgcagagtg     60

ggatgcatgc gttgtgagct gaggctcaag ctgcgctggc agaagagcag ggttgcctt    120

gtcagactcc agggtctctt tctctctgag cctgggaaag tgccacttta ttggatctat    180

aaagccgggg gggggggggg ggaggaatct caaggtgaag aggaagttca cagacccctc    240

taacgcctct attagaacct tccagctatt ctctcatact tgtacactga gctggcacac    300

agtataggca agttctattc gcatcacccc tctagttcct gtctccctgg ttatgcaagc    360

ctcatattta ggtagatgtg accttaggaa accaaaatat cctttaagat cttactaact    420

ggttgcctgt tcagcttttc cacattgatc ctgtagcccc ctcgaggagg tgaaggaaaa    480

aaatctcctc tttgtttctc taactcatta atgaatttta agggcactct gtaaggttcc    540

tttcccattc tggtctggtt cgtacattct gagaaacaca ctgtgtttgt gttgagagtt    600

ggctccctag ctacactgtc tgtcacattg atgctctgag tagggacagg gttcatctag    660

gaaatatatt ttcactcaca ctctgtatct tttcctagtt tggcatattc tagtctgcat    720

ttggctctct gtttaaatat aaaagaaaac taaaacacac ccttcagacg cctatgtctg    780

aaaaatctgg catttccgtg ggtttttctt taaggaggcc ttcatttgta accaacacca    840

tgctctcctt aaggaaatca atctcaatgc cctattatcc ttccctttc tttcctccca     900

gtttgaggct gcagttgcct tttttttct tatcccctgc tgaacctgaa aaaccctctc    960

ttttctacag ttttctgttc ccaggccccg ctgacttcct ttagagcatg gggggggggg   1020

ggatcaggat tgtgatgtgt gaactgggag gatcttgacc tactccgcta acccagtggc   1080

ctgagcaaat cacaaggagg attggagcca tctgcccagc cctcccccca cggcagcctg   1140

ctggaaagag acaagttagt cattcaaatg attggctttt tgcccgcttc ttctctaaat   1200

aagaaggcag cagcttctgc tgaggt                                        1226
```

<210> SEQ ID NO 11
<211> LENGTH: 82

<212> TYPE: DNA
<213> ORGANISM: Artificial Sequence
<220> FEATURE:
<223> OTHER INFORMATION: Synthetic

<400> SEQUENCE: 11
gtaagtatca aggttacaag acaggtttaa ggagaccaat agaaactggg cttgtcgaga 60
cagagaagac tcttgcgttt ct 82

<210> SEQ ID NO 12
<211> LENGTH: 51
<212> TYPE: DNA
<213> ORGANISM: Artificial Sequence
<220> FEATURE:
<223> OTHER INFORMATION: Synthetic

<400> SEQUENCE: 12
gataggcacc tattggtctt actgacatcc actttgcctt tctctccaca g 51

<210> SEQ ID NO 13
<211> LENGTH: 77
<212> TYPE: DNA
<213> ORGANISM: Artificial Sequence
<220> FEATURE:
<223> OTHER INFORMATION: Synthetic

<400> SEQUENCE: 13
gggattttgc cgatttcggc ctattggtta aaaaatgagc tgatttaaca aaaatttaac 60
gcgaatttta acaaaat 77

<210> SEQ ID NO 14
<211> LENGTH: 1307
<212> TYPE: DNA
<213> ORGANISM: Artificial Sequence
<220> FEATURE:
<223> OTHER INFORMATION: Synthetic

<400> SEQUENCE: 14
cccctctccc tccccccccc ctaacgttac tggccgaagc cgcttggaat aaggccggtg 60
tgcgtttgtc tatatgttat tttccaccat attgccgtct tttggcaatg tgagggcccg 120
gaaacctggc cctgtcttct tgacgagcat tcctaggggt ctttcccctc tcgccaaagg 180
aatgcaaggt ctgttgaatg tcgtgaagga agcagttcct ctggaagcct cttgaagaca 240
aacaacgtct gtagcgaccc tttgcaggca gcggaacccc ccacctggcg acaggtgcct 300
ctgcggccaa aagccacgtg tataagatac acctgcaaag gcggcacaac cccagtgcca 360
cgttgtgagt tggatagttg tggaaagagt caaatggctc tcctcaagcg tattcaacaa 420
ggggctgaag gatgcccaga aggtacccca ttgtatggga tctgatctgg ggcctcggtg 480
cacatgcttt acatgtgttt agtcgaggtt aaaaaaacgt ctaggccccc cgaaccacgg 540
ggacgtggtt ttcctttgaa aaacacgatg ataatatggc cacaaccatg gtgagcaagg 600
gcgaggagct gttcaccggg gtggtgccca tcctggtcga gctggacggc gacgtaaacg 660
gccacaagtt cagcgtgtcc ggcgagggcg agggcgatgc cacctacggc aagctgaccc 720
tgaagttcat ctgcaccacc ggcaagctgc ccgtgccctg gcccaccctc gtgaccaccc 780
tgacctacgg cgtgcagtgc ttcagccgct accccgacca catgaagcag cacgacttct 840
tcaagtccgc catgcccgaa ggctacgtcc aggagcgcac catcttcttc aaggacgacg 900
gcaactacaa gacccgcgcc gaggtgaagt tcgagggcga caccctggtg aaccgcatcg 960
agctgaaggg catcgacttc aaggaggacg gcaacatcct ggggcacaag ctggagtaca 1020
actacaacag ccacaacgtc tatatcatgg ccgacaagca gaagaacggc atcaaggtga 1080
acttcaagat ccgccacaac atcgaggacg gcagcgtgca gctcgccgac cactaccagc 1140
agaacacccc catcggcgac ggccccgtgc tgctgcccga caaccactac ctgagcaccc 1200
agtccgccct gagcaaagac cccaacgaga agcgcgatca catggtcctg ctggagttcg 1260
tgaccgccgc cgggatcact ctcggcatgg acgagctgta caagtaa 1307

<210> SEQ ID NO 15
<211> LENGTH: 197
<212> TYPE: DNA
<213> ORGANISM: Artificial Sequence
<220> FEATURE:
<223> OTHER INFORMATION: Synthetic

<400> SEQUENCE: 15
gatccagaca tgataagata cattgatgag tttggacaaa ccacaactag aatgcagtga 60
aaaaaatgct ttatttgtga aatttgtgat gctattgctt tatttgtaac cattataagc 120
tgcaataaac aagttaacaa caacaattgc attcatttta tgtttcaggt tcagggggag 180
gtgtgggagg ttttttta 197

<210> SEQ ID NO 16
<211> LENGTH: 237
<212> TYPE: DNA
<213> ORGANISM: Artificial Sequence
<220> FEATURE:
<223> OTHER INFORMATION: Synthetic

<400> SEQUENCE: 16
gtcgactaga gctcgctgat cagcctcgac tgtgccttct agttgccagc catctgttgt 60
ttgcccctcc cccgtgcctt ccttgaccct ggaaggtgcc actcccactg tcctttccta 120
ataaaatgag gaaattgcat cgcattgtct gagtaggtgt cattctattc tggggggtgg 180
ggtggggcag gacagcaagg gggaggattg ggaagacaat agcaggcatg ctgggga 237

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
tacccatacg acgtgcccga ctacgcc 27

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
gattacaaag acgacgacga taaa 24

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19
gtgcctacta tcgtgatggt ggacgcctac aagcgttaca ag 42

<210> SEQ ID NO 20
<211> LENGTH: 149
<212> TYPE: DNA
<213> ORGANISM: Artificial Sequence
<220> FEATURE:
<223> OTHER INFORMATION: Synthetic

<400> SEQUENCE: 20
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagat 149

<210> SEQ ID NO 21
<211> LENGTH: 139
<212> TYPE: DNA
<213> ORGANISM: Artificial Sequence
<220> FEATURE:
<223> OTHER INFORMATION: Synthetic

<400> SEQUENCE: 21
cccctagtga tggagttggc cactccctct ctgcgcgctc gctcgctcac tgaggccgcc 60
cgggcaaagc ccgggcgtcg ggcgaccttt ggtcgcccgg cctcagtgag cgagcgagcg 120
cgcagagagg gagtggcca 139

<210> SEQ ID NO 22
<211> LENGTH: 7438
<212> TYPE: DNA
<213> ORGANISM: Artificial Sequence
<220> FEATURE:
<223> OTHER INFORMATION: Synthetic

<400> SEQUENCE: 22
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accgacattg attattgact 180
agttattaat agtaatcaat tacggggtca ttagttcata gcccatatat ggagttccgc 240
gttacataac ttacggtaaa tggcccgcct ggctgaccgc ccaacgaccc ccgcccattg 300
acgtcaataa tgacgtatgt tcccatagta acgccaatag ggactttcca ttgacgtcaa 360
tgggtggagt atttacggta aactgcccac ttggcagtac atcaagtgta tcatatgcca 420
agtacgcccc ctattgacgt caatgacggt aaatggcccg cctggcatta tgcccagtac 480
atgaccttat gggactttcc tacttggcag tacatctacg tattagtcat cgctattacc 540
atggtgatgc ggttttggca gtacatcaat gggcgtggat agcggtttga ctcacgggga 600
tttccaagtc tccaccccat tgacgtcaat gggagtttgt tttggcacca aaatcaacgg 660
gactttccaa aatgtcgtaa caactccgcc ccattgacgc aaatgggcgg taggcgtgta 720
cggtgggagg tctatataag cagagctctc tggctaacta ccggtgccac catgttccta 780
cagtttgctg tctggaagtg tttaccccat gggatcctca ttgcctctct cttggtagtc 840
agctggggcc agtatgacga tgactggcaa tacgaggatt gcaaactagc taggggagga 900
ccaccagcta ctatcgtggc cattgatgaa gagagtcgaa acggtacaat tctggtggat 960
aacatgttga ttaaggggac tgccggagga ccagacccca ccatagagct ctctttaaag 1020
gacaacgtgg actactgggt gttgctggac cccgttaaac agatgctttt cctgaacagt 1080
accggaagag ttctggatag agacccacca atgaacatac actccattgt ggtgcaagtc 1140
cagtgtgtca acaagaaggt tggcacagtt atctatcatg aagtacgcat cgtggtgcga 1200
gatcggaatg acaactcccc cacattcaag catgaaagct actatgccac cgtgaatgag 1260
ctcactccag ttggcaccac gatattcacg ggttctcgg gagacaatgg agctacagac 1320
atagacgatg gccctaatgg acagatagaa tacgtgattc agtacaaccc agaagatccg 1380
acatccaacg acacctttga aattccactc atgctgactg gcaacgtggt actgaggaaa 1440
agactcaact atgaggataa gactcgctac tatgtcatca tccaagcaaa tgaccgtgca 1500
caaaatctga atgagaggcg aacaaccacc accaccctca cagtagatgt tctagatgga 1560
gatgacctgg gacctatgtt tctgccttgt gttcttgtgc caaacacacg tgactgtcgt 1620
ccactcacct accaagctgc cattcctgaa ctgaggactc cggaagaact gaaccctatt 1680
ttggtgacac cacctatcca agccattgat caggaccgaa acatccaacc accatctgat 1740
cgacctggca tcctctactc catccttgtc ggcacccctg aggattaccc ccgcttcttc 1800
catatgcatc ccaggactgc agaactcact ctcctggagc cagtaaacag agacttccat 1860
caaaaatttg atttggttat taaggctgag caggacaatg gccacccact tcctgccttt 1920
gctagtctgc acatcgaaat actagacgaa aacaatcaga gtccatactt cacaatgccc 1980
agctatcaag gatacatcct ggaatccgcc ccagtgggag ccaccatttc tgagagccta 2040
aacttaacca ctcctctgag aattgtagct ctggacaaag acatagaaga cgtgccacct 2100
ggtggagttc ctacaaaaga tccagagctc cacctcttcc tgaatgacta cacctcggtc 2160
ttcactgtga cacccactgg tatcacccgc tacctcaccc tgcttcaacc tgtggacagg 2220
gaggaacagc aaacctacac ctttctgata acagcgtttg atggcgtgca agaaagtgag 2280
ccagtcgtgg tcaatatccg agtgatggat gcaaatgata acacgcccac cttccctgaa 2340
atctcctatg atgtctatgt ttacacagac atgagtcctg ggacagcgt cattcagctg 2400
acagcggtag atgctgatga aggctctaat ggggagatct cctatgaaat actggtgggg 2460
ggcaagggag acttcgtgat caacaagacc acagggctgg tgagcattgc accaggcgtg 2520
gagctgatcg tgggacagac gtatgcgctc acagtgcagg cttcggacaa cgccccgcct 2580
gcagaaagaa ggcactccat ctgcacagtg tacatcgagg tgcttcctcc taacaaccag 2640
agccctcccc gcttcccgca gctgatgtac agtctggaag tcagcgaggc catgaggatc 2700
ggtgctattt tattaaatct acaggcaact gatcgagagg gagatccaat cacatatgcc 2760
atcgagaatg gagaccctca gagagttttt aatctttcag aaaccacagg gattctcagc 2820
ctagggaagg ctctagaccg cgagagcaca gaccgctaca tcctcatcgt cacagcctca 2880
gatggcagac cggatggaac ctcaactgcc actgtgaaca tagtggtgac ggacgtcaat 2940
gacaacgctc ccgtgttcga tccctatctg cccaggaacc tctctgtggt ggaggaagaa 3000
gccaatgcct ttgtgggtca agtccgggca acagacccag atgctgggat aaacggccaa 3060
gttcactaca gcctggggaa cttcaacaac ctcttccgca tcacatccaa cgggagcatt 3120
tacacagccg tgaagctgaa cagggaagcc agggaccact atgaactggt tgtcgtggca 3180
acagatggag cagtccaccc tcgacattca actctgacac tgtacatcaa ggtgttggac 3240
attgatgata acagtcctgt ttttaccaat tcaacgtaca cagttgtcgt tgaagagaat 3300
ctgccagccg ggacctcctt tcttcaaata gaggccaagg atgttgacct tggagccaat 3360
gtgtcatatc ggatcagaag cccagaagtg aaacaccttt ttgcactgca tccattcact 3420
ggagaattgt ctcttctgag gagtttggat tatgaggcct ttccggacca ggaggcaagc 3480
atcacattct tggtggaggc ctttgacatt tatgggacta tgccacctgg tatagcaaca 3540
gtcacggtaa ttgtgaagga catgaatgac taccctccag tgtttagcaa acgcatctac 3600
aaggggatgg tggctccaga tgcagtcaag ggacaccaa tcaccaccgt ttatgctgaa 3660
gatgcggacc cacctgggat gcctgcaagt agggtgaggt atcgagtgga cgacgtgcag 3720
tttccatacc cagccagtat ttttgatgta gaggaagatt ctggaagagt agtaacccgc 3780
gtcaatctta atgaagagcc tactacgatt ttcaagctgg tggttgtggc ttttgatgac 3840
ggcgaacctg tgatgtccag cagtgccacg gtgagaattc ttgtcttaca tcctggagag 3900
atcccacgct tcacccaaga ggaatacaga cctcctcctg taagtgagct tgcggccaga 3960
gggactgtag ttggtgtcat ttctgctgct gccattaatc agagcatcgt gtactccatt 4020
gtggcaggaa atgaggaaga caagtttgga atcaacaatg tcactggggt catctatgtg 4080
aattcaccat tggattacga gacaaggacc agctatgtgc tccgggtaca agcagattct 4140
ctggaagtgg tccttgccaa tctccgagtc ccttcaaaaa gcaatacagc taaggtgtac 4200
attgagattc aggatgaaaa cgatcacccc ccagtgttcc agaagaaatt ctacattgga 4260
ggtgtgtctg aagacgtaag tatcaaggtt acaagacagg tttaaggaga ccaatagaaa 4320
ctgggcttgt cgagacagag aagactcttg cgtttctggg attttgccga tttcggccta 4380
ttggttaaaa aatgagctga tttaacaaaa atttaacgcg aattttaaca aaatgcatgc 4440
tggggagaga tctaggaacc cctagtgatg gagttggcca ctccctctct gcgcgctcgc 4500
tcgctcactg aggccgcccg ggcaaagccc gggcgtcggg cgacctttgg tcgcccggcc 4560
tcagtgagcg agcgagcgcg cagagaggga gtggccatgc agccagctgg cgtaatagcg 4620
aagaggcccg caccgatcgc ccttcccaac agttgcgtag cctgaatggc gaatggcgcg 4680
acgcgccctg tagcggcgca ttaagcgcgg cgggtgtggt ggttacgcgc agcgtgaccg 4740
ctacacttgc cagcgcccta gcgcccgctc ctttcgcttt cttcccttcc tttctcgcca 4800
cgttcgccgg ctttccccgt caagctctaa atcgggggct ccctttaggg ttccgattta 4860
gtgctttacg gcacctcgac cccaaaaaac ttgattaggg tgatggttca cgtagtgggc 4920
catcgccctg atagacggtt tttcgccctt tgacgttgga gtccacgttc tttaatagtg 4980
gactcttgtt ccaaactgga acaacactca accctatctc ggtctattct tttgatttat 5040
aagggatttt gccgatttcg gcctattggt taaaaaatga gctgatttaa caaaaattta 5100
acgcgaattt taacaaaata ttaacgttta caatttcctg atgcggtatt ttctccttac 5160
gcatctgtgc ggtatttcac accgcatatg gtgcactctc agtacaatct gctctgatgc 5220
cgcatagtta agccagcccc gacacccgcc aacacccgct gacgcgccct gacgggcttg 5280
tctgctcccg gcatccgctt acagacaagc tgtgaccgtc tccgggagct gcatgtgtca 5340
gaggttttca ccgtcatcac cgaaacgcgc gagacgaaag ggcctcgtga tacgcctatt 5400
tttataggtt aatgtcatga taataatggt ttcttagacg tcaggtggca cttttcgggg 5460
aaatgtgcgc ggaaccccta tttgtttatt tttctaaata cattcaaata tgtatccgct 5520
catgagacaa taaccctgat aaatgcttca ataatattga aaaaggaaga gtatgagtat 5580
tcaacatttc cgtgtcgccc ttattccctt ttttgcggca ttttgccttc ctgtttttgc 5640
tcacccagaa acgctggtga aagtaaaaga tgctgaagat cagttgggtg cacgagtggg 5700
ttacatcgaa ctggatctca acagcggtaa gatccttgag agttttcgcc ccgaagaacg 5760
ttttccaatg atgagcactt ttaaagttct gctatgtggc gcggtattat cccgtattga 5820
cgccgggcaa gagcaactcg gtcgccgcat acactattct cagaatgact tggttgagta 5880
ctcaccagtc acagaaaagc atcttacgga tggcatgaca gtaagagaat tatgcagtgc 5940
tgccataacc atgagtgata acactgcggc caacttactt ctgacaacga tcggaggacc 6000
gaaggagcta accgcttttt tgcacaacat gggggatcat gtaactcgcc ttgatcgttg 6060
ggaaccggag ctgaatgaag ccataccaaa cgacgagcgt gacaccacga tgcctgtagc 6120
aatggcaaca acgttgcgca aactattaac tggcgaacta cttactctag cttcccggca 6180
acaattaata gactggatgg aggcggataa agttgcagga ccacttctgc gctcggccct 6240
tccggctggc tggtttattg ctgataaatc tggagccggt gagcgtgggt ctcgcggtat 6300
cattgcagca ctggggccag atggtaagcc ctcccgtatc gtagttatct acacgacggg 6360
gagtcaggca actatggatg aacgaaatag acagatcgct gagataggtg cctcactgat 6420
taagcattgg taactgtcag accaagttta ctcatatata ctttagattg atttaaaact 6480
tcatttttaa tttaaaagga tctaggtgaa gatccttttt gataatctca tgaccaaaat 6540
cccttaacgt gagttttcgt tccactgagc gtcagacccc gtagaaaaga tcaaaggatc 6600
ttcttgagat cctttttttc tgcgcgtaat ctgctgcttg caaacaaaaa aaccaccgct 6660
accagcggtg gtttgtttgc cggatcaaga gctaccaact ctttttccga aggtaactgg 6720
cttcagcaga gcgcagatac caaatactgt ccttctagtg tagccgtagt taggccacca 6780
cttcaagaac tctgtagcac cgcctacata cctcgctctg ctaatcctgt taccagtggc 6840
tgctgccagt ggcgataagt cgtgtcttac cgggttggac tcaagacgat agttaccgga 6900
taaggcgcag cggtcgggct gaacgggggg ttcgtgcaca cagcccagct tggagcgaac 6960
gacctacacc gaactgagat acctacagcg tgagcattga gaaagcgcca cgcttcccga 7020
agggagaaag gcggacaggt atccggtaag cggcagggtc ggaacaggag agcgcacgag 7080
ggagcttcca gggggaaacg cctggtatct ttatagtcct gtcgggtttc gccacctctg 7140
acttgagcgt cgatttttgt gatgctcgtc aggggggcgg agcctatgga aaaacgccag 7200
caacgcggcc tttttacggt tcctggcctt ttgctggcct tttgctcaca tgttctttcc 7260
tgcgttatcc cctgattctg tggataaccg tattaccgcc tttgagtgag ctgataccgc 7320
tcgccgcagc cgaacgaccg agcgcagcga gtcagtgagc gaggaagcgg aagagcgccc 7380
aatacgcaaa ccgcctctcc ccgcgcgttg gccgattcat taatgcagct gggctgca 7438

<210> SEQ ID NO 23
<211> LENGTH: 7518
<212> TYPE: DNA
<213> ORGANISM: Artificial Sequence
<220> FEATURE:
<223> OTHER INFORMATION: Synthetic

<400> SEQUENCE: 23
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accgggattt tgccgatttc 180
ggcctattgg ttaaaaaatg agctgattta acaaaaattt aacgcgaatt ttaacaaaat 240
gataggcacc tattggtctt actgacatcc actttgcctt tctctccaca ggcaaggatg 300
ttcgcatctg tgctcagagt gaaggccacc gacagggaca cgggtaatta cagtgccatg 360

```
gcctaccggc tcatcatacc gccgattaaa gagggcaaag aggggtttgt ggtggaaaca    420
tacacaggtc tcatcaagac agccatgctc ttccacaata tgagaagatc ctacttcaag    480
tttcaagtga ttgcaactga cgactacggg aaggggttga gcgggaaagc agacgtactg    540
gtctccgtgg tcaatcaact ggatatgcag gtcattgtct ccaatgtgcc ccctacacta    600
gtggaaaaga agatagaaga ccttacagag attttggatc gctacgttca ggagcaaatt    660
cctggtgcca aggttgtggt ggagtccata ggtgcccgtc gccatggaga cgcctactcc    720
ctagaagact atagcaagtg cgacctgact gtctatgcca tcgacccgca gaccaacaga    780
gccatcgaca gaaatgagct ttttaagttc ctggacggca aactgctcga tatcaataaa    840
gacttccagc cgtattacgg ggaaggaggg cgcattctgg agattcggac acctgaggca    900
gtgacgagca tcaagaagcg aggagaaagc ttggggtaca cagaagggc cttgctggcc    960
ttggccttca tcatcatcct ctgttgcatc ccagccatct tggtcgtctt agtaagctac   1020
cgacagttta aagtacgcca ggctgagtgc acgaagaccg caagaattca gtctgctatg   1080
cctgcagcca agcctgcagc tcctgtacca gctgcgcctg cgccgccccc gcccccgcca   1140
ccaccaccac caggagcaca tctctatgaa gaactgggag agagcgcaat gcataagtat   1200
gagatgcccc agtatggaag tcgccgtcga ctgctgccac ctgctggaca ggaggaatac   1260
ggcgaagtca ttggtgaagc tgaagaggaa tatgaagaag aagaggtaga gccagagaaa   1320
gttaaaaaac ccaaagttga aattagagag cctagtgagg aggaggtggt agtcaccgtt   1380
gagaagccac cagcggctga gcccacatac ccaacgtgga agagagccag gatattcccg   1440
atgattttta agaaagtcag aggtctcgct gagaaaagag gcattgacct tgagggcgag   1500
gagtggagga ggcgccttga tgaagaagac aaagactatc ttcaactgac tctagaccag   1560
gaggaagcta ccgaaagcac cgtggagtca gaggaggagt ccagcgacta cacagaatac   1620
acagaaacgg agtccgagtt cagcgagtcc gagacaactg aagaatcaga gtcggagacc   1680
ccatctgagg aagcggagga gagctctacc ccggagtcag aggagtctga gtccactgag   1740
tcagagggag agaaagcaag aaaaaacatc gtgctggcta gaagaaggcc tgtggtcgag   1800
gaaatccagg aggtgaaagg taagagagag gagcccccgg tggaagagga agaagagccc   1860
ccactagagg aggaagaacg ggcagaggaa ggagaagaaa gcgaagcagc tcccatggat   1920
gagtccacag acctggaggc tcaggatgtc ccagaggagg gcagtgcaga atcagtctcc   1980
atggagaggg gcgtggaaag tgaggagtca gagtcagaac tgagcagcag cagcagtacc   2040
agtgagagtc tctccggagg cccctggggc tttcaggtgc cagaatatga cagaaggaag   2100
gatgaagagc ccaagaaatc tccaggcgca aactccgaag gttacaacac agccctttag   2160
ctcgagtcta gagcccctct ccctcccccc cccctaacgt tactggccga agccgcttgg   2220
aataaggccg gtgtgcgttt gtctatatgt tattttccac catattgccg tcttttggca   2280
atgtgagggc ccggaaacct ggccctgtct tcttgacgag cattcctagg ggtctttccc   2340
ctctcgccaa aggaatgcaa ggtctgttga atgtcgtgaa ggaagcagtt cctctggaag   2400
cctcttgaag acaaacaacg tctgtagcga ccctttgcag gcagcggaac cccccacctg   2460
gcgacaggtg cctctgcggc caaaagccac gtgtataaga tacacctgca aaggcggcac   2520
aaccccagtg ccacgttgtg agttggatag ttgtggaaag agtcaaatgg ctctcctcaa   2580
gcgtattcaa caaggggctg aaggatgccc agaaggtacc ccattgtatg ggatctgatc   2640
tggggcctcg gtgcacatgc tttacatgtg tttagtcgag gttaaaaaaa cgtctaggcc   2700
```

ccccgaacca cggggacgtg gttttccttt gaaaaacacg atgataatat ggccacaacc 2760
atggtgagca agggcgagga gctgttcacc ggggtggtgc ccatcctggt cgagctggac 2820
ggcgacgtaa acggccacaa gttcagcgtg tccggcgagg gcgagggcga tgccacctac 2880
ggcaagctga ccctgaagtt catctgcacc accggcaagc tgcccgtgcc ctggcccacc 2940
ctcgtgacca ccctgaccta cggcgtgcag tgcttcagcc gctaccccga ccacatgaag 3000
cagcacgact tcttcaagtc cgccatgccc gaaggctacg tccaggagcg caccatcttc 3060
ttcaaggacg acggcaacta caagacccgc gccgaggtga agttcgaggg cgacaccctg 3120
gtgaaccgca tcgagctgaa gggcatcgac ttcaaggagg acggcaacat cctggggcac 3180
aagctggagt acaactacaa cagccacaac gtctatatca tggccgacaa gcagaagaac 3240
ggcatcaagg tgaacttcaa gatccgccac aacatcgagg acggcagcgt gcagctcgcc 3300
gaccactacc agcagaacac ccccatcggc gacggccccg tgctgctgcc cgacaaccac 3360
tacctgagca cccagtccgc cctgagcaaa gaccccaacg agaagcgcga tcacatggtc 3420
ctgctggagt tcgtgaccgc cgccgggatc actctcggca tggacgagct gtacaagtaa 3480
tctagaagat aatcaacctc tggattacaa aatttgtgaa agattgactg gtattcttaa 3540
ctatgttgct ccttttacgc tatgtggata cgctgcttta atgcctttgt atcatgctat 3600
tgcttcccgt atggctttca ttttctcctc cttgtataaa tcctggttgc tgtctcttta 3660
tgaggagttg tggcccgttg tcaggcaacg tggcgtggtg tgcactgtgt ttgctgacgc 3720
aacccccact ggttggggca ttgccaccac ctgtcagctc ctttccggga ctttcgcttt 3780
ccccctccct attgccacgg cggaactcat cgccgcctgc cttgcccgct gctggacagg 3840
ggctcggctg ttgggcactg acaattccgt ggtgttgtcg gggaagctga cgtcctttcc 3900
atggctgctc gcctgtgttg ccacctggat tctgcgcggg acgtccttct gctacgtccc 3960
ttcggccctc aatccagcgg accttccttc ccgcggcctg ctgccggctc tgcggcctct 4020
tccgcgtctt cgccttcgcc ctcagacgag tcggatctcc ctttgggccg cctccccgca 4080
tcggactaga gagatccaga catgataaga tacattgatg agtttggaca aaccacaact 4140
agaatgcagt gaaaaaaatg ctttatttgt gaaatttgtg atgctattgc tttatttgta 4200
accattataa gctgcaataa acaagttaac aacaacaatt gcattcattt tatgtttcag 4260
gttcaggggg aggtgtggga ggttttttag tcgactagag ctcgctgatc agcctcgact 4320
gtgccttcta gttgccagcc atctgttgtt tgcccctccc ccgtgccttc cttgaccctg 4380
gaaggtgcca ctcccactgt cctttcctaa taaaatgagg aaattgcatc gcattgtctg 4440
agtaggtgtc attctattct ggggggtggg gtggggcagg acagcaaggg ggaggattgg 4500
gaagacaata gcaggcatgc tggggagaga tctaggaacc cctagtgatg gagttggcca 4560
ctccctctct gcgcgctcgc tcgctcactg aggccgcccg ggcaaagccc gggcgtcggg 4620
cgacctttgg tcgcccggcc tcagtgagcg agcgagcgcg cagagaggga gtggccatgc 4680
agccagctgg cgtaatagcg aagaggcccg caccgatcgc ccttcccaac agttgcgtag 4740
cctgaatggc gaatggcgcg acgcgccctg tagcggcgca ttaagcgcgg cgggtgtggt 4800
ggttacgcgc agcgtgaccg ctacacttgc cagcgcccta gcgcccgctc ctttcgcttt 4860
cttcccttcc tttctcgcca cgttcgccgg ctttccccgt caagctctaa atcgggggct 4920
ccctttaggg ttccgattta gtgctttacg gcacctcgac cccaaaaaac ttgattaggg 4980
tgatggttca cgtagtgggc catcgccctg atagacggtt tttcgccctt tgacgttgga 5040
gtccacgttc tttaatagtg gactcttgtt ccaaactgga acaacactca accctatctc 5100

-continued

```
ggtctattct tttgatttat aagggatttt gccgatttcg gcctattggt taaaaaatga   5160
gctgatttaa caaaaattta acgcgaattt taacaaaata ttaacgttta caatttcctg   5220
atgcggtatt ttctccttac gcatctgtgc ggtatttcac accgcatatg gtgcactctc   5280
agtacaatct gctctgatgc cgcatagtta agccagcccc gacacccgcc aacacccgct   5340
gacgcgccct gacgggcttg tctgctcccg gcatccgctt acagacaagc tgtgaccgtc   5400
tccgggagct gcatgtgtca gaggttttca ccgtcatcac cgaaacgcgc gagacgaaag   5460
ggcctcgtga tacgcctatt tttataggtt aatgtcatga taataatggt ttcttagacg   5520
tcaggtggca cttttcgggg aaatgtgcgc ggaaccccta tttgtttatt tttctaaata   5580
cattcaaata tgtatccgct catgagacaa taaccctgat aaatgcttca ataatattga   5640
aaaaggaaga gtatgagtat tcaacatttc cgtgtcgccc ttattccctt ttttgcggca   5700
ttttgccttc ctgtttttgc tcacccagaa acgctggtga aagtaaaaga tgctgaagat   5760
cagttgggtg cacgagtggg ttacatcgaa ctggatctca acagcggtaa gatccttgag   5820
agttttcgcc ccgaagaacg ttttccaatg atgagcactt ttaaagttct gctatgtggc   5880
gcggtattat cccgtattga cgccgggcaa gagcaactcg gtcgccgcat acactattct   5940
cagaatgact tggttgagta ctcaccagtc acagaaaagc atcttacgga tggcatgaca   6000
gtaagagaat tatgcagtgc tgccataacc atgagtgata acactgcggc caacttactt   6060
ctgacaacga tcggaggacc gaaggagcta accgcttttt tgcacaacat gggggatcat   6120
gtaactcgcc ttgatcgttg ggaaccggag ctgaatgaag ccataccaaa cgacgagcgt   6180
gacaccacga tgcctgtagc aatggcaaca acgttgcgca aactattaac tggcgaacta   6240
cttactctag cttcccggca acaattaata gactggatgg aggcggataa agttgcagga   6300
ccacttctgc gctcggccct tccggctggc tggtttattg ctgataaatc tggagccggt   6360
gagcgtgggt ctcgcggtat cattgcagca ctggggccag atggtaagcc ctcccgtatc   6420
gtagttatct acacgacggg gagtcaggca actatggatg aacgaaatag acagatcgct   6480
gagataggtg cctcactgat taagcattgg taactgtcag accaagttta ctcatatata   6540
ctttagattg atttaaaact tcatttttaa tttaaaagga tctaggtgaa gatccttttt   6600
gataatctca tgaccaaaat cccttaacgt gagttttcgt tccactgagc gtcagacccc   6660
gtagaaaaga tcaaaggatc ttcttgagat cctttttttc tgcgcgtaat ctgctgcttg   6720
caaacaaaaa aaccaccgct accagcggtg gtttgtttgc cggatcaaga gctaccaact   6780
ctttttccga aggtaactgg cttcagcaga gcgcagatac caaatactgt ccttctagtg   6840
tagccgtagt taggccacca cttcaagaac tctgtagcac cgcctacata cctcgctctg   6900
ctaatcctgt taccagtggc tgctgccagt ggcgataagt cgtgtcttac cgggttggac   6960
tcaagacgat agttaccgga taaggcgcag cggtcgggct gaacgggggg ttcgtgcaca   7020
cagcccagct tggagcgaac gacctacacc gaactgagat acctacagcg tgagcattga   7080
gaaagcgcca cgcttcccga agggagaaag gcggacaggt atccggtaag cggcagggtc   7140
ggaacaggag agcgcacgag ggagcttcca gggggaaacg cctggtatct ttatagtcct   7200
gtcgggtttc gccacctctg acttgagcgt cgatttttgt gatgctcgtc aggggggcgg   7260
agcctatgga aaaacgccag caacgcggcc tttttacggt tcctggcctt ttgctggcct   7320
tttgctcaca tgttctttcc tgcgttatcc cctgattctg tggataaccg tattaccgcc   7380
tttgagtgag ctgataccgc tcgccgcagc cgaacgaccg agcgcagcga gtcagtgagc   7440
```

gaggaagcgg aagagcgccc aatacgcaaa ccgcctctcc ccgcgcgttg gccgattcat 7500
taatgcagct gggctgca 7518

<210> SEQ ID NO 24
<211> LENGTH: 1619
<212> TYPE: PRT
<213> ORGANISM: Homo sapiens

<400> SEQUENCE: 24

Asn Met Leu Ile Lys Gly Thr Ala Gly Gly Pro Asp Pro Thr Ile Glu
1 5 10 15

Leu Ser Leu Lys Asp Asn Val Asp Tyr Trp Val Leu Met Asp Pro Val
20 25 30

Lys Gln Met Leu Phe Leu Asn Ser Thr Gly Arg Val Leu Asp Arg Asp
35 40 45

Pro Pro Met Asn Ile His Ser Ile Val Val Gln Val Gln Cys Ile Asn
50 55 60

Lys Lys Val Gly Thr Ile Ile Tyr His Glu Val Arg Ile Val Val Arg
65 70 75 80

Asp Arg Asn Asp Asn Ser Pro Thr Phe Lys His Glu Ser Tyr Tyr Ala
85 90 95

Thr Val Asn Glu Leu Thr Pro Val Gly Thr Thr Ile Phe Thr Gly Phe
100 105 110

Ser Gly Asp Asn Gly Ala Thr Asp Ile Asp Asp Gly Pro Asn Gly Gln
115 120 125

Ile Glu Tyr Val Ile Gln Tyr Asn Pro Asp Asp Pro Thr Ser Asn Asp
130 135 140

Thr Phe Glu Ile Pro Leu Met Leu Thr Gly Asn Ile Val Leu Arg Lys
145 150 155 160

Arg Leu Asn Tyr Glu Asp Lys Thr Arg Tyr Phe Val Ile Ile Gln Ala
165 170 175

Asn Asp Arg Ala Gln Asn Leu Asn Glu Arg Arg Thr Thr Thr Thr Thr
180 185 190

Leu Thr Val Asp Val Leu Asp Gly Asp Asp Leu Gly Pro Met Phe Leu
195 200 205

Pro Cys Val Leu Val Pro Asn Thr Arg Asp Cys Arg Pro Leu Thr Tyr
210 215 220

Gln Ala Ala Ile Pro Glu Leu Arg Thr Pro Glu Glu Leu Asn Pro Ile
225 230 235 240

Ile Val Thr Pro Pro Ile Gln Ala Ile Asp Gln Asp Arg Asn Ile Gln
245 250 255

Pro Pro Ser Asp Arg Pro Gly Ile Leu Tyr Ser Ile Leu Val Gly Thr
260 265 270

Pro Glu Asp Tyr Pro Arg Phe Phe His Met His Pro Arg Thr Ala Glu
275 280 285

Leu Ser Leu Leu Glu Pro Val Asn Arg Asp Phe His Gln Lys Phe Asp
290 295 300

Leu Val Ile Lys Ala Glu Gln Asp Asn Gly His Pro Leu Pro Ala Phe
305 310 315 320

Ala Gly Leu His Ile Glu Ile Leu Asp Glu Asn Asn Gln Ser Pro Tyr
325 330 335

Phe Thr Met Pro Ser Tyr Gln Gly Tyr Ile Leu Glu Ser Ala Pro Val
340 345 350

```
Gly Ala Thr Ile Ser Asp Ser Leu Asn Leu Thr Ser Pro Leu Arg Ile
        355                 360                 365

Val Ala Leu Asp Lys Asp Ile Glu Asp Thr Lys Asp Pro Glu Leu His
    370                 375                 380

Leu Phe Leu Asn Asp Tyr Thr Ser Val Phe Thr Val Thr Gln Thr Gly
385                 390                 395                 400

Ile Thr Arg Tyr Leu Thr Leu Leu Gln Pro Val Asp Arg Glu Glu Gln
                405                 410                 415

Gln Thr Tyr Thr Phe Ser Ile Thr Ala Phe Asp Gly Val Gln Glu Ser
            420                 425                 430

Glu Pro Val Ile Val Asn Ile Gln Val Met Asp Ala Asn Asp Asn Thr
        435                 440                 445

Pro Thr Phe Pro Glu Ile Ser Tyr Asp Val Tyr Val Tyr Thr Asp Met
    450                 455                 460

Arg Pro Gly Asp Ser Val Ile Gln Leu Thr Ala Val Asp Ala Asp Glu
465                 470                 475                 480

Gly Ser Asn Gly Glu Ile Thr Tyr Glu Ile Leu Val Gly Ala Gln Gly
                485                 490                 495

Asp Phe Ile Ile Asn Lys Thr Thr Gly Leu Ile Thr Ile Ala Pro Gly
            500                 505                 510

Val Glu Met Ile Val Gly Arg Thr Tyr Ala Leu Thr Val Gln Ala Ala
        515                 520                 525

Asp Asn Ala Pro Pro Ala Glu Arg Arg Asn Ser Ile Cys Thr Val Tyr
    530                 535                 540

Ile Glu Val Leu Pro Pro Asn Asn Gln Ser Pro Pro Arg Phe Pro Gln
545                 550                 555                 560

Leu Met Tyr Ser Leu Glu Ile Ser Glu Ala Met Arg Val Gly Ala Val
                565                 570                 575

Leu Leu Asn Leu Gln Ala Thr Asp Arg Glu Gly Asp Ser Ile Thr Tyr
            580                 585                 590

Ala Ile Glu Asn Gly Asp Pro Gln Arg Val Phe Asn Leu Ser Glu Thr
        595                 600                 605

Thr Gly Ile Leu Thr Leu Gly Lys Ala Leu Asp Arg Glu Ser Thr Asp
    610                 615                 620

Arg Tyr Ile Leu Ile Ile Thr Ala Ser Asp Gly Arg Pro Asp Gly Thr
625                 630                 635                 640

Ser Thr Ala Thr Val Asn Ile Val Val Thr Asp Val Asn Asp Asn Ala
                645                 650                 655

Pro Val Phe Asp Pro Tyr Leu Pro Arg Asn Leu Ser Val Val Glu Glu
            660                 665                 670

Glu Ala Asn Ala Phe Val Gly Gln Val Lys Ala Thr Asp Pro Asp Ala
        675                 680                 685

Gly Ile Asn Gly Gln Val His Tyr Ser Leu Gly Asn Phe Asn Asn Leu
    690                 695                 700

Phe Arg Ile Thr Ser Asn Gly Ser Ile Tyr Thr Ala Val Lys Leu Asn
705                 710                 715                 720

Arg Glu Val Arg Asp Tyr Tyr Glu Leu Val Val Val Ala Thr Asp Gly
                725                 730                 735

Ala Val His Pro Arg His Ser Thr Leu Thr Leu Ala Ile Lys Val Leu
            740                 745                 750

Asp Ile Asp Asp Asn Ser Pro Val Phe Thr Asn Ser Thr Tyr Thr Val
        755                 760                 765
```

```
Leu Val Glu Glu Asn Leu Pro Ala Gly Thr Thr Ile Leu Gln Ile Glu
    770                 775                 780

Ala Lys Asp Val Asp Leu Gly Ala Asn Val Ser Tyr Arg Ile Arg Ser
785                 790                 795                 800

Pro Glu Val Lys His Phe Phe Ala Leu His Pro Phe Thr Gly Glu Leu
                805                 810                 815

Ser Leu Leu Arg Ser Leu Asp Tyr Glu Ala Phe Pro Asp Gln Glu Ala
            820                 825                 830

Ser Ile Thr Phe Leu Val Glu Ala Phe Asp Ile Tyr Gly Thr Met Pro
        835                 840                 845

Pro Gly Ile Ala Thr Val Thr Val Ile Val Lys Asp Met Asn Asp Tyr
    850                 855                 860

Pro Pro Val Phe Ser Lys Arg Ile Tyr Lys Gly Met Val Ala Pro Asp
865                 870                 875                 880

Ala Val Lys Gly Thr Pro Ile Thr Thr Val Tyr Ala Glu Asp Ala Asp
                885                 890                 895

Pro Pro Gly Leu Pro Ala Ser Arg Val Arg Tyr Arg Val Asp Asp Val
            900                 905                 910

Gln Phe Pro Tyr Pro Ala Ser Ile Phe Glu Val Glu Glu Asp Ser Gly
        915                 920                 925

Arg Val Ile Thr Arg Val Asn Leu Asn Glu Glu Pro Thr Thr Ile Phe
    930                 935                 940

Lys Leu Val Val Val Ala Phe Asp Asp Gly Glu Pro Val Met Ser Ser
945                 950                 955                 960

Ser Ala Thr Val Lys Ile Leu Val Leu His Pro Gly Glu Ile Pro Arg
                965                 970                 975

Phe Thr Gln Glu Glu Tyr Arg Pro Pro Pro Val Ser Glu Leu Ala Thr
            980                 985                 990

Lys Gly Thr Met Val Gly Val Ile  Ser Ala Ala Ala Ile  Asn Gln Ser
        995                 1000                1005

Ile Val  Tyr Ser Ile Val Ser  Gly Asn Glu Glu Asp  Thr Phe Gly
    1010                1015                1020

Ile Asn  Asn Ile Thr Gly Val  Ile Tyr Val Asn Gly  Pro Leu Asp
    1025                1030                1035

Tyr Glu  Thr Arg Thr Ser Tyr  Val Leu Arg Val Gln  Ala Asp Ser
    1040                1045                1050

Leu Glu  Val Val Leu Ala Asn  Leu Arg Val Pro Ser  Lys Ser Asn
    1055                1060                1065

Thr Ala  Lys Val Tyr Ile Glu  Ile Gln Asp Glu Asn  Asn His Pro
    1070                1075                1080

Pro Val  Phe Gln Lys Lys Phe  Tyr Ile Gly Gly Val  Ser Glu Asp
    1085                1090                1095

Ala Arg  Met Phe Thr Ser Val  Leu Arg Val Lys Ala  Thr Asp Lys
    1100                1105                1110

Asp Thr  Gly Asn Tyr Ser Val  Met Ala Tyr Arg Leu  Ile Ile Pro
    1115                1120                1125

Pro Ile  Lys Glu Gly Lys Glu  Gly Phe Val Val Glu  Thr Tyr Thr
    1130                1135                1140

Gly Leu  Ile Lys Thr Ala Met  Leu Phe His Asn Met  Arg Arg Ser
    1145                1150                1155

Tyr Phe  Lys Phe Gln Val Ile  Ala Thr Asp Asp Tyr  Gly Lys Gly
    1160                1165                1170
```

```
Leu Ser  Gly Lys Ala Asp Val  Leu Val Ser Val Val  Asn Gln Leu
    1175                 1180                 1185

Asp Met  Gln Val Ile Val Ser  Asn Val Pro Pro Thr  Leu Val Glu
    1190                 1195                 1200

Lys Lys  Ile Glu Asp Leu Thr  Glu Ile Leu Asp Arg  Tyr Val Gln
    1205                 1210                 1215

Glu Gln  Ile Pro Gly Ala Lys  Val Val Val Glu Ser  Ile Gly Ala
    1220                 1225                 1230

Arg Arg  His Gly Asp Ala Phe  Ser Leu Glu Asp Tyr  Thr Lys Cys
    1235                 1240                 1245

Asp Leu  Thr Val Tyr Ala Ile  Asp Pro Gln Thr Asn  Arg Ala Ile
    1250                 1255                 1260

Asp Arg  Asn Glu Leu Phe Lys  Phe Leu Asp Gly Lys  Leu Leu Asp
    1265                 1270                 1275

Ile Asn  Lys Asp Phe Gln Pro  Tyr Tyr Gly Glu Gly  Gly Arg Ile
    1280                 1285                 1290

Leu Glu  Ile Arg Thr Pro Glu  Ala Val Thr Ser Ile  Lys Lys Arg
    1295                 1300                 1305

Gly Glu  Ser Leu Gly Tyr Thr  Glu Gly Ala Leu Leu  Ala Leu Ala
    1310                 1315                 1320

Phe Ile  Ile Ile Leu Cys Cys  Ile Pro Ala Ile Leu  Val Val Leu
    1325                 1330                 1335

Val Ser  Tyr Arg Gln Phe Lys  Val Arg Gln Ala Glu  Cys Thr Lys
    1340                 1345                 1350

Thr Ala  Arg Ile Gln Ala Ala  Leu Pro Ala Ala Lys  Pro Ala Val
    1355                 1360                 1365

Pro Ala  Pro Ala Pro Val Ala  Ala Pro Pro Pro Pro  Pro Pro Pro
    1370                 1375                 1380

Pro Pro  Gly Ala His Leu Tyr  Glu Glu Leu Gly Asp  Ser Ser Met
    1385                 1390                 1395

His Lys  Tyr Glu Met Pro Gln  Tyr Gly Ser Arg Arg  Arg Leu Leu
    1400                 1405                 1410

Pro Pro  Ala Gly Gln Glu Glu  Tyr Gly Glu Val Val  Gly Glu Ala
    1415                 1420                 1425

Glu Glu  Glu Tyr Glu Glu Glu  Glu Trp Ala Arg Lys  Arg Met Ile
    1430                 1435                 1440

Lys Leu  Val Val Asp Arg Glu  Tyr Glu Thr Ser Ser  Thr Gly Glu
    1445                 1450                 1455

Asp Ser  Ala Pro Glu Cys Gln  Arg Asn Arg Leu His  His Pro Ser
    1460                 1465                 1470

Ile His  Ser Asn Ile Asn Gly  Asn Ile Tyr Ile Ala  Gln Asn Gly
    1475                 1480                 1485

Ser Val  Val Arg Thr Arg Arg  Ala Cys Leu Thr Asp  Asn Leu Lys
    1490                 1495                 1500

Val Ala  Ser Pro Val Arg Leu  Gly Gly Pro Phe Lys  Lys Leu Asp
    1505                 1510                 1515

Lys Leu  Ala Val Thr His Glu  Glu Asn Val Pro Leu  Asn Thr Leu
    1520                 1525                 1530

Ser Lys  Gly Pro Phe Ser Thr  Glu Lys Met Asn Ala  Arg Pro Thr
    1535                 1540                 1545

Leu Val  Thr Phe Ala Pro Cys  Pro Val Gly Thr Asp  Asn Thr Ala
    1550                 1555                 1560
```

```
Val Lys  Pro Leu Arg Asn Arg  Leu Lys Ser Thr Val  Glu Gln Glu
    1565                 1570                 1575

Ser Met  Ile Asp Ser Lys Asn  Ile Lys Glu Ala Leu  Glu Phe His
    1580                 1585                 1590

Ser Asp  His Thr Gln Ser Asp  Asp Glu Glu Leu Trp  Met Gly Pro
    1595                 1600                 1605

Trp Asn  Asn Leu His Ile Pro  Met Thr Lys Leu
    1610                 1615


<210> SEQ ID NO 25
<211> LENGTH: 13
<212> TYPE: PRT
<213> ORGANISM: Artificial Sequence
<220> FEATURE:
<223> OTHER INFORMATION: Synthetic

<400> SEQUENCE: 25

Ser Arg Leu Glu Glu Glu Leu Arg Arg Arg Leu Thr Glu
1               5                   10


<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

Gly Leu Asn Asp Ile Phe Glu Ala Gln Lys Ile Glu Trp His Glu
1               5                   10                  15


<210> SEQ ID NO 27
<211> LENGTH: 4
<212> TYPE: PRT
<213> ORGANISM: Artificial Sequence
<220> FEATURE:
<223> OTHER INFORMATION: Synthetic

<400> SEQUENCE: 27

Glu Pro Glu Ala
1


<210> SEQ ID NO 28
<211> LENGTH: 26
<212> TYPE: PRT
<213> ORGANISM: Artificial Sequence
<220> FEATURE:
<223> OTHER INFORMATION: Synthetic

<400> SEQUENCE: 28

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25


<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Glu Glu Glu Glu Glu Glu
1               5
```

<210> SEQ ID NO 30
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (6)..(9)
<223> OTHER INFORMATION: may be absent

<400> SEQUENCE: 30

```
Arg Arg Arg Arg Arg Arg Arg Arg Arg
1               5
```

<210> SEQ ID NO 31
<211> LENGTH: 13
<212> TYPE: PRT
<213> ORGANISM: Artificial Sequence
<220> FEATURE:
<223> OTHER INFORMATION: Synthetic

<400> SEQUENCE: 31

```
Gly Ala Pro Val Pro Tyr Pro Asp Pro Leu Glu Pro Arg
1               5                   10
```

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

```
Asp Tyr Lys Asp Asp Asp Asp Lys
1               5
```

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

```
Tyr Pro Tyr Asp Val Pro Asp Tyr Ala
1               5
```

<210> SEQ ID NO 34
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (6)..(10)
<223> OTHER INFORMATION: May be absent

<400> SEQUENCE: 34

```
His His His His His His His His His His
1               5                   10
```

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Glu Gln Lys Leu Ile Ser Glu Glu Asp Leu
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Thr Lys Glu Asn Pro Arg Ser Asn Gln Glu Glu Ser Tyr Asp Asp Asn
1               5                   10                  15

Glu Ser

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Thr Glu Thr Ser Gln Val Ala Pro Ala
1               5

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Lys Glu Thr Ala Ala Ala Lys Phe Glu Arg Gln His Met Asp Ser
1               5                   10                  15

<210> SEQ ID NO 39
<211> LENGTH: 38
<212> TYPE: PRT
<213> ORGANISM: Artificial Sequence
<220> FEATURE:
<223> OTHER INFORMATION: Synthetic

<400> SEQUENCE: 39

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 40
<211> LENGTH: 13
<212> TYPE: PRT
<213> ORGANISM: Artificial Sequence
<220> FEATURE:
<223> OTHER INFORMATION: Synthetic

<400> SEQUENCE: 40

Ser Leu Ala Glu Leu Leu Asn Ala Gly Leu Gly Gly Ser
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Thr Gln Asp Pro Ser Arg Val Gly
1               5

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Pro Asp Arg Val Arg Ala Val Ser His Trp Ser Ser
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

Trp Ser His Pro Gln Phe Glu Lys
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Met Ala Ser Met Thr Gly Gly Gln Gln Met Gly
1               5                   10

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Cys Cys Pro Gly Cys Cys
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic

<400> SEQUENCE: 46

Glu Val His Thr Asn Gln Asp Pro Leu Asp
1 5 10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Gly Lys Pro Ile Pro Asn Pro Leu Leu Gly Leu Asp Ser Thr
1 5 10

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Tyr Thr Asp Ile Glu Met Asn Arg Leu Gly Lys
1 5 10

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Asp Leu Tyr Asp Asp Asp Asp Lys
1 5

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Thr Asp Lys Asp Met Thr Ile Thr Phe Thr Asn Lys Lys Asp Ala Glu
1 5 10 15

<210> SEQ ID NO 51
<211> LENGTH: 13
<212> TYPE: PRT
<213> ORGANISM: Artificial Sequence
<220> FEATURE:
<223> OTHER INFORMATION: Synthetic

<400> SEQUENCE: 51

Ala His Ile Val Met Val Asp Ala Tyr Lys Pro Thr Lys
1 5 10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

```
Lys Leu Gly Asp Ile Glu Phe Ile Lys Val Asn Lys
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

```
Lys Leu Gly Ser Ile Glu Phe Ile Lys Val Asn Lys
1               5                   10
```

<210> SEQ ID NO 54
<211> LENGTH: 23
<212> TYPE: PRT
<213> ORGANISM: Artificial Sequence
<220> FEATURE:
<223> OTHER INFORMATION: Synthetic

<400> SEQUENCE: 54

```
Asp Ile Pro Ala Thr Tyr Glu Phe Thr Asp Gly Lys His Tyr Ile Thr
1               5                   10                  15

Asn Glu Pro Ile Pro Pro Lys
            20
```

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

```
Asp Pro Ile Val Met Ile Asp Asn Asp Lys Pro Ile Thr
1               5                   10
```

<210> SEQ ID NO 56
<211> LENGTH: 14
<212> TYPE: DNA
<213> ORGANISM: Artificial Sequence
<220> FEATURE:
<223> OTHER INFORMATION: Synthetic

<400> SEQUENCE: 56

```
ttcttttctt tcaa                                                       14
```

DUAL-AAV VECTOR DELIVERY OF PCDH15 AND USES THEREOF

RELATED APPLICATIONS

This application is a national stage filing under 35 U.S.C. § 371 of International PCT Application, PCT/US2021/050188, filed Sep. 14, 2021, which claims priority under 35 U.S.C. § 119(e) to U.S. Provisional Application, U.S. Ser. No. 63/077,911, filed Sep. 14, 2020, each of which is incorporated herein by reference.

FEDERALLY SPONSORED RESEARCH

This invention was made with Government support under DC016932 and DC016199 awarded by the National Institutes of Health. The Government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Mar. 9, 2023, is named H082470366US01-SEQ-LJG and is 108,969 bytes in size.

BACKGROUND OF INVENTION

Deafness and blindness are two of the most common and most devastating neurological disorders. In many cases, deafness and blindness result from single gene defects (e.g., PCDH15 mutation that causes Usher syndrome type 1F). However, effective therapy for treating Usher syndrome type 1F remains elusive.

Mutations in PCDH15 cause Usher 1F, a recessive syndrome characterized by profound congenital deafness and absence of vestibular function, and progressive blindness beginning in the second decade of life. Because patients who lack hearing and balance rely on vision for communication and mobility, the late-onset blindness is particularly devastating.

Currently, treatment for Usher 1F is limited to cochlear implants, and there is no treatment for the related blindness. Gene addition therapy could be an attractive treatment for those with homozygous recessive mutations. However, the PCDH15 coding sequence of ~5.8 kb is too large to fit into a single AAV capsid, which is limited to ~4.7 kb of transgene. There are no known methods to reconstitute wild-type PCDH15 expression in inner ear or eye cells currently.

SUMMARY

Currently, treatment for Usher 1F is limited to cochlear implants, and there is no treatment for the related blindness. Gene addition therapy could be an attractive treatment for those with homozygous recessive mutations. However, the PCDH15 coding sequence of ~5.8 kb is too large to fit into a single AAV capsid, which is limited to ~4.7 kb of transgene. There are no known methods to reconstitute wild-type PCDH15 expression in inner ear or eye cells currently.

Accordingly, in some aspects, the present disclosure provides a first 5' isolated nucleic acid comprising transgene, wherein the transgene comprises a nucleotide sequence encoding a first portion of a PCDH15 protein.

In some embodiments, in the first 5' isolated nucleic acid, the transgene further comprises a promoter operably linked to the nucleotide sequence encoding the first portion of the PCDH15 protein. In some embodiments, in the first 5' isolated nucleic acid, the promoter is a constitutive promoter, an inducible promoter, or a tissue specific promoter. In some embodiments, in the first 5' isolated nucleic acid, the promoter is a minimal promoter. In some embodiments, in the first 5' isolated nucleic acid, the promoter is a CMV promoter, a chicken beta actin promoter (CBA), a CAG promoter, a minimal CMV promoter, a human EF1-α promoter, or a ProA6 promoter.

In some embodiments, in the first 5' isolated nucleic acid, the transgene further comprises a nucleotide sequence encoding a splice donor of an intron. In some embodiments, in the first 5' isolated nucleic acid, the nucleotide sequence encoding the splice donor is positioned 3' to the nucleotide sequence encoding the first portion of the PCDH15 protein. In some embodiments, in the first 5' isolated nucleic acid, the nucleotide sequence encoding the splice donor comprises a nucleotide sequence at least 80% identical to SEQ ID NO: 11

In some embodiments, in the first 5' isolated nucleic acid, the PCDH15 protein is a human PCDH15 protein. In some embodiments, in the first 5' isolated nucleic acid, the nucleotide sequence encoding the first portion of PCDH15 comprises a sequence at least 80% identical to SEQ ID NO: 4.

In some embodiments, in the first 5' isolated nucleic acid, the transgene further comprises a Kozak sequence. In some embodiments, in the first 5' isolated nucleic acid, the transgene further comprises a beta-actin exon and/or a chimeric intron positioned between the promoter and the nucleotide sequence encoding the first portion of the PCDH15 protein.

In some embodiments, the first 5' isolated nucleic acid further comprises two adeno-associated virus inverted terminal repeats (ITRs) flanking the transgene. In some embodiments, in the first 5' isolated nucleic acid, the ITRs are of an AAV serotype selected from the group consisting of AAV1 ITR, AAV2 ITR, AAV3 ITR, AAV4 ITR, AAV5 ITR, and AAV6 ITR. In some embodiments, in the first 5' isolated nucleic acid, the AAV ITRs are AAV2 ITRs.

In some aspects, the present disclosure proves a first 3' isolated nucleic acid comprising a transgene encoding a second portion of a PCDH15 protein.

In some embodiments, in the first 3' isolated nucleic acid, the PCDH15 protein is human PCDH15 protein. In some embodiments, in the first 3' isolated nucleic acid, the nucleotide sequence encoding the second portion of the PCDH15 protein comprises a sequence at least 80% identical to any of SEQ ID NOs: 5-7.

In some embodiments, in the first 3' isolated nucleic acid, the transgene further comprises nucleotide sequence encoding a splice acceptor of an intron. In some embodiments, in the first 3' isolated nucleic acid, the splice acceptor derives from the same intron as the splice donor of the first 5' isolated nucleic acid. In some embodiments, in the first 3' isolated nucleic acid, the nucleotide sequence encoding the splice acceptor is positioned 5' to the nucleotide sequence encoding the second portion of the PCDH15 protein. In some embodiments, in the first 3' isolated nucleic acid, the nucleotide sequence encoding the splice acceptor comprises a nucleotide sequence at least 80% identical to SEQ ID NO: 12.

In some embodiments, in the first 3' isolated nucleic acid, the transgene further comprises a poly A tail. In some embodiments, in the first 3' isolated nucleic acid, the poly A tail is a SV40 poly A tail or a bovine growth hormone (BGH) poly A tail.

In some embodiments, in the first 3' isolated nucleic acid, the transgene further comprises a Woodchuck Hepatitis Virus (WHP) Posttranscriptional Regulatory Element (WPRE).

In some embodiments, in the first 3' isolated nucleic acid, the transgene further comprises a nucleotide sequence encoding a tag. In some embodiments, in the first 3' isolated nucleic acid, the tag is fused to the C-terminal of the second portion of the PCDH15 protein. In some embodiments, in the first 3' isolated nucleic acid, the tag is a HA-tag, a FLAG-tag, or a Spy Tag.

In some embodiments, in the first 3' isolated nucleic acid, the transgene further comprises a nucleotide sequence encoding a detectable protein. In some embodiments, in the first 3' isolated nucleic acid, the detectable protein is a fluorescent protein. In some embodiments, in the first 3' isolated nucleic acid, the fluorescent protein is an enhanced green fluorescent protein (eGFP).

In some embodiments, in the first 3' isolated nucleic acid, the transgene further comprises an internal ribosomal entering site (IRES) positioned between the nucleotide sequence encoding the second portion of the PCDH15 protein, and the nucleotide sequence encoding the detectable protein. In some embodiments, in the first 3' isolated nucleic acid, the transgene further comprises a nucleotide sequence encoding a 2A peptide positioned between the nucleotide sequence encoding the second portion of the PCDH15 protein, and the nucleotide sequence encoding the detectable protein.

In some embodiments, the first 3' isolated nucleic acid further comprises two adeno-associated virus inverted terminal repeats (ITRs) flanking the transgene. In some embodiments, in the first 3' isolated nucleic acid, the ITRs are of an AAV serotype selected from the group consisting of AAV1 ITR, AAV2 ITR, AAV3 ITR, AAV4 ITR, AAV5 ITR, and AAV6 ITR. In some embodiments, in the first 3' isolated nucleic acid, the AAV ITRs are AAV2 ITRs.

In some aspects, the present disclosure provides a second 5' isolated nucleic acid comprising transgene, wherein the transgene comprises a nucleotide sequence encoding a first portion of a PCDH15 protein.

In some embodiments, in the second 5' isolated nucleic acid, the transgene further comprises a promoter operably linked to the nucleotide sequence encoding the first portion of the PCDH15 protein.

In some embodiments, in the second 5' isolated nucleic acid, the promoter is a constitutive promoter, an inducible promoter, or a tissue specific promoter. In some embodiments, in the second 5' isolated nucleic acid, the promoter is a minimal promoter. In some embodiments, in the second 5' isolated nucleic acid, the promoter is a CMV promoter, a chicken beta actin promoter (CBA), a CAG promoter, a minimal CMV promoter, a human EF1-α promoter, or a ProA6 promoter.

In some embodiments, in the second 5' isolated nucleic acid, the transgene further comprises a nucleotide sequence encoding a splice donor of an intron. In some embodiments, in the second 5' isolated nucleic acid, the nucleotide sequence encoding the splice donor is positioned 3' to the nucleotide sequence encoding the first portion of the PCDH15 protein. In some embodiments, in the second 5' isolated nucleic acid, the nucleotide sequence encoding the splice donor comprises a nucleotide sequence at least 80% identical to SEQ ID NO: 11.

In some embodiments, in the second 5' isolated nucleic acid, the transgene further comprises a nucleotide sequence encoding a recombinogenic sequence. In some embodiments, in the second 5' isolated nucleic acid, the nucleotide sequence encoding the recombinogenic sequence is positioned 3' to the nucleotide sequence encoding the splice donor. In some embodiments, in the second 5' isolated nucleic acid, the nucleotide sequence encoding the recombinogenic sequence comp a nucleotide sequence at least 80% identical to SEQ ID NO: 13.

In some embodiments, in the second 5' isolated nucleic acid, the PCDH15 protein is a human PCDH15 protein. In some embodiments, in the second 5' isolated nucleic acid, the nucleotide sequence encoding the first portion of PCDH15 comprises a sequence at least 80% identical to SEQ ID NO: 4.

In some embodiments, in the second 5' isolated nucleic acid, the transgene further comprises a Kozak sequence. In some embodiments, in the second 5' isolated nucleic acid, the transgene further comprises a beta-actin exon and/or a chimeric intron positioned between the promoter and the nucleotide sequence encoding the first portion of the PCDH15 protein.

In some embodiments, the second 5' isolated nucleic acid further comprises two adeno-associated virus inverted terminal repeats (ITRs) flanking the transgene. In some embodiments, in the second 5' isolated nucleic acid, the ITRs are of an AAV serotype selected from the group consisting of AAV1 ITR, AAV2 ITR, AAV3 ITR, AAV4 ITR, AAV5 ITR, and AAV6 ITR. In some embodiments, in the second 5' isolated nucleic acid, the AAV ITRs are AAV2 ITRs.

In some aspects, the present disclosure provides a second 3' isolated nucleic acid comprising a transgene encoding a second portion of a PCDH15 protein.

In some embodiments, in the second 3' isolated nucleic acid, the PCDH15 protein is human PCDH15 protein. In some embodiments, in the second 3' isolated nucleic acid, the nucleotide sequence encoding the second portion of the PCDH15 protein comprises a sequence at least 80% identical to any of SEQ ID NOs: 5-7.

In some embodiments, in the second 3' isolated nucleic acid, the transgene further comprises nucleotide sequence encoding a splice acceptor of an intron. In some embodiments, in the second 3' isolated nucleic acid, the splice acceptor derives from the same intron as the splice donor of the first 3' isolated nucleic acid. In some embodiments, in the second 3' isolated nucleic acid, the nucleotide sequence encoding the splice acceptor is positioned 3' to the nucleotide sequence encoding the second portion of the PCDH15 protein. In some embodiments, in the second 3' isolated nucleic acid, the nucleotide sequence encoding the splice acceptor comprises a nucleotide sequence at least 80% identical to SEQ ID NO: 12.

In some embodiments, in the second 3' isolated nucleic acid, the transgene further comprises a nucleotide sequence encoding a recombinogenic sequence. In some embodiments, in the second 3' isolated nucleic acid, the nucleotide sequence encoding the recombinogenic sequence is positioned 3' to the nucleotide sequence encoding the splice acceptor. In some embodiments, in the second 3' isolated nucleic acid, the recombinogenic sequence of the second 3' isolated nucleic acid is the same as the recombinogenic sequence of the second 3' isolated nucleic acid. In some embodiments, in the second 3' isolated nucleic acid, the nucleotide sequence encoding the recombinogenic sequence comp a nucleotide sequence at least 80% identical to SEQ ID NO: 13.

In some embodiments, in the second 3' isolated nucleic acid, the transgene further comprises a poly A tail. In some embodiments, in the second 3' isolated nucleic acid, the poly A tail is a SV40 poly A tail or a bovine growth hormone (BGH) poly A tail.

In some embodiments, in the second 3' isolated nucleic acid, the transgene further comprises a Woodchuck Hepatitis Virus (WHP) Posttranscriptional Regulatory Element (WPRE).

In some embodiments, in the second 3' isolated nucleic acid, the transgene further comprises a nucleotide sequence encoding a tag. In some embodiments, in the second 3' isolated nucleic acid, the tag is fused to the C-terminal of the second portion of the PCDH15 protein. In some embodiments, in the second 3' isolated nucleic acid, the tag is a HA-tag, a FLAG-tag, or a Spy Tag.

In some embodiments, in the second 3' isolated nucleic acid, the transgene further comprises a nucleotide sequence encoding a detectable protein. In some embodiments, in the second 3' isolated nucleic acid, the detectable protein is a fluorescent protein. In some embodiments, in the second 3' isolated nucleic acid, the fluorescent protein is an enhanced green fluorescent protein (eGFP).

In some embodiments, in the second 3' isolated nucleic acid, the transgene further comprises an internal ribosomal entering site (IRES) positioned between the nucleotide sequence encoding the second portion of the PCDH15 protein, and the nucleotide sequence encoding the detectable protein. In some embodiments, in the second 3' isolated nucleic acid, the transgene further comprises a nucleotide sequence encoding a 2A peptide positioned between the nucleotide sequence encoding the second portion of the PCDH15 protein, and the nucleotide sequence encoding the detectable protein.

In some embodiments, the second 3' isolated nucleic acid further comprises two adeno-associated virus inverted terminal repeats (ITRs) flanking the transgene.

In some embodiments, in the second 3' isolated nucleic acid, the ITRs are of an AAV serotype selected from the group consisting of AAV1 ITR, AAV2 ITR, AAV3 ITR, AAV4 ITR, AAV5 ITR, and AAV6 ITR. In some embodiments, in the second 3' isolated nucleic acid, the AAV ITRs are AAV2 ITRs.

In some aspects, the present disclosure provides a vector comprising the first 5' isolated nucleic acid, the first 3' isolated nucleic acid, the second 5' isolated nucleic acid, or the second 3' isolated nucleic acid as described herein. In some embodiments, the vector is a plasmid, or a viral vector. In some embodiments, the vector is an adeno-associated virus vector.

In some embodiments, the rAAV vector encoding the first portion of PCDH15 comprises, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; and (g) a 3' ITR.

In some embodiments, the rAAV vector encoding the first portion of PCDH15 comprises, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; (g) a recombinogenic sequence, and (h) a 3' ITR.

In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a WPRE; (e) a SV40 poly A signal; (f) a BGH poly A signal; and (g) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a nucleotide sequence encoding an IRES; (e) a nucleotide encoding an eGFP; (f) a WPRE; (e) a SV40 poly A signal; (f) a BGH poly A signal; and (g) a 3' ITR. In some embodiments, the rAAV vector further comprises a nucleotide sequence encoding a tag. In some embodiments, the tag is a HA tag.

In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a WPRE; (f) a SV40 poly A signal; (g) a BGH poly A signal; and (h) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a nucleotide sequence encoding an IRES; (f) a nucleotide encoding an eGFP; (g) a WPRE; (h) a SV40 poly A signal; (i) a BGH poly A signal; and (j) a 3' ITR. In some embodiments, the rAAV vector further comprises a nucleotide sequence encoding a tag. In some embodiments, the tag is a HA tag.

In some embodiments, the vector comprising a nucleotide sequence at least 80% identical to any one of SEQ ID NOs: 22 or 23.

In some aspects, the present disclosure provides a first 5' rAAV comprising (i) an AAV capsid protein (e.g., AAV-S capsid protein or AAV9.PHP.B capsid protein); and (ii) a first 5' isolated nucleic acid comprising, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; and (g) a 3' ITR.

In some aspects, the present disclosure provides a first 3' rAAV comprising (i) an AAV capsid protein (e.g., AAV-S capsid protein or AAV9.PHP.B capsid protein); and (ii) a first 3' isolated nucleic acid comprising, from 5' to 3', from 5' to 3', (a) a 5' ITR; (b) a splice acceptor; (c) a nucleotide sequence encoding a second portion of the PCDH15 protein; (d) a WPRE; (e) a SV40 poly A signal; (f) a BGH poly A signal; and (g) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a nucleotide sequence encoding an IRES; (e) a nucleotide encoding an eGFP; (f) a WPRE; (e) a SV40 poly A signal; (f) a BGH poly A signal; and (g) a 3' ITR. In some embodiments, the first 3' isolated nucleic acid further comprises a nucleotide sequence encoding a tag. In some embodiments, the tag is a HA tag.

In some aspects, the present disclosure provides a second 5' rAAV comprising (i) an AAV capsid protein (e.g., AAV-S capsid protein or AAV9.PHP.B capsid protein); and (ii) a second 5' isolated nucleic acid comprising, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; (g) a recombinogenic sequence, and (h) a 3' ITR.

In some aspects, the present disclosure provides a second 3' rAAV comprising (i) an AAV capsid protein (e.g., AAV-S capsid protein or AAV9.PHP.B capsid protein); and (ii) a second 3' isolated nucleic acid comprising, from 5' to 3', from 5' to 3', (a) a 5' ITR; (b) a recombinogenic sequence; (c) a splice acceptor; (d) a nucleotide sequence encoding a second portion of the PCDH15 protein; (e) a WPRE; (f) a SV40 poly A signal; (g) a BGH poly A signal; and (h) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a nucleotide sequence encoding an IRES; (f) a nucleotide encoding an eGFP; (g) a WPRE; (h) a SV40 poly A signal; (i) a BGH poly A signal; and (j) a 3' ITR. In some embodiments, the second 3' isolated nucleic acid further comprises a nucleotide sequence encoding a tag. In some embodiments, the tag is a HA tag.

In some aspects, the present disclosure provides: (a) a first 5' recombinant adeno-associated (rAAV) virus comprising: (i) an adeno-associated virus capsid protein; and (ii) the first 5' isolated nucleic acid as described herein; (b) first 3' recombinant adeno-associated (rAAV) virus comprising: (i) an adeno-associated virus capsid protein; and (ii) the first 3' isolated nucleic acid as described herein. (c) a second 5' recombinant adeno-associated (rAAV) virus comprising: (i) an adeno-associated virus capsid protein; and (ii) the second 5' isolated nucleic acid as described herein; or (d) a second 3' recombinant adeno-associated (rAAV) virus comprising: (i) an adeno-associated virus capsid protein; and (ii) the second 3' isolated nucleic acid as described herein.

In some embodiments, the rAAV has tropism for cells of the cochlea and/or the retina.

In some embodiments, the rAAV has tropism for outer hair cell (OHCs), inner hair cell (IHCs), supporting cell, cells in spiral ganglion neuron, cells in piral limbus, outer sulcus cells, cells in lateral wall, cells in stria vascularis, cells in inner sulcus, cells in spiral ligament, or cells of the vestibular system.

In some embodiments, the rAAV has tropism for photoreceptor cells, other cells in the retina within the photoreceptor inner and outer segments (IS), cells of the outer plexiform layer (OPL), cells of the inner nuclei layer (INL), cells of the ganglion cell layer (GCL), cells of the inner plexiform layer (IPL), or retinal pigment epithelium (RPE) of the eye.

In some embodiments, the capsid protein is an AAV2 capsid protein, an AAV5 capsid protein, an AAV7 capsid protein, an AAV8 capsid protein, an AAV9 capsid protein, or a variant thereof. In some embodiments, the AAV capsid variant is an AAV9.PHP.B, an AAV-S capsid protein, an AAV9.PHP.eB capsid protein, an AAV2.7m8 capsid protein, an AAV9-7m8 capsid protein, an AAV8BP2 capsid protein, an exoAAV1 capsid protein, an exoAAV9 capsid protein, or an Anc80L65 capsid protein. In some embodiments, the AAV capsid protein is an AAV9.PHP.B capsid protein. In some embodiments, the AAV capsid protein is an AAV-S capsid protein.

In some aspects, the present disclosure provides: (a) a PCDH15 expression system comprising: (i) the first 5' rAAV; and (ii) the first 3' rAAV as described herein; or (b) a PCDH15 expression system comprising: (i) the second 5' rAAV; and (ii) the second 3' rAAV as described herein.

In some aspects, the present disclosure provides a host cell comprising the first 5' isolated nucleic acid, the first 3' isolated nucleic acid, the second 5' isolated nucleic acid, the second 3' isolated nucleic acid, the vector, the rAAV, or the PCDH15 expression system as described herein.

In some aspects, the present disclosure provides a pharmaceutical composition comprising the first 5' isolated nucleic acid, the first 3' isolated nucleic acid, the second 5' isolated nucleic acid, the second 3' isolated nucleic acid, the vector, the rAAV, or the PCDH15 expression system as described herein. In some embodiments, the pharmaceutical composition further comprising a pharmaceutically acceptable carrier.

In some aspects, the present disclosure provides a method for expressing a full length PCDH15 in a cell, the method comprising: delivering to the cell the first 5' isolated nucleic acid, the first 3' isolated nucleic acid, the second 5' isolated nucleic acid, the second 3' isolated nucleic acid, the vector, the rAAV, the PCDH15 expression system, or the pharmaceutical composition as described herein.

In some aspects, the present disclosure provides a method for treating hearing loss in a subject in need thereof, the method comprising: administering to the subject an effective amount of the first 5' isolated nucleic acid, the first 3' isolated nucleic acid, the second 5' isolated nucleic acid, the second 3' isolated nucleic acid, the vector, the rAAV, the PCDH15 expression system, or the pharmaceutical composition as described herein.

In some aspects, the present disclosure provides a method for treating vison loss in a subject in need thereof, the method comprising: administering to the subject an effective amount of the first 5' isolated nucleic acid, the first 3' isolated nucleic acid, the second 5' isolated nucleic acid, the second 3' isolated nucleic acid, the vector, the rAAV, the PCDH15 expression system, or the pharmaceutical composition as described herein.

In some aspects, the present disclosure provides a method for treating Usher Syndrome, Type 1F in a subject in need thereof, the method comprising: administering to the subject an effective amount of the first 5' isolated nucleic acid, the first 3' isolated nucleic acid, the second 5' isolated nucleic acid, the second 3' isolated nucleic acid, the vector, the rAAV, the PCDH15 expression system, or the pharmaceutical composition as described herein.

In some embodiments, the subject is a mammal. In some embodiments, the mammal is a human. In some embodiments, the mammal is a non-human mammal. In some embodiments, the non-human mammal is mouse, rat, or non-human primate.

In some embodiments, the subject has or is suspected of having Usher Syndrome type 1F. In some embodiments, the hearing loss and/or vision loss is associated with Usher syndrome type 1F.

In some embodiments, the hearing loss and/or vision loss is associated with a mutation in the PCDH15 gene. In some embodiments, the mutation in the PCDH15 gene is a point mutation, a missense mutation, a nonsense mutation, a deletion, an insertion, or a combination thereof. In some embodiments, the subject is human; and the mutation is one or more mutations listed in Table 1. In some embodiments, the mutation is c.733C>T.

In some embodiments, the administration results in expression of full-length PCDH15 protein in the inner ear of the subject. In some embodiments, the administration results in expression of full-length PCDH15 protein in the cochlea of the subject. In some embodiments, the administration results in expression of full-length PCDH15 protein in outer hair cell (OHCs), inner hair cell (IHCs), supporting cell, cells in spiral ganglion neuron, cells in piral limbus, outer sulcus cells, cells in lateral wall, cells in stria vascularis, cells in inner sulcus, cells in spiral ligament, or cells of the vestibular system.

In some embodiments, the administration results in expression of full-length PCDH15 protein in the eye of the subject. In some embodiments, the administration results in expression of full-length PCDH15 protein in the retina of the subject. In some embodiments, the administration results in expression of full-length PCDH15 protein photoreceptor cells, other cells in the retina within the photoreceptor inner and outer segments (IS), cells of the outer plexiform layer (OPL), cells of the inner nuclei layer (INL), cells of the ganglion cell layer (GCL), cells of the inner plexiform layer (IPL), or retinal pigment epithelium (RPE) of the eye.

In some embodiments, the administration is via injection. In some embodiments, the injection is through round window membrane of the inner ear, into a semicircular canal of the inner ear, or into the saccule or the utricle of the inner ear. In some embodiments, the injection into the eye is subretinal or intravitreal.

The details of one or more embodiments of the invention are set forth in the description below. Other features or advantages of the present invention will be apparent from the following drawing and detailed description of certain embodiments, and also from the appended claims.

BRIEF DESCRIPTION OF DRAWINGS

FIGS. 1A-1B are illustrations of the interaction of PCDH15 with Cadherin-23 in the inner ear. FIGS. 1C-1D are illustrations of PCDH15's functioning in the retina. FIG. 1E is a schematic illustration of PCDH15 mutations associated with deafness and/or blindness.

FIG. 2A shows a general strategy to deliver full-length PCDH15 to cells. FIG. 2B is a graph showing a dual AAV vector structure to deliver full-length PCDH15 using trans splicing. FIG. 2C shows dual AAV vector structure to deliver full-length PCDH15 and eGFP using cis splicing. With AAVs, the 3' and 5' ITRs tend to concatemerize. After transcription, trans-splicing can then occur from the splice donor site in vector 1 to the splice acceptor site in vector 2, creating a full-length PCDH15 coding sequence. FIGS. 2D-2E are AAV vector maps of the dual AAV vectors for delivering full-length PCDH15 to cells. FIG. 2F is a graph showing a dual AAV vector structure to deliver full-length PCDH15 using homologous recombination plus cis-splicing. FIG. 2G is a graph showing a dual AAV vector structure to deliver full-length PCDH15 and eGFP using homologous recombination plus cis-splicing. FIG. 2H is a structural model of PCDH15 with a small epitope tag, which enables detection with a binding protein. A hybrid strategy creates a full-length coding sequence by homologous recombination between two viral genomes. After transcription, the homologous recombination sequence is spliced out.

FIG. 3A shows immunofluorescence detection of full-length PCDH15 in cochlea cells after injection of dual AAV vectors in mice. FIG. 3B shows dual-vector delivery of PCDH15 rescues hearing in a conditional knockout model. The control mouse has sensitive hearing, measured as a low threshold across most stimulus frequencies. The knockout (mutant) has no response even with the loudest (85 dB) sounds. A mutant injected with dual vectors encoding PCDH15 has greatly enhanced sensitivity, shown by lower thresholds. The dual-vector PCDH15 delivered to wild-type mouse has normal thresholds indicating no toxicity for hearing. FIG. 3C shows dual-vector delivery of PCDH15 rescues hair bundle morphology in a conditional knockout model. The top panel shows the control mouse has well-developed hair bundles, seen at low (left) and high (right) magnification. The middle panel shows the mutant shows disorganized bundles, lacking many stereocilia. The bottom panel shows that in a mutant injected with dual vectors encoding PCDH15, many of the hair bundles are normal.

FIG. 4A shows that zebra fish retina is similar to human retina. FIGS. 4B-4C show electron microscopy of wild type zebra fish larva compared to a larva carrying PCDH15 mutation. Wild type zebra fish showed well-formed parallel calyceal processes (arrows) surrounding the outer segments of photoreceptors. Right, higher magnification. In mutant zebra fish, processes are fewer, not of uniform diameter, and sometimes branched. Outer segments are disorganized. FIG. 4D shows development of the electroretinogram (ERG) in zebrafish larvae. An electrical signal is recorded from the front of the eye in response to short flashes of increasing intensity. A robust ERG is present just 5-6 days after fertilization of the egg. FIG. 4E shows an optokinetic reflex test of zebra fish larvae.

FIG. 6A shows HA-tagged PCDH15 at the tips of OHC stereocilia in mice injected with dual vectors at P1. FIG. 6B shows the localization of HA-tagged PCDH15 in P30 OHC stereocilia, in CKO mice injected at P1 with dual vectors encoding HA-PCDH15. FIG. 6C shows immunogold SEM localization of HA-tagged PCDH15 in P30 OHC stereocilia in KO mice injected with Dual PCDH15-HA at P1.

Figure 1A:
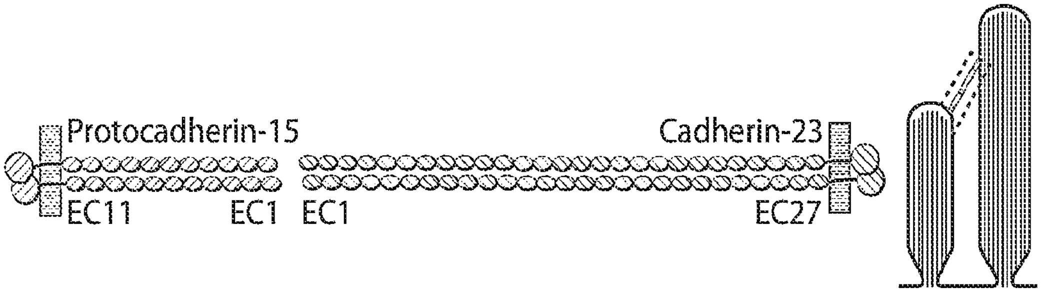
FIGS. 1A-1E are schematic illustrations of PCDH14 in the inner ear and the retina.

The accompanying drawings, which are incorporated in and constitute a part of this specification, illustrate certain embodiments, and together with the written description, serve to provide non-limiting examples of certain aspects of the compositions and methods disclosed herein. Any references cited in the present disclosure are incorporated by reference in their entirety.

DETAILED DESCRIPTION

The present disclosure, at least in part, relates to compositions, systems, nucleic acids, vectors, viruses, uses, and methods for treating certain genetic diseases, for example, autosomal recessive disorders (e.g., Usher Syndrome, Type 1F), etc. Autosomal recessive disorders are diseases that result from abnormal expression or function of both alleles of a gene. Usher syndrome, type 1F is an inherited disease that causes profound hearing loss from birth and impairs vision beginning in adolescence. Usher syndrome, type 1F is caused by mutations in the PCDH15 gene One aspect of the disclosure relates to delivering a full-length therapeutic protein (e.g., PCDH15) to the target cells (e.g., inner hair cells, outer hair cells, and photoreceptors) using a PCDH15 expression system as described herein (e.g., one or more recombinant adeno-associated virus (rAAV)).

Adeno-associated virus (AAV) mediated gene therapy is one approach for the treatment of various genetic diseases. Currently, treatment for Usher 1F is limited to cochlear implants, and there is no treatment for the blindness associated with Usher 1F. Gene addition therapy could be an attractive treatment for those with homozygous recessive mutations. However, the PCDH15 coding sequence of ~5.8 kb is too large to fit into a single AAV capsid, which is limited to ~4.7 kb of transgene.

This disclosure is based, in part, on gene therapy vectors, such as viral (e.g., rAAV) vectors, comprising one or more gene fragments encoding a therapeutic gene product (e.g., PCDH15) for delivery to target cells (e.g., inner hair cells, outer hair cells, and photoreceptors). In some embodiments, portions of the coding sequence of the therapeutic protein (e.g., PCDH15) are delivered to the target cells (e.g., inner hair cells, outer hair cells, and photoreceptors) by more than one rAAVs (e.g., dual rAAVs), and the portions of the coding sequences of PCDH15 recombines in the cell to generate a full-length PCDH15 coding sequence, thus generating a full-length PCDH15 protein in the target cell.

I. Dual-AAV Vector System Encoding Full-Length PCDH15

In some aspects, the disclosure provides a dual-AAV vector system (e.g., a 5' nucleic acid and/or a 3' nucleic acid) each encoding a different portion of a protein (e.g., a portion of PCDH15 protein) for expressing a gene product (e.g., full-length PCDH15) in a target cell (e.g., inner hair cells, outer hair cells, and photoreceptors).

In some embodiments, the dual AAV vector system for expressing full-length PCDH15 in a target cell comprises: (i) a 5' isolated nucleic acid comprising transgene, wherein the transgene comprises a nucleotide sequence encoding a first portion of a PCDH15 protein; and (ii) a 3' isolated nucleic acid comprising a transgene encoding a second portion of a PCDH15 protein. In some embodiments, the isolated nucleic acids described herein are useful for expressing a full-length PCDH15 in a target cell.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art.

The wild type PCDH15 coding sequence of ~5.8 kb is too large to fit into a single AAV capsid, which is limited to ~4.7 kb of transgene. The PCDH15 gene is a member of the cadherin superfamily. Family members encode integral membrane proteins that mediate calcium-dependent cell-cell adhesion. Full-length PCDH15 includes (from N-terminus to C-terminus): a signal peptide, eleven extracellular calcium-binding domains (EC domains, EC1-EC11), a membrane adjacent domain (MAD12), a transmembrane domain, and a unique cytoplasmic domain. PCDH15 is expressed in several isoforms differing in their cytoplasmic domains, suggesting that alternative splicing regulates PCDH15 function in hair cells. There are three prominent splice isoforms of PCDH15 according to its unique cytoplasmic domain: CD1, CD2, and CD3. PCDH15 plays an essential role in maintenance of normal retinal and cochlear function. It is thought to interact with cadherin related 23 (CDH23) to form tip-link filaments.

An exemplary amino acid sequence for full-length human PCDH15 (CD1 splice form; CBI Reference Sequence: NP_001136235.1) is set forth in SEQ ID NO: 1:

MFRQFYLWTCLASGIILGSLFEICLGQYDDDWQYEDCKLARGGPPATIVAIDEESRNGTILV

DNMLIKGTAGGPDPTIELSLKDNVDYWVLMDPVKQMLFLNSTGRVLDRDPPMNIHSIVVQVQ

CINKKVGTIIYHEVRIVVRDRNDNSPTFKHESYYATVNELTPVGTTIFTGFSGDNGATDIDD

-continued

GPNGQIEYVIQYNPDDPTSNDTFEIPLMLTGNIVLRKRLNYEDKTRYFVIIQANDRAQNLNE

RRTTTTTLTVDVLDGDDLGPMFLPCVLVPNTRDCRPLTYQAAIPELRTPEELNPIIVTPPIQ

AIDQDRNIQPPSDRPGILYSILVGTPEDYPRFFHMHPRTAELSLLEPVNRDFHQKFDLVIKA

EQDNGHPLPAFAGLHIEILDENNQSPYFTMPSYQGYILESAPVGATISDSLNLTSPLRIVAL

DKDIEDTKDPELHLFLNDYTSVFTVTQTGITRYLTLLQPVDREEQQTYTFSITAFDGVQESE

PVIVNIQVMDANDNTPTFPEISYDVYVYTDMRPGDSVIQLTAVDADEGSNGEITYEILVGAQ

GDFIINKTTGLITIAPGVEMIVGRTYALTVQAADNAPPAERRNSICTVYIEVLPPNNQSPPR

FPQLMYSLEISEAMRVGAVLLNLQATDREGDSITYAIENGDPQRVFNLSETTGILTLGKALD

RESTDRYILIITASDGRPDGTSTATVNIVVTDVNDNAPVFDPYLPRNLSVVEEEANAFVGQV

KATDPDAGINGQVHYSLGNFNNLFRITSNGSIYTAVKLNREVRDYYELVVVATDGAVHPRHS

TLTLAIKVLDIDDNSPVFTNSTYTVLVEENLPAGTTILQIEAKDVDLGANVSYRIRSPEVKH

FFALHPFTGELSLLRSLDYEAFPDQEASITFLVEAFDIYGTMPPGIATVTVIVKDMNDYPPV

FSKRIYKGMVAPDAVKGTPITTVYAEDADPPGLPASRVRYRVDDVQFPYPASIFEVEEDSGR

VITRVNLNEEPTTIFKLVVVAFDDGEPVMSSSATVKILVLHPGEIPRFTQEEYRPPPVSELA

TKGTMVGVISAAAINQSIVYSIVSGNEEDTFGINNITGVIYVNGPLDYETRTSYVLRVQADS

LEVVLANLRVPSKSNTAKVYIEIQDENNHPPVFQKKFYIGGVSEDARMFTSVLRVKATDKDT

GNYSVMAYRLIIPPIKEGKEGFVVETYTGLIKTAMLFHNMRRSYFKFQVIATDDYGKGLSGK

ADVLVSVVNQLDMQVIVSNVPPTLVEKKIEDLTEILDRYVQEQIPGAKVVVESIGARRHGDA

FSLEDYTKCDLTVYAIDPQTNRAIDRNELFKFLDGKLLDINKDFQPYYGEGGRILEIRTPEA

VTSIKKRGESLGYTEGALLALAFIIILCCIPAILVVLVSYRQFKVRQAECTKTARIQAALPA

AKPAVPAPAPVAAPPPPPPPPPGAHLYEELGDSSMHNLFLLYHFQQSRGNNSVSEDRKHQQV

VMPFSSNTIEAHKSAHVDGSLKSNKLKSARKFTFLSDEDDLSAHNPLYKENISQVSTNSDIS

QRTDFVDPFSPKIQAKSKSLRGPREKIQRLWSQSVSLPRRLMRKVPNRPEIIDLQQWQGTRQ

KAENENTGICTNKRGSSNPLLTTEEANLTEKEEIRQGETLMIEGTEQLKSLSSDSSFCFPRP

HFSFSTLPTVSRTVELKSEPNVISSPAECSLELSPSRPCVLHSSLSRRETPICMLPIETERN

IFENFAHPPNISPSACPLPPPPPISPPSPPPAPAPLAPPPDISPFSLFCPPPSPPSIPLPLP

PPTFFPLSVSTSGPPTPPLLPPFPTPLPPPPPSIPCPPPPSASFLSTECVCITGVKCTTNLM

PAEKIKSSMTQLSTTTVCKTDPQREPKGILRHVKNLAELEKSVANMYSQIEKNYLRTNVSEL

QTMCPSEVTNMEITSEQNKGSLNNIVEGTEKQSHSQSTSL

Another exemplary amino acid sequence for full-length human PCDH15 (CD2 splice form; NCBI Reference Sequence: NP_001136241.1) is set forth in SEQ ID NO: 2:

MFRQFYLWTCLASGIILGSLFEICLGQYDDDWQYEDCKLARGGPPATIVAIDEESRNGTILV

DNMLIKGTAGGPDPTIELSLKDNVDYWVLMDPVKQMLFLNSTGRVLDRDPPMNIHSIVVQVQ

CINKKVGTIIYHEVRIVVRDRNDNSPTFKHESYYATVNELTPVGTTIFTGFSGDNGATDIDD

GPNGQIEYVIQYNPDDPTSNDTFEIPLMLTGNIVLRKRLNYEDKTRYFVIIQANDRAQNLNE

RRTTTTTLTVDVLDGDDLGPMFLPCVLVPNTRDCRPLTYQAAIPELRTPEELNPIIVTPPIQ

AIDQDRNIQPPSDRPGILYSILVGTPEDYPRFFHMHPRTAELSLLEPVNRDFHQKFDLVIKA

EQDNGHPLPAFAGLHIEILDENNQSPYFTMPSYQGYILESAPVGATISDSLNLTSPLRIVAL

DKDIEDVPPSGVPTKDPELHLFLNDYTSVFTVTQTGITRYLILLQPVDREEQQTYTFSITAF

-continued

```
DGVQESEPVIVNIQVMDANDNTPTFPEISYDVYVYTDMRPGDSVIQLTAVDADEGSNGEITY

EILVGAQGDFIINKTTGLITIAPGVEMIVGRTYALTVQAADNAPPAERRNSICTVYIEVLPP

NNQSPPRFPQLMYSLEISEAMRVGAVLLNLQATDREGDSITYAIENGDPQRVFNLSETTGIL

TLGKALDRESTDRYILIITASDGRPDGTSTATVNIVVTDVNDNAPVFDPYLPRNLSVVEEEA

NAFVGQVKATDPDAGINGQVHYSLGNFNNLFRITSNGSIYTAVKLNREVRDYYELVVVATDG

AVHPRHSTLTLAIKVLDIDDNSPVFTNSTYTVLVEENLPAGTTILQIEAKDVDLGANVSYRI

RSPEVKHFFALHPFTGELSLLRSLDYEAFPDQEASITFLVEAFDIYGTMPPGIATVTVIVKD

MNDYPPVFSKRIYKGMVAPDAVKGTPITTVYAEDADPPGLPASRVRYRVDDVQFPYPASIFE

VEEDSGRVITRVNLNEEPTTIFKLVVVAFDDGEPVMSSSATVKILVLHPGEIPRFTQEEYRP

PPVSELATKGTMVGVISAAAINQSIVYSIVSGNEEDTFGINNITGVIYVNGPLDYETRTSYV

LRVQADSLEVVLANLRVPSKSNTAKVYIEIQDENNHPPVFQKKFYIGGVSEDARMFTSVLRV

KATDKDTGNYSVMAYRLIIPPIKEGKEGFVVETYTGLIKTAMLFHNMRRSYFKFQVIATDDY

GKGLSGKADVLVSVVNQLDMQVIVSNVPPTLVEKKIEDLTEILDRYVQEQIPGAKVVVESIG

ARRHGDAFSLEDYTKCDLTVYAIDPQTNRAIDRNELFKFLDGKLLDINKDFQPYYGEGGRIL

EIRTPEAVTSIKKRGESLGYTEGALLALAFIIILCCIPAILVVLVSYRQFKVRQAECTKTAR

IQAALPAAKPAVPAPAPVAAPPPPPPPPPGAHLYEELGDSSMHKYEMPQYGSRRRLLPPAGQ

EEYGEVVGEAEEEYEEEEEEPKKIKKPKVEIREPSEEEEVVVTIEKPPAAEPTYTTWKRARI

FPMIFKKVRGLADKRGIVDLEGEEWQRRLEEEDKDYLKLTLDQEEATESTVESEEESSSDYT

EYSEEESEFSESETTEEESESETPSEEEESSTPESEESESTESEGEKARKNIVLARRRPMVE

EVKEVKGRKEEPQEEQKEPKMEEEEHSEEEESGPAPVEESTDPEAQDIPEEGSAESASVEGG

VESEEESESGSSSSSSSESQSGGPWGYQVPAYDRSKNANQKKSPGANSEGYNTAL
```

An exemplary amino acid sequence for full-length human PCDH15 (CD3-a splice form; NCBI Reference Sequence: NP_001341349.1) is set forth in SEQ ID NO: 3:

```
MFRQFYLWTCLASGIILGSLFEICLGQYDDDCKLARGGPPATIVAIDEESRNGTILVDNMLI

KGTAGGPDPTIELSLKDNVDYWVLMDPVKQMLFLNSTGRVLDRDPPMNIHSIVVQVQCINKK

VGTIIYHEVRIVVRDRNDNSPTFKHESYYATVNELTPVGTTIFTGFSGDNGATDIDDGPNGQ

IEYVIQYNPDDPTSNDTFEIPLMLTGNIVLRKRLNYEDKTRYFVIIQANDRAQNLNERRTTT

TTLTVDVLDGDDLGPMFLPCVLVPNTRDCRPLTYQAAIPELRTPEELNPIIVTPPIQAIDQD

RNIQPPSDRPGILYSILVGTPEDYPRFFHMHPRTAELSLLEPVNRDFHQKFDLVIKAEQDNG

HPLPAFAGLHIEILDENNQSPYFTMPSYQGYILESAPVGATISDSLNLTSPLRIVALDKDIE

DTKDPELHLFLNDYTSVFTVTQTGITRYLTLLQPVDREEQQTYTFSITAFDGVQESEPVIVN

IQVMDANDNTPTFPEISYDVYVYTDMRPGDSVIQLTAVDADEGSNGEITYEILVGAQGDFII

NKTTGLITIAPGVEMIVGRTYALTVQAADNAPPAERRNSICTVYIEVLPPNNQSPPRFPQLM

YSLEISEAMRVGAVLLNLQATDREGDSITYAIENGDPQRVFNLSETTGILTLGKALDRESTD

RYILIITASDGRPDGTSTATVNIVVTDVNDNAPVFDPYLPRNLSVVEEEANAFVGQVKATDP

DAGINGQVHYSLGNFNNLFRITSNGSIYTAVKLNREVRDYYELVVVATDGAVHPRHSTLTLA

IKVLDIDDNSPVFTNSTYTVLVEENLPAGTTILQIEAKDVDLGANVSYRIRSPEVKHFFALH

PFTGELSLLRSLDYEAFPDQEASITFLVEAFDIYGTMPPGIATVTVIVKDMNDYPPVFSKRI

YKGMVAPDAVKGTPITTVYAEDADPPGLPASRVRYRVDDVQFPYPASIFEVEEDSGRVITRV
```

-continued

NLNEEPTTIFKLVVVAFDDGEPVMSSSATVKILVLHPGEIPRFTQEEYRPPPVSELATKGTM

VGVISAAAINQSIVYSIVSGNEEDTFGINNITGVIYVNGPLDYETRTSYVLRVQADSLEVVL

ANLRVPSKSNTAKVYIEIQDENNHPPVFQKKFYIGGVSEDARMFTSVLRVKATDKDTGNYSV

MAYRLIIPPIKEGKEGFVVETYTGLIKTAMLFHNMRRSYFKFQVIATDDYGKGLSGKADVLV

SVVNQLDMQVIVSNVPPTLVEKKIEDLTEILDRYVQEQIPGAKVVVESIGARRHGDAFSLED

YTKCDLTVYAIDPQTNRAIDRNELFKFLDGKLLDINKDFQPYYGEGGRILEIRTPEAVTSIK

KRGESLGYTEGALLALAFIIIILCCIPAILVVLVSYRQFKVRQAECTKTARIQAALPAAKPAV

PAPAPVAAPPPPPPPPPGAHLYEELGDSSMYEMPQYGSRRRLLPPAGQEEYGEVVGEAEEEY

EEEEWARKRMIKLVVDREYETSSTGEDSAPECQRNRLHHPSIHSNINGNIYIAQNGSVVRTR

RACLTDNLKVASPVRLGGPFKKLDKLAVTHEENVPLNTLSKGPFSTEKMNARPTLVTFAPCP

VGTDNTAVKPLRNRLKSTVEQESMIDSKNIKEALEFHSDHTQSDDEELWMGPWNNLHIPMTK

L

An exemplary amino acid sequence for full-length human PCDH15 (CD3-1 splice form; NCBI Reference Sequence: NP_001341349.1) is set forth in SEQ ID NO: 24:

NMLIKGTAGGPDPTIELSLKDNVDYWVLMDPVKQMLFLNSTGRVLDRDPPMNIHSIVVQVQC

INKKVGTIIYHEVRIVVRDRNDNSPTFKHESYYATVNELTPVGTTIFTGFSGDNGATDIDDG

PNGQIEYVIQYNPDDPTSNDTFEIPLMLIGNIVLRKRLNYEDKTRYFVIIQANDRAQNLNER

RTTTTTLTVDVLDGDDLGPMFLPCVLVPNTRDCRPLTYQAAIPELRTPEELNPIIVTPPIQA

IDQDRNIQPPSDRPGILYSILVGTPEDYPRFFHMHPRTAELSLLEPVNRDFHQKFDLVIKAE

QDNGHPLPAFAGLHIEILDENNQSPYFTMPSYQGYILESAPVGATISDSLNLTSPLRIVALD

KDIEDTKDPELHLFLNDYTSVFTVTQTGITRYLTLLQPVDREEQQTYTFSITAFDGVQESEP

VIVNIQVMDANDNTPTFPEISYDVYVYTDMRPGDSVIQLTAVDADEGSNGEITYEILVGAQG

DFIINKTTGLITIAPGVEMIVGRTYALTVQAADNAPPAERRNSICTVYIEVLPPNNQSPPRF

PQLMYSLEISEAMRVGAVLLNLQATDREGDSITYAIENGDPQRVFNLSETTGILTLGKALDR

ESTDRYILIITASDGRPDGTSTATVNIVVTDVNDNAPVFDPYLPRNLSVVEEEANAFVGQVK

ATDPDAGINGQVHYSLGNFNNLFRITSNGSIYTAVKLNREVRDYYELVVVATDGAVHPRHST

LTLAIKVLDIDDNSPVFTNSTYTVLVEENLPAGTTILQIEAKDVDLGANVSYRIRSPEVKHF

FALHPFTGELSLLRSLDYEAFPDQEASITFLVEAFDIYGTMPPGIATVTVIVKDMNDYPPVF

SKRIYKGMVAPDAVKGTPITTVYAEDADPPGLPASRVRYRVDDVQFPYPASIFEVEEDSGRV

ITRVNLNEEPTTIFKLVVVAFDDGEPVMSSSATVKILVLHPGEIPRFTQEEYRPPPVSELAT

KGTMVGVISAAAINQSIVYSIVSGNEEDTFGINNITGVIYVNGPLDYETRTSYVLRVQADSL

EVVLANLRVPSKSNTAKVYIEIQDENNHPPVFQKKFYIGGVSEDARMFTSVLRVKATDKDTG

NYSVMAYRLIIPPIKEGKEGFVVETYTGLIKTAMLFHNMRRSYFKFQVIATDDYGKGLSGKA

DVLVSVVNQLDMQVIVSNVPPTLVEKKIEDLTEILDRYVQEQIPGAKVVVESIGARRHGDAF

SLEDYTKCDLTVYAIDPQTNRAIDRNELFKFLDGKLLDINKDFQPYYGEGGRILEIRTPEAV

TSIKKRGESLGYTEGALLALAFIIIILCCIPAILVVLVSYRQFKVRQAECTKTARIQAALPAA

KPAVPAPAPVAAPPPPPPPPPGAHLYEELGDSSMHKYEMPQYGSRRRLLPPAGQEEYGEVVG

EAEEEYEEEEWARKRMIKLVVDREYETSSTGEDSAPECQRNRLHHPSIHSNINGNIYIAQNG

-continued

SVVRTRRACLTDNLKVASPVRLGGPFKKLDKLAVTHEENVPLNTLSKGPFSTEKMNARPTLV

TFAPCPVGTDNTAVKPLRNRLKSTVEQESMIDSKNIKEALEFHSDHTQSDDEELWMGPWNNL

HIPMTKL

In some embodiments, the dual-AAV vector system comprises two isolated nucleic acids, each encoding a portion of PCDH15, and once in the cell, is capable of expressing a full-length PCDH15. In some embodiments, the dual-AAV vector system forms a full-length PCDH15 coding sequence in the target cell by trans splicing. In other embodiments, the dual-AAV vector system forms a full-length PCDH15 coding sequence in the target cell by homologous recombination and splicing.

The isolated nucleic acids of the present disclosure may be recombinant adeno-associated virus (AAV) vectors (rAAV vectors). In some embodiments, an isolated nucleic acid comprises two adeno-associated virus (AAV) inverted terminal repeats (ITR). The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene, and 5' and 3' AAV inverted terminal repeats (ITRs). The transgene may comprise, as disclosed elsewhere herein, a nucleic acid sequence encoding a protein (e.g., a first portion of PCDH15 or a second portion of PCDH15). In some aspects, the dual-AAV vector system forms a full-length PCDH15 coding sequence in the target cell by trans splicing. In some embodiments, the present disclosure provides a first dual-AAV vector system including two isolated nucleic acids (e.g., a first 5' isolated nucleic acid and a first 3' isolated nucleic acid) in a way that the two isolated nucleic acids form a full length PCDH15 mRNA in a target cell by trans-splicing. Trans-splicing, as used herein, refers to a form of RNA processing where exons from a primary RNA transcript transcribed from concatemerized DNA (e.g., concatemerized rAAV genomes) are spliced together and processed into a mature mRNA. This process is mediated by the spliceosome. In some embodiments, the first 5' isolated nucleic acid comprises a nucleotide sequence encoding a splice donor 3' to the nucleotide sequence encoding the first portion of PCDH15. In addition, the first 3' isolated nucleic acid comprises a nucleotide sequence encoding a splice acceptor 5' to the nucleotide sequence encoding the second portion of PCDH15. In eukaryotic cells, mRNA splicing occurs at intronic sites. A splice donor (e.g., 5' end of the intron) and a splice acceptor (e.g., 3' end of the intron) are required for splicing. Once the first 5' isolated nucleic acid and the first 3' isolated nucleic acid are delivered to a target cell (e.g., by rAAVs), the two isolated nucleic acids undergo head to tail concatemerization from 3' ITR of the first 5' isolated nucleic acid and 5' ITR of the first 3' isolated nucleic acid, such that the first 5' isolated nucleic acid and the first 3' isolated nucleic acid are combined into one single nucleic acid (e.g., a single DNA molecule), which can be transcribed into pre-mRNA. The pre-mRNA comprises the PCDH15 first portion mRNA, splice site comprising the splicing donor and splicing acceptor, and PCDH15 second portion mRNA. As part of the RNA splicing mechanism, the spliceosome of the cell can splice out the splice site and stitches the PCDH15 first portion mRNA and PCDH15 second portion mRNA together to form a complete mRNA encoding a full-length PCDH15.

In other aspects, the dual-AAV vector system forms a full-length PCDH15 coding sequence in the target cell by homologous recombination and splicing. In other aspects, the present disclosure provides a second dual-AAV vector system including two isolated nucleic acids (e.g., a second 5' isolated nucleic acid and a second 3' isolated nucleic acid) in a way that the two isolated nucleic acids form a full length PCDH15 mRNA in a target cell by homologous recombination and splicing. Homologous recombination, as used herein, refers to a type of genetic recombination in which nucleotide sequences are exchanged between two similar or identical molecules of double-stranded or single-stranded nucleic acids (e.g., DNA or RNA). In some embodiments, the second 5' isolated nucleic acid further comprises a nucleotide sequence encoding a splice donor and a first recombinogenic sequence 3' to the nucleotide sequence encoding the first portion of PCDH15. In addition, the second 3' isolated nucleic acid further comprises a second recombinogenic sequence, and a nucleotide sequence encoding a splice acceptor 5' to the nucleotide sequence encoding the second portion of PCDH15. Once the second 5' isolated nucleic acid and the second 3' isolated nucleic acid are delivered to a target cell (e.g., by rAAVs), the first recombinogenic sequence and the second recombinogenic sequence undergo homologous recombination such that the second 5' isolated nucleic acid and the second 3' isolated nucleic acid are combined into one single nucleic acid molecule (e.g., a single DNA molecule), which can be transcribed into pre-mRNA. In some embodiments, the first recombinogenic sequence and the second recombinogenic sequence are the same. After transcription, the pre-mRNA comprises the PCDH15 first portion mRNA, splicing site comprises recombinogenic sequence flanked by the splicing donor. The recombinogenic sequence, the splicing acceptor, and PCDH15 second portion mRNA. As part of the RNA splicing mechanism, the spliceosome in the cell will then splice out the splicing site and stitch the PCDH15 first portion mRNA and PCDH15 second portion mRNA to form a complete mRNA encoding a full-length PCDH15.

In some embodiments, a 5' isolated nucleic acid (e.g., the first 5' isolated nucleic acid or the second 5' isolated nucleic acid), as used herein, refers to an isolated nucleic acid comprising a transgene, wherein the transgene comprises a nucleotide sequence encoding a first portion (e.g., N-terminal portion) of a protein (e.g., full-length PCDH15 protein. In some embodiments, the transgene of the 5' isolated nucleic acid further comprises a promoter operably linked to a nucleotide sequence encoding a first portion of a gene product (e.g., PCDH15 protein).

In some embodiments, a 3' isolated nucleic acid (e.g., the first 3' isolated nucleic acid or the second 3' isolated nucleic acid), as used herein, refers to an isolated nucleic acid comprising a transgene, wherein the transgene comprises a nucleotide sequence encoding a second portion (e.g., C-terminal portion) of a protein (e.g., full-length PCDH15 protein.

In some embodiments, the PDCH15 is a human PCDH15. Human PCDH15 full-length amino acid sequences are set forth in SEQ ID NOs: 1-3. In some embodiments, the full-length PCDH15 expressed by the PCDH15 expression system is the CD1 splice form of PCDH15. In some embodiments, the PCDH15 expressed by the PCDH15 expression system is at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 1. In some embodiments, the full-length PCDH15 expressed by the PCDH15 expression system is the CD2 splice form of PCDH15. In some embodiments, the PCDH15 expressed by the PCDH15 expression system is at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 2. In some embodiments, the full-length PCDH15 expressed by the PCDH15 expression system is the CD3 splice form of PCDH15. In some embodiments, the PCDH15 expressed by the PCDH15 expression system is at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 3.

In some embodiments, the 5' isolated nucleic acid (e.g., the first 5' isolated nucleic acid or the second 5' isolated nucleic acid) comprises a nucleotide sequence encoding a first portion of PCDH15. In some embodiments, the 3' isolated nucleic acid (e.g., the first 3' isolated nucleic acid or the second 3' isolated nucleic acid) comprises a nucleotide sequence encoding a first portion of PCDH15. The PCDH15 gene includes 33 exons. In some embodiment, the split site of the PCDH15 coding sequence between the 5' isolated nucleic acid and the 3' isolated nucleic acid can occur anywhere at the joining site between two consecutive exons of the full-length PCDH15 coding sequence (e.g., between exons 1 and 2, between exons 2 and 3, between exons 3 and 4, between exons 4 and 5, between exons 5 and 6, between exons 6 and 7, between exons 7 and 8, between exons 8 and 9, between exons 9 and 10, between exons 10 and 11, between exons 11 and 12, between exons 12 and 13, between exons 13 and 14, between exons 14 and 15, between exons 15 and 16, between exons 16 and 17, between exons 17 and 18, between exons 18 and 19, between exons 19 and 20, between exons 20 and 21, between exons 21 and 22, between exons 22 and 23, between exons 23 and 24, between exons 24 and 25, between exons 25 and 26, between exons 26 and 27, between exons 27 and 28, between exons 28 and 29, between exons 30 and 31, between exons 31 and 32, or between exons 32 and 33). In some embodiments, the split site of the PCDH15 coding sequence between the 5' isolated nucleic acid and the 3' isolated nucleic acid can occur anywhere between two consecutive codons of the full-length PCDH15 coding sequence (e.g., any two consecutive codons between codons 500 and 600, any two consecutive codons between codons 600 and 700, any two consecutive codons between codons 700 and 800, any two consecutive codons between codons 800 and 900, any two consecutive codons between codons 900 and 1000, any two consecutive codons between codons 1000 and 1100, any two consecutive codons between codons 1100 and 1200, any two consecutive codons between codons 1200 and 1300, any two consecutive codons between codons 1300 and 1400, any two consecutive codons between codons 1400 and 1500, etc.). In some embodiments, the split site of the PCDH15 coding sequence between the 5' isolated nucleic acid and the 3' isolated nucleic acid occurs between codons 1168 and 1169, or any two consecutive codons 50 codons upstream or downstream of codon 1168, or any two consecutive codons 40 codons upstream or downstream of codon 1168, or any two consecutive codons 30 codons upstream or downstream of codon 1168, or any two consecutive codons 25 codons upstream or downstream of codon 1168, or any two consecutive codons 20 codons upstream or downstream of codon 1168, or any two consecutive codons 15 codons upstream or downstream of codon 1168, or any two consecutive codons 10 codons upstream or downstream of codon 1168, or any two consecutive codons 5 codons upstream or downstream of codon 1168, or any two consecutive codons 4 codons upstream or downstream of codon 1168, or any two consecutive codons 3 codons upstream or downstream of codon 1168, or any two consecutive codons 2 codons upstream or downstream of codon 1168, or any two consecutive codons 50 codons upstream or downstream of codon 1168. In some embodiments, and the split site of the PCDH15 coding sequence between the 5' isolated nucleic acid and the 3' isolated nucleic acid occurs between codons 1161 and 1162, or any two consecutive codons 50 codons upstream or downstream of codon 1161, or any two consecutive codons 40 codons upstream or downstream of codon 1161, or any two consecutive codons 30 codons upstream or downstream of codon 1161, or any two consecutive codons 25 codons upstream or downstream of codon 1161, or any two consecutive codons 20 codons upstream or downstream of codon 1161, or any two consecutive codons 15 codons upstream or downstream of codon 1161, or any two consecutive codons 10 codons upstream or downstream of codon 1161, or any two consecutive codons 5 codons upstream or downstream of codon 1161, or any two consecutive codons 4 codons upstream or downstream of codon 1161, or any two consecutive codons 3 codons upstream or downstream of codon 1161, or any two consecutive codons 2 codons upstream or downstream of codon 1161, or any two consecutive codons 50 codons upstream or downstream of codon 1161. In some embodiments, the split site of the PCDH15 coding sequence between the 5' isolated nucleic acid and the 3' isolated nucleic acid occurs between codons 1156 and 1157, or any two consecutive codons 50 codons upstream or downstream of codon 1156, or any two consecutive codons 40 codons upstream or downstream of codon 1156, or any two consecutive codons 30 codons upstream or downstream of codon 1156, or any two consecutive codons 25 codons upstream or downstream of codon 1156, or any two consecutive codons 20 codons upstream or downstream of codon 1156, or any two consecutive codons 15 codons upstream or downstream of codon 1156, or any two consecutive codons 10 codons upstream or downstream of codon 1156, or any two consecutive codons 5 codons upstream or downstream of codon 1156, or any two consecutive codons 4 codons upstream or downstream of codon 1156, or any two consecutive codons 3 codons upstream or downstream of codon 1156, or any two consecutive codons 2 codons upstream or downstream of codon 1156, or any two consecutive codons 50 codons upstream or downstream of codon 1156.

In some embodiments, the nucleotide sequence encoding the first portion of PCDH15 encodes the N-terminal portion of PCDH15 protein. In some embodiments, the nucleotide sequence encoding the first portion of PCDH15 comprises a sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 4. An exemplary nucleotide sequence encoding the first portion of PCDH15 is set forth in SEQ ID NO: 4.

```
ATGTTTCGACAGTTTTATCTCTGGACATGTTTAGCTTCAGGGATCATCCTGGGCTCTCTCTT
TGAAATCTGCTTGGGCCAGTATGATGATGACTGGCAATATGAGGATTGCAAACTAGCTAGGG
GAGGACCACCAGCTACCATAGTTGCTATTGATGAAGAAAGTCGGAATGGTACAATTCTGGTG
GACAACATGCTGATCAAAGGGACTGCTGGAGGACCAGACCCCACCATAGAACTTTCTTTAAA
GGATAATGTGGATTACTGGGTGTTGATGGATCCTGTTAAGCAAATGCTTTTCCTGAACAGCA
CCGGAAGAGTTCTGGATAGAGATCCACCGATGAACATACACTCCATTGTGGTGCAGGTCCAG
TGCATCAACAAAAAAGTGGGCACTATTATCTACCATGAAGTGCGAATAGTGGTGAGAGACAG
GAATGACAACTCACCCACTTTCAAGCATGAAAGCTACTATGCCACAGTGAATGAGCTCACTC
CAGTTGGTACCACAATATTCACAGGATTTTCAGGAGACAATGGAGCTACAGATATAGATGAT
GGACCAAATGGACAGATAGAGTATGTTATTCAGTATAATCCAGATGATCCGACATCCAATGA
CACCTTTGAAATTCCCCTAATGTTGACTGGAAATATAGTGTTAAGGAAGAGGCTCAACTATG
AAGATAAGACTCGCTACTTTGTCATAATCCAAGCTAATGACCGTGCCCAAAATCTGAATGAG
AGGCGAACCACCACCACCACTCTCACAGTGGATGTTCTGGATGGAGATGACTTGGGTCCAAT
GTTTCTTCCTTGTGTCCTTGTGCCAAACACTCGTGATTGCCGTCCACTCACTTATCAAGCTG
CCATACCTGAGTTGAGAACTCCGGAAGAACTGAACCCCATTATTGTTACGCCACCAATCCAA
GCCATTGATCAGGACCGGAATATTCAACCGCCATCAGATAGGCCAGGAATCCTCTATTCCAT
CCTTGTTGGGACTCCTGAGGATTACCCACGATTTTTCCATATGCATCCTAGGACAGCAGAAC
TTAGTCTCCTGGAGCCAGTAAACAGAGACTTTCACCAGAAATTTGATTTGGTTATTAAGGCT
GAACAAGACAATGGTCATCCTCTTCCTGCCTTTGCCGGTCTACACATTGAAATACTGGATGA
AAACAATCAAAGTCCATATTTTACAATGCCCAGTTATCAAGGCTATATCCTGGAATCTGCCC
CAGTGGGAGCAACCATTTCGGACAGTCTCAATTTGACTTCACCTTTAAGAATAGTAGCTCTG
GACAAGGACATAGAAGATGTTCCACCCAGTGGAGTTCCTACAAAAGACCCAGAGCTTCACCT
TTTTCTGAATGACTACACCTCAGTCTTCACCGTCACACAGACTGGTATTACTCGCTACCTCA
CCTTACTTCAACCAGTGGACAGGGAAGAACAGCAAACTTACACCTTTTCGATAACAGCATTT
GATGGTGTACAAGAAAGTGAGCCAGTCATCGTCAATATTCAAGTGATGGATGCAAATGATAA
CACGCCAACCTTCCCTGAAATATCCTATGATGTGTATGTTTATACAGACATGAGACCTGGGG
ACAGTGTCATACAGCTCACTGCAGTCGACGCAGACGAAGGGTCAAATGGGGAGATCACATAT
GAAATCCTTGTTGGGGCTCAGGGAGACTTCATCATCAATAAAACAACAGGGCTTATCACCAT
CGCTCCAGGGGTGGAAATGATAGTCGGGCGGACTTACGCACTCACGGTCCAAGCAGCGGATA
ATGCTCCTCCTGCAGAGCGAAGGAACTCCATCTGCACTGTGTATATTGAAGTGCTTCCACCA
AATAATCAAAGCCCTCCTCGCTTCCCACAGCTGATGTATAGCCTTGAAATTAGTGAAGCCAT
GAGGGTTGGTGCTGTTTTATTAAATCTACAGGCAACTGATCGAGAGGGAGACTCAATAACAT
ATGCCATTGAGAATGGAGATCCTCAGAGAGTTTTTAATCTTTCAGAAACCACGGGGATTCTA
ACCTTAGGGAAAGCACTGGACAGGGAAAGCACTGATCGCTACATTCTGATCATCACAGCTTC
AGATGGCAGGCCAGATGGGACCTCAACTGCCACAGTAAACATAGTGGTGACAGATGTCAATG
ACAATGCTCCAGTGTTTGATCCTTATCTGCCAAGAAATTTATCTGTGGTGGAAGAAGAAGCC
AATGCCTTTGTGGGTCAAGTAAAAGCAACAGACCCTGATGCTGGAATAAATGGTCAAGTGCA
CTACAGTTTGGGTAACTTTAATAATCTTTTTCGTATCACATCCAATGGGAGCATTTACACAG
```

-continued

```
CAGTGAAGCTTAACAGAGAAGTCAGGGACTACTATGAACTTGTTGTTGTGGCAACAGATGGA

GCAGTACACCCTCGTCATTCAACTCTAACCTTGGCCATCAAGGTTTTGGACATTGATGATAA

CAGTCCTGTGTTCACCAATTCAACATACACTGTCCTTGTTGAAGAGAATTTGCCAGCTGGGA

CTACCATCCTTCAAATAGAGGCCAAAGATGTCGACCTTGGAGCAAATGTGTCTTACCGGATA

AGAAGCCCAGAAGTGAAGCACTTTTTTGCACTACATCCATTTACAGGAGAACTATCGCTTTT

AAGGAGTTTAGATTATGAGGCATTTCCAGACCAAGAAGCAAGTATCACTTTTCTGGTAGAGG

CCTTTGATATTTATGGAACAATGCCACCTGGTATTGCTACTGTCACAGTGATTGTAAAGGAT

ATGAATGATTATCCTCCTGTCTTTAGTAAACGAATATACAAAGGGATGGTGGCTCCGGATGC

AGTCAAGGGTACACCTATCACAACAGTTTATGCTGAAGATGCAGACCCTCCTGGATTACCTG

CAAGTCGTGTGAGGTATAGAGTAGATGATGTACAGTTTCCTTACCCTGCCAGTATTTTTGAA

GTGGAAGAAGATTCCTGGAAGAGTAATAACACGAGTCAATCTTAATGAAGAACCTACAACAAT

TTTTAAGTTGGTGGTGGTTGCTTTTGATGATGGGGAGCCTGTGATGTCCAGCAGTGCCACAG

TGAAGATTCTTGTCTTACATCCTGGTGAGATCCCACGCTTCACACAGGAGGAATATAGACCT

CCTCCAGTAAGTGAACTTGCCACCAAAGGGACCATGGTTGGTGTAATTTCTGCTGCTGCCAT

TAATCAAAGTATTGTGTACTCCATTGTTTCAGGAAATGAAGAAGATACATTTGGAATTAATA

ACATCACAGGTGTTATCTATGTGAATGGACCTCTGGATTATGAGACCAGGACAAGCTATGTA

CTTCGAGTCCAAGCTGATTCCCTGGAAGTGGTCCTTGCCAATCTCCGAGTTCCTTCAAAAAG

CAATACAGCTAAAGTATACATTGAGATTCAGGATGAAAATAATCATCCCCCAGTGTTTCAGA

AAAAATTCTACATCGGAGGTGTATCTGAAGAT
```

In some embodiments, the 5' isolated nucleic acid (e.g., the first 5' isolated nucleic acid or the second 5' isolated nucleic acid) comprises a promoter operably linked to a nucleic acid sequence encoding the first portion of PCDH15.

A "promoter" refers to a DNA sequence recognized by the synthetic machinery of the cell, or introduced synthetic machinery, required to initiate the specific transcription of a gene. The phrases "operatively positioned," "under control," or "under transcriptional control" means that the promoter is in the correct location and orientation in relation to the nucleic acid to control RNA polymerase initiation and transcription of the gene.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence, and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins being translated in frame.

In some embodiments, the promoter is a constitutive promoter. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., *Cell,* 41:521-530 (1985)), the SV40 promoter, the dihydrofolate reductase promoter, the β-actin promoter, the phosphoglycerol kinase (PGK) promoter, and the EF1-α promoter (Invitrogen). In some embodiments, the promoter is hybrid cytomegalovirus (CMV) immediate-early/Chicken beta-actin promoter (CAG promoter). In some embodiments, a promoter is a chicken beta-actin (CBA) promoter. In some embodiments, the promoter is a minimal promoter. A minimal promoter is a part of a promoter located between ~35 to +35 region with respect to the transcription start site. It has one or more of 3 conservative sequences, i.e., Tata box, initiator region, binding site for RNA polymerase, and downstream promoter element. Exemplary minimal promoters can be less than 400, 400, 200, 195, 190, 185, 180, or less nucleotides in length. In some examples, the minimal promoter is a minimal CMV promoter (e.g., CMV584 bp promoter). In some embodiments, the minimal promoter is a JeT promoter. In some embodiments, the minimal promoter is a human EF1-α core promoter. In some embodiments, the promoter comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 8 or SEQ ID NO: 9.

An exemplary mini-CMV promoter nucleotide sequence is set forth in SEQ ID NO: 8:

```
GACATTGATTATTGACTAGTTATTAATAGTAATCAATTACGGGGTCATTAGTTCATAGCCCA
TATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCC
ATTGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTATGC
CCAGTACATGACCTTATGGGACTTTCCTACTTGGCAGTACATCTACGTATTAGTCATCGCTA
TTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACG
GGACTTTCCAAAATGTCGTAACAACTCCGCCCCATTGACGCAAATGGGCGGTAGGCGTGTAC
GGTGGGAGGTCTATATAAGCAGAGCTCTCTGGCTAACT
```

An exemplary human EF1-ca promoter sequence is set forth in SEQ ID NO: 9:

```
GGATCTGCGATCGCTCCGGTGCCCGTCAGTGGGCAGAGCGCACATCGCCCACAGTCCCCGAG
AAGTTGGGGGGAGGGGTCGGCAATTGAACGGGTGCCTAGAGAAGGTGGCGCGGGGTAAACTG
GGAAAGTGATGTCGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGAACACAG
```

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., *Proc. Natl. Acad. Sci. USA,* 93:3346-3351 (1996)), the tetracycline-repressible system (Gossen et al., *Proc. Natl. Acad. Sci. USA,* 89:5547-5551 (1992)), the tetracycline-inducible system (Gossen et al., *Science,* 268:1766-1769 (1995), see also Harvey et al., *Curr. Opin. Chem. Biol.,* 2:512-518 (1998)), the RU486-inducible system (Wang et al., *Nat. Biotech.,* 15:239-243 (1997) and Wang et al., *Gene Ther.,* 4:432-441 (1997)) and the rapamycin-inducible system (Magari et al., *J. Clin. Invest.,* 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene is used. The native promoter may be preferred when native expression of the transgene is desired. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites, or Kozak consensus sequences, may also be used to mimic the native expression. In some embodiments, the 5' isolated nucleic acid (e.g., the first 5' isolated nucleic acid or the second 5' isolated nucleic acid) comprises a Kozak sequence (GCCACC). In some embodiments, the promoter is a native promoter. In some examples, the promoter can drive the transgene expression (e.g., mini-PCDH15) in the cells of the eye (e.g., rods, cones, horizontal cells, bipolar cells, and muller glias, etc.) (Angueyra et al., Leveraging Zebrafish to Study Retinal Degeneration, *Front Cell Dev Biol.* 2018; 6: 110). Non-limiting exemplary native promoters can be a Methyl-CpG Binding Protein 2 (MeCP2) promoter, a Ubiquitin-C (UbiC) promoter, a Bestrophin 1 (Best1) (retina native) promoter, a human red opsin (RedO) promoter, a human rhodopsin kinase (RK) promoter, a mouse cone arrestin (CAR) promoter, a human rhodopsin (Rho) promoter, a UV opsin-specific 1 (opn1sw1) promoter, a UV opsin-specific 2 (opn1sw2) promoter, an Opsin 1, Medium Wave Sensitive 2 (opn1mw2) promoter, an opsin 1, long-wave-sensitive 1 (opn1lw1) promoter, a blue cone specific promoter (sws2), an L-opsin (opn1lw1-cxxc1) promoter, a thyroid hormone receptor β (thrb) promoter, an LIM Homeobox 1a (lhx1a) promoter, a connexin 55.5 (cx55.5) promoter, a metabotropic glutamate receptor 6b (grm6b), a glial fibrillar acidic protein (gfap) promoter, a cone transducin alpha subunit (gnat2) promoter, a connexin 52.7 (cx52.7) promoter, a connexin 52.9 (cx52.9) promoter, a heat shock cognate 70-kd protein, -like (hsp70l) promoter, a yeast transcription activator protein-(GAL4-VP16) promoter, a upstream activation sequence (UAS), a visual system homeobox 1 (vsx1) promoter, or a rhodopsin (zop) promoter. In some embodiments, the promoter is a tissue specific promoter. In some embodiments, the promoter is a short photoreceptor-specific promoter. In some embodiments, the short photoreceptor-specific promoter is ProA6. In some embodiments, the promoter comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 10. An exemplary nucleotide sequence for the ProA6 promoter is set forth in SEQ ID NO: 10:

```
CTAGCACAGCACTAGGCTAAAGCGTACTGAGCCCT
TGTCTTCCGTGGGAGCTGCAGAGTGGGATGCATGC
GTTGTGAGCTGAGGCTCAAGCTGCGCTGGCAGAAG
AGCAGGGGTTGCCTTGTCAGACTCCAGGGTCTCTT
TCTCTCTGAGCCTGGGAAAGTGCCACTTTATTGGA
TCTATAAAGCCGGGGGGGGGGGGGGGGAGGAATCT
CAAGGTGAAGAGGAAGTTCACAGACCCCTCTAACG
CCTCTATTAGAACCTTCCAGCTATTCTCTCATACT
TGTACACTGAGCTGGCACACAGTATAGGCAAGTTC
TATTCGCATCACCCCTCTAGTTCCTGTCTCCCTGG
TTATGCAAGCCTCATATTTAGGTAGATGTGACCTT
AGGAAACCAAAATATCCTTTAAGATCTTACTAACT
GGTTGCCTGTTCAGCTTTTCCACATTGATCCTGTA
GCCCCCTCGAGGAGGTGAAGGAAAAAAATCTCCTC
TTTGTTTCTCTAACTCATTAATGAATTTTAAGGGC
ACTCTGTAAGGTTCCTTTCCCATTCTGGTCTGGTT
CGTACATTCTGAGAAACACACTGTGTTTGTGTTGA
GAGTTGGCTCCCTAGCTACACTGTCTGTCACATTG
ATGCTCTGAGTAGGGACAGGGTTCATCTAGGAAAT
ATATTTTCACTCACACTCTGTATCTTTTCCTAGTT
TGGCATATTCTAGTCTGCATTTGGCTCTCTGTTTA
AATATAAAAGAAAACTAAAACACACCCTTCAGACG
CCTATGTCTGAAAAATCTGGCATTTCCGTGGGTTT
TTCTTTAAGGAGGCCTTCATTTGTAACCAACACCA
TGCTCTCCTTAAGGAAATCAATCTCAATGCCCTAT
TATCCTTCCCTTTTCTTTCCTCCCAGTTTGAGGCT
GCAGTTGCCTTTTTTTTTCTTATCCCCTGCTGAAC
CTGAAAAACCCTCTCTTTTCTACAGTTTTCTGTTC
CCAGGCCCCGCTGACTTCCTTTAGAGCATGGGGGG
GGGGGGGATCAGGATTGTGATGTGTGAACTGGGAG
GATCTTGACCTACTCCGCTAACCCAGTGGCCTGAG
CAAATCACAAGGAGGATTGGAGCCATCTGCCCAGC
CCCTCCCCCACGGCAGCCTGCTGGAAAGAGACAAG
TTAGTCATTCAAATGATTGGCTTTTTGCCCGCTTC
TTCTCTAAATAAGAAGGCAGCAGCTTCTGCTGAGG
T
```

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is an eye-specific promoter. Examples of eye-specific promoters include, but are not limited to, a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, and an opsin promoter (e.g., a red opsin promoter, a blue opsin promoter, etc.). In some embodiments, the tissue-specific promoter is an inner ear cell-specific promoter. Examples of inner ear cell-specific promoters include, but are not limited to, the Myosin 7 promoter, Myosin 15 promoter, and TMC1 promoter.

In some embodiments, the 3' isolated nucleic acid (e.g., the first 3' isolated nucleic acid or the second 3' isolated nucleic acid) comprises a nucleotide sequence encoding a second portion of PCDH15. In some embodiments, the nucleotide sequence encoding the second portion of PCDH15 encodes the C-terminal portion of PCDH15 protein. Accordingly, in some embodiments, the nucleotide sequence encoding the second portion of PCDH15 encodes the CD1, CD2, or CD3 splice form of PCDH15.

In some embodiments, the nucleotide sequence encoding the second portion of PCDH15 comprises a sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 5. An exemplary nucleotide sequence encoding the second portion of PCDH15 in CD1 splice form is set forth in SEQ ID NO: 5.

```
GCAAGAATGTTTACTTCTGTACTCAGAGTGAAGGC
TACTGATAAAGATACTGGCAATTATAGTGTCATGG
CCTACAGACTCATAATACCACCAATTAAAGAGGGA
AAAGAAGGATTTGTAGTGGAAACATATACAGGGCT
TATCAAAACTGCTATGCTCTTCCATAATATGAGGA
GATCCTACTTCAAGTTTCAAGTTATTGCAACTGAC
GACTATGGGAAGGGACTGAGCGGCAAAGCCGATGT
ACTCGTCTCCGTGGTCAATCAGCTGGATATGCAAG
TCATTGTTTCCAATGTGCCTCCTACTCTAGTGGAA
AAAAAGATAGAAGATCTTACAGAGATCTTGGATCG
CTATGTTCAGGAACAAATTCCTGGTGCCAAGGTCG
TAGTGGAGTCCATTGGAGCTCGCCGGCATGGAGAT
GCCTTTTCCCTAGAAGATTACACCAAATGTGACTT
GACTGTCTATGCAATTGACCCCCAAACCAACAGAG
CCATCGATAGAAATGAGCTTTTTAAATTTTTGGAT
GGCAAACTACTTGATATCAATAAAGACTTTCAGCC
GTATTATGGGGAAGGAGGACGCATTCTGGAGATCC
GGACTCCAGAGGCAGTGACCAGCATTAAAAAGAGA
GGAGAAAGTCTAGGATACACAGAAGGGGCCTTGTT
GGCTCTGGCCTTCATCATCATCCTCTGCTGCATTC
CTGCCATCTTGGTGGTTTTGGTCAGCTACAGACAG
```

-continued

TTTAAAGTACGTCAAGCTGAGTGTACAAAGACTGC
ACGAATTCAGGCCGCATTACCCGCGGCTAAACCAG
CAGTGCCGGCTCCTGCACCAGTGGCAGCGCCCCCG
CCGCCGCCGCCGCCTCCGCCAGGTGCGCATCTCTA
TGAAGAACTTGGAGACAGCTCAATGCATAATCTTT
TCCTTCTCTACCATTTTCAACAAAGCAGGGGAAAT
AACTCAGTCTCAGAAGACAGGAAACATCAACAAGT
TGTGATGCCCTTTTCTTCCAATACTATTGAGGCTC
ACAAGTCAGCTCATGTAGACGGATCACTTAAGAGC
AACAAACTGAAGTCTGCAAGAAAATTCACATTTCT
ATCTGATGAGGATGACTTAAGTGCCCATAATCCCC
TTTATAAGGAAAACATAAGTCAAGTATCAACAAAT
TCAGACATTTCACAGAGAACAGATTTTGTAGACCC
ATTTTCACCCAAAATACAAGCCAAGAGTAAGTCTC
TGAGGGGCCCAAGAGAAAAGATTCAGAGGCTGTGG
AGTCAGTCAGTCAGCTTACCCAGGAGGCTGATGAG
GAAAGTTCCAAATAGACCAGAGATCATAGATCTGC
AGCAGTGGCAAGGCACCAGGCAGAAAGCTGAAAAT
GAAAACACTGGAATCTGTACAAACAAAAGAGGTAG
CAGCAATCCATTGCTTACAACTGAAGAGGCAAATT
TGACAGAGAAAGAGGAAATAAGGCAAGGTGAAACA
CTGATGATAGAAGGAACAGAACAGTTGAAATCTCT
CTCTTCAGACTCTTCATTTTGCTTTCCCAGGCCTC
ACTTCTCATTCTCCACTTTGCCAACTGTTTCAAGA
ACTGTGGAACTCAAATCAGAACCTAATGTCATCAG
TTTCTAGGAGAGAGACACCTATTTGTATGTTACCT
ATTGAAACCGAAAGAAATATTTTTGAAAATTTTGC
CCATCCACCAAACATCTCTCCTTCTGCCTGTCCCC
TTCCCCCTCCTCCTCCTATTTCTCCTCCTTCTCCT
CCTCCTGCTCCTGCTCCTCTTGCTCCTCCTCCTGA
CATTTCTCCTTTTTCTCTTTTTTGTCCTCCTCCCT
CTCCTCCTTCTATCCCTCTTCCTCTTCCTCCTCCT
ACATTTTTTCCACTTTCCGTTTCAACGTCTGGTCC
CCCAACACCACCTCTTCTACCTCCATTTCCAACTC
CTCTTCCTCCACCACCTCCTTCTATTCCTTGCCCT
CCACCTCCTTCAGCTTCATTTCTGTCCACAGAGTG
TGTCTGTATAACAGGTGTTAAATGCACGACCAACT
TGATGCCTGCCGAGAAAATTAAGTCCTCTATGACA
CAGCTATCAACAACGACAGTGTGTAAAACAGACCC
TCAGAGAGAACCAAAAGGCATCCTCAGACACGTTA

-continued

AAAACTTAGCAGAACTTGAAAAATCAGTAGCTAAC
CCCTTCAGAAGTAACAAATATGGAAATCACATCTG
AACAAAACAAGGGGAGTTTGAACAATATTGTCGAG
GGAACTGAAAAACAATCTCACAGTCAATCTACTTC
ACTGTAA

In some embodiments, the nucleotide sequence encoding the second portion of PCDH15 comprises a sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 6. An exemplary nucleotide sequence encoding the second portion of PCDH15 in CD2 splice form is set forth in SEQ ID NO: 6.

GCAAGAATGTTTACTTCTGTACTCAGAGTGAAGGC
TACTGATAAAGATACTGGCAATTATAGTGTCATGG
CCTACAGACTCATAATACCACCAATTAAAGAGGGA
AAAGAAGGATTTGTAGTGGAAACATATACAGGGCT
TATCAAAACTGCTATGCTCTTCCATAATATGAGGA
GATCCTACTTCAAGTTTCAAGTTATTGCAACTGAC
GACTATGGGAAGGGACTGAGCGGCAAAGCCGATGT
ACTCGTCTCCGTGGTCAATCAGCTGGATATGCAAG
TCATTGTTTCCAATGTGCCTCCTACTCTAGTGGAA
AAAAAGATAGAAGATCTTACAGAGATCTTGGATCG
CTATGTTCAGGAACAAATTCCTGGTGCCAAGGTCG
TAGTGGAGTCCATTGGAGCTCGCCGGCATGGAGAT
GCCTTTTCCCTAGAAGATTACACCAAATGTGACTT
GACTGTCTATGCAATTGACCCCCAAACCAACAGAG
CCATCGATAGAAATGAGCTTTTTAAATTTTTGGAT
GGCAAACTACTTGATATCAATAAAGACTTTCAGCC
GTATTATGGGGAAGGAGGACGCATTCTGGAGATCC
GGACTCCAGAGGCAGTGACCAGCATTAAAAAGAGA
GGAGAAAGTCTAGGATACACAGAAGGGGCCTTGTT
GGCTCTGGCCTTCATCATCATCCTCTGCTGCATTC
CTGCCATCTTGGTGGTTTTGGTCAGCTACAGACAG
TTTAAAGTACGTCAAGCTGAGTGTACAAAGACTGC
ACGAATTCAGGCCGCATTACCCGCGGCTAAACCAG
CAGTGCCGGCTCCTGCACCAGTGGCAGCGCCCCCG
CCGCCGCCGCCGCCTCCGCCAGGTGCGCATCTCTA
TGAAGAACTTGGAGACAGCTCAATGCATAAGTATG
AAATGCCTCAATATGGGAGTCGCCGTCGATTGTTA
CCACCAGCTGGACAGGAGGAATATGGTGAGGTGGT
TGGTGAAGCTGAGGAAGAATATGAGGAGGAAGAGG

-continued

```
AAGAGCCAAAGAAAATTAAAAAACCAAAGGTTGAA
ATTAGAGAGCCTAGTGAGGAGGAAGAAGTAGTTGT
AACTATCGAAAAACCACCAGCAGCTGAGCCTACAT
ACACAACATGGAAGAGAGCCAGAATATTCCCCATG
ATTTTTAAGAAAGTTAGAGGATTAGCTGATAAAAG
AGGAATCGTTGACCTTGAGGGTGAAGAGTGGCAGA
GACGCCTTGAGGAAGAAGATAAAGATTATTTGAAA
CTCACTCTGGACCAAGAGGAAGCAACAGAAAGCAC
TGTAGAATCAGAGGAGGAATCCTCCAGCGACTATA
CTGAATACAGTGAAGAAGAGTCTGAGTTCAGTGAG
TCTGAGACTACAGAAGAGGAATCTGAGTCAGAGAC
ACCCTCTGAGGAGGAGGAGAGTTCCACCCCTGAAT
CAGAAGAATCGGAATCCACAGAGTCAGAAGGAGAA
AAAGCAAGGAAAAACATTGTGCTTGCAAGAAGAAG
GCCCATGGTTGAGGAGGTCAAGGAAGTCAAGGGTA
GGAAAGAGGAGCCACAAGAAGAACAAAAAGAACCT
AAGATGGAAGAAGAAGAACACTCAGAAGAAGAAGA
AAGTGGACCAGCCCCTGTGGAAGAAAGTACAGACC
CTGAAGCTCAAGATATCCCTGAAGAGGGCAGTGCA
GAATCAGCTTCGGTGGAAGGAGGTGTGGAAAGTGA
GGAGGAATCAGAATCAGGTAGTAGTAGCAGTAGTA
GCGAAAGTCAGTCTGGAGGTCCATGGGGCTATCAG
GTACCAGCGTATGACAGAAGCAAGAATGCAAACCA
AAAGAAGTCGCCAGGAGCAAACTCTGAAGGTTACA
ACACAGCACTTTGA
```

In some embodiments, the nucleotide sequence encoding the second portion of PCDH15 comprises a sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 7. An exemplary nucleotide sequence encoding the second portion of PCDH15 in CD3 splice form is set forth in SEQ ID NO: 7.

```
GCAAGAATGTTTACTTCTGTACTCAGAGTGAAGGC
TACTGATAAAGATACTGGCAATTATAGTGTCATGG
CCTACAGACTCATAATACCACCAATTAAAGAGGGA
AAAGAAGGATTTGTAGTGGAAACATATACAGGGCT
TATCAAAACTGCTATGCTCTTCCATAATATGAGGA
GATCCTACTTCAAGTTTCAAGTTATTGCAACTGAC
GACTATGGGAAGGGACTGAGCGGCAAAGCCGATGT
ACTCGTCTCCGTGGTCAATCAGCTGGATATGCAAG
TCATTGTTTCCAATGTGCCTCCTACTCTAGTGGAA
```

-continued

```
AAAAAGATAGAAGATCTTACAGAGATCTTGGATCG
CTATGTTCAGGAACAAATTCCTGGTGCCAAGGTCG
TAGTGGAGTCCATTGGAGCTCGCCGGCATGGAGAT
GCCTTTTCCCTAGAAGATTACACCAAATGTGACTT
GACTGTCTATGCAATTGACCCCCAAACCAACAGAG
CCATCGATAGAAATGAGCTTTTTAAATTTTTGGAT
GGCAAACTACTTGATATCAATAAAGACTTTCAGCC
GTATTATGGGGAAGGAGGACGCATTCTGGAGATCC
GGACTCCAGAGGCAGTGACCAGCATTAAAAAGAGA
GGAGAAAGTCTAGGATACACAGAAGGGGCCTTGTT
GGCTCTGGCCTTCATCATCATCCTCTGCTGCATTC
CTGCCATCTTGGTGGTTTTGGTCAGCTACAGACAG
TTTAAAGTACGTCAAGCTGAGTGTACAAAGACTGC
ACGAATTCAGGCCGCATTACCCGCGGCTAAACCAG
CAGTGCCGGCTCCTGCACCAGTGGCAGCGCCCCCG
CCGCCGCCGCCGCCTCCGCCAGGTGCGCATCTCTA
TGAAGAACTTGGAGACAGCTCAATGTATGAAATGC
CTCAATATGGGAGTCGCCGTCGATTGTTACCACCA
GCTGGACAGGAGGAATATGGTGAGGTGGTTGGTGA
AGCTGAGGAAGAATATGAGGAGGAAGAGTGGGCAA
GAAAAAGAATGATCAAGTTAGTTGTTGATCGAGAG
TATGAAACCAGCTCAACTGGAGAAGACAGTGCTCC
TGAATGTCAGAGAAACCGTCTTCACCATCCTAGTA
TCCACAGTAATATCAACGGCAATATATATATTGCA
CAGAATGGTTCTGTGGTGAGAACCCGCCGTGCCTG
CCTCACGGACAACTTAAAAGTTGCTTCCCCTGTTC
GACTGGGAGGGCCCTTTAAGAAACTAGACAAGTTG
GCAGTGACACATGAGGAGAATGTACCTCTGAACAC
ATTATCAAAGGGGCCATTTTCTACTGAAAAAATGA
ATGCAAGACCAACTCTGGTTACATTTGCCCCTTGC
CCTGTGGGGACTGACAATACAGCGGTGAAGCCACT
AAGGAACAGGCTGAAAAGCACAGTTGAACAGGAGT
CCATGATTGACAGTAAGAACATCAAGGAGGCTTTG
GAATTTCATAGTGACCACACACAGTCTGATGATGA
AGAGCTTTGGATGGGCCCCTGGAACAACCTCCATA
TACCAATGACAAAACTGTGA
```

In some embodiments, the transgene of the 5' isolated nucleic acid (e.g., the first 5' isolated nucleic acid or the second 5' isolated nucleic acid) further comprises a splice donor of an intron. Introns always have two distinct nucleotides at either end. At the 5' end the DNA nucleotides are GT (GU in the pre-messenger RNA (pre-mRNA)); at the 3' end they are AG. The GT/AG pair form part of the splicing sites. Any known intronic splice donor/splice acceptor pair can be used to form the splice site of the present disclosure, for example, the splice sites described in Burset et al, SpliceDB: database of canonical and non-canonical mammalian splice sites, *Nucleic Acids Res.* 2001 Jan. 1; 29(1): 255-259, the entire contents of which is incorporated herein by reference).

In some embodiments, the nucleotide sequence encoding the splicing donor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 11. An exemplary nucleotide sequence of a splicing donor is set forth in SEQ ID NO: 11.

```
GTAAGTATCAAGGTTACAAGACAGGTTTAAGGAGA
CCAATAGAAACTGGGCTTGTCGAGACAGAGAAGAC
TCTTGCGTTTCT
```

In some embodiments, the transgene of the 3' isolated nucleic acid (e.g., the first 3' isolated nucleic acid or the second 3' isolated nucleic acid) comprises a splice acceptor of an intron. In some embodiments, the splice acceptor is derived from the same intron as the splice acceptor.

In some embodiments, the nucleotide sequence encoding the splicing acceptor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 12. An exemplary nucleotide sequence of a splicing acceptor is set forth in SEQ ID NO: 12:

```
GATAGGCACCTATTGGTCTTACTGACATCCACTTT
GCCTTTCTCTCCACAG
```

In some embodiments, the second 5' isolated nucleic acid and the second 3' isolated nucleic acid further comprises a recombinogenic sequence. Any suitable known recombinogenic sequence can be used in the isolated nucleic acids of the present disclosure. In some embodiments, the recombinogenic sequence is at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 13. An exemplary first and second recombinogenic sequence is set forth in SEQ ID NO: 13.

```
GGGATTTTGCCGATTTCGGCCTATTGGTTAAAAAA
TGAGCTGATTTAACAAAAATTTAACGCGAATTTTA
ACAAAAT
```

In some embodiments, the 5 isolated nucleic acid (e.g., the first 3 isolated nucleic acid or the second 3' isolated nucleic acid) and/or the 3' isolated nucleic acid (e.g., the first 3' isolated nucleic acid or the second 3' isolated nucleic acid) further comprise a nucleotide sequence encoding a detectable protein. The nucleotide sequence encoding the detectable protein can be anywhere (e.g., in the 5' isolated nucleic acid or the 3' isolated nucleic acid). In some embodiments, the nucleotide sequence encoding the detectable protein is placed in the 3' isolated nucleic acid 3' to the nucleotide sequence encoding the second portion of PCDH15. Further, the nucleotide sequence encoding the detectable protein can be positioned in any order (e.g., at the 5' end or the 3' end of the nucleotide sequence encoding the first or the second portion of the PCDH15 protein). In some embodiments, the 3' isolated nucleic acid comprises the nucleotide sequence encoding the detectable protein. In some embodiments, the nucleotide sequence encoding the detectable protein is placed 3' to the nucleotide sequence encoding the second portion of the PCDH15 protein. In some embodiments, a nucleotide sequence encoding an internal ribosome entry site (IRES) is placed between the nucleotide sequence encoding the second portion of PCDH15, and the nucleotide sequence encoding the detectable protein.

In some embodiments, the transgene encodes a detectable molecule, such as a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used as a detectable protein in the sensor circuit of the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes a substrate to produce a detectable signal (e.g., a chemiluminescent signal). Such enzymes include, without limitation, beta-galactosidase (encoded by LacZ), horseradish peroxidase, or luciferase. In some embodiments, the detectable molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used include, without limitation, Spinach and Broccoli (e.g., as described in Paige et al., Science Vol. 333, Issue 6042, pp. 642-646, 2011, incorporated herein by reference). In some embodiments, the detectable protein is a green fluorescence protein. Non-limiting examples of a detectable protein include eGFP, eYFP, eCFP, mKate2, mCherry, mPlum, mGrape2, mRaspberry, mGrape1, mStrawberry, mTangerine, mBanana, and mHoneydew.

In some embodiments, an IRES sequence is used to produce more than one polypeptide from a single gene transcript. An IRES sequence would be used to produce a protein that contains more than one polypeptide chains. Selection of these and other common vector elements are conventional, and many such sequences are known (see, e.g., Sambrook et al., molecular cloning: a laboratory manual. 2nd ed. Cold Spring Harbor, N.Y: Cold Spring Harbor Laboratory; 1989) and references cited therein at, for example, pages 3.18-3.26 and 16.17-16.27 and Ausubel et al., *Current Protocols in Molecular Biology*, John Wiley & Sons, New York, 1989]).

In other embodiments, nucleotide sequence encoding a self-cleavage peptide is placed between the nucleotide sequence encoding the detectable protein and the nucleotide sequence encoding the first or the second portion of the PCDH15 protein. In other embodiments, nucleotide sequence encoding a self-cleavage peptide is placed between the nucleotide sequence encoding the detectable protein and the nucleotide sequence encoding the second portion of the PCDH15 protein. In some embodiments, a Foot and Mouth Disease Virus 2A sequence is included in a polyprotein; this is a small peptide (approximately 18 amino acids in length) that has been shown to mediate the cleavage of polyproteins (Ryan, M D et al., *EMBO,* 1994; 4: 928-933; Mattion, N M et al., *J Virology*, November 1996; p. 8124-8127; Furler, S et al., *Gene Therapy,* 2001; 8: 864-873; and Halpin, C et al., *The Plant Journal,* 1999; 4: 453-459). The cleavage activity of the 2A sequence has previously been demonstrated in artificial systems including plasmids and gene therapy vectors (AAV and retroviruses) (Ryan, M D et al., *EMBO,* 1994; 4: 928-933; Mattion, N M et al., *J Virology*, November 1996; p. 8124-8127; Furler, S. et al., *Gene Therapy,* 2001; 8: 864-873; and Halpin, C et al., *The Plant Journal,* 1999; 4: 453-459; de Felipe, P et al., *Gene Therapy,* 1999; 6: 198-208; de Felipe, P et al., *Human Gene Therapy,* 2000; 11: 1921-1931.; and Klump, H et al., *Gene Therapy,* 2001; 8: 811-817).

In some embodiments, the 3' isolated nucleic acid (e.g., the first 3' isolated nucleic acid or the second 3' isolated nucleic acid) comprises a nucleotide sequence encoding an IRES and an eGFP at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 14. An exemplary nucleotide sequence encoding IRES and eGFP is set forth in SEQ ID NO: 14:

```
CCCCTCTCCCTCCCCCCCCCCTAACGTTACTGGCC
GAAGCCGCTTGGAATAAGGCCGGTGTGCGTTTGTC
TATATGTTATTTTCCACCATATTGCCGTCTTTTGG
CAATGTGAGGGCCCGGAAACCTGGCCCTGTCTTCT
TGACGAGCATTCCTAGGGGTCTTTCCCCTCTCGCC
AAAGGAATGCAAGGTCTGTTGAATGTCGTGAAGGA
AGCAGTTCCTCTGGAAGCCTCTTGAAGACAAACAA
CGTCTGTAGCGACCCTTTGCAGGCAGCGGAACCCC
CCACCTGGCGACAGGTGCCTCTGCGGCCAAAAGCC
ACGTGTATAAGATACACCTGCAAAGGCGGCACAAC
CCCAGTGCCACGTTGTGAGTTGGATAGTTGTGGAA
AGAGTCAAATGGCTCTCCTCAAGCGTATTCAACAA
GGGGCTGAAGGATGCCCAGAAGGTACCCCATTGTA
TGGGATCTGATCTGGGGCCTCGGTGCACATGCTTT
ACATGTGTTTAGTCGAGGTTAAAAAAACGTCTAGG
CCCCCCGAACCACGGGGACGTGGTTTTCCTTTGAA
AAACACGATGATAATATGGCCACAACCATGGTGAG
CAAGGGCGAGGAGCTGTTCACCGGGGTGGTGCCCA
TCCTGGTCGAGCTGGACGGCGACGTAAACGGCCAC
AAGTTCAGCGTGTCCGGCGAGGGCGAGGGCGATGC
CACCTACGGCAAGCTGACCCTGAAGTTCATCTGCA
CCACCGGCAAGCTGCCCGTGCCCTGGCCCACCCTC
GTGACCACCCTGACCTACGGCGTGCAGTGCTTCAG
CCGCTACCCCGACCACATGAAGCAGCACGACTTCT
TCAAGTCCGCCATGCCCGAAGGCTACGTCCAGGAG
CGCACCATCTTCTTCAAGGACGACGGCAACTACAA
```

-continued

```
GACCCGCGCCGAGGTGAAGTTCGAGGGCGACACCC
TGGTGAACCGCATCGAGCTGAAGGGCATCGACTTC
AAGGAGGACGGCAACATCCTGGGGCACAAGCTGGA
GTACAACTACAACAGCCACAACGTCTATATCATGG
CCGACAAGCAGAAGAACGGCATCAAGGTGAACTTC
AAGATCCGCCACAACATCGAGGACGGCAGCGTGCA
GCTCGCCGACCACTACCAGCAGAACACCCCCATCG
GCGACGGCCCCGTGCTGCTGCCCGACAACCACTAC
CTGAGCACCCAGTCCGCCCTGAGCAAAGACCCCAA
CGAGAAGCGCGATCACATGGTCCTGCTGGAGTTCG
TGACCGCCGCCGGGATCACTCTCGGCATGGACGAG
CTGTACAAGTAA
```

For nucleic acids encoding proteins, a polyadenylation sequence generally is inserted following the coding sequences and before the 3' AAV ITR sequence. Any suitable know poly A signal can be used in the isolated nucleic acids described in the present disclosure. In some embodiments, the 3' isolated nucleic acid (e.g., the first 3' isolated nucleic acid or the second 3' isolated nucleic acid) further comprises a poly A sequence at the 3' end of any of the coding sequences described herein.

In some embodiments, the poly A sequence is a SV40 poly A as set forth in SEQ ID NO: 15.

```
GATCCAGACATGATAAGATACATTGATGAGTTTGG
ACAAACCACAACTAGAATGCAGTGAAAAAAATGCT
TTATTTGTGAAATTTGTGATGCTATTGCTTTATTT
GTAACCATTATAAGCTGCAATAAACAAGTTAACAA
CAACAATTGCATTCATTTTATGTTTCAGGTTCAGG
GGGAGGTGTGGGAGGTTTTTTA
```

In some embodiments, the poly A sequence is a BGH poly A sequence as set forth in SEQ ID NO: 16.

```
GTCGACTAGAGCTCGCTGATCAGCCTCGACTGTGC
CTTCTAGTTGCCAGCCATCTGTTGTTTGCCCCTCC
CCCGTGCCTTCCTTGACCCTGGAAGGTGCCACTCC
CACTGTCCTTTCCTAATAAAATGAGGAAATTGCAT
CGCATTGTCTGAGTAGGTGTCATTCTATTCTGGGG
GGTGGGGTGGGGCAGGACAGCAAGGGGGAGGATTG
GGAAGACAATAGCAGGCATGCTGGGGA
```

In some embodiments, the isolated nucleic acid further comprises a nucleotide sequence encoding a protein tag. A protein tag can be placed at either the N-terminus or the C-terminus of the PCDH15 protein. In some embodiments, the tag is at the N terminus of the full-length PCDH15. Any suitable known protein tag can be used in the present disclosure, for example, the ALFA-tag (SRLEEELRRRLTE (SEQ ID NO: 25)), AviTag (GLNDIFEAQKIEWHE (SEQ ID NO: 26)), C-tag (EPEA (SEQ ID NO: 27)), Calmodulin-tag (KRRWKKNFIAVSAANRFKKISSSGAL (SEQ ID NO: 28)), polyglutamate tag (EEEEEE (SEQ ID NO: 29)), polyarginine tag, (from 5 to 9 consecutive R (SEQ ID NO: 30)), E-tag (GAPVPYPDPLEPR (SEQ ID NO: 31)), FLAG-tag (DYKDDDDK (SEQ ID NO: 32)), HA-tag (YPYDVPDYA (SEQ ID NO: 33)), His-tag (5-10 Histidine (SEQ ID NO: 34)), Myc-tag (EQKLISEEDL (SEQ ID NO: 35)), NE-tag (TKENPRSNQEESYDDNES (SEQ ID NO: 36)), RholD4-tag (TETSQVAPA (SEQ ID NO: 37)), S-tag (KETAAAKFERQHMDS (SEQ ID NO: 38)), SBP-tag (MDEKTTGWRGGHVVEGLAGELEQLRAR-LEHHPQGQREP (SEQ ID NO: 39)), Softag (SLAEL-LNAGLGGS (SEQ ID NO: 40)), Softag 3 (TQDPSRVG (SEQ ID NO: 41)), Spot-tag (PDRVRAVSHWSS (SEQ ID NO: 42)), Strep-tag (Strep-tag II: WSHPQFEK (SEQ ID NO: 43)), T7-tag (MASMTGGQQMG (SEQ ID NO: 44)), TC tag (CCPGCC (SEQ ID NO: 45)), Ty tag (EVHTNQDPLD (SEQ ID NO: 46)), V5 tag (GKPIPN-PLLGLDST (SEQ ID NO: 47)), VSV-tag (YTDI-EMNRLGK (SEQ ID NO: 48)), Xpress tag (DLYDDDDK (SEQ ID NO: 49)), Isopeptag (TDKDMTITFTNKKDAE (SEQ ID NO: 50)), SpyTag (AHIVMVDAYKPTK (SEQ ID NO: 51)), SnoopTag (KLGDIEFIKVNK (SEQ ID NO: 52)), Second generation, SnoopTagJr (KLGSIEFIKVNK (SEQ ID NO: 53)), DogTag (DIPATYEFTDGKHYITNEPIPPK (SEQ ID NO: 54)), SdyTag (DPIVMIDNDKPIT (SEQ ID NO: 55)), BCCP (Biotin Carboxyl Carrier Protein), Glutathione-S-transferase-tag, GFP-tag, HaloTag, SNAP-tag, CLIP-tag, HUH-tag, Maltose binding protein-tag, Nus-tag, Thioredoxin-tag, Fc-tag, Carbohydrate Recognition Domain or CRDSAT-tag.

In some embodiments, the tag is expressed at the C-terminus of the full-length PCDH15. In some embodiments, the tag is capable of facilitating the detection of the presence of full-length PCDH15 in a target cell. In some embodiments, the tag is an HA tag, a FLAG-tag or a Spy tag. In some embodiments, the 5' isolated nucleic acid or the 3' isolated nucleic acid comprises a nucleotide sequence encoding an HA tag as set forth in SEQ ID NO: 17: TACCCATACGACGTGCCCGACTACGCC. In some embodiments, the 5' isolated nucleic acid or the 3' nucleic acid comprises a nucleotide sequence encoding a FLAG tag as set forth in SEQ ID NO: 18: GATTACAAA-GACGACGACGATAAA. In some embodiments, the 5' isolated nucleic acid or the 3' nucleic acid comprises a nucleotide sequence encoding an Spy tag as set forth in SEQ ID NO: 19:

GTGCCTACTATCGTGATGGTGGACGCCTACAAGCG

TTACAAG

The 5' and 3' isolated nucleic acids as described herein, may be incorporated into a vector. In addition to the major elements identified above for the recombinant AAV vector, the vector may also include conventional control elements which are operably linked with elements of the transgene in a manner that permits its transcription, translation, and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter, and enhancer sequences; efficient RNA processing signals such as splicing and polyadenylation (polyA) signals; sequences that stabilize cytoplasmic mRNA; sequences that enhance translation efficiency (i.e., Kozak consensus sequence GCCACC); sequences that enhance protein stability; and when desired, sequences that enhance secretion of the encoded product. A number of expression control sequences, including promoters which are native, constitutive, inducible, and/or tissue-specific, are known in the art and may be utilized. In some embodiments, the transgene comprises a Kozak consensus sequence at the 5' end of the nucleic acid sequence encoding the transgene (e.g., the nucleotide sequence encoding the first portion of PCDH15). A rAAV construct useful in the present disclosure may also contain an intron, desirably located between the promoter/enhancer sequence and the coding sequences. In some embodiments, the intron is a chimeric intron. In some embodiments, the intron is SV-40 intron. A rAAV construct useful in the present disclosure may also contain an exon (e.g., (3-actin exon).

As used herein, the term "sequence identity" refers to the percentage of amino acid (or nucleic acid) residues of a candidate sequence that are identical to the amino acid (or nucleic acid) residues of a reference sequence, e.g., any of the sequences disclosed herein, after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alteration of the amino acid sequence or nucleic acid coding sequences can be obtained by deletion, addition, or substitution of residues of the reference sequence. Alignment for purposes of determining percent identity can be achieved in various ways that are within the skill in the art, for instance, using publicly available computer software, such as BLAST, BLAST-2, BLAST-P, BLAST-N, BLAST-X, WU-BLAST-2, ALIGN, ALIGN-2, CLUSTAL, or Megalign (DNASTAR) software. Those skilled in the art can determine appropriate parameters for measuring alignment, including any algorithms needed to achieve maximal alignment over the full length of the sequences being compared. For instance, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100\times(\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In particular, a reference sequence aligned for comparison with a candidate sequence can show that the candidate sequence exhibits from, e.g., 50% to 100% identity across the full length of the candidate sequence or a selected portion of contiguous amino acid (or nucleic acid) residues of the candidate sequence. The length of the candidate sequence aligned for comparison purpose is at least 30%, 40%, 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

In some embodiments, the 5' isolated nucleic acid (e.g., the first 5' isolated nucleic acid or the second 5' isolated nucleic acid) and the 3' isolated nucleic acid (e.g., the first 3' isolated nucleic acid or the second 3' isolated nucleic acid) comprises two adeno-associated virus inverted terminal repeats (ITR) flanking the 5' end and 3' end of the isolated nucleic acids. Generally, ITR sequences are about 145 bp in length. Preferably, substantially the entire sequences encoding the ITRs are used in the molecule, although some degree of minor modification of these sequences is permissible. The ability to modify these ITR sequences is within the skill of one in the art. (See, e.g., texts such as Sambrook et al., *Molecular Cloning. A Laboratory Manual,* 2d ed., Cold Spring Harbor Laboratory, New York (1989); and K. Fisher et al., *J. Virol.,* 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid comprises at least one ITR having a serotype selected from AAV1, AAV2, AAV5, AAV6, AAV6.2, AAV7, AAV8, AAV9, AAV10, and AAV11, and variants thereof. In some embodiments, the ITRs are AAV2 ITRs.

In some embodiments, the isolated nucleic acid further comprises a region (e.g., a second region, a third region, a fourth region, etc.) comprising a second AAV ITR. In embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is an AAV2 ITR.

In some embodiments, the 5' isolated nucleic acid (e.g., the first 5' isolated nucleic acid or the second 5' isolated nucleic acid) and the 3' isolated nucleic acid (e.g., the first 3' isolated nucleic acid or the second 3' isolated nucleic acid) comprises a 5' ITR having the nucleotide sequence as set forth in SEQ ID NO: 20:

```
TTGGCCACTCCCTCTCTGCGCGCTCGCTCGCTCAC

TGAGGCCGGGCGACCAAAGGTCGCCCGACGCCCGG

GCTTTGCCCGGGCGGCCTCAGTGAGCGAGCGAGCG

CGCAGAGAGGGAGTGGCCAACTCCATCACTAGGGG

TTCCTAGAT
```

In some embodiments, the 5' isolated nucleic acid (e.g., the first 5' isolated nucleic acid or the second 5' isolated nucleic acid) and the 3' isolated nucleic acid (e.g., the first 3' isolated nucleic acid or the second 3' isolated nucleic acid) comprises a 3' ITR having the nucleotide sequence as set forth in SEQ ID NO: 21:

```
CCCCTAGTGATGGAGTTGGCCACTCCCTCTCTGCG

CGCTCGCTCGCTCACTGAGGCCGCCCGGGCAAAGC

CCGGGCGTCGGGCGACCTTTGGTCGCCCGGCCTCA

GTGAGCGAGCGAGCGCGCAGAGAGGGAGTGGCCA
```

In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example, as described by McCarthy (2008) *Molecular Therapy* 16(10):1648-1656.

The present disclosure provides a 5' isolated nucleic acid (e.g., the first 5' isolated nucleic acid or the second 5' isolated nucleic acid) and the 3' isolated nucleic acid (e.g., the first 3' isolated nucleic acid or the second 3' isolated nucleic acid) and/or vectors (e.g., AAV vectors) for expressing a transgene (e.g., full-length PCDH15). In addition, the vector can further comprise certain regulatory elements (e.g., enhancers, kozak sequences, Woodchuck Hepatitis Virus (WHP) Posttranscriptional Regulatory Element (WPRE) and poly adenylation sites (e.g., SV40 poly A signa and/or bovine growth hormone polyadenylation (BGH-PolyA) signal)). In some embodiments, the isolated nucleic acids and/or vectors does not comprise a WPRE. In some embodiments, the isolated nucleic acids and/or vectors comprise a WPRE. In some embodiments, the isolated nucleic acids and/or vectors comprise a BGH signal. In some embodiments, the isolated nucleic acids and/or vectors comprise AAV2 ITRs flanking a CMV584 bp promoter operably linked to a transgene (e.g., mini-PCDH15), a BGH poly (A) signal and no WPRE.

Exemplary dual-AAV vectors encoding the first portion of a mouse PCDH15 CD2 isoform and the second portion of a mouse PCDH15 CD2 isoform are set forth in SEQ ID NO: 22 and SEQ ID NO: 23, receptively. It is within the skill of artisans in the art to replace the mouse PCDH15 coding sequences with PCDH15 coding sequences of another species (e.g., first portion of human PCDH15 coding sequences and second portion of human PCDH15 coding sequences described in the present disclosure).

In some embodiments, the rAAV vector encoding the first portion of PCDH15 comprises, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; and (g) a 3' ITR.

In some embodiments, the rAAV vector encoding the first portion of PCDH15 comprises, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; (g) a recombinogenic sequence, and (h) a 3' ITR.

In some embodiments, the rAAV vector encoding the first portion of PCDH15 (e.g., mouse PCDH15 CD2 isoform) comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to the nucleotide sequence as set forth in SEQ ID NO: 22 (first portion of the PCDH15 coding sequences underlined, splice donor sequence in bold face):

TTGGCCACTCCCTCTCTGCGCGCTCGCTCGCTCACTGAGGCCGGGCGACCAAAGGTCGCCCG

ACGCCCGGGCTTTGCCCGGGCGGCCTCAGTGAGCGAGCGAGCGCGCAGAGAGGGAGTGGCCA

ACTCCATCACTAGGGGTTCCTAGATCTGAATTCGGTACCGACATTGATTATTGACTAGTTAT

TAATAGTAATCAATTACGGGGTCATTAGTTCATAGCCCATATATGGAGTTCCGCGTTACATA

ACTTACGGTAAATGGCCCGCCTGGCTGACCGCCCAACGACCCCCGCCCATTGACGTCAATAA

TGACGTATGTTCCCATAGTAACGCCAATAGGGACTTTCCATTGACGTCAATGGGTGGAGTAT

TTACGGTAAACTGCCCACTTGGCAGTACATCAAGTGTATCATATGCCAAGTACGCCCCCTAT

TGACGTCAATGACGGTAAATGGCCCGCCTGGCATTATGCCCAGTACATGACCTTATGGGACT

TTCCTACTTGGCAGTACATCTACGTATTAGTCATCGCTATTACCATGGTGATGCGGTTTTGG

CAGTACATCAATGGGCGTGGATAGCGGTTTGACTCACGGGGATTTCCAAGTCTCCACCCCAT

TGACGTCAATGGGAGTTTGTTTTGGCACCAAAATCAACGGGACTTTCCAAAATGTCGTAACA

ACTCCGCCCCATTGACGCAAATGGGCGGTAGGCGTGTACGGTGGGAGGTCTATATAAGCAGA

GCTCTCTGGCTAACTACCGGTGCCACCATGTTCCTACAGTTTGCTGTCTGGAAGTGTTTACC

CCATGGGATCCTCATTGCCTCTCTCTTGGTAGTCAGCTGGGGCCAGTATGACGATGACTGGC

AATACGAGGATTGCAAACTAGCTAGGGGAGGACCACCAGCTACTATCGTGGCCATTGATGAA

GAGAGTCGAAACGGTACAATTCTGGTGGATAACATGTTGATTAAGGGGACTGCCGGAGGACC

AGACCCCACCATAGAGCTCTCTTTAAAGGACAACGTGGACTACTGGGTGTTGCTGGACCCCG

TTAAACAGATGCTTTTCCTGAACAGTACCGGAAGAGTTCTGGATAGAGACCCACCAATGAAC

ATACACTCCATTGTGGTGCAAGTCCAGTGTGTCAACAAGAAGGTTGGCACAGTTATCTATCA

TGAAGTACGCATCGTGGTGCGAGATCGGAATGACAACTCCCCCACATTCAAGCATGAAAGCT

ACTATGCCACCGTGAATGAGCTCACTCCAGTTGGCACCACGATATTCACGGGGTTCTCGGGA

GACAATGGAGCTACAGACATAGACGATGGCCCTAATGGACAGATAGAATACGTGATTCAGTA

CAACCCAGAAGATCCGACATCCAACGACACCTTTGAAATTCCACTCATGCTGACTGGCAACG

TGGTACTGAGGAAAAGACTCAACTATGAGGATAAGACTCGCTACTATGTCATCATCCAAGCA

AATGACCGTGCACAAAATCTGAATGAGAGGCGAACAACCACCACCACCCTCACAGTAGATGT

TCTAGATGGAGATGACCTGGGACCTATGTTTCTGCCTTGTGTTCTTGTGCCAAACACACGTG

ACTGTCGTCCACTCACCTACCAAGCTGCCATTCCTGAACTGAGGACTCCGGAAGAACTGAAC

CCTATTTTGGTGACACCACCTATCCAAGCCATTGATCAGGACCGAAACATCCAACCACCATC

TGATCGACCTGGCATCCTCTACTCCATCCTTGTCGGCACCCCTGAGGATTACCCCCGCTTCT

TCCATATGCATCCCAGGACTGCAGAACTCACTCTCCTGGAGCCAGTAAACAGAGACTTCCAT

CAAAAATTTGATTTGGTTATTAAGGCTGAGCAGGACAATGGCCACCCACTTCCTGCCTTTGC

TAGTCTGCACATCGAAATACTAGACGAAAACAATCAGAGTCCATACTTCACAATGCCCAGCT

ACCACTCCTCTGAGAATTGTAGCTCTGGACAAAGACATAGAAGACGTGCCACCTGGTGGAGT

TCCTACAAAAGATCCAGAGCTCCACCTCTTCCTGAATGACTACACCTCGGTCTTCACTGTGA

CACCCACTGGTATCACCCGCTACCTCACCCTGCTTCAACCTGTGGACAGGGAGGAACAGCAA

ACCTACACCTTTCTGATAACAGCGTTTGATGGCGTGCAAGAAAGTGAGCCAGTCGTGGTCAA

TATCCGAGTGATGGATGCAAATGATAACACGCCCACCTTCCCTGAAATCTCCTATGATGTCT

ATGTTTACACAGACATGAGTCCTGGGGACAGCGTCATTCAGCTGACAGCGGTAGATGCTGAT

GAAGGCTCTAATGGGGAGATCTCCTATGAAATACTGGTGGGGGGCAAGGGAGACTTCGTGAT

CAACAAGACCACAGGGCTGGTGAGCATTGCACCAGGCGTGGAGCTGATCGTGGGACAGACGT

ATGCGCTCACAGTGCAGGCTTCGGACAACGCCCCGCCTGCAGAAAGAAGGCACTCCATCTGC

-continued

ACAGTGTACATCGAGGTGCTTCCTCCTAACAACCAGAGCCCTCCCCGCTTCCCGCAGCTGAT

GTACAGTCTGGAAGTCAGCGAGGCCATGAGGATCGGTGCTATTTTATTAAATCTACAGGCAA

CTGATCGAGAGGGAGATCCAATCACATATGCCATCGAGAATGGAGACCCTCAGAGAGTTTTT

AATCTTTCAGAAACCACAGGGATTCTCAGCCTAGGGAAGGCTCTAGACCGCGAGAGCACAGA

CCGCTACATCCTCATCGTCACAGCCTCAGATGGCAGACCGGATGGAACCTCAACTGCCACTG

TGAACATAGTGGTGACGGACGTCAATGACAACGCTCCCGTGTTCGATCCCTATCTGCCCAGG

AACCTCTCTGTGGTGGAGGAAGAAGCCAATGCCTTTGTGGGTCAAGTCCGGGCAACAGACCC

AGATGCTGGGATAAACGGCCAAGTTCACTACAGCCTGGGGAACTTCAACAACCTCTTCCGCA

TCACATCCAACGGGAGCATTTACACAGCCGTGAAGCTGAACAGGGAAGCCAGGGACCACTAT

GAACTGGTTGTCGTGGCAACAGATGGAGCAGTCCACCCTCGACATTCAACTCTGACACTGTA

CATCAAGGTGTTGGACATTGATGATAACAGTCCTGTTTTTACCAATTCAACGTACACAGTTG

TCGTTGAAGAGAATCTGCCAGCCGGGACCTCCTTTCTTCAAATAGAGGCCAAGGATGTTGAC

CTTGGAGCCAATGTGTCATATCGGATCAGAAGCCCAGAAGTGAAACACCTTTTTGCACTGCA

TCCATTCACTGGAGAATTGTCTCTTCTGAGGAGTTTGGATTATGAGGCCTTTCCGGACCAGG

AGGCAAGCATCACATTCTTGGTGGAGGCCTTTGACATTTATGGGACTATGCCACCTGGTATA

GCAACAGTCACGGTAATTGTGAAGGACATGAATGACTACCCTCCAGTGTTTAGCAAACGCAT

CTACAAGGGGATGGTGGCTCCAGATGCAGTCAAGGGGACACCAATCACCACCGTTTATGCTG

AAGATGCGGACCCACCTGGGATGCCTGCAAGTAGGGTGAGGTATCGAGTGGACGACGTGCAG

TTTCCATACCCAGCCAGTATTTTTGATGTAGAGGAAGATTCTGGAAGAGTAGTAACCCGCGT

CAATCTTAATGAAGAGCCTACTACGATTTTCAAGCTGGTGGTTGTGGCTTTTGATGACGGCG

AACCTGTGATGTCCAGCAGTGCCACGGTGAGAATTCTTGTCTTACATCCTGGAGAGATCCCA

CGCTTCACCCAAGAGGAATACAGACCTCCTCCTGTAAGTGAGCTTGCGGCCAGAGGGACTGT

AGTTGGTGTCATTTCTGCTGCTGCCATTAATCAGAGCATCGTGTACTCCATTGTGGCAGGAA

ATGAGGAAGACAAGTTTGGAATCAACAATGTCACTGGGGTCATCTATGTGAATTCACCATTG

GATTACGAGACAAGGACCAGCTATGTGCTCCGGGTACAAGCAGATTCTCTGGAAGTGGTCCT

TGCCAATCTCCGAGTCCCTTCAAAAAGCAATACAGCTAAGGTGTACATTGAGATTCAGGATG

AAAACGATCACCCCCCAGTGTTCCAGAAGAAATTCTACATTGGAGGTGTGTCTGAAGACGTA

AGTATCAAGGTTACAAGACAGGTTTAAGGAGACCAATAGAAACTGGGCTTGTCGAGACAGAG

AAGACTCTTGCGTTTCTGGGATTTTGCCGATTTCGGCCTATTGGTTAAAAAATGAGCTGATT

TAACAAAAATTTAACGCGAATTTTAACAAAATGCATGCTGGGGAGAGATCTAGGAACCCCTA

GTGATGGAGTTGGCCACTCCCTCTCTGCGCGCTCGCTCGCTCACTGAGGCCGCCCGGGCAAA

GCCCGGGCGTCGGGCGACCTTTGGTCGCCCGGCCTCAGTGAGCGAGCGAGCGCGCAGAGAGG

GAGTGGCCATGCAGCCAGCTGGCGTAATAGCGAAGAGGCCCGCACCGATCGCCCTTCCCAAC

AGTTGCGTAGCCTGAATGGCGAATGGCGCGACGCGCCCTGTAGCGGCGCATTAAGCGCGGCG

GGTGTGGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAATCGGG

GGCTCCCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACGTTGGA

GTCCACGTTCTTTAATAGTGGACTCTTGTTCCAAACTGGAACAACACTCAACCCTATCTCGG

TCTATTCTTTTGATTTATAAGGGATTTTGCCGATTTCGGCCTATTGGTTAAAAAATGAGCTG

-continued

ATTTAACAAAAATTTAACGCGAATTTTAACAAAATATTAACGTTTACAATTTCCTGATGCGG

TATTTTCTCCTTACGCATCTGTGCGGTATTTCACACCGCATATGGTGCACTCTCAGTACAAT

CTGCTCTGATGCCGCATAGTTAAGCCAGCCCCGACACCCGCCAACACCCGCTGACGCGCCCT

GACGGGCTTGTCTGCTCCCGGCATCCGCTTACAGACAAGCTGTGACCGTCTCCGGGAGCTGC

ATGTGTCAGAGGTTTTCACCGTCATCACCGAAACGCGCGAGACGAAAGGGCCTCGTGATACG

CCTATTTTTATAGGTTAATGTCATGATAATAATGGTTTCTTAGACGTCAGGTGGCACTTTTC

GGGGAAATGTGCGCGGAACCCCTATTTGTTTATTTTTCTAAATACATTCAAATATGTATCCG

CTCATGAGACAATAACCCTGATAAATGCTTCAATAATATTGAAAAAGGAAGAGTATGAGTAT

TCAACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTGGGTTAC

ATCGAACTGGATCTCAACAGCGGTAAGATCCTTGAGAGTTTTCGCCCCGAAGAACGTTTTCC

AATGATGAGCACTTTTAAAGTTCTGCTATGTGGCGCGGTATTATCCCGTATTGACGCCGGGC

AAGAGCAACTCGGTCGCCGCATACACTATTCTCAGAATGACTTGGTTGAGTACTCACCAGTC

ACAGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAACCG

CTTTTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTTGCG

CAAACTATTAACTGGCGAACTACTTACTCTAGCTTCCCGGCAACAATTAATAGACTGGATGG

AGGCGGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCAGATGG

TAAGCCCTCCCGTATCGTAGTTATCTACACGACGGGGAGTCAGGCAACTATGGATGAACGAA

ATAGACAGATCGCTGAGATAGGTGCCTCACTGATTAAGCATTGGTAACTGTCAGACCAAGTT

TACTCATATATACTTTAGATTGATTTAAAACTTCATTTTTAATTTAAAAGGATCTAGGTGAA

GATCCTTTTTGATAATCTCATGACCAAAATCCCTTAACGTGAGTTTTCGTTCCACTGAGCGT

CAGACCCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTCCTTCTAG

TGTAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGACTC

AAGACGATAGTTACCGGATAAGGCGCAGCGGTCGGGCTGAACGGGGGGTTCGTGCACACAGC

CCAGCTTGGAGCGAACGACCTACACCGAACTGAGATACCTACAGCGTGAGCATTGAGAAAGC

GCCACGCTTCCCGAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTCCTGTCGGGTTTC

GCCACCTCTGACTTGAGCGTCGATTTTTGTGATGCTCGTCAGGGGGGCGGAGCCTATGGAAA

AACGCCAGCAACGCGGCCTTTTTACGGTTCCTGGCCTTTTGCTGGCCTTTTGCTCACATGTT

CTTTCCTGCGTTATCCCCTGATTCTGTGGATAACCGTATTACCGCCTTTGAGTGAGCTGATA

CCGCTCGCCGCAGCCGAACGACCGAGCGCAGCGAGTCAGTGAGCGAGGAAGCGGAAGAGCGC

CCAATACGCAAACCGCCTCTCCCCGCGCGTTGGCCGATTCATTAATGCAGCTGGGCTGCA

In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a WPRE; (e) a SV40 poly A signal; (f) a BGH poly A signal; and (g) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a nucleotide sequence encoding an IRES; (e) a nucleotide encoding an eGFP; (f) a WPRE; (e) a SV40 poly A signal; (f) a BGH poly A signal; and (g) a 3' ITR. In some embodiments, the rAAV vector further comprises a nucleotide sequence encoding a tag. In some embodiments, the tag is a HA tag. In some embodiments, the tag placed at the C-terminus of the PCDH15 protein.

In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a WPRE; (f) a SV40 poly A signal; (g) a BGH poly A signal; and (h) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a nucleotide sequence encoding an IRES; (f) a nucleotide encoding an eGFP; (g) a WPRE; (h) a SV40 poly A signal; (i) a BGH poly A signal; and (j) a 3' ITR. In some embodiments, the rAAV vector further comprises a nucleotide sequence encoding a tag. In some embodiments, the tag is a HA tag. In some embodiments, the tag placed at the C-terminus of the PCDH15 protein.

In some embodiments, the rAAV vector encoding the second portion of PCDH15 (e.g., mouse PCDH15 isoform 2) comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to a nucleotide sequence as set forth in SEQ ID NO: 23 (splice acceptor in bold face; second portion of the PCDH15 coding sequence underlined):

TTGGCCACTCCCTCTCTGCGCGCTCGCTCGCTCACTGAGGCCGGGCGACCAAAGGTCGCCCG

ACGCCCGGGCTTTGCCCGGGCGGCCTCAGTGAGCGAGCGAGCGCGCAGAGAGGGAGTGGCCA

ACTCCATCACTAGGGGTTCCTAGATCTGAATTCGGTACCGGGATTTTGCCGATTTCGGCCTA

TTGGTTAAAAAATGAGCTGATTTAACAAAAATTTAACGCGAATTTTAACAAAATGATAGGCA

CCTATTGGTCTTACTGACATCCACTTTGCCTTTCTCTCCACAGGCAAGGATGTTCGCATCTG

TGCTCAGAGTGAAGGCCACCGACAGGGACACGGGTAATTACAGTGCCATGGCCTACCGGCTC

ATCATACCGCCGATTAAAGAGGGCAAAGAGGGGTTTGTGGTGGAAACATACACAGGTCTCAT

CTGACGACTACGGGAAGGGGTTGAGCGGGAAAGCAGACGTACTGGTCTCCGTGGTCAATCAA

CTGGATATGCAGGTCATTGTCTCCAATGTGCCCCCTACACTAGTGGAAAAGAAGATAGAAGA

CCTTACAGAGATTTTGGATCGCTACGTTCAGGAGCAAATTCCTGGTGCCAAGGTTGTGGTGG

AGTCCATAGGTGCCCGTCGCCATGGAGACGCCTACTCCCTAGAAGACTATAGCAAGTGCGAC

CTGACTGTCTATGCCATCGACCCGCAGACCAACAGAGCCATCGACAGAAATGAGCTTTTTAA

GTTCCTGGACGGCAAACTGCTCGATATCAATAAAGACTTCCAGCCGTATTACGGGGAAGGAG

GGCGCATTCTGGAGATTCGGACACCTGAGGCAGTGACGAGCATCAAGAAGCGAGGAGAAAGC

TTGGGGTACACAGAAGGGGCCTTGCTGGCCTTGGCCTTCATCATCATCCTCTGTTGCATCCC

AGCCATCTTGGTCGTCTTAGTAAGCTACCGACAGTTTAAAGTACGCCAGGCTGAGTGCACGA

AGACCGCAAGAATTCAGTCTGCTATGCCTGCAGCCAAGCCTGCAGCTCCTGTACCAGCTGCG

CCTGCGCCGCCCCCGCCCCCGCCACCACCACCACCAGGAGCACATCTCTATGAAGAACTGGG

AGAGAGCGCAATGCATAAGTATGAGATGCCCCAGTATGGAAGTCGCCGTCGACTGCTGCCAC

CTGCTGGACAGGAGGAATACGGCGAAGTCATTGGTGAAGCTGAAGAGGAATATGAAGAAGAA

GAGGTAGAGCCAGAGAAAGTTAAAAAACCCAAAGTTGAAATTAGAGAGCCTAGTGAGGAGGA

GGTGGTAGTCACCGTTGAGAAGCCACCAGCGGCTGAGCCCACATACCCAACGTGGAAGAGAG

CCAGGATATTCCCGATGATTTTTAAGAAAGTCAGAGGTCTCGCTGAGAAAAGAGGCATTGAC

-continued

CTTGAGGGCGAGGAGTGGAGGAGGCGCCTTGATGAAGAAGACAAAGACTATCTTCAACTGAC
TCTAGACCAGGAGGAAGCTACCGAAAGCACCGTGGAGTCAGAGGAGGAGTCCAGCGACTACA
CAGAATACACAGAAACGGAGTCCGAGTTCAGCGAGTCCGAGACAACTGAAGAATCAGAGTCG
GAGACCCCATCTGAGGAAGCGGAGGAGAGCTCTACCCCGGAGTCAGAGGAGTCTGAGTCCAC
TGAGTCAGAGGGAGAGAAAGCAAGAAAAAACATCGTGCTGGCTAGAAGAAGGCCTGTGGTCG
AGGAAATCCAGGAGGTGAAAGGTAAGAGAGAGGAGCCCCCGGTGGAAGAGGAAGAAGAGCCC
CCACTAGAGGAGGAAGAACGGGCAGAGGAAGGAGAAGAAAGCGAAGCAGCTCCCATGGATGA
GTCCACAGACCTGGAGGCTCAGGATGTCCCAGAGGAGGGCAGTGCAGAATCAGTCTCCATGG
AGAGGGGCGTGGAAAGTGAGGAGTCAGAGTCAGAACTGAGCAGCAGCAGCAGTACCAGTGAG
AGTCTCTCCGGAGGCCCCTGGGGCTTTCAGGTGCCAGAATATGACAGAAGGAAGGATGAAGA
GCCCAAGAAATCTCCAGGCGCAAACTCCGAAGGTTACAACACAGCCCTTTAGCTCGAGTCTA
GAGCCCCTCTCCCTCCCCCCCCCCTAACGTTACTGGCCGAAGCCGCTTGGAATAAGGCCGGT
GTGCGTTTGTCTATATGTTATTTTCCACCATATTGCCGTCTTTTGGCAATGTGAGGGCCCGG
AAACCTGGCCCTGTCTTCTTGACGAGCATTCCTAGGGGTCTTTCCCCTCTCGCCAAAGGAAT
GCAAGGTCTGTTGAATGTCGTGAAGGAAGCAGTTCCTCTGGAAGCCTCTTGAAGACAAACAA
CGTCTGTAGCGACCCTTTGCAGGCAGCGGAACCCCCCACCTGGCGACAGGTGCCTCTGCGGC
CAAAAGCCACGTGTATAAGATACACCTGCAAAGGCGGCACAACCCCAGTGCCACGTTGTGAG
ATGCCCAGAAGGTACCCCATTGTATGGGATCTGATCTGGGGCCTCGGTGCACATGCTTTACA
TGTGTTTAGTCGAGGTTAAAAAAACGTCTAGGCCCCCCGAACCACGGGGACGTGGTTTTCCT
TTGAAAAACACGATGATAATATGGCCACAACCATGGTGAGCAAGGGCGAGGAGCTGTTCACC
GGGGTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGTTCATCTGCACCACCG
GCAAGCTGCCCGTGCCCTGGCCCACCCTCGTGACCACCCTGACCTACGGCGTGCAGTGCTTC
AGCCGCTACCCCGACCACATGAAGCAGCACGACTTCTTCAAGTCCGCCATGCCCGAAGGCTA
CGTCCAGGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTG
CCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGCTGT
ACAAGTAATCTAGAAGATAATCAACCTCTGGATTACAAAATTTGTGAAAGATTGACTGGTAT
TCTTAACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTGCTGTCTCTT
AACCCCCACTGGTTGGGGCATTGCCACCACCTGTCAGCTCCTTTCCGGGACTTTCGCTTTCC
CCCTCCCTATTGCCACGGCGGAACTCATCGCCGCCTGCCTTGCCCGCTGCTGGACAGGGGCT
CGGCTGTTGGGCACTGACAATTCCGTGGTGTTGTCGGGGAAGCTGACGTCCTTTCCATGGCT
GCTCGCCTGTGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTCTT
CGCCTTCGCCCTCAGACGAGTCGGATCTCCCTTTGGGCCGCCTCCCCGCATCGGACTAGAGA

-continued

GATCCAGACATGATAAGATACATTGATGAGTTTGGACAAACCACAACTAGAATGCAGTGAAA

AAAATGCTTTATTTGTGAAATTTGTGATGCTATTGCTTTATTTGTAACCATTATAAGCTGCA

ATAAACAAGTTAACAACAACAATTGCATTCATTTTATGTTTCAGGTTCAGGGGGAGGTGTGG

GAGGTTTTTTAGTCGACTAGAGCTCGCTGATCAGCCTCGACTGTGCCTTCTAGTTGCCAGCC

ATCTGTTGTTTGCCCCTCCCCCGTGCCTTCCTTGACCCTGGAAGGTGCCACTCCCACTGTCC

TTTCCTAATAAAATGAGGAAATTGCATCGCATTGTCTGAGTAGGTGTCATTCTATTCTGGGG

GGTGGGGTGGGGCAGGACAGCAAGGGGGAGGATTGGGAAGACAATAGCAGGCATGCTGGGGA

GAGATCTAGGAACCCCTAGTGATGGAGTTGGCCACTCCCTCTCTGCGCGCTCGCTCGCTCAC

TGAGGCCGCCCGGGCAAAGCCCGGGCGTCGGGCGACCTTTGGTCGCCCGGCCTCAGTGAGCG

AGCGAGCGCGCAGAGAGGGAGTGGCCATGCAGCCAGCTGGCGTAATAGCGAAGAGGCCCGCA

CCGATCGCCCTTCCCAACAGTTGCGTAGCCTGAATGGCGAATGGCGCGACGCGCCCTGTAGC

GGCGCATTAAGCGCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCGCCGGCTTTCCCC

GTCAAGCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACGGTTTT

TCGCCCTTTGACGTTGGAGTCCACGTTCTTTAATAGTGGACTCTTGTTCCAAACTGGAACAA

CACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGTT

TACAATTTCCTGATGCGGTATTTTCTCCTTACGCATCTGTGCGGTATTTCACACCGCATATG

GTGCACTCTCAGTACAATCTGCTCTGATGCCGCATAGTTAAGCCAGCCCCGACACCCGCCAA

CACCCGCTGACGCGCCCTGACGGGCTTGTCTGCTCCCGGCATCCGCTTACAGACAAGCTGTG

ACCGTCTCCGGGAGCTGCATGTGTCAGAGGTTTTCACCGTCATCACCGAAACGCGCGAGACG

AAAGGGCCTCGTGATACGCCTATTTTTATAGGTTAATGTCATGATAATAATGGTTTCTTAGA

CGTCAGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATATTGAAA

AAGGAAGAGTATGAGTATTCAACATTTCCGTGTCGCCCTTATTCCCTTTTTTGCGGCATTTT

GCCTTCCTGTTTTTGCTCACCCAGAAACGCTGGTGAAAGTAAAAGATGCTGAAGATCAGTTG

GGTGCACGAGTGGGTTACATCGAACTGGATCTCAACAGCGGTAAGATCCTTGAGAGTTTTCG

CCCCGAAGAACGTTTTCCAATGATGAGCACTTTTAAAGTTCTGCTATGTGGCGCGGTATTAT

CCCGTATTGACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGATCGGAG

GACCGAAGGAGCTAACCGCTTTTTTGCACAACATGGGGGATCATGTAACTCGCCTTGATCGT

TGGGAACCGGAGCTGAATGAAGCCATACCAAACGACGAGCGTGACACCACGATGCCTGTAGC

AATGGCAACAACGTTGCGCAAACTATTAACTGGCGAACTACTTACTCTAGCTTCCCGGCAAC

AATTAATAGACTGGATGGAGGCGGATAAAGTTGCAGGACCACTTCTGCGCTCGGCCCTTCCG

GCTGGCTGGTTTATTGCTGATAAATCTGGAGCCGGTGAGCGTGGGTCTCGCGGTATCATTGC

AGCACTGGGGCCAGATGGTAAGCCCTCCCGTATCGTAGTTATCTACACGACGGGGAGTCAGG

CAACTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGAGT

-continued

```
TTTCGTTCCACTGAGCGTCAGACCCCGTAGAAAAGATCAAAGGATCTTCTTGAGATCCTTTT

TTTCTGCGCGTAATCTGCTGCTTGCAAACAAAAAAACCACCGCTACCAGCGGTGGTTTGTTT

GCCGGATCAAGAGCTACCAACTCTTTTTCCGAAGGTAACTGGCTTCAGCAGAGCGCAGATAC

CAAATACTGTCCTTCTAGTGTAGCCGTAGTTAGGCCACCACTTCAAGAACTCTGTAGCACCG

CCTACATACCTCGCTCTGCTAATCCTGTTACCAGTGGCTGCTGCCAGTGGCGATAAGTCGTG

TCTTACCGGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATACCTACAG

CGTGAGCATTGAGAAAGCGCCACGCTTCCCGAAGGGAGAAAGGCGGACAGGTATCCGGTAAG

CGGCAGGGTCGGAACAGGAGAGCGCACGAGGGAGCTTCCAGGGGGAAACGCCTGGTATCTTT

ATAGTCCTGTCGGGTTTCGCCACCTCTGACTTGAGCGTCGATTTTTGTGATGCTCGTCAGGG

GGGCGGAGCCTATGGAAAAACGCCAGCAACGCGGCCTTTTTACGGTTCCTGGCCTTTTGCTG

GCCTTTTGCTCACATGTTCTTTCCTGCGTTATCCCCTGATTCTGTGGATAACCGTATTACCG

CCTTTGAGTGAGCTGATACCGCTCGCCGCAGCCGAACGACCGAGCGCAGCGAGTCAGTGAGC

GAGGAAGCGGAAGAGCGCCCAATACGCAAACCGCCTCTCCCCGCGCGTTGGCCGATTCATTA

ATGCAGCTGGGCTGCA
```

II. Recombinant Adeno-Associated Viruses (rAAV) for Delivering Full-Length PCDH15 to a Target Cell In some aspects, the present disclosure provides a first 5' rAAV comprising (i) an AAV capsid protein (e.g., AAV-S capsid protein or AAV9.PHP.B capsid protein); and (ii) a first 5' isolated nucleic acid comprising, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; and (g) a 3' ITR.

In some aspects, the present disclosure provides a first 3' rAAV comprising (i) an AAV capsid protein (e.g., AAV-S capsid protein or AAV9.PHP.B capsid protein); and (ii) a first 3' isolated nucleic acid comprising, from 5' to 3', from 5' to 3', (a) a 5' ITR; (b) a splice acceptor; (c) a nucleotide sequence encoding a second portion of the PCDH15 protein; (d) a WPRE; (e) a SV40 poly A signal; (f) a BGH poly A signal; and (g) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a splice acceptor; (c) a nucleotide sequence encoding a second portion of the PCDH15 protein; (d) a nucleotide sequence encoding an IRES; (e) a nucleotide encoding an eGFP; (f) a WPRE; (e) a SV40 poly A signal; (f) a BGH poly A signal; and (g) a 3' ITR. In some embodiments, the first 3' isolated nucleic acid further comprises a nucleotide sequence encoding a tag. In some embodiments, the tag is a HA tag. In some embodiments, the tag placed at the C-terminus of the PCDH15 protein.

In some aspects, the present disclosure provides a PCDH15 expression system comprising the first 5' rAAV as described herein; and the first 3' rAAV as described herein.

In some aspects, the present disclosure provides a second 5' rAAV comprising (i) an AAV capsid protein (e.g., AAV-S capsid protein or AAV9.PHP.B capsid protein); and (ii) a second 5' isolated nucleic acid comprising, from 5' to 3', (a) a 5' ITR; (b) a Human Cytomegalovirus Early Enhancer (CMV enhancer); (c) a Cytomegalovirus (CMV) promoter; (d) a Kozak sequence; (e) a nucleotide sequence encoding a first portion of the PCDH15 protein; (f) a splice donor; (g) a recombinogenic sequence, and (h) a 3' ITR.

In some aspects, the present disclosure provides a second 3' rAAV comprising (i) an AAV capsid protein (e.g., AAV-S capsid protein or AAV9.PHP.B capsid protein); and (ii) a second 3' isolated nucleic acid comprising, from 5' to 3', from 5' to 3', (a) a 5' ITR; (b) a recombinogenic sequence; (c) a splice acceptor; (d) a nucleotide sequence encoding a second portion of the PCDH15 protein; (e) a WPRE; (f) a SV40 poly A signal; (g) a BGH poly A signal; and (h) a 3' ITR. In some embodiments, the rAAV vector further comprises a nucleotide encoding a detectable protein (e.g., eGFP). In some embodiments, the rAAV vector further comprises a nucleotide sequence encoding an IRES or a nucleotide sequence encoding a 2A peptide between the nucleotide sequence encoding the second portion of the PCDH15 protein and the nucleotide sequence encoding eGFP. Accordingly, In some embodiments, the rAAV vector encoding the second portion of PCDH15 comprises, from 5' to 3', (a) a 5' ITR; (b) a recombinogenic sequence; (c) a splice acceptor; (d) a nucleotide sequence encoding a second portion of the PCDH15 protein; (e) a nucleotide sequence encoding an IRES; (f) a nucleotide encoding an eGFP; (g) a WPRE; (h) a SV40 poly A signal; (i) a BGH poly A signal; and (j) a 3' ITR. In some embodiments, the second 3' isolated nucleic acid further comprises a nucleotide sequence encoding a tag. In some embodiments, the tag is a HA tag. In some embodiments, the tag placed at the C-terminus of the PCDH15 protein.

In some aspects, the present disclosure provides a PCDH15 expression system comprising the second 5' rAAV as described herein; and the second 3' rAAV as described herein.

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected. In some aspects, the present disclosure provides a first 5' recombinant adeno-associated (rAAV) virus comprising: (i) an adeno-associated virus capsid protein; and (ii) the first 5' isolated nucleic acid as described herein. In some aspects, the present disclosure provides a first 3' recombinant adeno-associated (rAAV) virus comprising: (i) an adeno-associated virus capsid protein; and (ii) the first 3' isolated nucleic acid as described herein. In some aspects, the present disclosure provides a second 5' recombinant adeno-associated (rAAV) virus comprising: (i) an adeno-associated virus capsid protein; and (ii) the second 5' isolated nucleic acid as described herein. In some aspects, the present disclosure provides a second 3' recombinant adeno-associated (rAAV) virus comprising: (i) an adeno-associated virus capsid protein; and (ii) the second 3' isolated nucleic acid as described herein.

Methods for obtaining recombinant AAVs having a desired capsid protein are well known in the art. (See, for example, U.S. Patent Application Publication US 2003-0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa, and about 62 kDa. In some embodiments, upon translation, capsid proteins form a spherical 60-mer protein shell around the viral genome. In some embodiments, the functions of the capsid proteins are to protect the viral genome, deliver the genome, and interact with the host. In some aspects, capsid proteins deliver the viral genome to a host in a tissue specific manner.

The present disclosure is based on the finding that exemplary AAV serotype capsids are capable of delivering the transgene (e.g., PCDH15) to the ear (e.g., inner hair cells and outer hair cells, spiral ganglion neurons) or the eyes (e.g., photoreceptors). In some embodiments, an AAV capsid protein is of an AAV serotype selected from the group consisting of AAV-S, AAV9.PHP.B, AAV2.7m8, AAV8BP2, exoAAV, Anc80, AAV1, AAV2, AAV3, AAV4, AAV5, AAV6, AAV7, AAV8, AAVrh8, AAV9, AAV10, and AAVrh10. In some embodiments, the capsid protein is AAV2.7m8 or AAV8BP2. AAV2.7m8, which is capable of delivering a transgene to cochlear hair cells and supporting cells and the retina. AAV8BP2 shows enhanced transduction rate to the retina (Isgrig et al., AAV2.7m8 is a powerful viral vector for inner ear gene therapy, Nature Communications, volume 10, Article number: 427 (2019)). In some embodiments, the capsid protein is of AAV serotype 9 (AAV9). In some embodiments, an AAV capsid protein is of a serotype derived from AAV9 (e.g., AAV9.PHP.B, AAV9.PHP.eB). In some embodiments, the AAV capsid is an exoAAV. An exoAAV, refers to an exosome-associated AAV. An exoAAV capsid protein can be selected from the group consisting of AAV1, AAV2, AAV3, AAV4, AAV5, AAV6, AAV7, AAV8, AAVrh8, AAV9, AAV10, AAVrh10, and AAV.PHP.B. In some examples, the exoAAV is exoAAV1 or exoAAV9. In other embodiments, the AAV capsid protein is Anc80 or Anc80L65. Anc80 is an in silico predicted ancestor of the widely studied AAV serotypes 1, 2, 8, and 9. Anc80 is a highly potent in vivo gene therapy AAV capsid for targeting liver, muscle, and retina. The present disclosure, at least in part, is based on the capability of AAV capsids (e.g., AAV9.PHPeB) to deliver the transgene (e.g., full-length PCDH15) to most of cells in the ear (e.g., inner hair cells, outer hair cells) and cells in the eye (e.g., photoreceptors). In some embodiments, the AAV capsid is an AAV9.PHP.B capsid protein. In some embodiments, the AAV capsid is an AAV9.PHP.eB capsid protein. In some embodiments, the AAV capsid is an AAV-S capsid protein.

AAV-S is an AAV9 capsid protein variant originally developed for targeting the central nervous system (CNS) (Hanlon et al., Selection of an Efficient AAV Vector for Robust CNS Transgene Expression, *Molecular Therapy Method & Clinical Development*, vol. 15, 320-332, Dec. 13, 2019, and PCT/US20/25720, which are incorporated herein by reference). The present disclosure, at least in part, is based on the surprising discovery that AAV-S has good transducing efficiency for inner ear cells (e.g., inner hair cells, outer hair cells, and fibrocytes) and/or cells of the eye (e.g., retina cells, such as photoreceptors). In some embodiments, the AAV-S capsid protein is capable of transducing a wide variety of ear cells (see, e.g., Hanlon et al., AAV-S: A novel AAV vector selected in brain transduces the inner ear with high efficiency, *Molecular Therapy* Vol 18 No 4S1, Apr. 28, 2020, Abstract 151, which is incorporated herein by reference), including, but not limited to: outer hair cells (OHCs), inner hair cells (IHCs), supporting cells (e.g., border cell, inner phalangeal cell, inner pillar cell, outer pillar cell, Deiters' cell, Hensen's, or Claudius' cell), spiral ganglion neuron, spiral limbus cells (e.g., glial cell or interdental cell), outer sulcus cells, lateral wall, stria vascularis (e.g., basal cell and intermediate cell), inner sulcus, spiral ligament (e.g., fibrocytes), or cells of the vestibular system. In some embodiments, the AAV-S capsid protein is capable of transducing a wide variety of eye cells, including, but not limited to, photoreceptor cells (e.g., rods and cones), cells in the retina within the photoreceptor inner and outer segments (IS), cells of the outer plexiform layer (OPL), cells of the inner nuclei layer (INL), cells of the ganglion cell layer (GCL), cells of the inner plexiform layer (IPL), or retinal pigment epithelium (RPE) cells.

The skilled artisan will also realize that conservative amino acid substitutions may be made to provide functionally equivalent variants, or homologs, of the capsid proteins. In some aspects, the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequences known to one of ordinary skill in the art such as are found in references that compile such methods, e.g., *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

In some aspects, the present disclosure provides a PCDH15 expression system comprising: (i) the first 5' rAAV, and (ii) the first 3' rAAV. In other aspects, the present disclosure provides a PCDH15 expression system comprising: (i) the second 5' rAAV; and (ii) the second 3' rAAV. In some embodiments, co-delivery of the first 5' rAAV and the first 3' rAAV results in expression of a full-length PCDH15 in a target cell. In some embodiments, co-delivery of the second 5' rAAV and the second 3' rAAV results in expression of a full-length PCDH15 in a target cell.

In some embodiments, the rAAV, as provided herein, is capable of delivering the (e.g., full-length PCDH15) to a mammal. In some examples, the mammal is a human or a non-human mammal, such as a mouse, a rat, or a non-human primate (e.g., cynomolgus monkey).

In some embodiments, the rAAVs, as provided herein, is capable of delivering the transgene (e.g., full-length PCDH15) to the ear. In some instances, the rAAVs as provided herein, is capable of delivering the transgene (e.g., full-length PCDH15) to the cells in the inner ear (e.g., cochlea). In other embodiments, the cells are cells of the eye. In some examples, the cells are photoreceptors. Non-limiting examples of target cells are outer hair cells (OHC), inner hair cells (IHC), supporting cell, cells in spiral ganglion neuron, cells in piral limbus, outer sulcus cells, cells in lateral wall, cells in stria vascularis, cells in inner sulcus, cells in spiral ligament, or cells of the vestibular system, photoreceptor cells, other cells in the retina within the photoreceptor inner and outer segments (IS), cells of the outer plexiform layer (OPL), cells of the inner nuclei layer (INL), cells of the ganglion cell layer (GCL), cells of the inner plexiform layer (IPL), or retinal pigment epithelium (RPE) of the eye.

In some embodiments, the instant disclosure relates to a host cell containing the first and/or second nucleic acid or the 5' and/or the 3' rAAV as described herein. In some embodiments, the host cell is a mammalian cell (e.g., a human cell), a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, N.Y. Similarly, methods of generating rAAV virions are well known and the selection of a suitable method is not a limitation on the present disclosure. See, e.g., K. Fisher et al., *J. Virol.,* 70:520-532 (1993) and U.S. Pat. No. 5,478,745. The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, recombinant AAVs may be produced using the triple transfection method (described in detail in U.S. Pat. No. 6,001,650, which is incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses, such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid, such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements, and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed.

The foregoing methods for packaging recombinant vectors in desired AAV capsids to produce the rAAVs of the disclosure are not meant to be limiting and other suitable methods will be apparent to the skilled artisan.

III. Pharmaceutical Composition for Delivering Transgenes to the Ear and Eye

The isolated nucleic acids and the rAAVs as described herein may be delivered to a subject in compositions according to any appropriate methods known in the art. The rAAV, preferably suspended in a physiologically compatible carrier (e.g., in a composition), may be administered to a subject, e.g., host animal. In some embodiments, the host animal is a mammal. In some examples, the mammal is a human. In other embodiments, the mammal can be a non-human mammal, such as a human, mouse, rat, cat, dog, sheep, rabbit, horse, cow, goat, pig, guinea pig, hamster, chicken, turkey, or a non-human primate (e.g., cynomolgus monkey).

Delivery of the 5' and the 3' rAAVs described herein to a mammalian subject may be by, for example, injection to the ear or the eye. In some embodiments, the injection is to the ear through round window membrane of the inner ear, into a semicircular canal of the inner ear, into the saccule or the utricle of the inner ear, or topical administration (e.g., ear drops). In some embodiments, the injection is injection into the eye (e.g., intravitreal or subretinal injection) or topical administration (e.g., eye drops). Combinations of administration methods (e.g., topical administration and injection through round window membrane of the inner ear) can also be used.

In some embodiments, a composition further comprises a pharmaceutically acceptable carrier. Suitable carriers may be readily selected by one of skill in the art in view of the indication for which the rAAV is directed. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., *Remington: The Science and Practice of Pharmacy* 20th Ed. (2000) Lippincott Williams and Wilkins, Ed. K. E. Hoover. For example, one acceptable carrier includes saline, which may be formulated with a variety of buffering agents (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

The rAAV containing pharmaceutical composition disclosed herein may further comprise a suitable buffering agent. A buffering agent is a weak acid or base used to maintain the pH of a solution near a chosen value after the addition of another acid or base. In some examples, the buffering agent disclosed herein can be a buffering agent capable of maintaining physiological pH despite changes in carbon dioxide concentration (produced by cellular respiration). Exemplary buffering agents include, but are not limited to, HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAV containing pharmaceutical composition described herein comprises one or more suitable surface-active agents, such as a surfactant. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example, mannitol or other pharmaceutically acceptable vehicles, if necessary.

The rAAVs are administered in sufficient amounts to transfect the cells of a desired tissue (e.g., inner hair cells, outer hair cells, or photoreceptors of the eye) and to provide sufficient levels of gene transfer and expression without undue adverse effects. Examples of pharmaceutically acceptable routes of administration include, but are not limited to, direct delivery to the selected organ (e.g., the ear and the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in viral genome copies/per kilogram of body weight (GC/kg or VG/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of a rAAV is an amount sufficient to infect an animal (e.g., mouse, rat, non-human primate or human), target a desired tissue (e.g., the inner ear or the eye). The effective amount will depend primarily on factors, such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies are appropriate. In certain embodiments, about $10^9$ rAAV genome copies are effective to target inner ear tissue (e.g., inner hair cells, outer hair cells, or photoreceptors of the eye). In some embodiments, a dose more concentrated than $10^9$ rAAV genome copies is toxic when administered to the eye of a subject. Therefore, in certain embodiments, no more than about $10^9$ rAAV genome copies are effective to target inner ear tissue (e.g., inner hair cells, outer hair cells, or photoreceptors of the eye). In some embodiments, an effective amount is produced using multiple doses of an rAAV composition.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 days. In some embodiments, a dose of rAAV is administered to a subject no more than once per calendar week (e.g., 7 days). In some embodiments, a dose of rAAV is administered to a subject no more than bi-weekly (e.g., once in a two-week period). In some embodiments, a dose of rAAV is administered to a subject no more than once per month (e.g., once in 30 days). In some embodiments, a dose of rAAV is administered to a subject no more than once per six months. In some embodiments, a dose of rAAV is administered to a subject no more than once per year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation may be used, including, for example, the addition of surfactants, pH adjustment, salt concentration adjustment, etc. (See, e.g., Wright et al., *Molecular Therapy* (2005) 12, 171-178, the contents of which are incorporated herein by reference.)

Formulation of pharmaceutically acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient (e.g., the rAAV or the isolated nucleic acids described herein) or more, although the percentage of the active ingredient(s) may, of course, be varied and may conveniently be between about 1 or 2% and about 70% or 80% or more of the weight or volume of the total formulation. Naturally, the amount of active ingredient (e.g., the rAAV or the isolated nucleic acids described herein) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to inner ear tissue (e.g., inner hair cells, outer hair cells, or photoreceptors of the eye). In other embodiments, the target tissue is an eye. The rAAVs in suitably formulated pharmaceutical compositions disclosed herein are delivered directly to the eye (e.g., photoreceptors). However, in certain circumstances it may be desirable to separately or in addition deliver the rAAV-based therapeutic constructs via another route, e.g., subcutaneously, intranasally, parenterally, intravenously, intramuscularly, or orally. In some embodiments, the administration modalities as described in U.S. Pat. Nos. 5,543,158; 5,641,515, and 5,399,363 (each of which is incorporated herein by reference in its entirety) may be used to deliver rAAVs.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous administration, intramuscular administration, subcutaneous administration, intraperitoneal administration, subretinal administration, intravitreal administration, and injection through round window membrane of the inner ear. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, *Remington's Pharmaceutical Sciences* 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation and in such amount as is therapeutically effective. The formulations are easily administered in a variety of dosage forms, such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, a nanoparticle, or the like.

Such formulations may be preferred for the introduction of pharmaceutically acceptable formulations of PCDH15 expression system disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587, each of which are incorporated herein by reference).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors, and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

IV. Therapeutic Applications

The present disclosure also provides methods for delivering a transgene (e.g., full-length PCDH15) to the ear or the eye for treating hearing loss and/or blindness (e.g., Usher Syndrome type 1F).

In some embodiments, the subject can be a mammal. In some embodiments, the subject is a human. In other embodiments, the subject is a non-human mammal such as mouse, rat, cow, goat, pig, camel, or non-human primate (e.g., cynomolgus monkey).

In some embodiments, the subject is having or suspected of having hearing loss and/or blindness. In some examples, the subject is diagnosed with having Usher Syndrome type 1F. In further examples, the hearing loss and/or blindness is associated with a mutation in the PCDH15 gene. In some examples, the mutation of PCDH15 gene is a point mutation, a missense mutation, a nonsense mutation, a deletion, an insertion, or a combination thereof. Non-limiting exemplary mutations in PCDH15 are shown in Table 1. A mutation, as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4th ed., Cold Spring Harbor Laboratory Press, Cold Spring Harbor, N.Y. (2012)).

TABLE 1

| Exemplary mutations in PCDH15 | | |
|---|---|---|
| Accession NO: | Mutation | Amino Acid Change |
| NM_033056.3(PCDH15) | c.400C > G | p.Arg134Gly |
| NM_033056.3(PCDH15) | c.733C > T | p.Arg245Ter |
| NM_033056.3(PCDH15) | c.785G > A | p.Gly262Asp |
| NM_033056.3(PCDH15) | c.1583T > A | p.Val528Asp |
| NM_033056.3(PCDH15) | c.3316C > T | p.Arg1106Ter |
| NM_001142769.2(PCDH15) | c.4726C > T | p.Gln1576Ter |
| NM_033056.3(PCDH15) | c.4035T > A | p.Tyr1345Ter |
| NM_033056.3(PCDH15) | c.1997 + 1G > A | |
| NM_033056.3(PCDH15) | c.3984 − 1G > C | |
| | GRCh38/hg3810q21.1 (chr10: 53954459-54098171)x0 | |
| NM_033056.3(PCDH15) | c.158 − 1G > A | |
| NM_033056.3(PCDH15) | c.16delT | p.Tyr6Ilefs |
| NM_001142763.1(PCDH15) | c.2986C > T | p.Arg996Ter |
| NM_033056.3(PCDH15) | c.1998 − 2A > G | |
| NM_033056.3(PCDH15) | c.1927C > T | p.Arg643Ter |
| NM_033056.3(PCDH15) | c.3358C > T ( ) | p.Arg1120Ter |
| PCDH15, IVS27, A-G, -2 | | |
| NM_033056.3(PCDH15) | c.(?_ − 15)_(876_?) | del |
| NM_033056.3(PCDH15) | c.706-3_717delCAGGACCGTGCCCAA | |
| NM_033056.3(PCDH15) | c.(?_3374)_(3501_?) | del (p.(?)) |
| NM_033056.3(PCDH15) | c.1940C > G | p.Ser647Ter |
| NM_033056.3(PCDH15) | c.1086delT | p.Leu363Trpfs |
| NM_001142772.1(PCDH15) | c.400C > T | p.Arg134Ter |
| NM_033056.3(PCDH15) | c.2419dupA | p.Ile807Asnfs |
| NM_033056.3(PCDH15) | c.7C > T | p.Arg3Ter |
| PCDH15, | 3-BP DEL, 5601AAC | |
| NM_033056.3(PCDH15) | c.394dupG | p.Glu132Glyfs |
| PCDH15, | 1-BP DEL, 16T | |
| NM_001142763.1(PCDH15) | c.(?_ − 1)_(2235 + 1_2236 − 1) | del |
| NM_001142763.1(PCDH15) | c.5385_5394delTCCTCTTCCT | p.Pro1796Leufs |
| NC_000010.10 | g.56104359_56108448del4090 | |
| NC_000010.10 | g.55829578_56723036del893459 | |
| NM_033056.3(PCDH15) | c.157 + 1G > C | |
| NM_033056.3(PCDH15) | c.3885_3889dup | p.Ala1297Glufs |
| NM_033056.3(PCDH15) | c.2825delG | p.Gly942Valfs |
| NM_033056.3(PCDH15) | c.3983 + 1G > T | |
| NM_033056.3(PCDH15) | c.1770_1771delTC | p.Pro591Cysfs |
| NM_001142763.1 | c.-189197_c.610-5166del | |
| NM_033056.3(PCDH15) | c.416_444del29 ( ) | p.Asp139Alafs |
| NM_033056.3(PCDH15) | c.3653delT | p.Phe1218Serfs |
| NM_033056.3(PCDH15) | c.3717 + 1G > A | |
| NM_033056.3(PCDH15) | c.2624C > A | p.Ser875Ter |
| NM_033056.3(PCDH15) | c.2785C > T ( ) | p.Arg929Ter |
| NM_033056.3(PCDH15) | c.4313delC ( ) | p.Pro1438Argfs |
| NM_033056.3(PCDH15) | c.2487dupA ( ) | p.Glu830Argfs |
| NM_033056.3(PCDH15) | c.4368 − 2A > T | |
| NM_033056.3(PCDH15) | c.4368-15_4368-2delTTCTTTTCTTTCAA (SEQ ID NO: 56) | |
| NM_033056.3(PCDH15) | c.1785 − 2A > C | |
| NM_033056.3(PCDH15) | c.4227T > A ( ) | p.Cys1409Ter |
| NM_033056.3(PCDH15) | c.594 + 1G > T | |
| NM_033056.3(PCDH15) | c.1006C > T ( ) | p.Arg336Ter |
| NM_033056.3(PCDH15) | c.1305 + 1G > A | |
| NM_033056.3(PCDH15) | c.901dupA | p.Thr301Asnfs |
| NM_033056.3(PCDH15) | c.3211delA | p.Ile1071Leufs |
| NM_033056.3(PCDH15) | c.333dupA | p.His112Thrfs |
| NM_033056.3(PCDH15) | c.3341delT | p.Val1114Glyfs |
| NM_033056.3(PCDH15) | c.4367 + 1G > A | |
| NM_033056.3(PCDH15) | c.1627delG | p.Glu543Argfs |
| NM_033056.3(PCDH15) | c.4197_4198insGTAG | p.Arg1400Valfs |
| NM_033056.3(PCDH15) | c.4211 + 2dupT | |
| NM_033056.3(PCDH15) | c.1806T > G | p.Tyr602Ter |
| NM_033056.3(PCDH15) | c.3441dupA | p.Phe1148Ilefs |
| NM_033056.3(PCDH15) | c.3082delC | p.His1028Ilefs |
| NM_033056.3(PCDH15) | c.1830_1833delTCAA | p.Asn610Lysfs |
| NM_033056.3(PCDH15) | c.1737C > G | p.Tyr579Ter |
| NM_033056.3(PCDH15) | c.358_359delTG | p.Cys120Hisfs |
| NM_033056.3(PCDH15) | c.3023delC | p.Ala1008Valfs |
| NM_033056.3(PCDH15) | c.1915C > T | p.Gln639Ter |
| NM_033056.3(PCDH15) | c.*12348A > G | |
| NM_033056.3(PCDH15) | c.5435C > T | p.Pro1812Leu |
| NM_001142771.1(PCDH15) | c.4627G > A | p.Gly1543Ser |
| NM_033056.3(PCDH15) | c.2367_2369delTGT | p.Val790del |

TABLE 1-continued

| Exemplary mutations in PCDH15 | | |
|---|---|---|
| Accession NO: | Mutation | Amino Acid Change |
| NM_033056.3(PCDH15) | c.1362C > T | p.Val454= |
| NM_033056.3(PCDH15) | c.3502 − 8C > T | |
| NM_033056.3(PCDH15) | c.330C > T | p.Asn110= |
| NM_033056.3(PCDH15) | c.5601_5603delAAC | p.Thr1869del |
| NM_033056.3(PCDH15) | c.5280_5342del63 | p.Ala1761_Pro1781del |
| NM_033056.3(PCDH15) | c.243G > A | p.Val81= |
| NM_033056.3(PCDH15) | c.5287_5292delGCTCCT | p.Ala1763_Pro1764del |
| NM_033056.3(PCDH15) | c.2885G > T | p.Arg962Leu |
| NM_033056.3(PCDH15) | c.2424G > C | p.Lys808Asn |
| NM_033056.3(PCDH15) | c.3195A > G | p.Gln1065= |
| NM_033056.3(PCDH15) | c.4812G > T ( ) | p.Arg1604Ser |
| NM_033056.3(PCDH15) | c.5353T > C ( ) | p.Ser1785Pro |
| NM_033056.3(PCDH15) | c.5283T > A | p.Ala1761= |
| NM_033056.3(PCDH15) | c.4783A > C | p.Ile1595Leu |
| NM_033056.3(PCDH15) | c.475 − 3C > T | |
| NM_033056.3(PCDH15) | c.4334C > G | p.Ala1445Gly |
| NM_033056.3(PCDH15) | c.2884C > T | p.Arg962Cys |
| NM_033056.3(PCDH15) | c.3983 + 12T > C | |
| NM_033056.3(PCDH15) | c.960A > G | p.Pro320= |
| NM_033056.3(PCDH15) | c.546A > G | p.Gly182= |
| NM_033056.3(PCDH15) | c.1910A > G | p.Asn637Ser |
| NM_033056.3(PCDH15) | c.2625G > A | p.Ser875= |
| NM_033056.3(PCDH15) | c.5359C > T | p.Pro1787Ser |
| NM_001142763.1(PCDH15) | c.4871A > G | p.Asn1624Ser |
| NM_033056.3(PCDH15) | c.2563C > T | p.Arg855Trp |
| NM_033056.3(PCDH15) | c.5254_5256delCCT | p.Pro1752del |
| NM_033056.3(PCDH15) | c.3018G > T | p.Val1006= |
| NM_033056.3(PCDH15) | c.4831_4834dupAACA | p.Thr1612Lysfs |
| NM_033056.3(PCDH15) | c.5565C > T | p.Ala1855= |
| NM_033056.3(PCDH15) | c.3795A > T | p.Glu1265Asp |
| NM_033056.3(PCDH15) | c.4080G > A | p.Val1360= |
| NM_033056.3(PCDH15) | c.1360G > A | p.Val454Ile |
| NM_033056.3(PCDH15) | c.3936A > G | p.Ala1312= |

Aspects of the present disclosure relate to methods of treating hearing loss and/or blindness (e.g., Usher Syndrome type 1F) by delivering a functional gene product (e.g., full-length PCDH15) using gene therapy (e.g., full-length PCDH15 encoded by dual AAV vectors) to a target cells (e.g., inner hair cell, outer hair cell, and photoreceptors), which comprise one or more mutations in both alleles in a relevant gene (e.g., PCDH15) that results in absence or malfunction of the gene product.

Aspects of the invention relate to certain protein-encoding transgenes (e.g., full-length PCDH15) that when delivered to a subject at an effective amount for promoting cell adhesion the inner ear and in the retina of the subject. In some embodiments, the subject has or is suspected of having hearing loss and/or blindness. In some examples, the hearing loss and/or blindness is associated with a mutation in the PCDH15 gene. In one example, the subject is diagnosed with Usher Syndrome, type 1F.

Accordingly, the methods and compositions of the disclosure are useful, in some embodiments, for the treatment of Usher syndrome, Type 1F. Usher syndrome, Type 1F is associated with one or more mutations or deletions of PCDH15 gene, and the symptoms include hearing loss, deafness, and/or progressive vision loss, and blindness.

Methods for delivering a transgene (e.g., full-length PCDH15) to a subject are provided by the disclosure. The methods typically involve administering to a subject an effective amount of the isolated nucleic acids (e.g., the 5' isolated nucleic acid and the 3' isolated nucleic acids), the 5' rAAV and the 3' rAAV, or the PCDH15 expression system as described herein for expression of a full-length PCDH15.

In some embodiments, the hearing loss and/or blindness is associated with Usher syndrome type 1F. Generally, a mutation or mutations in PCDH15 account for Usher syndrome type 1F. In some embodiments, the PCDH15 mutation can be, but are not limited to, point mutations, missense mutations, nonsense mutations, insertions, or deletions. In some examples, the PCDH15 gene mutations associated with Usher syndrome, type 1F include, but are not limited to, mutations in Table 1 (ClinVar, NCBI). In some embodiments, the mutation in PCDH15 is c.733C>T. Mutations in a PCDH15 gene of a subject (e.g., a subject having or suspected of having Usher Syndrome type 1F associated with a deletion or mutation of PCDH15 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological sample obtained from a subject, and nucleic acid sequencing is performed in order to identify a mutation in the PCDH15 gene. Examples of nucleic acids sequencing techniques include, but are not limited to, Maxam-Gilbert sequencing, pyrosequencing, chain-termination sequencing, massively parallel signature sequencing, single-molecule sequencing, nanopore sequencing, Illumina sequencing, etc. In some embodiments, a mutation in PCDH15 gene is detected indirectly, for example, by quantifying full-length PCDH15 protein expression (e.g., by Western blot) or function (e.g., by analyzing structure, function, etc.), or by direct sequencing of the DNA and comparing the sequence obtained to a control DNA sequence (e.g., a wild-type PCDH15 DNA sequence).

In some aspects, the disclosure provides a method for treating an Usher syndrome type 1F in a subject in need thereof, the method comprising administering to a subject having or suspected of having Usher syndrome type 1F a therapeutically effective amount of isolated nucleic acids (e.g., the 5' isolated nucleic acid and the 3' isolated nucleic acids), the 5' rAAV and the 3' rAAV, or the PCDH15 expression system as described herein through injections through the round window membrane of the inner ear, into a semicircular canal of the inner ear, or into the saccule or the utricle of the inner ear as described herein. In other embodiments, the injection is into the eye (e.g., subretinal or intravitreal injection).

An effective amount may also depend on the rAAV used. The invention is based, in part on the recognition that rAAV comprising capsid proteins having a particular serotype (e.g., AAV9.PHP.B, exoAAV, Anc80, or AAV-S) mediate more efficient transduction of cochlear (e.g., inner hair cells, outer hair cells) tissue than rAAV comprising capsid proteins having a different serotype.

In certain embodiments, the effective amount of rAAV is $10^{10}$, $10^{11}$, $10^{12}$, $10^{13}$, or $10^{14}$ genome copies per kg body weight of a subject. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting a cochlear (e.g., inner hair cells, and outer hair cells) tissue by injection through the round window membrane of the inner ear may require different (e.g., higher or lower) doses, in some cases, than targeting a cochlear (e.g., inner hair cells, outer hair cells) tissue by another method (e.g., systemic administration, topical administration). In other cases, targeting the eye (e.g., photoreceptors) by injection behind the eye (e.g., subretinal injection and intravitreal injection) may require different doses, in some cases, than targeting the eye (e.g., photoreceptors) by another method (e.g., systemic administration, topical administration). Thus, in some embodiments, the injection is injection through the round window membrane of the inner ear. In some embodiments, the administration is via injection, optionally subretinal injection or intravitreal injection. In some embodiments, the administration is topical administration (e.g., topical administration to an ear). In some embodiments, the administration is posterior semicircular canal injection. In some cases, multiple doses of a rAAV are administered.

Without wishing to be bound by any particular theory, efficient transduction of cochlear (e.g., inner hair cells, outer hair cells, or photoreceptors) cells by rAAV described herein may be useful for the treatment of a subject having a hereditary hearing loss and/or vision loss (e.g., Usher syndrome type 1F). Accordingly, methods and compositions for treating hereditary hearing loss and/or vision loss are also provided herein.

In some embodiments, the 5' rAAV and the 3' rAAV, or the PCDH15 expression system as described herein can be administered to the patients (e.g., patients with Usher 1F syndrome or hereditary hearing loss) at age of 6 month, 1 year, 2 years, 3 years, 5 years, 6 years, 7 years, 8 years, 9, years, 10 years, 11 years, 12 years, 13 years, 14 years, 15 years, 16 years, 17 years, 18 years, or older. In some embodiments, the patient is an infant, a child, or an adult. In some embodiments, the 5' rAAV and the 3' rAAV, or the PCDH15 expression system as described herein are administered to the patient (e.g., patient with Usher 1F syndrome once in a life time, every 5 years, every 2 years, every year, every 6 months, every 3 months, every month, every two weeks, or every week. In other embodiments, the administration of the 5' rAAV and the 3' rAAV, or the PCDH15 expression system as described herein can be administered to the patients (e.g., patients with Usher 1F syndrome or hereditary hearing loss) in combination with other known treatment methods for Usher 1F syndrome (e.g., Vitamin A supplementation).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All patents, patent applications, and publications cited herein are incorporated herein by reference for the purposes or subject matter referenced herein.

EXAMPLES

Example 1. Dual AAV Vectors for Delivering Full-Length PCDH15 in Hair Cells and Retina Cells Hearing loss, congenital, or acquired, affects ~30 million people in the United States alone (Lin et al., 2011). Congenital hearing loss occurs in about 1/1,000 births (Mason et al., 1998); about half have a defined genetic cause. So far, >150 genes and more than 8000 mutations have been causally linked to hearing loss. For congenital recessive deafness, gene addition is possible, while congenital dominant forms might be treated either by silencing or by correcting the mutated allele. Because the cochlea is surgically accessible and relatively immune-protected, gene therapy using viral vectors is an attractive approach to treatment. Gene therapy also holds promise for genetically complex forms of deafness such as age-related hearing loss, by enhancing survival of hair cells or spiral ganglion neurons (Wise et al., 2011) or by inducing trans-differentiation of supporting cells into hair cells (Li et al., 2015).

Significant advances have been made in gene therapy for deafness, primarily with gene addition therapy for small genes whose coding sequence will fit in an AAV (Kohrman & Raphael, 2013; Sacheli et al., 2013; Lustig & Akil, 2018). However, many deafness genes encode large proteins with coding sequences that do not fit, and more creative approaches must be developed to express therapeutic proteins within the target cells. Also, although conventional rAAV are safe and are currently used in clinical trials, none has led to efficient expression in all hair cells. In previous studies, AAVs transduced inner hair cells (IHCs) efficiently (Akil et al., 2012; Askew et al., 2015; Al-Moyed et al., 2019), leading to striking success in animal models for genes used only by inner hair cells (e.g., Vglut3, Otof). But few outer hair cells (OHCs) are transduced by conventional rAAV, so they are not sufficient for most deafness genes. Recently, new variants of AAV (exoAAV1, Anc80, AAV9-PHP.B) have been developed that are far more efficient in transducing OHCs, and these have been used for gene addition to both IHCs and OHCs (Pan et al., 2017; György et al., 2017; György et al., 2018). Significant but incomplete rescue of hearing has been demonstrated in mice lacking functional LHFPL5, TMC1 or CLRN1, because the best capsid, such as AAV9-PHP.B, still do not transduce 100% of OHCs. Thus, two major challenges remain: AAV capsids capable of efficient transduction of inner ear cells (e.g., inner hair cell and/or outer hair cell) of many species are needed, and strategies for delivering of deafness genes that are too large to be packaged into single AAV genomes are needed.

Diseases of the eye have been an attractive target for gene therapy as well. Many involve progressive retinal degeneration, so that a decades-long window for treatment exists in the early stages. The eye is a closed compartment, so that a much smaller amount of viral vector is needed; it is thought to be immune-privileged, so that AAV will elicit a muted immune response; and the retina is easily viewed, so that progression or reversal of the disease is easily monitored. The remaining problems for gene therapy in the retina include, but not limited to, the delivery of a large gene which exceeds the packaging capacity of AAVs into the eyes.

Usher Syndrome type 1 (USH1) is a recessively inherited syndrome characterized by profound congenital deafness and absence of vestibular function, and progressive blindness beginning in the second decade. Because patients who lack hearing and balance rely on vision for communication and mobility, the late-onset blindness is particularly devastating. Mutations in the PCDH15 gene, which encodes the protocadherin-15 protein (PCDH15) cause Usher syndrome type 1F (USH1F). In the ClinVar database, there are 80 pathogenic or likely pathogenic variants. In the Ashkenazi Jewish population, however, a single, founder mutation (c.733C>T; p.R245X) accounts for 64% of cases (Ben-Yosef et al., 2003). In the United States about 40 children are born each year with Usher 1F and there are 2500-3500 patients total. There are perhaps 10,000-15,000 USH1F patients worldwide. Gene therapy, to replace or repair the mutant gene, could prevent or repair the blindness and deafness. There are mild mutations (e.g. R134G, G262D and V528D) that do not cause blindness or compromise balance (Ahmed et al., 2003; Doucette et al., 2009), and these are associated with later onset hearing loss that may be treatable. Progressive blindness can be targeted by Usher 1F therapy in that it occurs over several decades. It is likely that there is a large window of opportunity for treatment and a potential patient pool of about 1,000 who retain some vision. Any therapies that preserve hearing in mouse models are likely to prevent blindness in human.

Figure 1B:
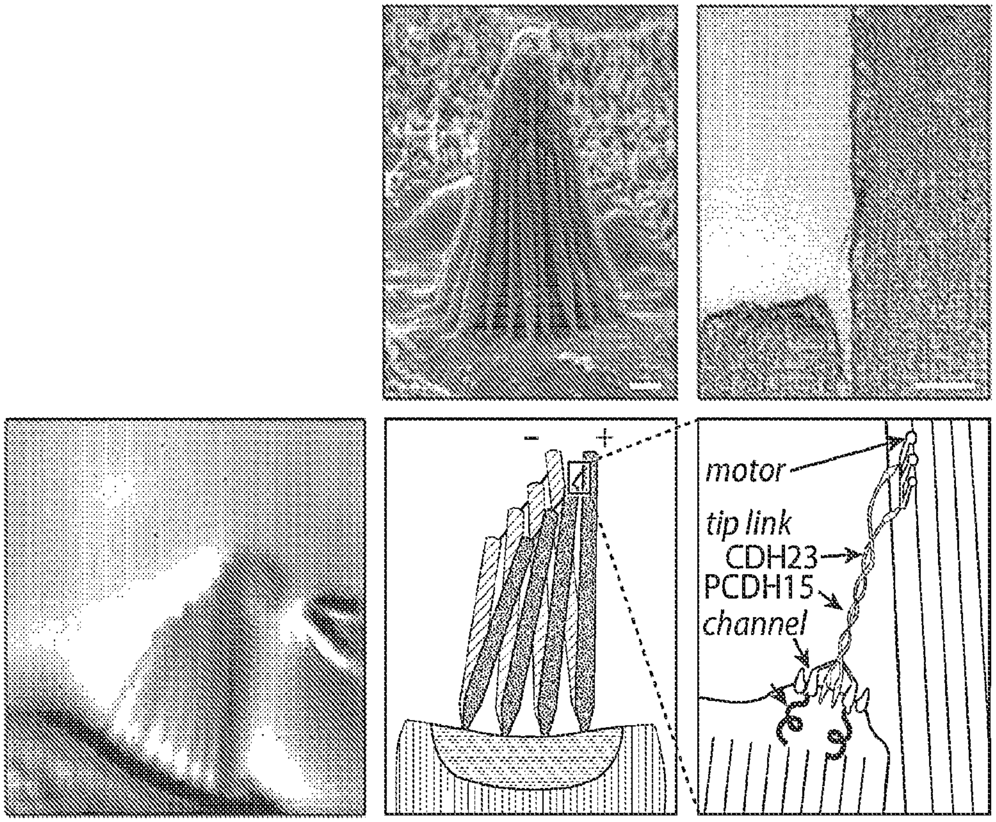

In hair cells of the inner ear, the PCDH15 protein forms the 'tip link' between adjacent stereocilia (Kazmierczak et al., 2007), pulling directly on ion channels to initiate the electrical response to sound (FIG. 1B). PCDH15 is a large protein of up to 1955 amino acids, forming 11 link-like 'extracellular cadherin' (EC) repeats and a transmembrane domain (FIG. 1A) (Ahmed et al., 2001; Ge et al., 2018). The X-ray crystal structure of the PCDH15 extracellular domain has been solved, so the structure of PCDH15 is known at the level of single atoms (Sotomayor et al., 2012; Araya-Secchi et al., 2016; Powers et al., 2017; Narui and Sotomayor, 2018; De-la-Torre et al., 2018).

Usher 1F patients have profound deafness at birth, so it may be that hair cells in newborn human Usher 1F cochleas have already degenerated beyond repair and that the therapeutic opportunity for deafness is limited. On the other hand, the blindness in Usher 1F does not appear until the second decade and is often not complete before the fourth decade. It is characterized first by the loss of rod photoreceptor cells (used in dim light) causing night blindness, and by subsequent loss of the cone photoreceptors, producing complete blindness. There is thus a long window for treatment-perhaps 20-30 years—and a potential patient population of 1500-2500 in the U.S. Therefore, it is meaningful to test the best strategy in the eye because the therapeutic possibilities for reversing blindness are great.

Figure 1C:
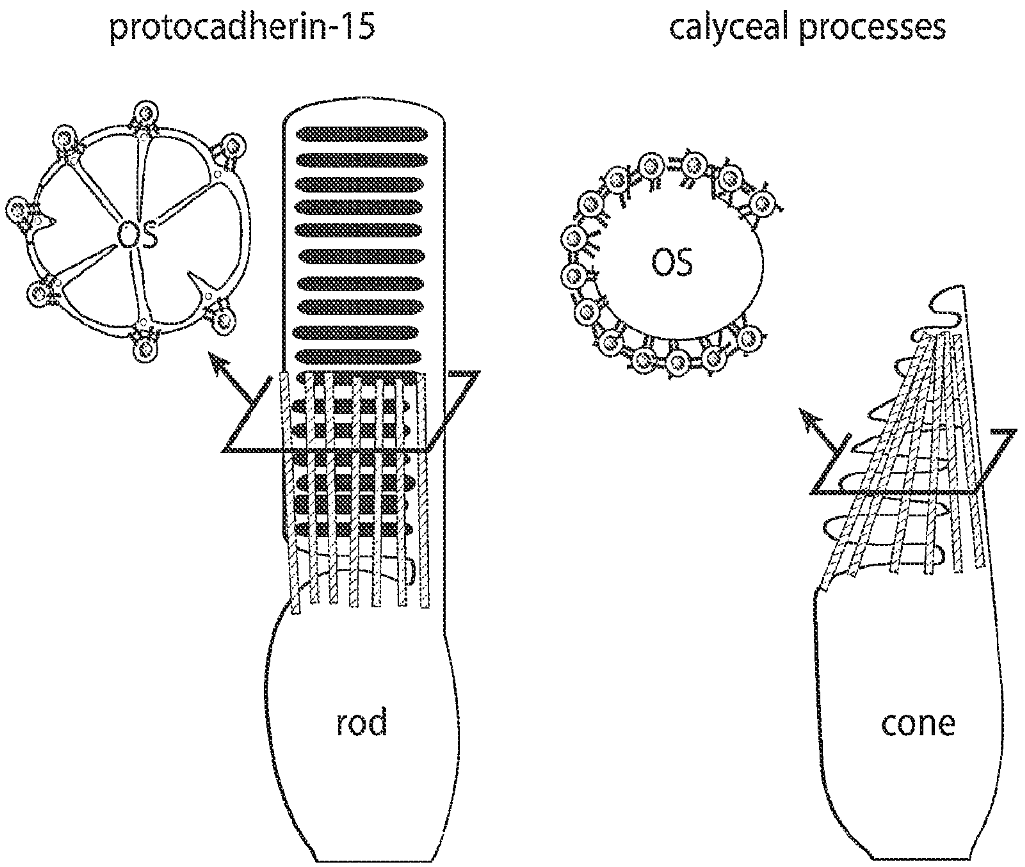
Figure 1D:
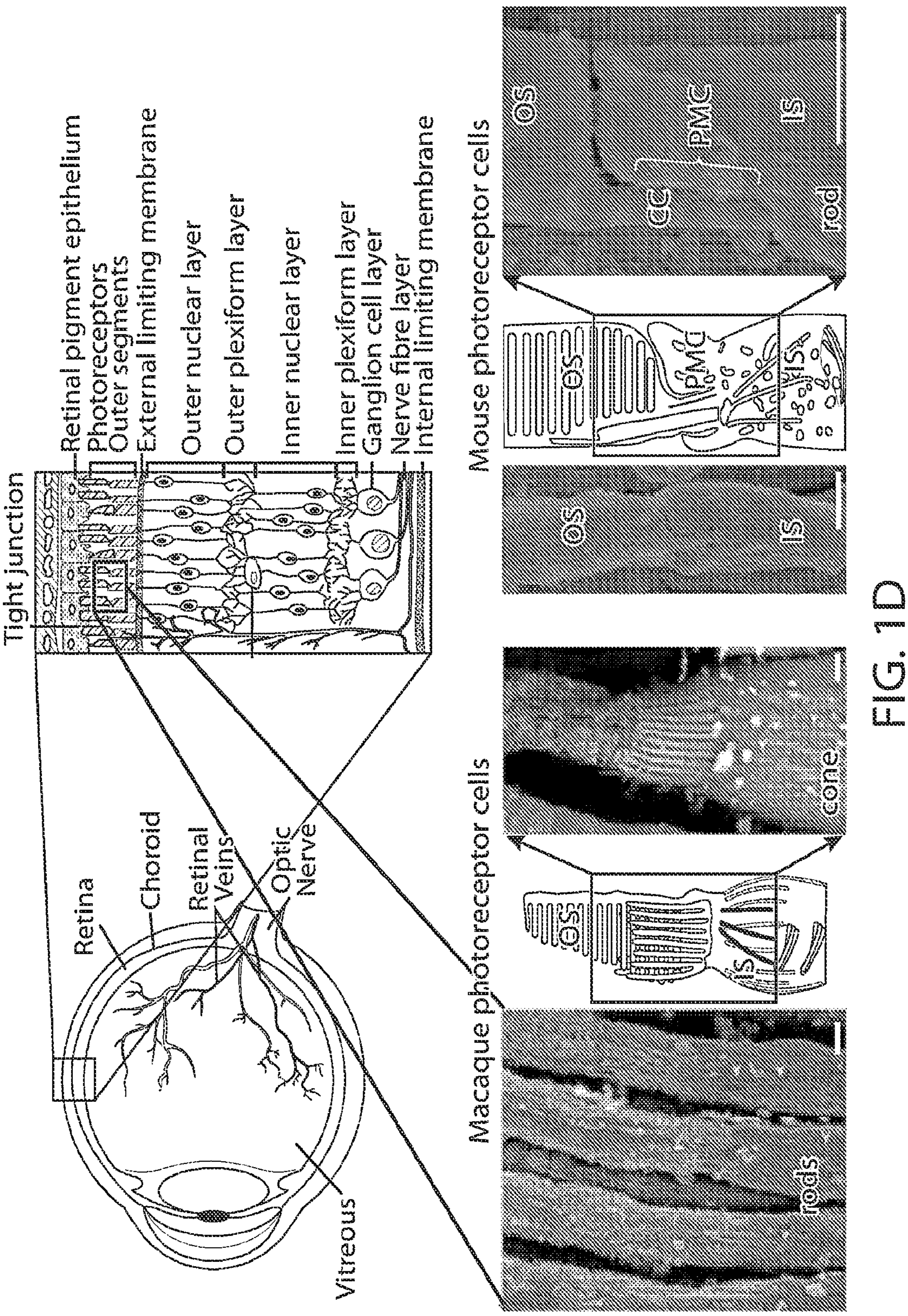
Figure 1E:
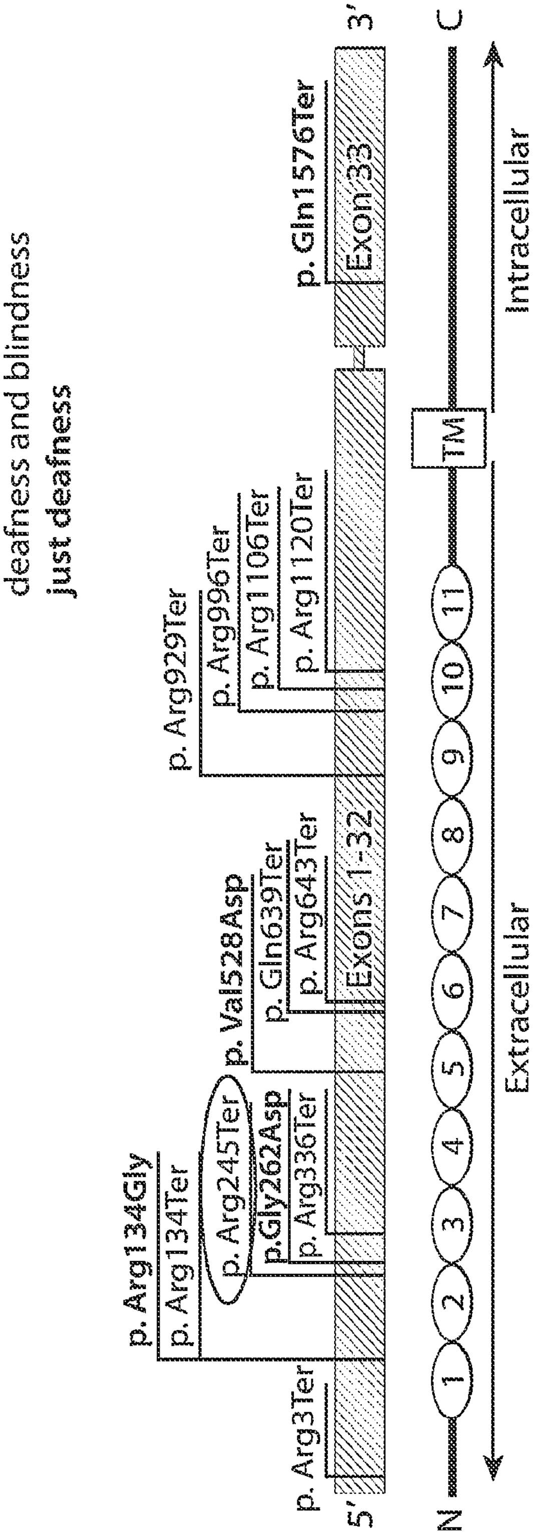

In the retina, PCDH15 is found in the photoreceptor cells, both rods and cones (FIG. 1C). These cells have an inner segment, which contains the nucleus and synaptic machinery, and an outer segment, which has the light-sensing opsin proteins. Inner and outer segments are connected by a narrow, fragile, cilium-based stalk. In humans, the outer segment is stabilized by "calyceal processes" that emanate from the inner segment and form a cup- or basket-like structure around the outer segment (FIG. 1C-1D). It is thought that PCDH15 ties the processes to each other or to the outer segment, and that mutations in PCDH15 destabilize the outer segment.

Accordingly, the present disclosure relates to the development of two AAV vectors that together encode full-length PCDH15 for treating deafness and blindness (e.g., Usher syndrome type 1F).

(i) Dual Vector AAV Delivery of Full-Length AAV in the Inner Ear

Figure 2A:
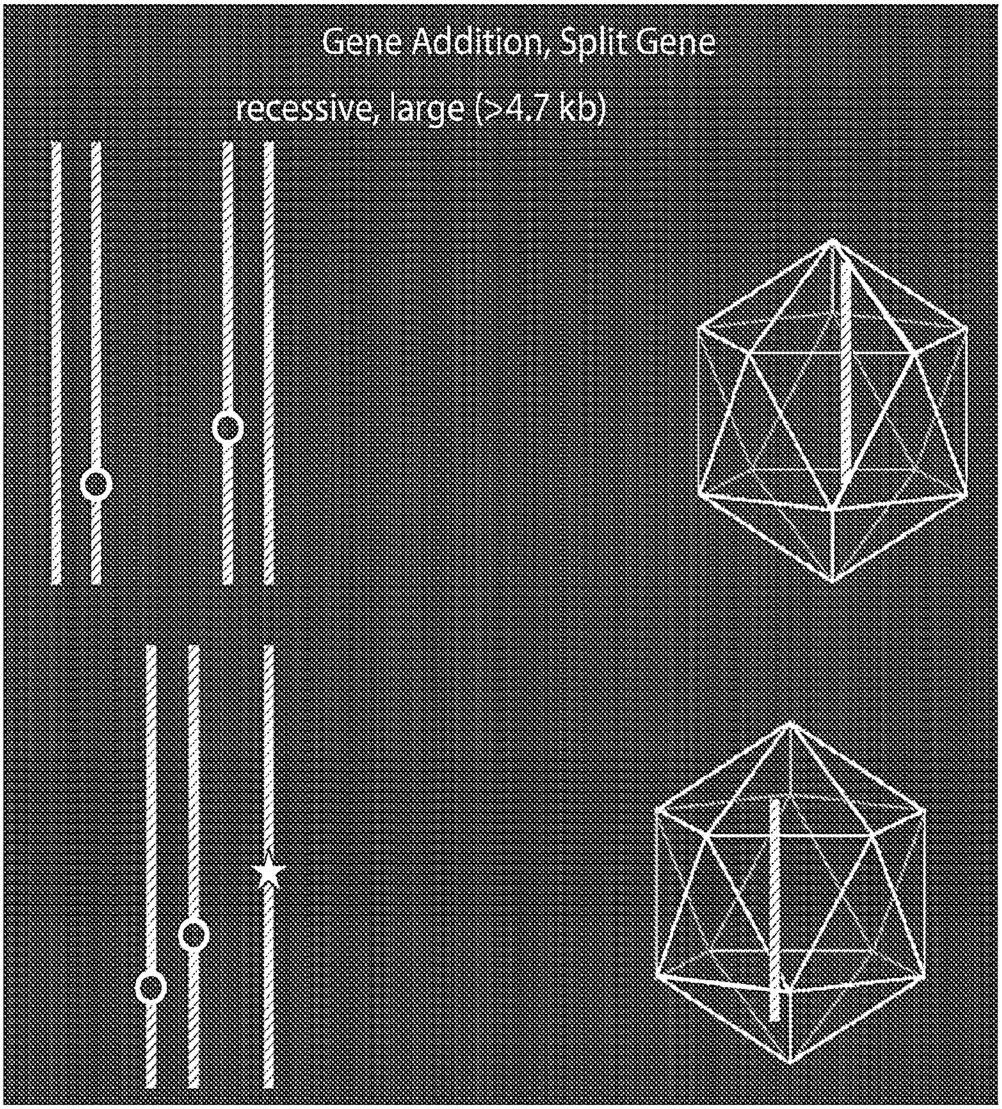
FIGS. 2A-2H are schematic illustrations of dual AAV vectors for delivering full-length PCDH15 to cells.
Figure 2B:
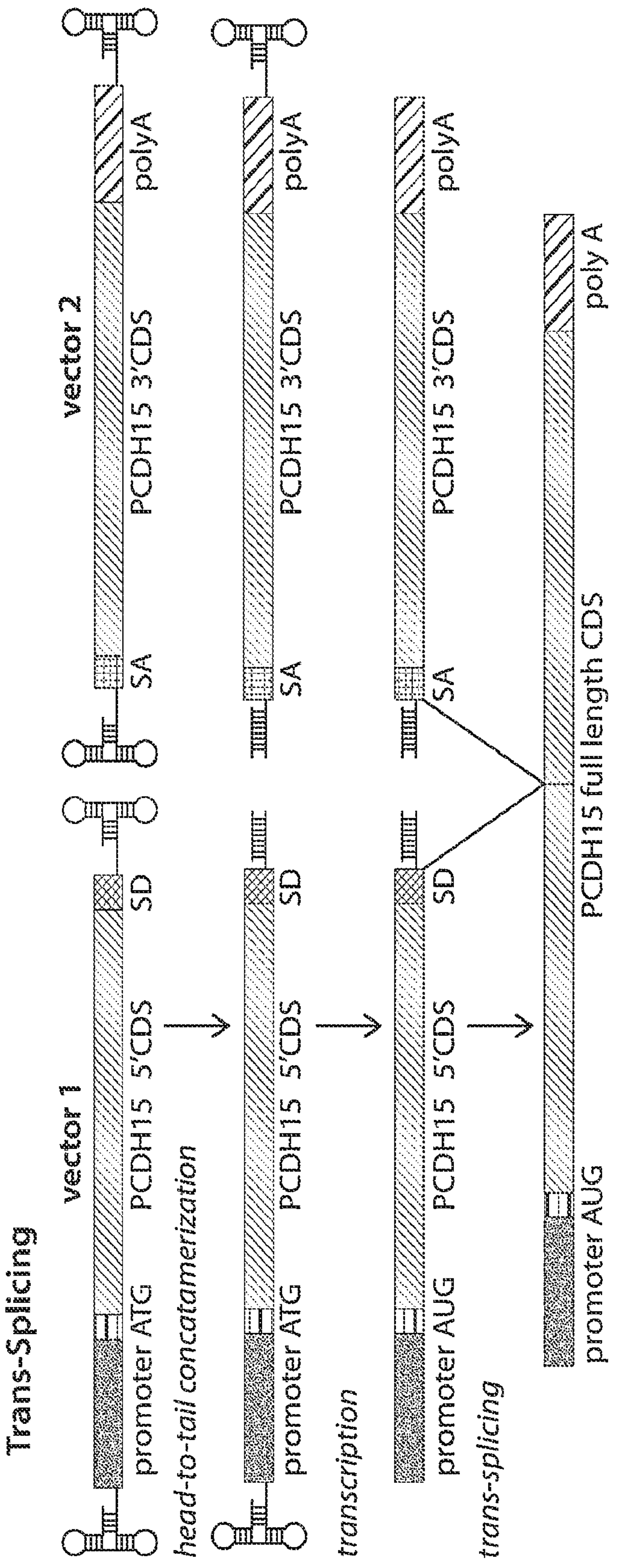
Figure 2C:
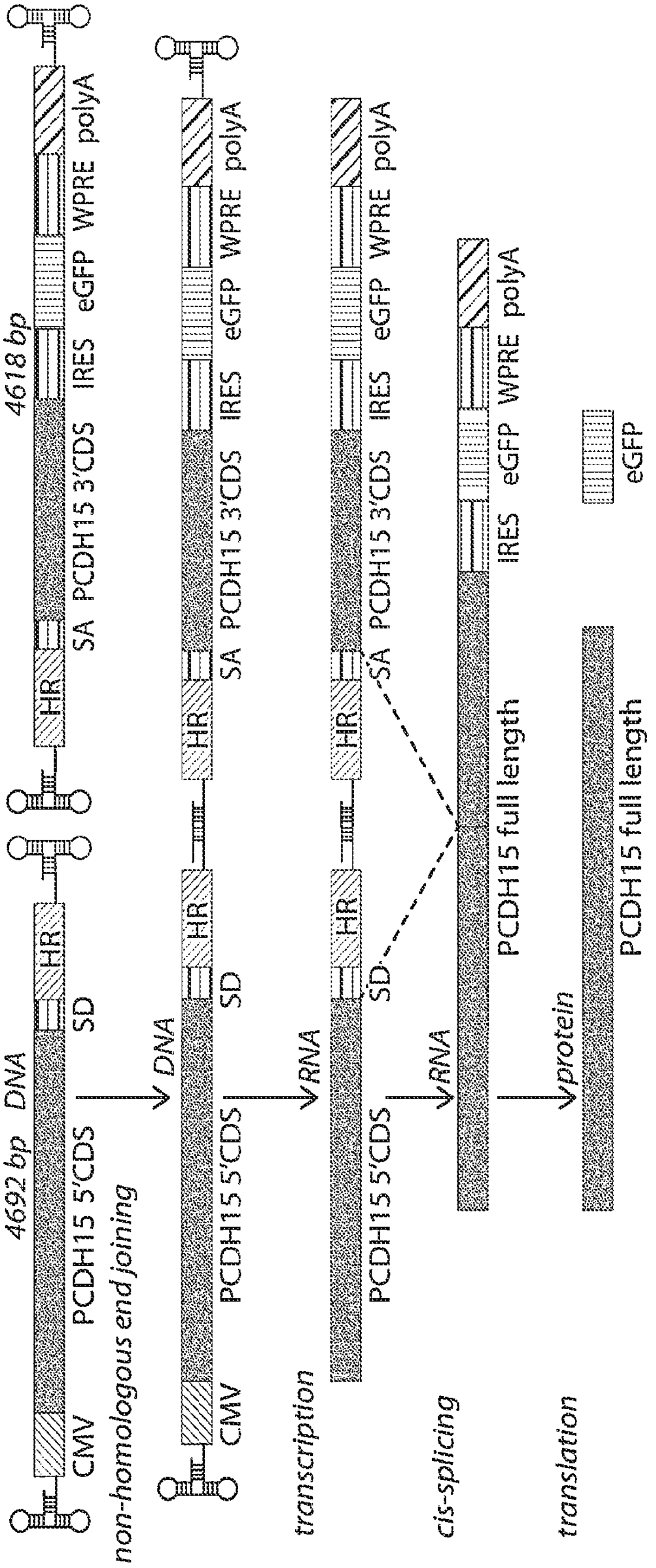
Figure 2D:
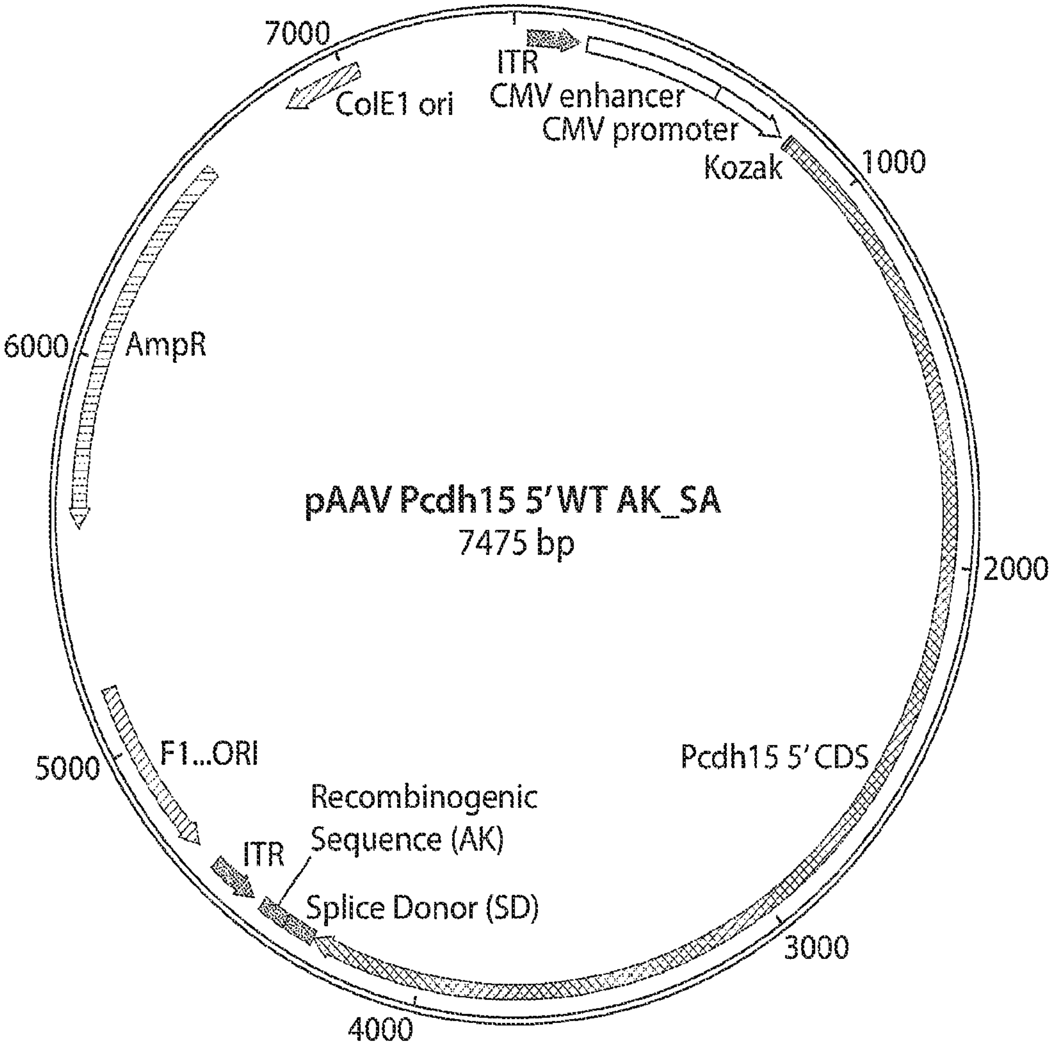
Figure 2E:
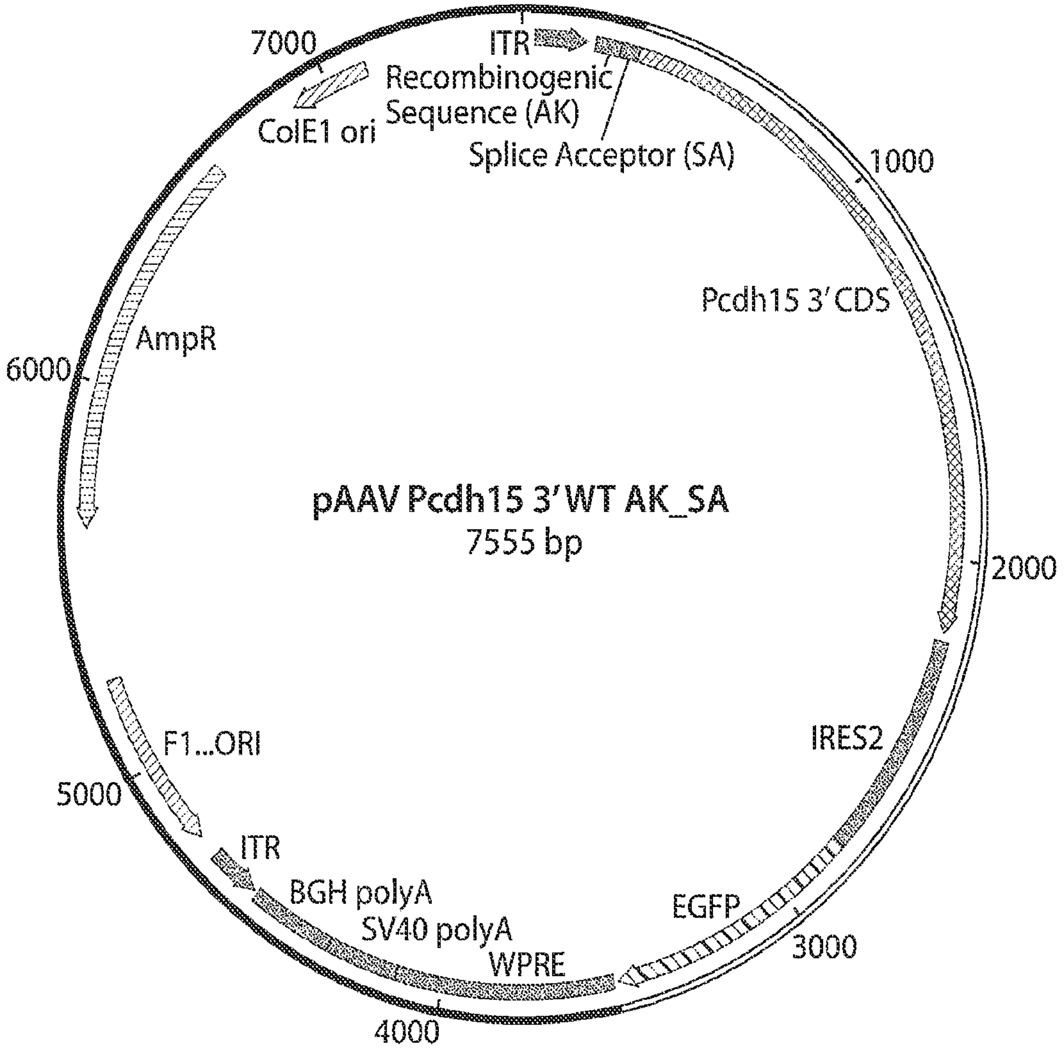

Both trans-splicing and hybrid methods are used to recombine and express a split PCDH15 coding sequence (FIG. 2A). First two AAV vectors are produced. Vector 1 includes a promoter, the N-terminal half of PCDH15, and a splice donor site. Vector 2 includes a splice acceptor, the C-terminal half of PCDH15, an HA tag, and a poly-A segment (FIG. 2B). Vector 2 can also include an IRES and eGFR coding sequence following the C-terminal half of PCDH15. A WPRE sequence can also to be added between coding sequences and poly A segment (FIG. 2C). Once in the same cell, concatemerization of the ITRs can lead to the internal ITR flanked by mRNA splice sites and splicing that creates a full-length PCDH15 coding sequence (FIG. 2B-2C). This method has worked well for dual-vector expression of otoferlin in inner hair cells of the cochlea (Al-Moyed et al., 2018). FIGS. 2D-2E are schematic illustration of vector maps of AAV vector 1 and vector 2 for delivering full-length PCDH15 to cells.

Figure 2F:
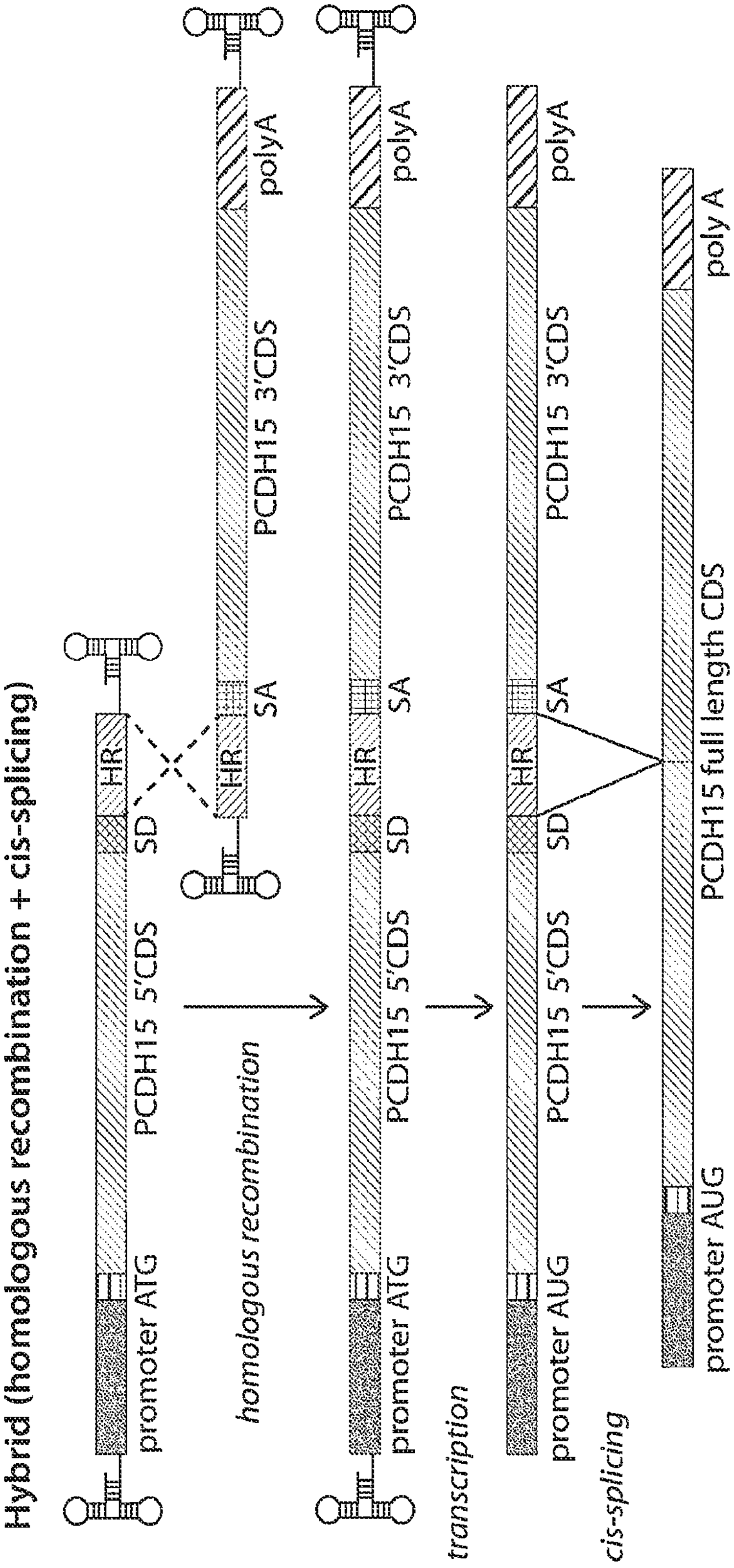
Figure 2G:
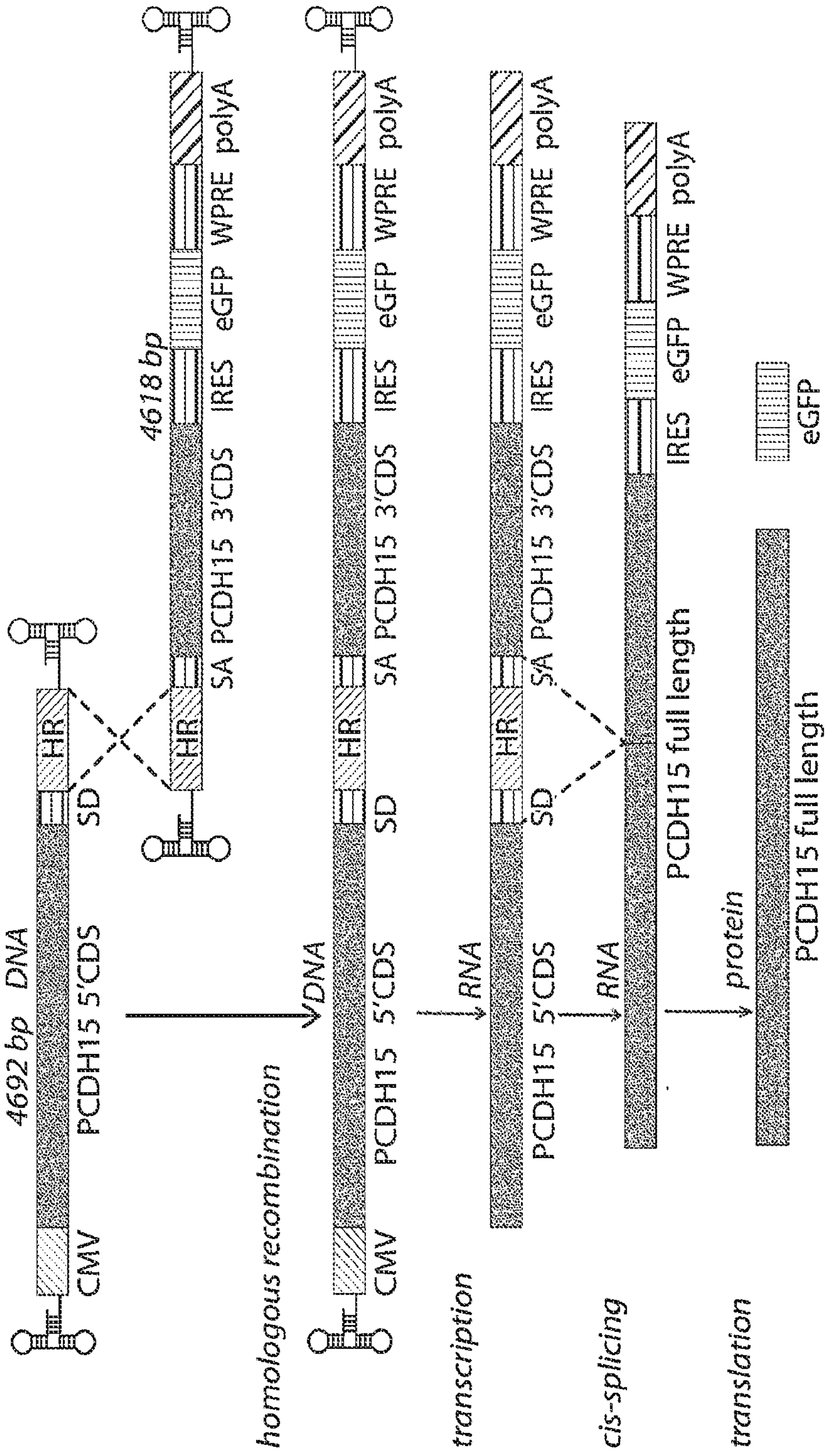

Alternatively, a hybrid method is also tested, in which the splice donor of vector 1 is followed by a highly recombinogenic sequence from F1 phage (HR), and the splice acceptor of vector 2 is preceded by the HR sequence. In the same cell, the F1 sequence recombines creating an artificial intron, which is spliced out to create full-length coding sequence (FIG. 2F). This has also been used for otoferlin, with an efficiency similar to trans-splicing.

Figure 2H:
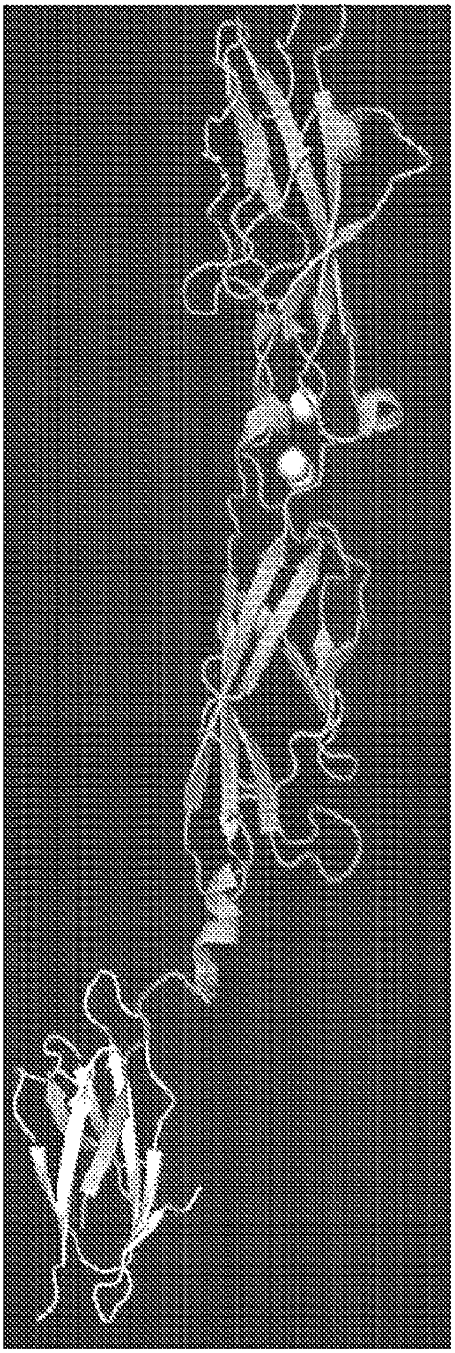

The dual vectors were packaged in the AAV9-PHP.B capsid. HEK cells were first transduced with both N- and C-terminal vectors and proper recombination with RT-PCR across the splice junction is evaluated. Expression of full-length PCDH15 was detected with an antibody to an HA tag introduced at the C-terminus (FIG. 2H). Proper membrane targeting of PCDH15 in HEK cells using live-cell labeling with the antibody to the extracellular N-terminal domain was then evaluated.

Expression of PCDH15 and rescue of function in knockout mice was then tested. The dual AAVs were injected into the cochleae of P1 conditional knockout mice, and expression of full-length PCDH15 was evaluated at P5 or P30. At P5, expression and localization of full-length PCDH15 in hair cells was evaluated with antibody labeling, using both light and electron microscopy. Efficiency of recombination can be tested by comparing the number of PCDH15-labeled cells in these cochleas, to the number in cochleas transduced with a single vector expressing a short, HA-tagged protein (LHFPL5; György et al., 2017). Rescue of hair-cell development was then tested with SEM. Finally, hair-cell mechanotransduction with FM1-43 loading and physiology was then tested. If virus-injected ears have hair cells that label with FM1-43, single-cell electrophysiology was used to test whether dye-labeled cells have functional receptor currents. In adult animals (P30, P60), hearing of injected mice were tested by ABR. Vestibular function was also tested with assays for circling and swimming.

Figure 3A:
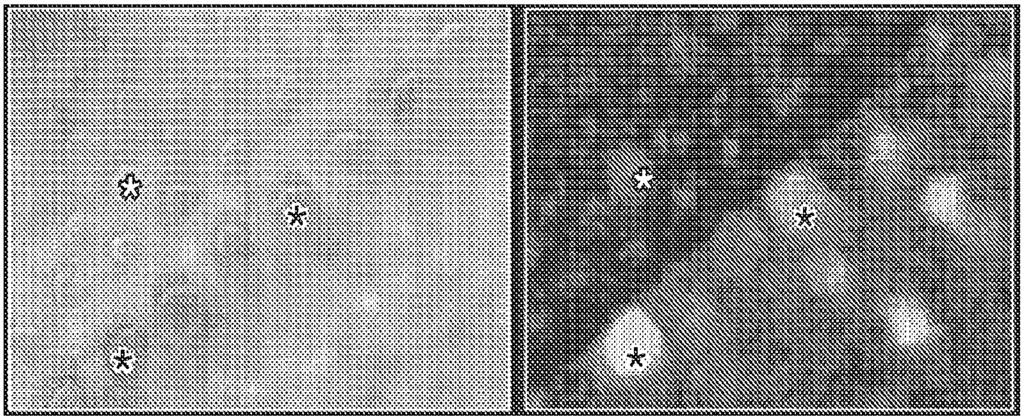
FIGS. 3A-3C are graphs showing dual vector AAV for delivering full-length PCDH15 to the inner ear.
Figure 3B:
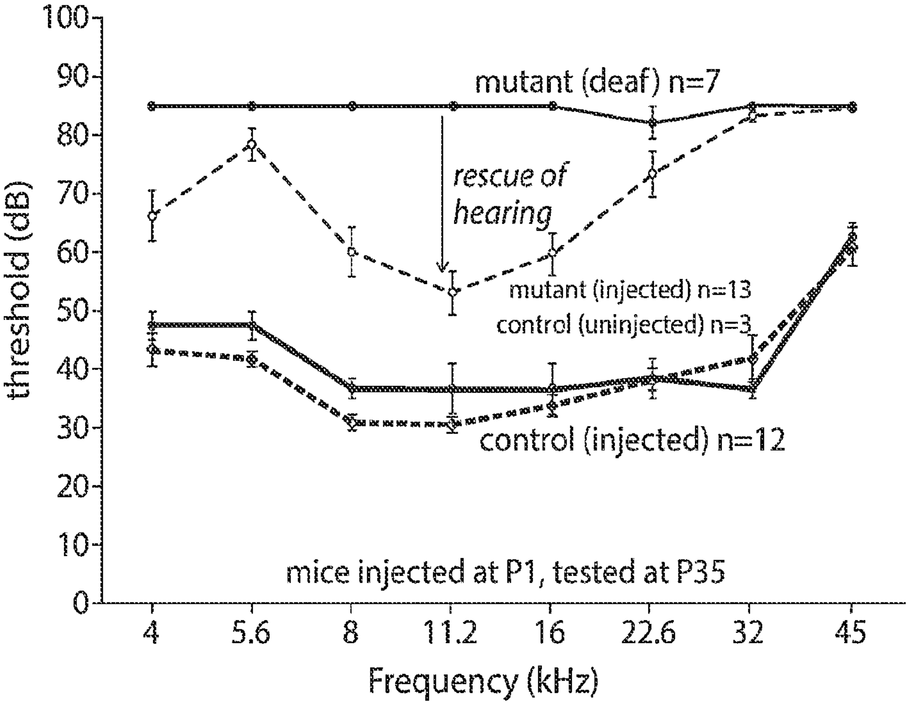
Figure 3C:
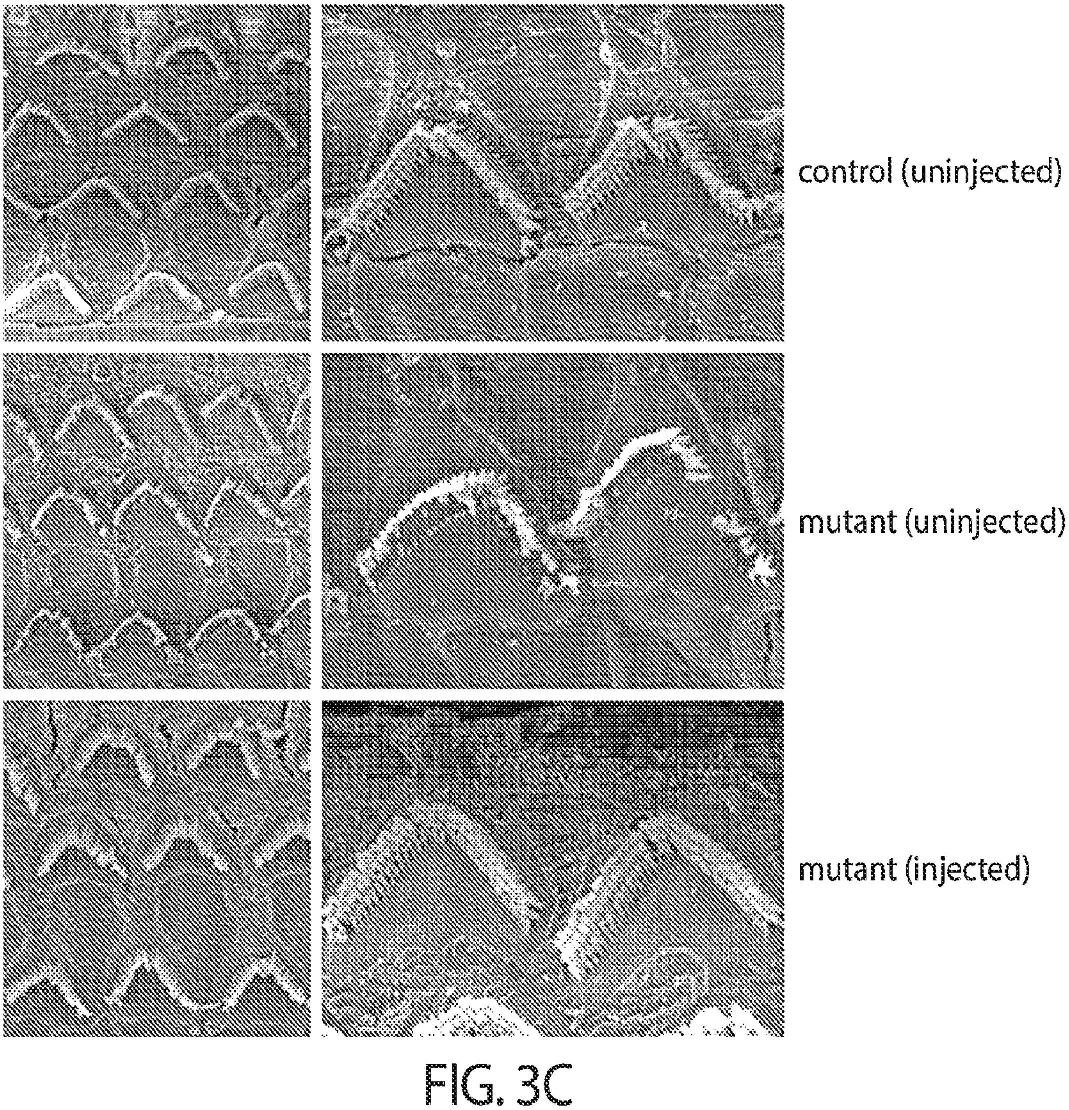

First, dual AAV vectors for PCDH15 and a HA tag (FIG. 2H) have been produced that encode full-length PCDH15 and have been injected into the inner ears of postnatal Pcdh15fl/fl×Gfi1-Cre mice. The recombination and splicing in cochlea cells were test. Test expression and localization of full-length PCDH15 in hair cells. Rescue of mechanotransduction at was tested at P5, and rescue of hearing and balance was tested at P30. Full length PCDH15 expression was detected in hair cells of neonatal mouse (FIG. 3A). These vectors also show substantial rescue of hearing, as assessed by ABR recording (FIG. 3B). Electron microscopy shows that dual-vector delivery of PCDH15 rescued hair bundle morphology in the conditional knockout mouse model, as shown in FIG. 3C. The control mouse has well-developed hair bundles, seen at low (left) and high (right) magnification (top panel of FIG. 3C). The mutant shows disorganized bundles, lacking many stereocilia (middle panel of FIG. 3C). In a mutant injected with dual vectors encoding PCDH15, many of the hair bundles are normal (bottom panel of FIG. 3C).

Further, dual-AAV delivery of the primate PCDH15 coding sequence leads to production of a tagged PCDH15 in non-human primate hair cells is tested using the dual-AAV vector system. The AAV9-PHP.B capsid is used initially, and other enhanced capsid proteins for primates are also tested. Again, the PCDH15 coding sequence includes a small epitope tag (either 3×HA or tandem GCN) in the extracellular MAD12 domain. The dual vectors are injected through the round window membrane in *Macaca fascicularis* monkeys (György et al., 2018). After one month, animals are sacrificed and expression of tagged PCDH15 assessed with an antibody to the tag. Robust expression in hair cells, and antibody label near the tips of the shorter stereocilia is expected. Toxicity with ABR for hearing and histology for inflammation and cell death is assessed.

(ii) Dual Vector AAV Delivery of Full-Length AAV in the Eye

First, rescue of visual pathology was tested in the mouse retina, using the best-performing therapy for the inner ear. It was confirm that the conditional Pcdh15$^{R245X/R245X}$ knockout mice of Usher 1F have vision loss. A variety of AAV capsids are tested (e.g., AAV8, AAV9, AAV-BP2 and AAV9-PHP.B) for effective transduction of photoreceptors. AAV-PHP.B worked well. Further, effective promoters for driving gene expression in photoreceptors were previously identified, and ProA6 promoter showed good efficacy (Jüttner et al, 2019). These mice produce no functional PCDH15 protein so they are a good model for this strategy.

Two weeks after dual-AAV vector injection into retina, expression and localization of the PCDH15 protein was evaluated. Confocal microscopy and electron microscopy are used to assay expression and localization by immunoreactivity in photoreceptors, with antibodies to the tag or to PCDH15. Mouse photoreceptors do not have calyceal processes so localization to processes cannot be evaluated, but whether the PCDH15 protein is made by photoreceptors can still be assessed.

In older mice, functional rescue by measuring the electroretinogram (ERG), a small electrical signal in the retina induced by a short flash of light, is tested after dual AAV vector injection. At six months of age, mice lacking PCDH15 show moderate (~50%) reduction of the ERG amplitude (Haywood-Watson et al., 2006; Ahmed et al., 2008). Therefore, restoration of ERG amplitude in Pcdh15R245X/R245X photoreceptors is assessed six months after injection. The ERG amplitude is restored to nearly normal level.

Figure 4A:
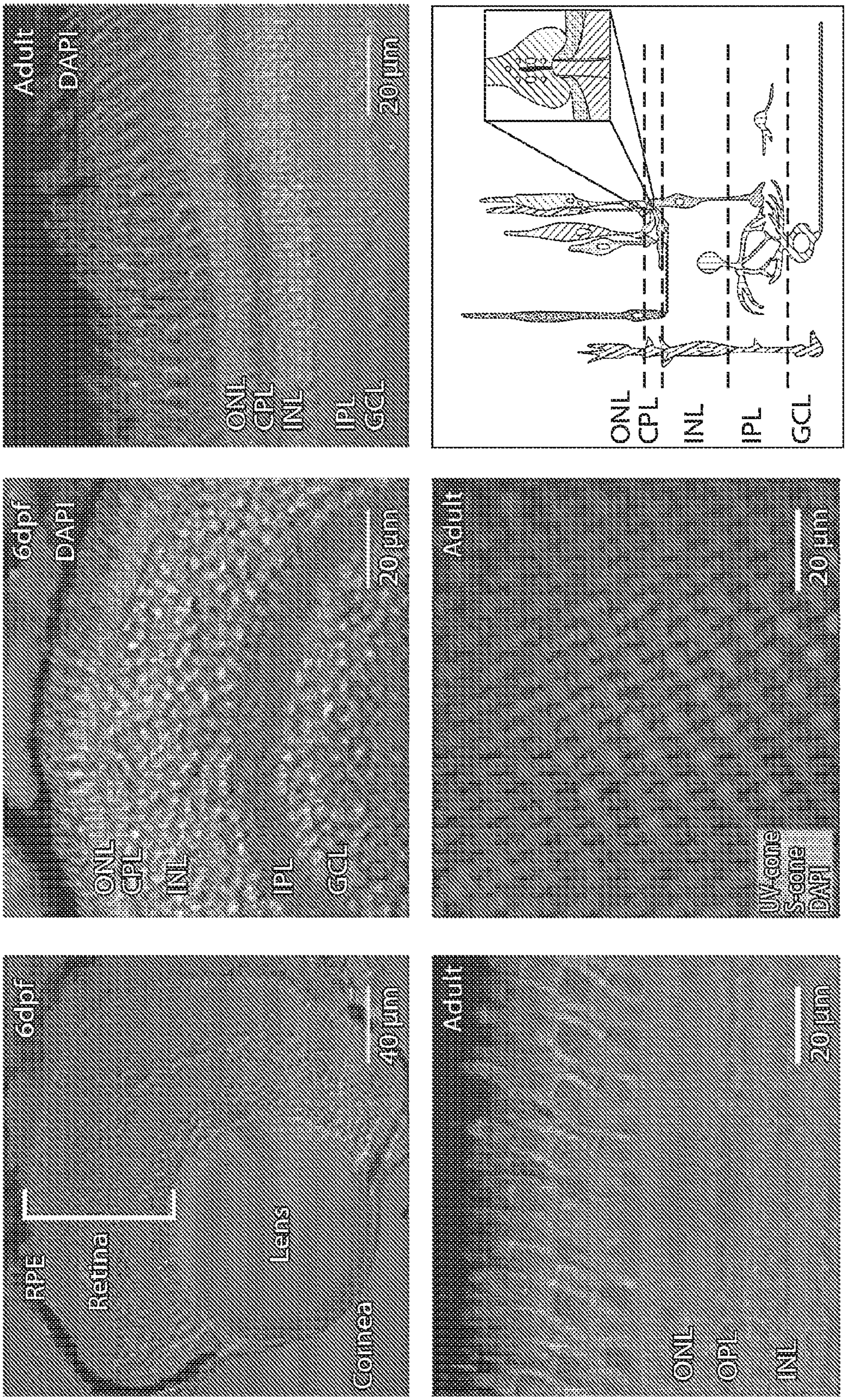
FIGS. 4A-4E are graphs showing PCDH15 expression in the retina.
Figure 4B:
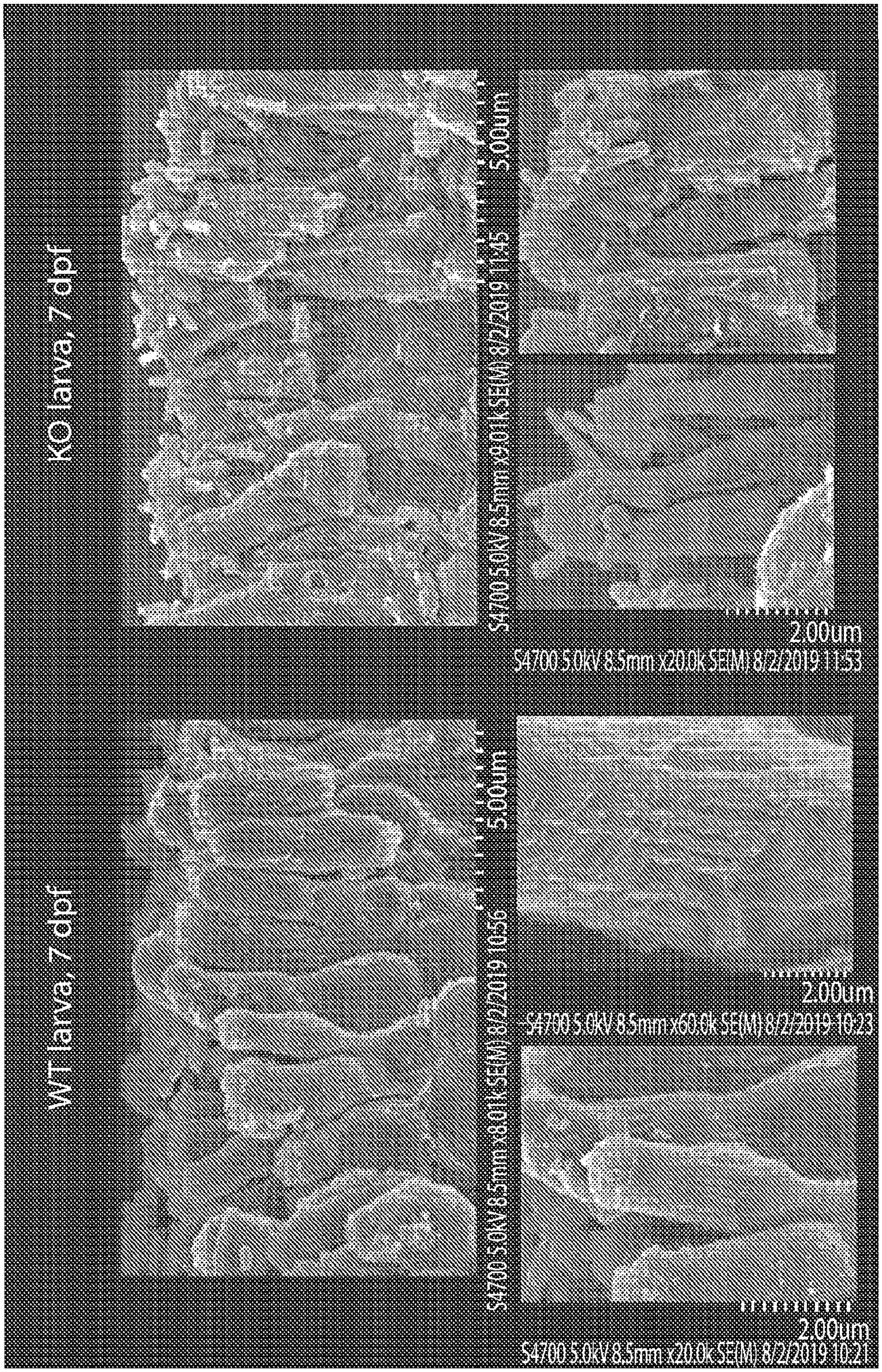
Figure 4C:
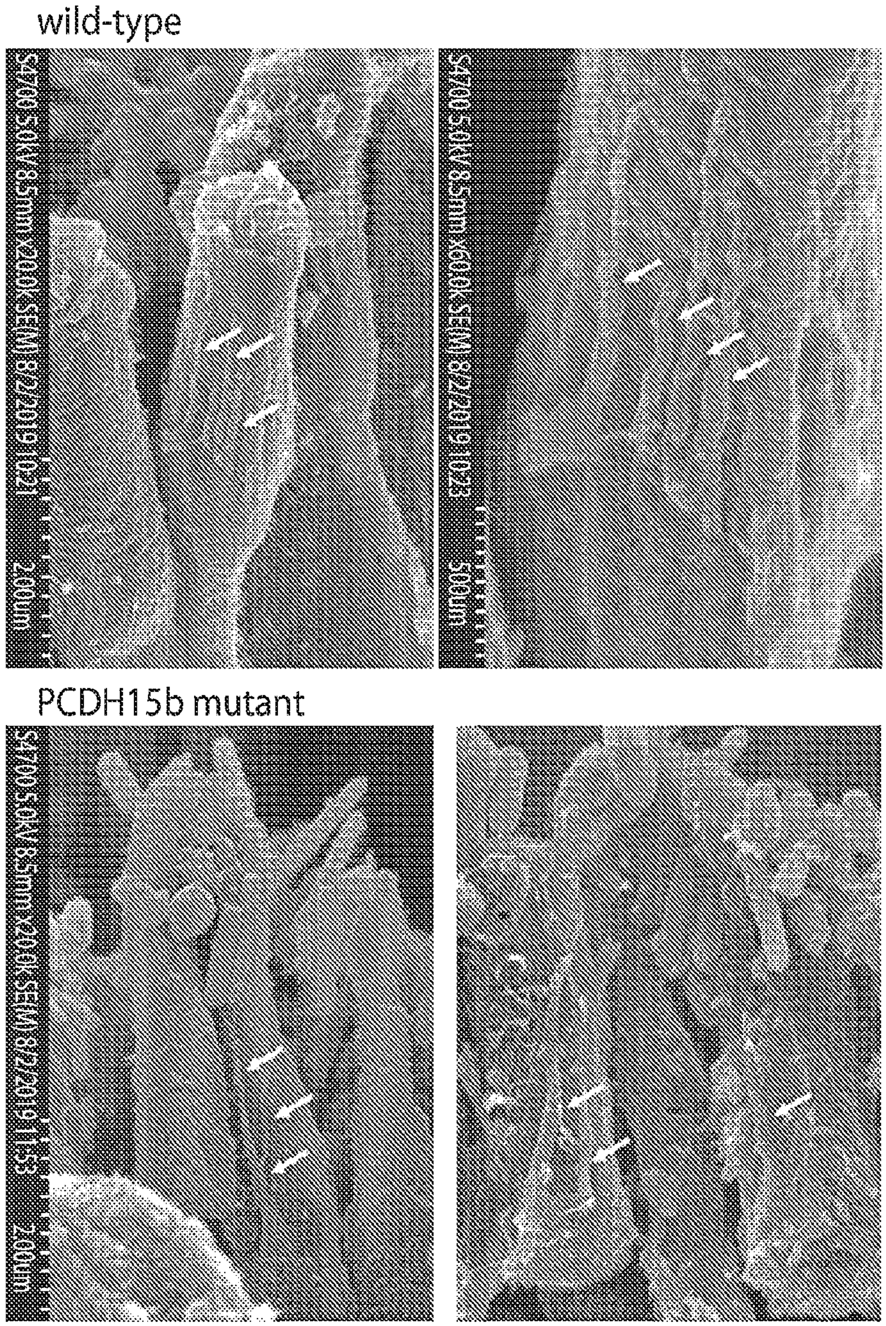
Figure 4D:
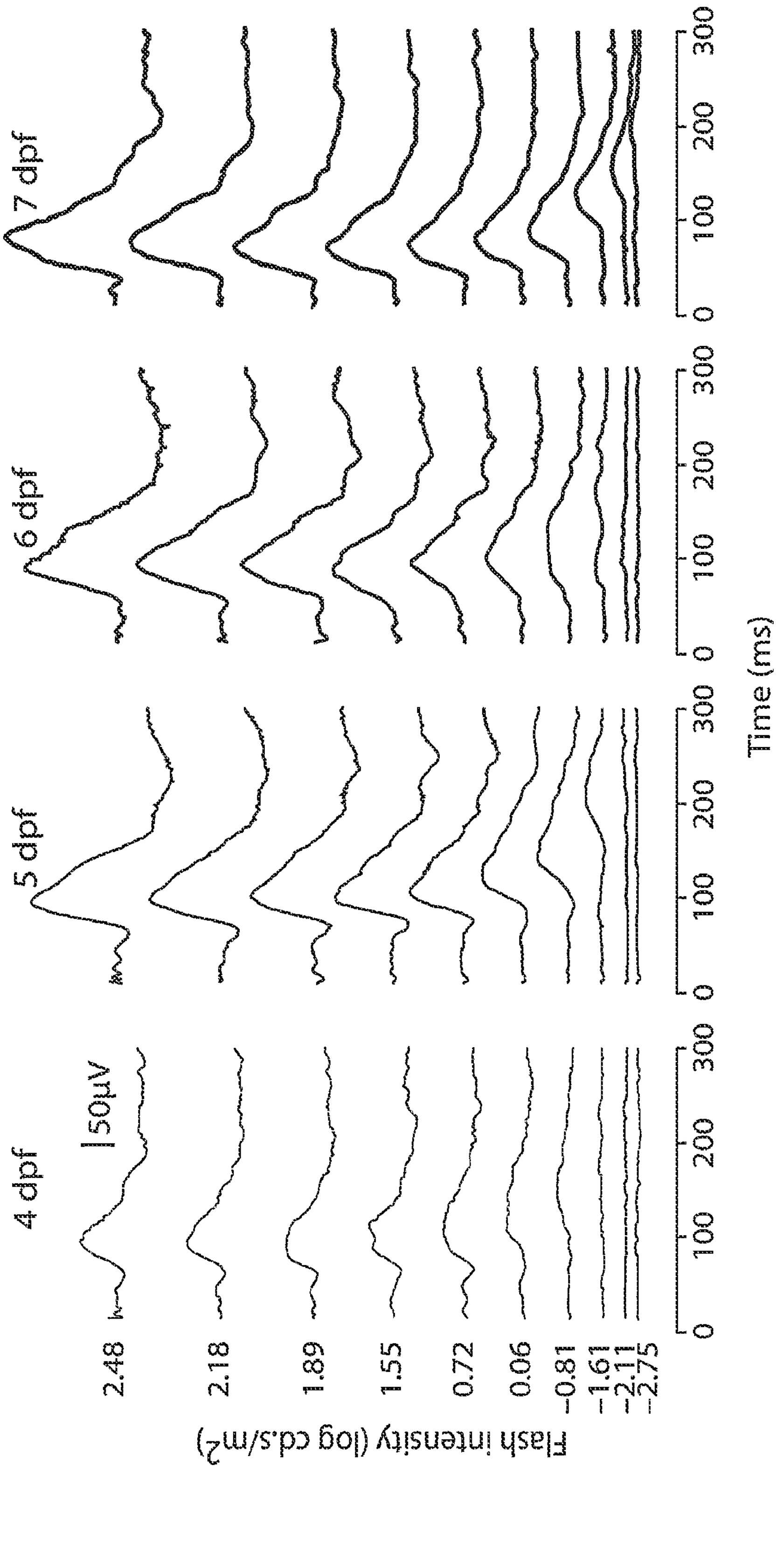

If the visual deficit in the Usher 1F mouse model is too weak for robust assessment of rescue, a different animal model for Usher 1F which does have a pronounced visual deficit can be used: the zebrafish. Zebrafish are an excellent model for studying Usher syndrome in the retina. The zebrafish retina is more like the human retina than is the mouse: zebrafish and human retinas have mostly cone photoreceptors (cone-dominated retina; 40% rods and 60% cones) (FIG. 4A), whereas mice have mostly rods. Zebrafish and human photoreceptors have calyceal processes, whereas mice do not. A further advantage is that zebrafish have functional retinas just 7 days after the egg is fertilized and retinas in the Pcdh15b knockout fish show pathology by that age, compared to six months in mice, so testing would be far faster and cheaper. They have the same USH genes and USH gene mutations produce retinal cell death. Phillips and Westerfield used CRISPR/Cas9 gene editing to delete Pcdh15b in zebrafish. WT and KO larva are shown in FIG. 4B. An electroretinogram of early development in WT larvae is shown in FIG. 4C. A robust ERG is present just 5-6 days after fertilization of the egg. Overall visual function with the opto-kinetic reflex (OKR) assay (FIG. 4D).

Figure 4E:
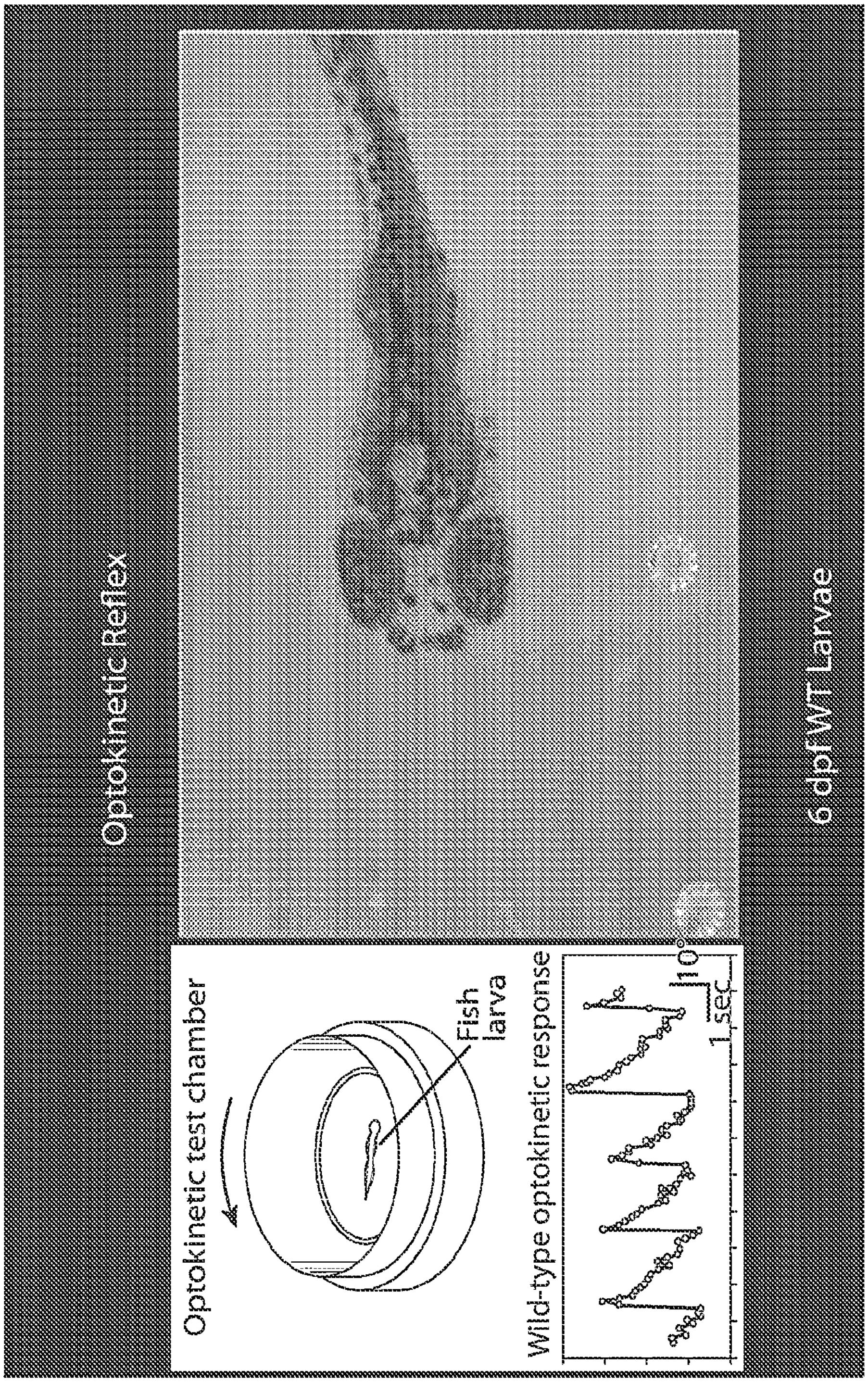

A line of zebrafish carrying a mutation in the Pcdh15b gene is used. Photoreceptor pathology in larval zebrafish retinas are shown in FIG. 4E. Wild-type zebra fish showed well-formed parallel calyceal processes (arrows) surround the outer segments of photoreceptors (right panel shows higher magnification). Mutant zebra fish showed fewer processes with un-uniform diameter, and sometimes branched morphology. Outer segments are disorganized. Dual-AAV vector encoding the full-length PCDH15 is injected to Zebra fish retina using at the one-cell stage. Gene expression will be restricted to retinal photoreceptors by driving expression with the cone-specific ProA7 promoter. Rescue of function at 7 days post-fertilization is tested. The development of the retina is evaluated with light microscopy and scanning electron microscopy, and retinal function is tested with ERG recording. Overall visual function with the opto-kinetic reflex (OKR), in which immobilized zebrafish will follow a moving visual pattern by moving their eyes Further, this strategy is tested in non-human primates. In retinas of non-human primates, AAVs encoding the most effective therapy from mouse studies is injected. PCDH15 expression is assessed in photoreceptor cells. Toxicity by ERG and histopathology is also evaluated. Subretinal injections of AAVs encoding epitope-tagged PCDH15 under the cone-specific ProA7 promoter is performed. After three weeks, animals are euthanized, and retinas obtained for histological analysis. Protein expression and localization to calyceal processes is assessed with an antibody to the epitope tag, to specifically label the delivered PCDH15 protein and distinguish it from endogenous. Immune response is evaluated by evaluating multifocal mononuclear cell infiltration. Toxicity is tested both with histology and with physiology. The ERG is measured from both eyes before the injection, and then just before euthanasia.

Example 2. Morphological Hair Bundle Rescue in Pcdh15 Conditional Knockout Mice

Figure 5:
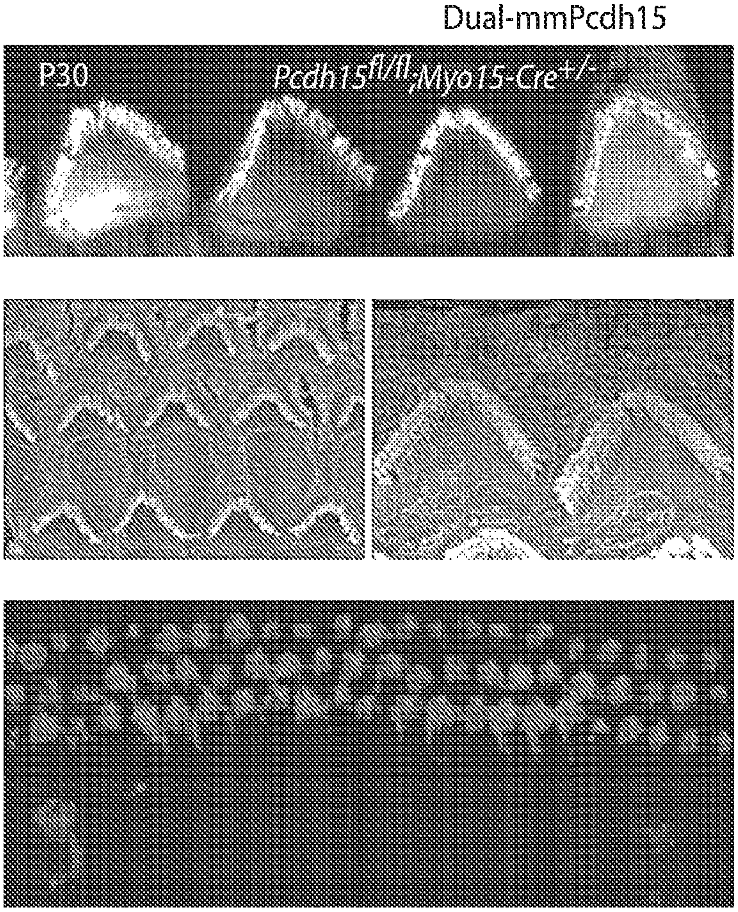
FIG. 5 shows the effects of dual-vector delivery of PCDH15 on hair bundle morphology in a Pcdh15fl/fl; Myo15-Cre+ mouse model of Usher 1F at P30. The top model shows phalloidin staining of CKO mice treated with dual vectors. The middle panel shows a scanning electron microscopy of a treated cochlea. The bottom panel shows the rescue of FM1-43 uptake in a treated cochlea.

Pcdh15 conditional knockout (Pcdh15fl/fl;Myo15-Cre+ mouse model of Usher 1F) were injected at P30 with dual AAV vectors encoding full-length PCDH15. Actin staining (FIG. 5, top panel) and scanning electron microscopy (SEM, FIG. 5, middle panel) showed robust hair bundle morphology at P30. Hair bundles in these mice appeared like those in wild-type mice. FM1-43 labeling at P30 demonstrated robust rescue of mechanotransduction in outer hair cells (OHCs), and significant rescue of FM1-43 loading in inner hair cells (IHCs), as compared to normal hearing littermates (FIG. 5, bottom panel).

Example 3. HA-Tagged PCDH15 Trafficking to the Stereocilia

Figure 6A:
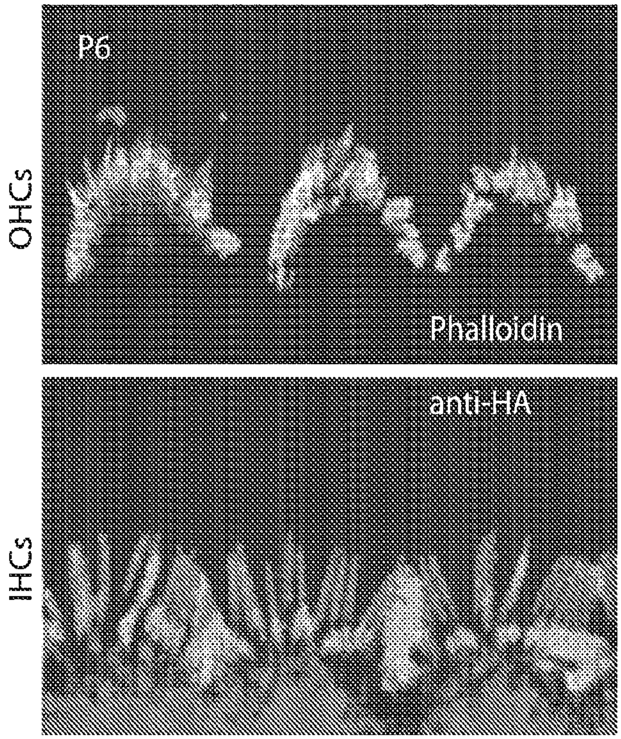
FIGS. 6A-6C show the effects of N-terminal HA tag on PCDH15 trafficking to the stereocilia.
Figure 6B:
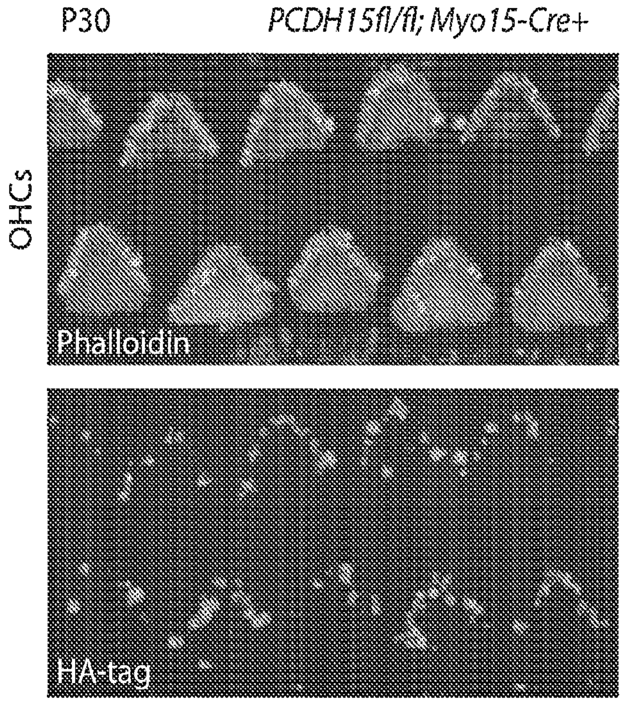
Figure 6C:
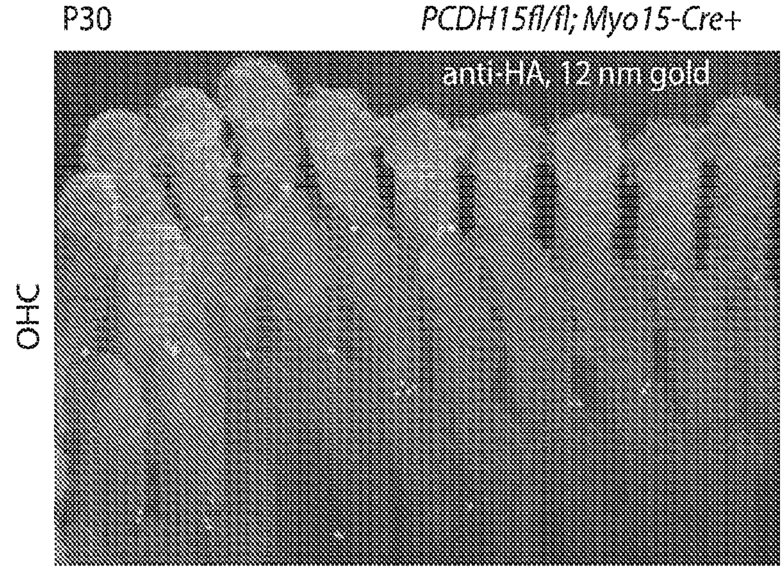

Neonatal Pcdh15 conditional knockout mice were injected at P1 with dual vectors encoding PCDH15 with an N-terminal HA tag to test if the HA epitope tag affects proper trafficking of PCDH15 to the tips of stereocilia. Hair bundles were labeled with phalloidin and antibody to the HA tag. With confocal imaging, strong anti-HA signal was detected at the tips of stereocilia in cochleas at ages P6 and P30 (FIGS. 6A and 6B). Immunogold SEM was also used to localize the HA-PCDH15 to the tips of outer hair cell stereocilia. Gold beads localized specifically at the position of the tip links (FIG. 6C). Multiple 12 nm gold beads (white dots) were detected in the SEM imaging, confirming that HA-tagged PCDH15 goes to the tips of stereocilia, and hence that the HA epitope tag does not adversely affect PCDH15 trafficking to the tips of the stereocilia.

Example 4. Hearing Rescue Using Dual Vectors Encoding PCDH15 or HA-PCDH15

Figure 7:
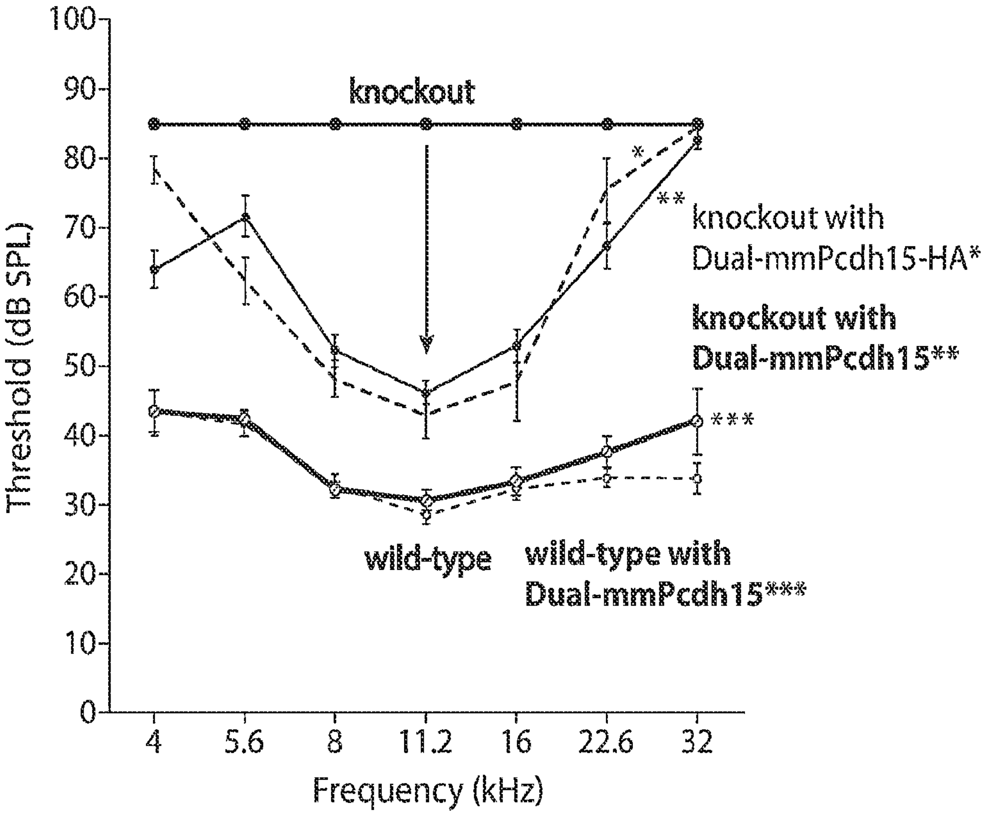
FIG. 7 is a graph of auditory brainstem evoked response (ABR) evaluation showing the effects of dual-vector delivery of PCDH15 on hearing rescue in a conditional knockout model. Knockouts injected with dual vectors encoding untagged PCDH15 or tagged HA-PCDH15 both have robust rescue of hearing. Wild-type mice injected with the vectors have normal thresholds indicating no toxicity for hearing.

Auditory brainstem evoked response (ABR) was conducted on conditional knockout (CKO) mice treated with dual vectors encoding PCDH15 or HA-PCDH15. Wild-type mice have best (lowest) threshold of 30 dB (FIG. 7, dashed line). Untreated Pcdh15 CKO mice were deaf at P30, with no response at the loudest test level delivered (FIG. 7; threshold above 85 dB, the highest tested). CKO mice treated with dual vectors encoding either PCDH15 or HA-PCDH15, showed robust rescue of hearing (FIG. 7). The threshold in rescued animals treated with either version was the same, confirming that HA-tagged PCDH15 is fully functional. The PCDH15 delivered with dual vectors to wild-type mice had the same thresholds compared to untreated wild-type indicating no toxicity for hearing (FIG. 7). These results indicate the effectiveness of dual-vector delivery.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A 3' isolated nucleic acid comprising a transgene, wherein the transgene comprises a nucleotide sequence encoding a second portion of a PCDH15 protein, and wherein the nucleotide sequence encoding the second portion of the PCDH15 protein comprises a sequence at least 95% identical to SEQ ID NO: 6.

2. A 3' isolated nucleic acid comprising a transgene, wherein the transgene comprises a nucleotide sequence encoding a second portion of a PCDH15 protein, a nucleotide sequence encoding a splice acceptor of an intron, and a nucleotide sequence encoding a recombinogenic sequence, and wherein the nucleotide sequence encoding the second portion of the PCDH15 protein comprises a sequence at least 95% identical to SEQ ID NO: 6.

3. A PCDH15 expression system comprising:

(i) a first 5' recombinant adeno-associated virus (rAAV) comprising an adeno-associated virus capsid protein and a first 5' isolated nucleic acid comprising a transgene, wherein the transgene of the first 5' isolated nucleic acid comprises a nucleotide sequence encoding a first portion of a PCDH15 protein and a nucleotide sequence encoding a splice donor of an intron, and wherein the nucleotide sequence encoding the first portion of the PCDH15 protein comprises a sequence at least 95% identical to SEQ ID NO: 4, and (ii) a first 3' rAAV comprising an adeno-associated virus capsid protein and a first 3' isolated nucleic acid comprising a transgene, wherein the transgene of the first 3' isolated nucleic acid comprises a nucleotide sequence encoding a second portion of a PCDH15 protein, and wherein the nucleotide sequence encoding the second portion of the PCDH15 protein comprises a sequence at least 95% identical to SEQ ID NO: 6.

4. A PCDH15 expression system comprising:

(i) a second 5' rAAV comprising an adeno-associated virus capsid protein and a second 5' isolated nucleic acid comprising a transgene, wherein the transgene of the second 5' isolated nucleic acid comprises a nucleotide sequence encoding a first portion of a PCDH15 protein, a nucleotide sequence encoding a splice donor of an intron, and a nucleotide sequence encoding a recombinogenic sequence, and wherein the nucleotide sequence encoding the first portion of the PCDH15 protein comprises a sequence at least 95% identical to SEQ ID NO: 4, and (ii) a second 3' rAAV comprising an adeno-associated virus capsid protein and a second 3' isolated nucleic acid comprising a transgene, wherein the transgene of the second 3' isolated nucleic acid comprises a nucleotide sequence encoding a second portion of a PCDH15 protein, a nucleotide sequence encoding a splice acceptor of an intron, and a nucleotide sequence encoding a recombinogenic sequence, and wherein the nucleotide sequence encoding the second portion of the PCDH15 protein comprises a sequence at least 95% identical to SEQ ID NO: 6.

* * * * *